(12) United States Patent
Greenlee et al.

(10) Patent No.: US 8,487,099 B2
(45) Date of Patent: Jul. 16, 2013

(54) GAMMA SECRETASE MODULATORS

(75) Inventors: William J. Greenlee, Teaneck, NJ (US); Zhaoning Zhu, Plainsboro, NJ (US); Theodros Asberom, West Orange, NJ (US); Xianhai Huang, Warren, NJ (US); Hubert B. Josien, Jersey City, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 171 days.

(21) Appl. No.: 12/739,315

(22) PCT Filed: Nov. 3, 2008

(86) PCT No.: PCT/US2008/082227
§ 371 (c)(1),
(2), (4) Date: Jul. 21, 2010

(87) PCT Pub. No.: WO2009/061699
PCT Pub. Date: May 14, 2009

(65) Prior Publication Data
US 2012/0107328 A1    May 3, 2012

Related U.S. Application Data

(60) Provisional application No. 60/985,453, filed on Nov. 5, 2007.

(51) Int. Cl.
| | | |
|---|---|---|
| C07D 487/10 | (2006.01) |
| C07D 487/20 | (2006.01) |
| C07D 493/10 | (2006.01) |
| C07D 493/20 | (2006.01) |
| C07D 493/22 | (2006.01) |
| C07F 7/08 | (2006.01) |
| C07F 9/6571 | (2006.01) |
| A61K 31/397 | (2006.01) |
| A61K 31/4245 | (2006.01) |
| A61K 31/438 | (2006.01) |
| A61P 25/28 | (2006.01) |

(52) U.S. Cl.
USPC ............................................ 546/19; 514/278

(58) Field of Classification Search
USPC ............................................ 546/19; 514/278
See application file for complete search history.

(56) References Cited

U.S. PATENT DOCUMENTS

| | | | |
|---|---|---|---|
| 5,883,096 A | 3/1999 | Lowe et al. |
| 5,889,006 A | 3/1999 | Lowe et al. |
| 5,935,958 A | 8/1999 | Kozlowski et al. |
| 5,952,349 A | 9/1999 | Asberom et al. |
| 5,977,138 A | 11/1999 | Wang et al. |
| 6,037,352 A | 3/2000 | Lowe et al. |
| 6,043,255 A | 3/2000 | Lowe et al. |
| 6,066,636 A | 5/2000 | Kozlowski et al. |
| 6,294,554 B1 | 9/2001 | Clader et al. |
| 6,458,812 B1 | 10/2002 | McKittrick et al. |
| 8,168,641 B2 | 5/2012 | Wu et al. |
| 2005/0043290 A1 | 2/2005 | Cumming et al. |
| 2005/0119227 A1 | 6/2005 | Cumming et al. |
| 2006/0004013 A1 | 1/2006 | Kimura et al. |
| 2006/0040948 A1 | 2/2006 | Stamford et al. |
| 2006/0040994 A1 | 2/2006 | Huang et al. |
| 2006/0111370 A1 | 5/2006 | Zhu et al. |
| 2006/0281729 A1 | 12/2006 | Iserloh et al. |
| 2006/0281730 A1 | 12/2006 | Zhu et al. |
| 2006/0287294 A1 | 12/2006 | Zhu et al. |
| 2007/0010667 A1 | 1/2007 | McKittrick et al. |
| 2007/0060575 A1 | 3/2007 | Zhu et al. |
| 2007/0072852 A1 | 3/2007 | Zhu et al. |
| 2007/0099875 A1 | 5/2007 | Zhu et al. |
| 2007/0099898 A1 | 5/2007 | Zhu et al. |
| 2007/0117798 A1 | 5/2007 | Kimura et al. |
| 2007/0117839 A1 | 5/2007 | Kimura et al. |
| 2010/0016341 A1 | 1/2010 | Zhu et al. |
| 2010/0069406 A1 | 3/2010 | Zhu et al. |

FOREIGN PATENT DOCUMENTS

| | | |
|---|---|---|
| WO | WO2004071431 | 8/2004 |
| WO | WO2004110350 | 12/2004 |
| WO | WO2005014540 | 2/2005 |
| WO | WO2005016876 | 2/2005 |
| WO | WO2005058311 | 6/2005 |

(Continued)

OTHER PUBLICATIONS

Wolfe, M., J. Neurochem. (2012) 120 (Suppl. 1), 89-98.*
Mancuso et al. Expert Opin. Investig. Drugs (2011) 20(9):1243-1261.*
Wolff Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
West, Anthony R., Solid State Chemistry and its Applications, Wiley, New York, 1988, pp. 358 & 365.*

(Continued)

*Primary Examiner* — Venkataraman Balasubramanian
(74) *Attorney, Agent, or Firm* — Susan L. Hess; Gerard M. Devlin

(57) ABSTRACT

This invention provides novel compounds that are modulators of gamma secretase. The compounds have the formula (I). Also disclosed are methods of modulating gamma secretase activity and methods of treating Alzheimer's Disease using the compounds of formula (I).

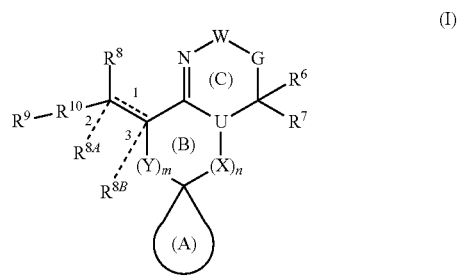

10 Claims, No Drawings

FOREIGN PATENT DOCUMENTS

| | | |
|---|---|---|
| WO | WO2005110422 | 11/2005 |
| WO | WO2006001877 | 1/2006 |
| WO | WO2006014762 | 2/2006 |
| WO | WO2006014944 | 2/2006 |
| WO | WO2006045554 | 5/2006 |
| WO | WO2006065277 | 6/2006 |
| WO | WO2006138192 | 12/2006 |
| WO | WO2006138195 | 12/2006 |
| WO | WO2006138217 | 12/2006 |
| WO | WO2006138230 | 12/2006 |
| WO | WO2006138264 | 12/2006 |
| WO | WO2006138265 | 12/2006 |
| WO | WO2006138266 | 12/2006 |
| WO | WO2007050721 | 5/2007 |
| WO | WO2007053506 | 5/2007 |
| WO | WO2007058305 | 5/2007 |
| WO | WO2007102580 | 9/2007 |
| WO | WO2007120454 | 10/2007 |

OTHER PUBLICATIONS

Vippagunta et al., Advanced Drug Delivery Reviews 48: 3-26, 2001.*
Freshney et al.,Culture of Animal Cells, A Manual of Basic Technique, Alan R. Liss, Inc., 1983, New York, p. 4.*
Dermer et al., Bio/Technology, 1994, 12:320.*
Berge, et al., "Pharmaceutical Salts," Journal of Pharmaceutical Sciences, vol. 66, No. 1, pp. 1-19, 1977.
Bingham, et al., "Over one hundred solvates of sulfathiazole," Chem. Comm. pp. 603-604, 2001.
Caira, et al., "Preparation and Crystal Characterization of a Polymorph, a Monohydrate, and an Ethyl Acetate Solvate of the Antifungal Fluconazole," J. Pharmaceutical Sci., vol. 93, vol. 3, pp. 601-611, 2004.
Forman, et al., Differential Effects of the Swedish Mutant Amyloid Precursor Protein on β-Amyloid Accumulation and Secretion in Neurons and Nonneuronal Cells., The Journal of Biological Chemistry, vol. 272, No. 51, pp. 32247-32253, 1997.
Frangione, et al., "Familial cerebral amyloid angiopathy related to stroke and dementia," Amyloid: J. Protein Folding Disord. 8,Suppl. 1, pp. 36-42, 2001.
Getchell, et al., "3-Nitrotyrosine immunoreactivity in olfactory receptor neurons of patients with Alzhemier's disease: implications for impaired odor sensitivity," Neurobiology of Aging, vol. 24, pp. 663-673, 2003.
Glenner, et al., "Alzheimer's Disease: Initial Report of the Purification and Characterization of a Novel Cerebrovascular Amyloid Protein," Biochem and Biophys. Res. Comm., vol. 120, No. 3, pp. 885-890, 1984.
von Tonder, et al., "Preparation and Physicochemical Characterization of 5 Niclosamide Solvates and 1 Hemisolvate," AAPS Pharm Sci Tech., vol. 5, No. 1, Article 12, 2004.
Gould, "Salt selection for basic drugs," Interrnational Journal of Pharmaceutics, vol. 33, pp. 201-217, 1986.
Gouras, et al., Intraneuronal Aβ Accumulation in Human Brain, American Journal of Pathology, vol. 156, No. 1, pp. 15-20, 2000.
Guo, et al., "Targeting amyloid-β in glaucome treatment," PNAS, vol. 104, No. 33, pp. 13444-13449, 2007.
Hock, et al., "Antibodies against β-Amyloid Slow Cognitive Decline in Alzheimer's Disease," Neuron, vol. 38, pp. 547-554, 2003.
Jarrett, et al., "The Carboxy Terminus of the β Amyloid Protein Is Critical for the Seeding of Amyloid Formation: Implications for the Pathogenesis of Alzheimer's Disease," Biochemistry, vol. 32, No. 18, pp. 4693-4697., 1993.
Lambert, et al., "Diffusible, nonfibrillar ligands derived from Aβ1-42 are potent central nervous system neurotoxins," PNAS Sci. USA, vol. 95, pp. 6448-6453, 1998.
Masters, et al., "Amyloid plaque core protein in Alzheimer's disease and Down syndrome," PNAS Sci USA, vol. 82, pp. 4245-4249, 1985.
Scheuner, et al., "Secreted Amyloid β-protein simila to that in the senile plaques of Alzhemier's disease is increased in vivo by the presenilin 1 and 2 and APP mutations linked to familial Alzheimer's disease," Nature Medicine, vol. 2, No. 8, Aug. 1996.
Shearman, et al., "L-685,458, an Aspartyl Protease Transition State Mimic, Is a Potent Inhibitor of Amyloid β-Protein Precursor y-Secretase Activity," Biochemistry, vol. 39, pp. 8698-8704, 2000.
Murata et al., "Palladium (0)-Catalyzed Silylation of Aryl Halides with Triorganosilanes: Syntehsis of Aryl (2-Furyl) Silanes", Synthesis, 2006, vol. 11, pp. 1771.
Tobisu et al., "Rh(I)-Catalyzed Silylation of Aryl and Alkenyl Cyanides Involving the Cleavage of C-C and Si-Si Bonds", J. Am. Chem Soc., 2006, vol. 128, pp. 8152.
Wong et al., Synlett., "A Facile Synthesis of 1-Substituted Cyclopropylsulfonamides", 2006, vol. 5, pp. 725.
Ensley et al., "Total synthesis of dl-Tazetitine", J. Am. Soc., 1980, pp. 2838.
International Search Report for PCT/US2008/082227, dated Feb. 27, 2009.
Kaim et al., "New Trimethylaluminum-Induced Mannich-Type Reaction of Hydrazones", J. Org. Chem., vol. 68, pp. 8734, 2003.
Subramanian et al., "Artificial Neural Network as an Alternative to Multiple Regression Analysis in Optimizing Formulation Parameters of Cytarabine Liposomes", AAPS PharmaSciTech, vol. 5, pp. 1-9, 2004.

* cited by examiner

GAMMA SECRETASE MODULATORS

REFERENCE TO RELATED APPLICATION

This application is a 371 of PCT/US2008/082227 filed Nov. 3, 2008, which in turn claims the benefit of U.S. Provisional Application Ser. No. 60/985,453 filed Nov. 2, 2007.

FIELD OF THE INVENTION

The present invention relates to certain heterocyclic compounds useful as gamma secretase modulators (including inhibitors, antagonists and the like), pharmaceutical compositions containing the compounds, and methods of treatment using the compounds and compositions to treat various diseases including central nervous system disorders such as, for example, neurodegenerative diseases such as Alzheimer's disease and other diseases relating to the deposition of amyloid protein. They are especially useful for reducing Amyloid beta (hereinafter referred to as Aβ) production which is effective in the treatment of diseases caused by Aβ such as, for example, Alzheimers and Down Syndrome.

BACKGROUND OF THE INVENTION

Alzheimer's disease is a disease characterized by degeneration and loss of neurons and also by the formation of senile plaques and neurofibrillary change. Presently, treatment of Alzheimer's disease is limited to symptomatic therapies with a symptom-improving agent represented by an acetylcholinesterase inhibitor, and the basic remedy which prevents progress of the disease has not been developed. A method of controlling the cause of onset of pathologic conditions needs to be developed for creation of the basic remedy of Alzheimer's disease.

Aβ protein, which is a metabolite of amyloid precursor protein (hereinafter referred to as APP), is considered to be greatly involved in degeneration and loss of neurons as well as onset of demential conditions (for example, see Klein W L, et al *Proceeding National Academy of Science USA*, Sep. 2, 2003, 100(18), p. 10417-22, suggest a molecular basis for reversible memory loss.

Nitsch R M, and 16 others, *Antibodies against β-amyloid slow cognitive decline in Alzheimer's disease, Neuron,* May 22, 2003, 38(4), p. 547-554) suggest that the main components of Aβ protein are Aβ40 consisting of 40 amino acids and Aβ42 having two additional amino acids at the C-terminal. The Aβ40 and Aβ42 tend to aggregate (for example, see Jarrell J T et al, *The carboxy terminus of the β amyloid protein is critical for the seeding of amyloid formation: implications for the pathogenesis of Alzheimer's disease*, Biochemistry, May 11, 1993, 32(18), p. 4693-4697) and constitute main components of senile plaques (for example, (Glenner G G, et al, *Alzheimer's disease: initial report of the purification and characterization of a novel cerebrovascular amyloid protein*, Biochemical and Biophysical Research Communications, May 16, 1984, 120(3), p. 885-90. See also Masters C L, et al, *Amyloid plaque core protein in Alzheimer disease and Down syndrome*, Proceeding National Academy of Science USA, June 1985, 82(12), p. 4245-4249.).

Furthermore, it is known that mutations of APP and presenelin genes, which is observed in familial Alzheimer's disease, increase production of Aβ40 and Aβ42 (for example, see Gouras G K, et al, *Intraneuronal Aβ142 accumulation in human brain*, American Journal of Pathology, January 2000, 156(1), p. 15-20. Also, see Scheuner D, et al, Nature Medicine, August 1996, 2(8), p. 864-870; and Forman M S, et al, *Differential effects of the Swedish mutant amyloid precursor protein on β-amyloid accumulation and secretion in neurons and nonneuronal cells*, Journal of Biological Chemistry, Dec. 19, 1997, 272(51), p. 32247-32253.). Therefore, compounds which reduce production of Aβ40 and Aβ542 are expected as an agent for controlling progress of Alzheimer's disease or for preventing the disease.

These Aβs are produced when APP is cleaved by beta secretase and subsequently clipped by gamma secretase. In consideration of this, creation of inhibitors of γ secretase and β secretase has been attempted for the purpose of reducing production of Aβs. Many of these secretase inhibitors already known are peptides or peptidomimetics such as L-685,458. L-685,458, an aspartyl protease transition stale mimic, is a potent inhibitor of amyloid β-protein precursor γ-secretase activity, Biochemistry, Aug. 1, 2000, 39(30), p. 8698-8704).

Also of interest in connection with the present invention are US 2007/0117798 (Eisai, published May 24, 2007); US 2007/0117839 (Eisai, published May 24, 2007); US 2006/0004013 (Eisai, published Jan. 5, 2006); WO 20051110422 (Boehringer Ingelheim, published Nov. 24, 2005); WO 2006/045554 (Cellzone AG, published May 4, 2006); WO 2004/110350 (Neurogenetics, published Dec. 23, 2004); WO 20041071431 (Myriad Genetics, published Aug. 26, 2004); US 2005/0042284 (Myriad Genetics, published Feb. 23, 2005) and WO 20061001877 (Myriad Genetics, published Jan. 5, 2006).

There is a need for new compounds, formulations, treatments and therapies to treat diseases and disorders associated with Aβ. It is, therefore, an object of this invention to provide compounds useful in the treatment or prevention or amelioration of such diseases and disorders.

SUMMARY OF THE INVENTION

In its many embodiments, the present invention provides a novel class of heterocyclic compounds as gamma secretase modulators (including inhibitors, antagonists and the like), methods of preparing such compounds, pharmaceutical compositions comprising one or more such compounds, methods of preparing pharmaceutical formulations comprising one or more such compounds, and methods of treatment, prevention, inhibition or amelioration of one or more diseases associated with the Aβ using such compounds or pharmaceutical compositions.

One embodiment, of the present invention is directed to compounds of formula (I):

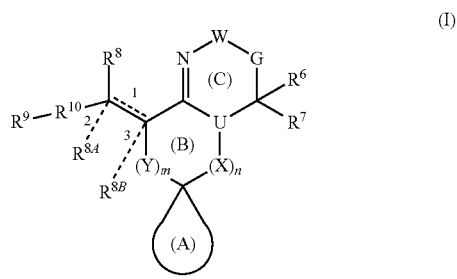

or a pharmaceutically acceptable salt, solvate, ester or prodrug thereof.

This invention also provides compounds of formula (I).

This invention also provides compounds of formula (I) in pure and isolated form.

This invention also provides compounds of formula (I) selected from the group consisting of: compounds IA, IB, IB.1, IC, ID, ID.1, ID.2, ID.3, IE, IF, IF.1, IG, IH, IH.1, II, IJ, IJ.1, IK, IL, IL.1, IM, IN, IN.1, IO, IP, IP.1, IQ, IR, IR.1, IS, IT, IT.1, IU, IV, IV.1, IW, IX, IX.1, IY, IZ, IZ.1, IAA, IAB, IAB.1, IAC, IAD, IAD.1, IAE, IAF, IAF.1, IAG, IAH, IAH.1, IAI, IAJ, IAJ.1, IAK, IAL, IAL.1, IAM, IAN, IAN.1, IAO, IAP, IAP.1, IAQ, IAR, IAR.1, IAS, IAT, IAT.1, IAU, IAV, IAV.1, IAW, IAX, IAX.1, IAY, IAZ, IAZ.1, IBA, IBB, IBB.1, IBC, IBD, IBD.1, IBE, IBF, IBF.1, IBG, IBH, IBH.1, IBI, IBJ, IBJ.1, IBK, IBL, IBL.1, IBM, IBN, IBN.1, IBO, IBP, IBP.1, 1c to 104c, A10 (e.g., A10a and A10b) to A30, E11 to E38, F8 to F25, G3 to G24, H1 to H17, I1 to I17, J1, J3 to J38, K9 to K24, L8, L10 to L21, M1 to M17, N1 to N22, O1 to O22, P6 to P15, Q1 to Q11, R7 to R19, S1 to S15, T3 to T18, U1, and U2.

This invention also provides compounds of formula (I) selected from the group consisting of: compounds IA, IB, IB.1, IC, ID, ID.1, ID.2, ID.3, IE, IF, IF.1, IG, IH, IH.1, II, IJ, IJ.1, IK, IL, IL.1, IM, IN, IN.1, IO, IP, IP.1, IQ, IR, IR.1, IS, IT, IT.1, IU, IV, IV.1, IW, IX, IX.1, IY, IZ, IZ.1, IAA, IAB, IAB.1, IAC, IAD, IAD.1, IAE, IAF, IAF.1, IAG, IAH, IAH.1, IAI, IAJ, IAJ.1, IAK, IAL, IAL.1, IAM, IAN, IAN.1, IAO, IAP, IAP.1, IAQ, IAR, IAR.1, IAS, IAT, IAT.1, IAU, IAV, IAV.1, IAW, IAX, IAX.1, IAY, IAZ, IAZ.1, IBA, IBB, IBB.1, IBC, IBD, IBD.1, IBE, IBF, IBF.1, IBG, IBH, IBH.1, IBI, IBJ, IBJ.1, IBK, IBL, IBL.1, IBM, IBN, IBN.1 IBO, IBP, and IBP.1.

This invention also provides compounds of formula (I) selected from the group consisting of: compounds 1c to 104c.

This invention also provides compounds of formula (I) selected from the group consisting of: compounds A10 (e.g., A10a and A10b) to A30, E11 to E38, F8 to F25, G3 to G24, H1 to H17, I1 to I17, J1, J3 to J38, K9 to K24, L8, L10 to L21, M1 to M17, N1 to N22, O1 to O22, P6 to P15, Q1 to Q11, R7 to R19, S1 to S15, T3 to T18, U1 and U2.

This invention also provides pharmaceutical compositions comprising an effective amount of one or more (e.g., one) compounds of formula (I), or a pharmaceutically acceptable salt, ester or solvate thereof, and a pharmaceutically acceptable carrier.

This invention also provides pharmaceutical compositions comprising an effective amount of one or more (e.g., one) compounds of formula (I), or a pharmaceutically acceptable salt, ester or solvate thereof, and an effective amount of one or more (e.g., one) other pharmaceutically active ingredients (e.g., drugs), and a pharmaceutically acceptable carrier.

The compounds of Formula (I) can be useful as gamma secretase modulators and can be useful in the treatment and prevention of diseases such as, for example, central nervous system disorders such as Alzheimers disease and Downs Syndrome.

Thus, this invention also provides methods for: (1) method for modulating (including inhibiting, antagonizing and the like) gamma-secretase; (2) treating one or more neurodegenerative diseases; (3) inhibiting the deposition of amyloid protein (e.g., amyloid beta protein) in, on or around neurological tissue (e.g., the brain); (4) Alzheimer's disease; and (5) treating Downs syndrome; wherein each method comprises administering an effective amount of one or more (e.g., one) compounds of formula (I) to a patient in need of such treatment.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of an effective amount of one or more (e.g. one) compounds of formula (I) and the administration of an effective amount of one or more (e.g., one) other pharmaceutical active ingredients (e.g., drugs).

This invention also provides methods for: (1) treating mild cognitive impairment; (2) treating glaucoma; (3) treating cerebral amyloid angiopathy; (4) treating stroke; (5) treating dementia; (6) treating microgliosis; (7) treating brain inflammation; and (8) treating olfactory function loss; wherein each method comprises administering an effective amount of one or more (e.g., one) compounds of formula (I) to a patient in need of such treatment.

This invention also provides a kit comprising, in separate containers, in a single package, pharmaceutical compositions for use in combination, wherein one container comprises an effective amount of a compound of formula (I) in a pharmaceutically acceptable carrier, and another container (i.e., a second container) comprises an effective amount of another pharmaceutically active ingredient (as described below), the combined quantities of the compound of formula (I) and the other pharmaceutically active ingredient being effective to treat the diseases or conditions mentioned in any of the above methods.

This invention also provides any of the above mentioned methods, pharmaceutical compositions or kit wherein the compound of formula (I) is selected from the group consisting of: IA, IB, IB.1, IC, ID, ID.1, ID.2, ID.3, IE, IF, IF.1, IG, IH, IH.1, II, IJ, IJ.1, IK, IL, IL.1, IM, IN, IN.1, IO, IP, IP.1, IQ, IR, IR.1, IS, IT, IT.1, IU, IV, IV.1, IW, IX, IX.1, IY, IZ, IZ.1, IAA, IAB, IAB.1, IAC, IAD, IAD.1, IAE, IAF, IAF.1, IAG, IAH, IAH.1, IAI, IAJ, IAJ.1, IAK, IAL, IAL.1, IAM, IAN, IAN.1, IAO, IAP, IAP.1, IAQ, IAR, IAR.1, IAS, IAT, IAT.1, IAU, IAV, IAV.1, IAW, IAX, IAX.1, IAY, IAZ, IAZ.1, IBA, IBB, IBB.1, IBC, IBD, IBD.1, IBE, IBF, IBF.1, IBG, IBH, IBH.1, IBI, IBJ, IBJ.1, IBK, IBL, IBL.1, IBM, IBN, IBN.1 IBO, IBP, and IBP.1.

This invention also provides any of the above mentioned methods, pharmaceutical compositions or kit wherein the compound of formula (I) is selected from the group consisting of: compounds 1c to 104c.

This invention also provides any of the above mentioned methods, pharmaceutical compositions or kit wherein the compound of formula (I) is selected from the group consisting of: compounds A10 (e.g., A10a and A10b) to A30, E11 to E38, F8 to F25, G3 to G24, H1 to H17, I1 to I17, J1, J3 to J38, K9 to K24, L8, L10 to L21, M1 to M17, N1 to N22, O1 to O22, P6 to P15, Q1 to Q11, R7 to R19, S1 to S15, T3 to T18, U1, and U2.

DETAILED DESCRIPTION OF THE INVENTION

This invention provides compounds, useful as gamma secretase modulators, of formula (I):

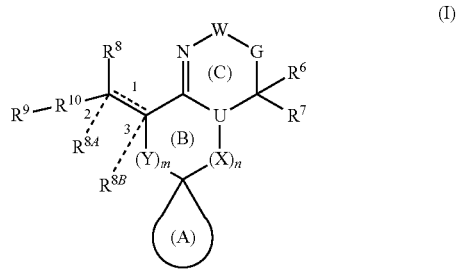

or a pharmaceutically acceptable salt, solvate, ester or prodrug thereof, wherein:

U, G, W, $R^6$, $R^7$, $R^8$, $R^{8A}$, $R^{8B}$, $R^9$, $R^{10}$, Y, X, m and n are independently selected;

(A), (B) and (C) in formula (I) are Fetters used to identify the rings in formula (I);

the dotted lines (-----) represent optional bonds, and the numbers 1, 2 and 3 are used to identify the optional bonds;

when optional Bond 1 (the optional bond from the Ring (B) carbon to the carbon to which $R^8$ is bound) is present, then optional Bonds 2 and 3 are absent (that is, there is no $R^{8A}$ moiety and there is no $R^{8B}$ moiety);

when optional Bond 1 is absent then:
(a) optional Bonds 2 and 3 are present and the $R^{8A}$ moiety and the $R^{8B}$ moiety are present; or
(b) optional Bonds 2 and 3 are present and $R^{8A}$ and $R^{8B}$, taken together with the carbon atoms to which they are bound, form a ring selected from the group consisting of: cycloalkyl, cycloalkenyl, heterocycloalkyl, and heterocycloalkenyl, wherein:
  (i) said cycloalkyl ring is a 3 to 8 carbon membered ring (and in one example a said ring is cyclopropyl), and
  (ii) said cycloalkenyl ring is a 5 to 8 carbon membered ring comprising one or two double bonds (and in one example one double bond, and in another example two double bonds), provided that $R^8$ is absent when there is a double bond to the carbon to which $R^{10}$ is bound, and provided that there is no double bond to the carbon common to Ring (B) and said cycloalkenyl ring, and
  (iii) said heterocycloalkyl ring is a 4 to 8 membered ring comprising 1 to 3 ring members independently selected from the group consisting of: O, S, $NR^2$, S(O), and $S(O)_2$, and wherein the remaining ring members are selected from the group consisting of carbon and C(O), and
  (iv) said heterocycloalkenyl ring is a 5 to 8 membered ring comprising one or two double bonds (and in one example one double bond, and in another example two double bonds), and comprising 1 to 3 ring members independently selected from the group consisting of: O, S, $NR^2$, S(O), and $S(O)_2$, and wherein the remaining ring members are selected from the group consisting of carbon and C(O), provided that $R^8$ is absent when there is a double bond to the carbon to which $R^{10}$ is bound, and provided that there is no double bond to the carbon common to Ring (B) and said heterocycloalkenyl ring, and
  (v) said cycloalkyl, cycloalkenyl, heterocycloalkyl, or heterocycloalkenyl ring is optionally substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —$OR^{15}$ (e.g., —$CH_3$), —$C(O)R^{15}$, —$C(O)OR^{15}$, —$C(O)N(R^{15})(R^{16})$, —$S(O)N(R^{15})(R^{16})$, —$S(O)_2N(R^{15})(R^{16})$, —$C(=NOR^{15})R^{16}$, and —$P(O)(OR^{15})(OR^{16})$;

Spiro Ring (A) is selected from the group consisting of: cycloalkyl, cycloalkenyl, heterocycloalkyl, and heterocycloalkenyl, wherein:
(a) said cycloalkyl ring (A) is a 3 to 8 carbon membered ring (including the carbon atom common to both rings (A) and (B)), and
(b) said cycloalkenyl ring (A) is a 5 to 8 carbon membered ring (including the carbon atom common to both rings (A) and (B)) comprising one or two double bonds (and in one example one double bond, and in another example two double bonds), provided that there is no double bond to the carbon common to Rings (A) and (B) and
(c) said heterocycloalkyl Ring (A) is a 4 to 8 membered ring (including the carbon atom common to Rings (A) and (B)) comprising 1 to 3 ring members independently selected from the group consisting of: O, S, $NR^2$, P(O)alkyl (e.g., $P(O)CH_3$), P(O)Oalkyl (e.g., $P(O)OCH_3$), S(O), and $S(O)_2$, and wherein the remaining ring members are independently selected from the group consisting of carbon and C(O), and
(d) said heterocycloalkenyl Ring (A) is a 5 to 8 membered ring (including the carbon atom common to Rings (A) and (B)) comprising one or two double bonds (and in one example one double bond, and in another example two double bonds), and comprising 1 to 3 ring members independently selected from the group consisting of: O, S, $NR^2$, P(O)alkyl (e.g., $P(O)CH_3$), P(O)Oalkyl (e.g., $P(O)OCH_3$), S(O), and $S(O)_2$, and wherein the remaining ring members are independently selected from the group consisting of carbon and C(O), provided that there is no double bond to the carbon common to Rings (A) and (B), and
(e) wherein said Spiro Ring (A) is optionally fused with an aryl ring (e.g. phenyl), or is optionally fused with a heteroaryl ring (e.g., pyridyl), to form a fused Spiro Ring (A) moiety, and
(f) wherein said Spiro Ring (A) is optionally substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, —$C(O)R^{15}$, —$C(O)OR^{15}$, —$C(O)N(R^{15})(R^{16})$, —$S(O)N(R^{15})(R^{16})$, —$S(O)_2N(R^{15})(R^{16})$, —$C(=NOR^{15})R^{16}$, —$P(O)(OR^{15})(OR^{16})$, —$OR^{15}$ (e.g., —$OCH_3$), and —$S(O)_2R^{15A}$ (e.g., —$S(O)_2CH_3$);

each X is independently selected from the group consisting of: —C(O)—, —$NR^2$—, —O—, —S—, —S(O)—, —$S(O)_2$— and —$C(R^3)_2$— (wherein each $R^3$ is independently selected);

each Y is independently selected from the group consisting of: —C(O)—, —$NR^2$—, —O—, —S—, —S(O)—, —$S(O)_2$— and —$C(R^3)_2$— (wherein each $R^3$ is independently selected);

m and n are each independently 0, 1, 2, or 3, provided that the sum of m and n is 0, 1, 2, or 3;

G is selected from the group consisting of: —$CF_2$—, —C(O)—, —O—, —S—, —$OC(R^3)_2$— (wherein each $R^3$ is independently selected), —$C(R^3)_2$— (wherein each $R^3$ is independently selected), and —$SC(R^3)_2$— (wherein each $R^3$ is independently selected); or G is —$C(R^3)_2$ wherein each $R^3$ is taken together with the carbon atom to which they are bound to form a 3 to 8 membered cycloalkyl or heterocycloalkyl ring, said heterocycloalkyl ring comprising 1 to 3 ring members independently selected from the group consisting of: O, S, $NR^2$, P(O)alkyl (e.g., $P(O)CH_3$), P(O)Oalkyl (e.g., $P(O)OCH_3$), S(O), and $S(O)_2$, and wherein the remaining ring members are selected from the group consisting of carbon and C(O);

U is selected from the group consisting of:

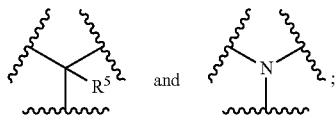

W is selected from the group consisting of: a bond; —C(O)—; —NR²—, —C(R³)₂— (wherein each R³ is independently selected), —S(O)—; and —S(O)₂—;

R² is selected from the group consisting of: H, —S(O)R⁴, —S(O)(OR⁴), —S(O)₂R⁴, —S(O)₂(OR⁴), —S(O)NHR⁴, —S(O)N(R⁴)₂ (wherein each R⁴ is independently selected), —S(O)NH₂, —S(O)₂NHR⁴, —S(O)₂N(R⁴)₂ (wherein each R⁴ is independently selected), —S(O)₂NH₂, —CN, —C(O)₂R⁴, —C(O)NHR⁴, —C(O)N(R⁴)₂ (wherein each R⁴ is independently selected), —C(O)NH₂, —C(O)R⁴, unsubstituted aryl, substituted aryl, unsubstituted heteroaryl, substituted heteroaryl, unsubstituted alkyl, substituted alkyl, unsubstituted arylalkyl-, substituted arylalkyl-, unsubstituted heteroarylalkyl-, substituted heteroarylalkyl-, unsubstituted alkenyl, substituted alkenyl, unsubstituted alkynyl, substituted alkynyl, unsubstituted cycloalkyl, and substituted cycloalkyl, wherein said substituted aryl, heteroaryl, alkyl, arylalkyl-, heteroarylalkyl-, alkenyl, alkynyl and cycloalkyl groups are substituted with 1 to 5 independently selected R²¹ groups;

R³, R⁵, R⁶, R⁷, R¹¹, and R¹² are each independently selected from the group consisting of: H, alkyl-, alkenyl-, alkynyl-, aryl-, arylalkyl-, alkylaryl-, cycloalkyl-, cycloalkylalkyl-, heteroaryl-, heteroarylalkyl-, heterocyclyl-, heterocyclylalkyl-, -arylfusedheteroaryl (i.e., and aryl ring fused to a heteroaryl ring, e.g., -phenylfusedheteroaryl), -arylfusedheterocycloalkyl (i.e., an aryl ring fused to a heterocycloalkyl ring, e.g., -phenylfusedheterocycloalkyl), and -heterocycloalkylfusedaryl (i.e., a heterocycloalkyl ring fused to a aryl ring), and (a) wherein the heteroaryl moiety in said -arylfusedheteroaryl substituent is a 5 to 8 membered heteroaryl ring (including the atoms common to both rings), and wherein the arylfusedheteroaryl ring is bound through the aryl moiety to the rest of the molecule, and (b) wherein the heterocycloalkyl moiety in said -arylfusedheterocycloalkyl substituent is a 4 to 8 membered heterocycloalkyl ring (including the atoms common to both rings), and wherein the arylfusedheterocycloalkyl ring is bound through the aryl moiety to the rest of the molecule, and (c) wherein the heterocycloalkyl moiety in said -heterocycloalkylfusedaryl substituent is a 4 to 8 membered heterocycloalkyl ring (including the atoms common to both rings) (and in one example a five membered ring comprising a nitrogen atom), and wherein the heterocycloalkylfusedaryl ring is bound through the heterocycloalkyl moiety to the rest of the molecule, and (d) wherein said heteroaryl moiety of said -arylfusedheteroaryl substituent, and said heterocycloalkyl moiety of said -arylfusedheterocycloalkyl substituent, and said heterocycloalkyl moiety of said -heterocycloalkylfusedaryl substituent comprise 1 to 3 independently selected heteroatoms selected from the group consisting of: O, S, NR², P(O)alkyl (e.g., P(O)CH₃), P(O)Oalkyl (e.g., P(O)OCH₃), Si, Si(R¹⁵ᴬ)₁₋₃, S(O), and S(O)₂, and wherein the remaining ring members are selected from the group consisting of carbon and C(O), and in one example the R¹⁵ᴬ of the Si(R¹⁵ᴬ)₁₋₃ moiety is selected from the group consisting of alkyl (e.g., methyl, ethyl and propyl), and aryl (e.g., phenyl), and (e) wherein independently each of said alkyl-, alkenyl- and alkynyl-, aryl-, alkylaryl-, cycloalkyl-, cycloalkylalkyl-, heteroaryl-, heteroarylalkyl-, heterocyclyl-, heterocyclylalkyl-, -arylfusedheteroaryl, -arylfusedheterocycloalkyl, and -heterocycloalkylfusedaryl is optionally substituted with 1 to 5 independently selected R²¹ groups; or R⁶ and R⁷, together with the carbon atom to which they are bound, form a 3 to 8 membered (including the carbon atom common to both rings) spiro ring selected from the group consisting of: cycloalkyl, cycloalkenyl, heterocycloalkyl, heterocycloalkenyl, cycloalkyl fused to an aryl, cycloalkyl fused to a heteroaryl ring, cycloalkenyl fused to an aryl, cycloalkenyl fused to a heteroaryl, heterocycloalkyl fused to an aryl, heterocycloalkyl fused to a heteroaryl, heterocycloalkenyl fused to an aryl, and heterocycloalkenyl fused to a heteroaryl wherein:

(i) said cycloalkyl ring is a 3 to 8 carbon membered ring (and in one example a said ring is cyclopropyl), and (ii) said cycloalkenyl ring is a 5 to 8 carbon membered ring comprising one or two double bonds (and in one example one double bond, and in another example two double bonds), provided that there is no double bond to the carbon atom common to Ring (C) and said cycloalkenyl ring, and (iii) said heterocycloalkyl ring is a 4 to 8 membered ring comprising 1 to 3 ring members selected from the group consisting of: O, S, NR², S(O), and S(O)₂, and wherein the remaining ring members are selected from the group consisting of carbon and C(O), and (iv) said heterocycloalkenyl ring is a 5 to 8 membered ring comprising one or two double bonds (and in one example one double bond, and in another example two double bonds), and comprising 1 to 3 ring members selected from the group consisting of: O, S, NR², S(O), and S(O)₂, and wherein the remaining ring members are selected from the group consisting of carbon and C(O), provided that there is no double bond to the carbon atom common to Ring (C) and said heterocycloalkenyl ring, and (v) said cycloalkyl, cycloalkenyl, heterocycloalkyl, or heterocycloalkenyl spiro ring is optionally substituted with 1 to 4 independently selected R²¹ groups; and (vi) said cycloalkyl, cycloalkenyl, heterocycloalkyl, heterocycloalkenyl, aryl and heteroaryl moieties of the fused spiro rings are each optionally substituted with 1 to 4 independently selected R²¹ groups (that is, each ring of the fused ring is optionally substituted with 1 to 4 independently selected R²¹ groups);

each R⁴ is independently selected from the group consisting of: unsubstituted aryl, substituted aryl, unsubstituted heteroaryl, substituted heteroaryl, unsubstituted alkyl, substituted alkyl, unsubstituted arylalkyl-, substituted arylalkyl-, unsubstituted heteroaryalkyl-, substituted heteroarylalkyl-, unsubstituted alkenyl, substituted alkenyl, unsubstituted alkynyl, substituted alkynyl, unsubstituted cycloalkyl, and substituted cycloalkyl, wherein said substituted aryl, heteroaryl, alkyl, arylalkyl-, heteroarylalkyl-, alkenyl, alkynyl and cycloalkyl groups are substituted with 1 to 5 independently selected R²¹ groups;

R⁸ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein independently each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1 to 3 independently selected $R^{21}$ groups;

$R^{8A}$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein independently each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1 to 3 independently selected $R^{21}$ groups;

$R^{8B}$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein independently each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1 to 3 independently selected $R^{21}$ groups;

$R^9$ is selected from the group consisting of H, alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein independently each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1 to 3 independently selected $R^{21}$ groups;

$R^{10}$ is selected from the group consisting of a bond, alkyl-, alkenyl- and alkynyl-, aryl-, arylalkyl-, alkylaryl-, cycloalkyl-, cycloalkylalkyl-, heteroaryl-, heteroarylalkyl-, heterocyclyl-, heterocyclylalkyl-,

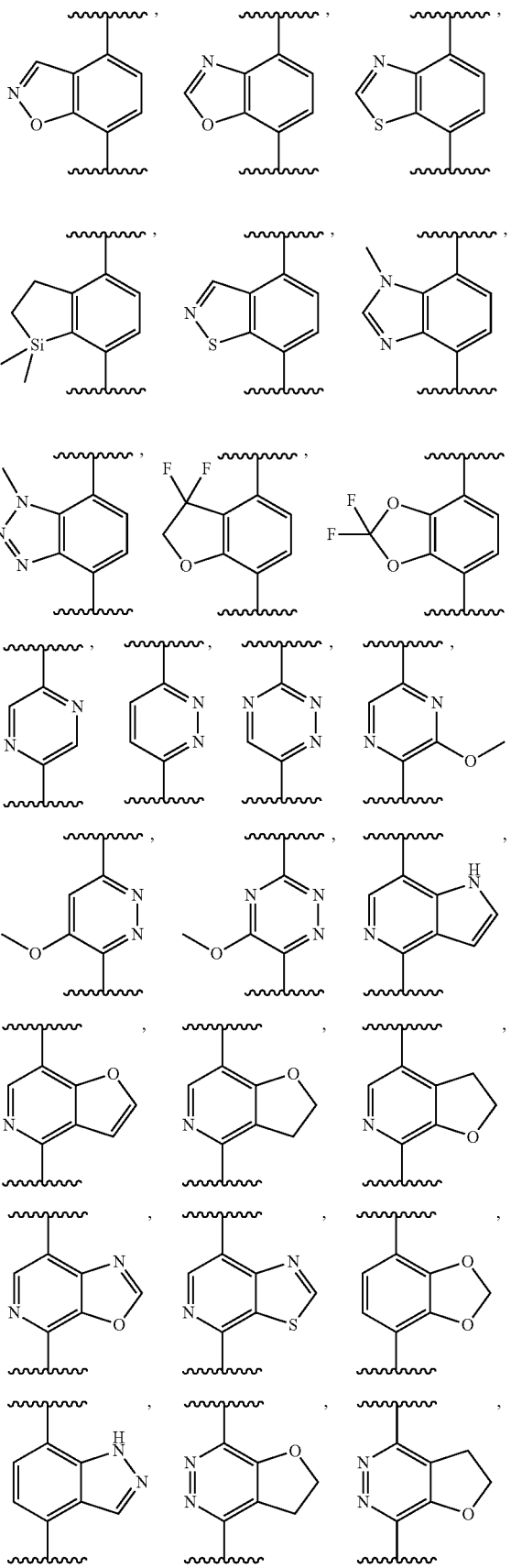

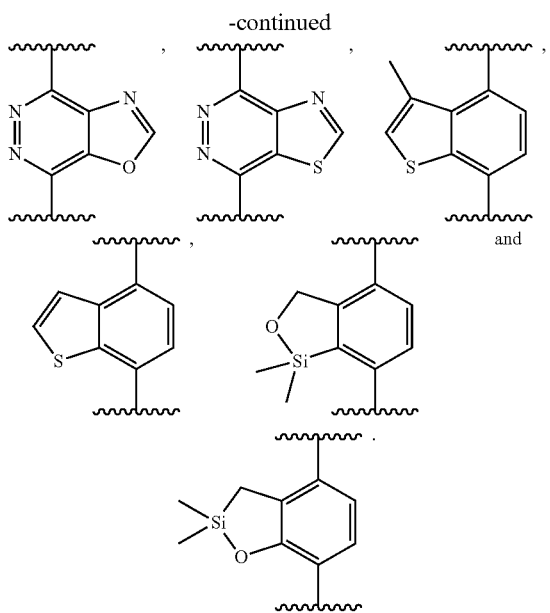

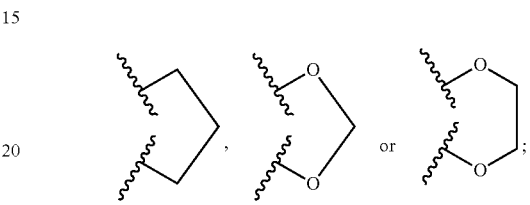

wherein $X^1$ is O, $N(R^{14})$ or S; and wherein independently each $R^{10}$ moiety (except the bond) is optionally substituted with 1 to 3 independently selected $R^{21}$ groups;

$R^{14}$ is selected from the group consisting of H, alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$), and wherein independently each of said alkyl, alkenyl, alkynyl, cycloalkyl, cycloalkylalkyl, cycloalkenyl, heterocyclyl, heterocyclylalkyl, aryl, arylalkyl, heteroaryl, and heteroarylalkyl is optionally substituted with 1 to 5 independently selected $R^{21}$ groups;

Each $R^{15A}$ is independently selected from the group consisting of alkyl, alkenyl, alkynyl, cycloalkyl, cycloalkylalkyl, heterocyclyl, heterocyclylalkyl, aryl, arylalkyl, heteroaryl, heteroarylalkyl, arylcycloalkyl, arylheterocyclyl, (R$^{18}$)$_q$-alkyl, (R$^{18}$)$_q$-cycloalkyl, R$^{18}$)$_q$-cycloalkylalkyl, (R$^{18}$)$_q$-heterocyclyl, (R$^{18}$)$_q$-heterocyclylalkyl, (R$^{18}$)$_q$-aryl, (R$^{18}$)$_q$-arylalkyl, (R$^{18}$)$_q$-heteroaryl and (R$^{18}$)$_q$-heteroarylalkyl, wherein q is 1 to 5 and each $R^{18}$ is independently selected (and those skilled in the art will appreciate that the $R^{18}$ moieties can be bound to any available substitutable atom);

$R^{15}$, $R^{16}$, and $R^{17}$ are independently selected from the group consisting of H, alkyl, alkenyl, alkynyl, cycloalkyl, cycloalkylalkyl, heterocyclyl, heterocyclylalkyl, aryl, arylalkyl, heteroaryl, heteroarylalkyl, arylcycloalkyl, arylheterocyclyl, (R$^{18}$)$_q$-alkyl, (R$^{18}$)$_q$-cycloalkyl, (R$^{18}$)$_q$-cycloalkylalkyl, (R$^{18}$)$_q$-heterocyclyl, (R$^{18}$)$_q$-heterocyclylalkyl, (R$^{18}$)$_q$-aryl, (R$^{18}$)$_q$-arylalkyl, (R$^{18}$)$_q$-heteroaryl and (R$^{18}$)$_q$-heteroarylalkyl, wherein q is 1 to 5 and each $R^{18}$ is independently selected (and those skilled in the art will appreciate that the $R^{18}$ moieties can be bound to any available substitutable atom); or each $R^{18}$ is independently selected from the group consisting of alkyl, alkenyl, alkynyl, cycloalkyl, aryl, arylalkyl, arylalkynyl, —NO$_2$, halo, heteroaryl, HO-alkyoxyalkyl, —CF$_3$, —CN, alkyl-CN, —C(O)R$^{19}$, —C(O)OH, —C(O)OR$^{19}$, —C(O)NHR$^{20}$, —C(O)NH$_2$, —C(O)NH$_2$—C(O)N(alkyl)$_2$, —C(O)N(alkyl)(aryl), —C(O)N(alkyl)(heteroaryl), —SR$^{19}$, —S(O)$_2$R$^{20}$, —S(O)NH$_2$, —S(O)NH (alkyl), —S(O)N(alkyl)(alkyl), —S(O)NH(aryl), —S(O)$_2$NH$_2$, —S(O)$_2$NHR$^{19}$, —S(O)$_2$NH(heterocyclyl), —S(O)$_2$N(alkyl)$_2$, —S(O)$_2$N(alkyl)(aryl), —OCF$_3$, —OH, —OR$^{20}$, —O-heterocyclyl, —O-heterocyclylalkyl, —NH$_2$, —NHR$^{20}$, —N(alkyl)$_2$, —N(arylalkyl)$_2$, —N(arylalkyl)-(heteroarylalkyl), —NHC(O)R$^{20}$, —NHC(O)NH$_2$, —NHC(O)NH(alkyl), —NHC(O)N(alkyl)(alkyl), —N(alkyl)C(O) NH(alkyl), —N(alkyl)C(O)N(alkyl)(alkyl), —NHS(O)$_2$R$^{20}$, —NHS(O)$_2$NH(alkyl), —NHS(O)$_2$N(alkyl)(alkyl), —N(alkyl)S(O)$_2$NH(alkyl) and —N(alkyl)S(O)$_2$N(alkyl)(alkyl); or alternately, two $R^{18}$ moieties on adjacent carbons can be linked together to form:

$R^{19}$ is alkyl, cycloalkyl, aryl, arylalkyl or heteroarylalkyl;
$R^{20}$ is alkyl, cycloalkyl, aryl, halo substituted aryl, arylalkyl, heteroaryl or heteroarylalkyl;

each $R^{21}$ group is independently selected from the group consisting of alkyl, alkenyl, alkynyl, cycloalkyl, cycloalkylalkyl, cycloalkenyl, heterocyclyl (i.e., heterocycloalkyl), heterocyclylalkyl (i.e., heterocycloalkylalkyl), aryl, arylalkyl, heteroaryl, heteroarylalkyl, halo, —CN, —OR$^{15}$, —C(O) OR$^{15}$, —C(O)N(R$^{15}$)(R$^{16}$), —SF$_5$, —OSF$_5$, —Si(R$^{15A}$)$_3$ wherein each R$^{15A}$ is independently selected, —SR$^{15}$, —S(O) N(R$^{15}$)(R$^{16}$), —CH(R$^{15}$)(R$^{16}$), —S(O)$_2$N(R$^{15}$)(R$^{16}$), —C(=NOR$^{15}$)R$^{16}$, —O, —P(O)(OR$^{15}$)(OR$^{16}$), —N(R$^{15}$) (R$^{16}$), -alkyl-N(R$^{15}$)(R$^{16}$), —N(R$^{15}$)C(O)R$^{16}$, —CH$_2$—N (R$^{15}$)C(O)R$^{16}$, —CH$_2$—N(R$^{15}$)C(O)N(R$^{16}$)(R$^{17}$), —CH$_2$—R$^{15}$; —CH$_2$N(R$^{15}$)(R$^{16}$), —N(R$^{15}$)S(O)R$^{16}$, —N(R$^{15}$)S(O)$_2$ R$^{16}$, —CH$_2$—N(R$^{15}$)S(O)$_2$R$^{16}$, —N(R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$)(R$^{17}$), —N(R$^{15}$)C(O)OR$^{16}$—CH$_2$—N(R$^{15}$)C(O)OR$^{16}$, —S(O)R$^{15}$, =NOR$^{15}$, —N$_3$, —NO$_2$ and —S(O)$_2$R$^{15}$; and wherein independently each of the alkyl, cycloalkenyl, cycloalkyl, cycloalkylalkyl, heterocyclyl, heterocyclylalkyl, aryl, arylalkyl, heteroaryl, heteroarylalkyl, alkenyl and alkynyl $R^{21}$ groups is optionally substituted by 1 to 5 independently selected $R^{22}$ groups wherein each $R^{22}$ group is independently selected from the group consisting of alkyl, cycloalkyl, cycloalkenyl, heterocyclyl, aryl, heteroaryl, halo, —CF$_3$, —CN, —OR$^{15}$, —C(O)R$^{15}$, —C(O)OR$^{15}$, -alkyl-C (O)OR$^{15}$, C(O)N(R$^{15}$)(R$^{16}$), —SF$_5$, —OSF$_5$, —Si(R$^{15A}$)$_3$ wherein each R$^{15A}$ is independently selected, —SR$^{15}$, S(O) N(R$^{15}$)(R$^{16}$), —S(O)$_2$N(R$^{15}$)(R$^{16}$), —C(=NOR$^{15}$)R$^{16}$, —P(O)(OR$^{15}$)(OR$^{16}$), —N(R$^{15}$)(R$^{16}$), -alkyl-N(R$^{15}$)(R$^{16}$), —N(R$^{15}$)C(O)R$^{16}$, —CH$_2$—N(R$^{15}$)C(O)R$^{16}$, —N(R$^{15}$)S (O)R$^{16}$, —N(R$^{15}$)S(O)$_2$R$^{16}$, —CH$_2$—N(R$^{15}$)S(O)$_2$R$^{16}$—N (R$^{15}$)S(O)$_2$N(R$^{16}$)(R$^{17}$), —N(R$^{15}$)S(O)N(R$^{16}$)(R$^{17}$), —N(R$^{15}$)C(O)N(R$^{16}$)(R$^{17}$), —CH$_2$—N(R$^{15}$)C(O)N(R$^{16}$) (R$^{17}$), —N(R$^{15}$)C(O)OR$^{16}$, —CH$_2$—N(R$^{15}$)C(O)OR$^{16}$, —N$_3$, =NOR$^{15}$, —NO$_2$, —S(O)R$^{15}$ and —S(O)$_2$R$^{15}$; and provided that
(1) the rings in formula (I) comprising hetero atoms:
(a) do not have two adjacent —O— atoms in the ring (i.e., the rings do not have —O—O— moieties in the rings), and (b) do not have a —S— adjacent to an —O— in the rings (i.e., the rings do not have —S—O— moieties, or a —O—S— moieties, in the rings), (c) do not have a —S— adjacent to a —S—, or a —S— adjacent to a —S(O)—, or a —S— adjacent to a —S(O)$_2$—, or a —S(O)— adjacent to a —S(O)—, or a —S(O)— adjacent to a —S(O)$_2$—, or a —S(O)$_2$— adjacent to a —S(O)$_2$ in the rings (i.e., the rings do not have —S—S—, —S—S(O)—, —S(O)—S—, —S—S(O)$_2$—, —S(O)$_2$—S—, —S(O)—S(O)—, —S(O)—S(O)$_2$—, —S(O)$_2$—S(O)—, or —S(O)$_2$—S(O)$_2$— moieties in the rings), and (d) do not have three consecutive ring atoms selected from the group consisting of: —O—, —N— (i.e., —NR$^2$—) and —S—, and (e) do not have more than two adjacent groups in the rings that are selected from the group consisting of: —C(O)—, —S(O)—, and —S(O)$_2$—, and (f) examples of the rings comprising heteroatoms include the heterocycloalkyl and the heterocycloalkenyl rings of the Spiro (A) ring moiety, the heterocycloalkyl and the heterocycloalkenyl rings formed when R$^{8A}$ and R$^{8B}$ are taken together with the carbon atoms to which they are bound, the heterocycloalkyl and the heterocycloalkenyl rings formed when R$^6$ and R$^7$ are taken together with the carbon atoms to which they are bound, and Ring (B) when U, X and Y are not all carbon; and (2) when X is —O— then Y is not —NR$^2$—; and
(3) when X is —NR$^2$— then Y is not —O—; and
(4) when Y is —O— then X is not —NR$^2$—; and
(5) when Y is —NR$^2$— then X is not —O—.

The compounds of this invention are useful for treating central nervous system disorders such as, for example, neurodegenerative diseases such as Alzheimer's disease and other diseases relating to the deposition of amyloid protein. They are especially useful for reducing Amyloid beta (hereinafter referred to as Aβ) production which is effective in the treatment of diseases caused by Aβ such as, for example, Alzheimers and Down Syndrome.

Thus, for example, the compounds of this invention can be used to treat the following diseases or conditions: Alzheimers disease, mild cognitive impairment (MCI), Downs Syndrome, Glaucoma (Guo et. al., Proc. Natl. Acad. Sci. USA 104, 13444-13449 (2007)), Cerebral amyloid angiopathy, stroke or dementia (Frangione et al., Amyloid: J. Protein folding Disord. 8, suppl. 1, 36-42 (2001), Microgliosis and brain inflammation (M P Lamber, Proc. Natl. Acad. Sci. USA 95, 6448-53 (1998)), and Olfactory function loss (Getchell, et. al. Neurobiology of Aging, 663-673, 24, 2003).

In one embodiment of this invention G is —CF$_2$—.
In another embodiment of this invention G is —C(O)—.
In another embodiment of this invention G is —O—.
In another embodiment of this invention G is —S—.
In another embodiment of this invention G is —C(R$^3$)$_2$— (wherein each R$^3$ is independently selected). In one example, G is —CH$_2$—. In another example, G is —CF$_2$—.

In another embodiment of this invention, G is —C(R$^3$)$_2$ wherein each R$^3$ is taken together with the carbon atom to which they are bound to form a 3 to 8 membered cycloalkyl or heterocycloalkyl ring, said heterocycloalkyl ring comprising 1 to 3 ring members independently selected from the group consisting of: O, S, NR$^2$, P(O)alkyl (e.g., P(O)CH$_3$), P(O)Oalkyl (e.g., P(O)OCH$_3$), S(O), and S(O)$_2$, and wherein the remaining ring members are selected from the group consisting of carbon and C(O).

In another embodiment of this invention G is —OC(R$^3$)$_2$— (wherein each R$^3$ is independently selected), wherein the —O— is bound to the ring N.

In another embodiment of this invention G is —SC(R$^3$)$_2$— (wherein each R$^3$ is independently selected) wherein the —S— is bound to the ring N.

In another embodiment of this invention U is a CR$^5$ moiety; that is U is:

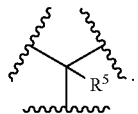

In another embodiment of this invention U is N; that is U is:

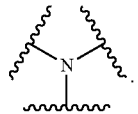

In another embodiment of this invention W is a bond, that is, the G moiety is bound directly to the N.

In another embodiment of this invention W is —NR$^2$—. In one example R$^2$ is H, e W is —NH—. In another example. R$^2$ is alkyl (such as, for example, methyl or ethyl), i.e., W is —NCH$_3$— or —NC$_2$H$_5$—.

In another embodiment of this invention W is —C(R$^3$)$_2$— (wherein each R$^3$ is independently selected).

In another embodiment of this invention W is —C(O)—.
In another embodiment of this invention W is —S(O)—.
In another embodiment of this invention W is —S(O)$_2$—.
In another embodiment m+n is 0.
In another embodiment m+n is 1.
In another embodiment m+n is 2.
In another embodiment m+n is 3.
In another embodiment of this invention n is 1.
In another embodiment of this invention m is 1.
In another embodiment of this invention m is 1 and n is 1.
In another embodiment of this invention X is —C(O)—.
In another embodiment of this invention X is —NR$^2$—.
In another embodiment of this invention X is —O—.
In another embodiment of this invention X is —S—.
In another embodiment of this invention X is —S(O)—.
In another embodiment of this invention X is —S(O)$_2$—.
In another embodiment of this invention X is —C(R$^3$)$_2$— (wherein each R$^3$ is independently selected).
In another embodiment of this invention X is —C(R$^3$)$_2$— wherein each R$^3$ is H, that is X is —CH$_2$—.
In another embodiment of this invention X is —C(R$^3$)$_2$— wherein each R$^3$ is H, and n is 1, that is X is —CH$_2$— and n is 1.
In another embodiment of this invention X is —NR$^2$— and n is 1.
In another embodiment of this invention X is —O— and n is 1.
In another embodiment of this invention X is —S— and n is 1.
In another embodiment of this invention X is —S(O)— and n is 1.
In another embodiment of this invention X is —S(O)$_2$— and n is 1.

In another embodiment of this invention X is —C(R$^3$)$_2$— (wherein each R$^3$ is independently selected) and n is 1.

In another embodiment of this invention X is —C(R$^3$)$_2$— wherein each R$^3$ is H, that is X is —CH$_2$—, and n is 1.

In another embodiment of this invention Y is —C(O)—

In another embodiment of this invention Y is —NR$^2$—.

In another embodiment of this invention Y is —O—.

In another embodiment of this invention Y is —S—.

In another embodiment of this invention Y is —S(O)—.

In another embodiment of this invention Y is —S(O)$_2$—.

In another embodiment of this invention Y is —C(R$^3$)$_2$— (wherein each R$^3$ is independently selected).

In another embodiment of this invention Y is —C(R$^3$)$_2$— wherein each R$^3$ is H, that is Y is —CH$_2$—.

In another embodiment of this invention Y is —C(R$^3$)$_2$— wherein each R$^3$ is H, and m is 1, that is Y is —CH$_2$— and m is 1.

In another embodiment of this invention Y is —NR$^2$— and m is 1.

In another embodiment of this invention Y is —O— and m is 1.

In another embodiment of this invention Y is —S— and m is 1.

In another embodiment of this invention Y is —S(O)— and m is 1.

In another embodiment of this invention Y is —S(O)$_2$— and m is 1.

In another embodiment of this invention Y is —C(R$^3$)$_2$— (wherein each R$^3$ is independently selected) and m is 1.

In another embodiment of this invention Y is —C(R$^3$)$_2$— wherein each R$^3$ is H, that is Y is —CH$_2$—, and m is 1.

In another embodiment of this invention X is —C(R$^3$)$_2$— (wherein each R$^3$ is independently selected), and Y is —C(R$^3$)$_2$— (wherein each R$^3$ is independently selected).

In another embodiment of this invention X is —C(R$^3$)$_2$— (wherein each R$^3$ is independently selected), and Y is —C(R$^3$)$_2$— (wherein each R$^3$ is independently selected), and each R$^3$ is H, that is, X is —CH$_2$— and Y is —CH$_2$—.

In another embodiment of this invention X is —C(R$^3$)$_2$— (wherein each R$^3$ is independently selected), and Y is —C(R$^3$)$_2$— (wherein each R$^3$ is independently selected), and m is 1, and n is 1.

In another embodiment of this invention X is —C(R$^3$)$_2$— (wherein each R$^3$ is independently selected), and Y is —C(R$^3$)$_2$— (wherein each R$^3$ is independently selected), and each R$^3$ is H, that is, X is —CH$_2$— and Y is —CH$_2$—, and m is 1, and n is 1.

In another embodiment of this invention X is —S(O)$_2$, and Y is —C(R$^3$)$_2$— (wherein each R$^3$ is independently selected), and m is 1.

In another embodiment of this invention X is —S(O)$_2$, and Y is —CH$_2$—, and m is 1.

In another embodiment of this invention X is —C(R$^3$)$_2$— (wherein each R$^3$ is independently selected), and Y is O, and m is 1.

In another embodiment of this invention X is —C(R$^3$)$_2$— (wherein each R$^3$ is independently selected), and Y is O, and m is 1, and n is 1.

In another embodiment of this invention X is —CH$_2$— (wherein each R$^3$ is independently selected), and Y is O, and m is 1.

In another embodiment of this invention X is —CH$_2$— (wherein each R$^3$ is independently selected), and Y is O, and m is 1, and n is 1.

In another embodiment of this invention there are 1 to 5 R$^{21}$ groups present in formula (I), wherein said R$^{21}$ groups are independently selected from the group consisting of: halo (e.g., F and Cl), alkyl substituted with 1 to 3 halos (e.g., alkyl substituted with 1 to 3 F, such as methyl substituted with 1 to 3 F, such as —CF$_3$), —CN, —SF$_5$, —OSF$_5$, and —Si(R$^{15A}$)$_3$ (such as for example, —Si(CH$_3$)$_3$, —Si(CH$_3$)$_2$phenyl, and —Si(CH$_2$CH$_3$)$_2$CH$_3$).

In another embodiment of this invention there are 1 to 3 R$^{21}$ groups present in formula (I), wherein said R$^{21}$ groups are independently selected from the group consisting of: halo (e.g., F and Cl), alkyl substituted with 1 to 3 halos (e.g., alkyl substituted with 1 to 3 F, such as methyl substituted with 1 to 3 F, such as —CF$_3$), —CN, —SF$_5$, —OSF$_5$, and —Si(R$^{15A}$)$_3$ (such as for example, —Si(CH$_3$)$_3$, —Si(CH$_3$)$_2$phenyl, and —Si(CH$_2$CH$_3$)$_2$CH$_3$).

In another embodiment of this invention, there are 1 to 5 R$^{21}$ groups present in formula (I), and at least one (e.g., 1 to 2) R$^{21}$ is selected from the group consisting of: —SF$_5$, —OSF$_5$ and —Si(R$^{15A}$)$_3$, wherein each R$^{15A}$ is independently selected.

In another embodiment of this invention, there are 1 to 5 R$^{21}$ groups present in formula (I), and at least one R$^{21}$ is selected from the group consisting of: —SF$_5$, —OSF$_5$, and —Si(R$^{15A}$)$_3$, wherein each R$^{15A}$ is independently selected from the group consisting of alkyl and aryl (e.g., phenyl). Examples of said —Si(R$^{15}$)$_3$ moiety include, for example, —Si(CH$_3$)$_3$, —Si(CH$_3$)$_2$phenyl, and —Si(CH$_2$CH$_3$)$_2$CH$_3$.

In another embodiment of this invention, there are 1 to 5 R$^{21}$ groups present in formula (I), and at least one R$^{21}$ is selected from the group consisting of: —SF$_5$ and —Si(R$^{15A}$)$_3$, wherein each R$^{15A}$ is independently selected from the group consisting of alkyl and aryl (e.g., phenyl). Examples of said —Si(R$^{15A}$)$_3$ moiety include, for example, —Si(CH$_3$)$_3$, —Si(CH$_3$)$_2$phenyl, and —Si(CH$_2$CH$_3$)$_2$CH$_3$.

In another embodiment of this invention, there are 1 to 5 R$^{21}$ groups present in formula (I), and at least one R$^{21}$ is selected from the group consisting of: —SF$_5$ and —Si(R$^{15A}$)$_3$, and each R$^{15A}$ is the same or different alkyl group.

In another embodiment of this invention, there are 1 to 5 R$^{21}$ groups present in formula (I), and at least one R$^{21}$ is selected from the group consisting of: —SF$_5$, —OSF$_5$, —Si(CH$_3$)$_3$, —Si(CH$_3$)$_2$phenyl, and —Si(CH$_2$CH$_3$)$_2$CH$_3$.

In another embodiment of this invention, there are 1 to 5 R$^{21}$ groups present in formula (I), and at least one R$^{21}$ is selected from the group consisting of: —SF$_5$, —OSF$_5$ and —Si(CH$_3$)$_3$.

In another embodiment of this invention, there are 1 to 5 R$^{21}$ groups present in formula (I), and one of the R$^{21}$ groups is selected from the group consisting of: —SF$_5$, OSF$_5$ and —Si(R$^{15A}$)$_3$.

In another embodiment of this invention, there are 1 to 5 R$^{21}$ groups present in formula (I), and one R$^{21}$ is selected from the group consisting of: —SF$_5$, —OSF$_5$, and —Si(R$^{15A}$)$_3$, wherein each R$^{15A}$ is independently selected from the group consisting of alkyl and aryl (e.g., phenyl). Examples of said —Si(R$^{15A}$)$_3$ moiety include, for example, —Si(CH$_3$)$_3$, —Si(CH$_3$)$_2$phenyl, and —Si(CH$_2$CH$_3$)$_2$CH$_3$.

In another embodiment of this invention, there are 1 to 5 R$^{21}$ groups present in formula (I), and one of the R$^{21}$ groups is selected from the group consisting of: —SF$_5$, OSF$_5$ and —Si(R$^{15A}$)$_3$, and each R$^{15A}$ is the same or different alkyl group.

In another embodiment of this invention, there are 1 to 5 R$^{21}$ groups present in formula (I), and one R$^{21}$ is selected from the group consisting of: —SF$_5$, —OSF$_5$, —Si(CH$_3$)$_3$, —Si(CH$_3$)$_2$phenyl, and —Si(CH$_2$CH$_3$)$_2$CH$_3$.

In another embodiment of this invention, there are 1 to 5 R$^{21}$ groups present in formula (I), and one of the R$^{21}$ groups is selected from the group consisting of: —SF$_5$, —OSF$_5$, —Si(CH$_3$)$_3$, —Si(CH$_3$)$_2$phenyl, and —Si(CH$_2$CH$_3$)$_2$CH$_3$.

In another embodiment of this invention, there are 2 to 5 $R^{21}$ groups present in formula (I), and two of the $R^{21}$ groups are selected from the group consisting of: —$SF_5$, $OSF_5$ and —$Si(R^{15A})_3$, wherein each $R^{15A}$ is independently selected.

In another embodiment of this invention, there are 2 to 5 $R^{21}$ groups present in formula (I), and two of the $R^{21}$ groups are selected from the group consisting of: —$SF_5$, $OSF_5$ and —$Si(R^{15A})_3$, wherein each $R^{15A}$ is independently selected from the group consisting of alkyl and aryl (e.g., phenyl). Examples of said —$Si(R^{15A})_3$ moiety include, for example, —$Si(CH_3)_3$, —$Si(CH_3)_2phenyl$, and —$Si(CH_2CH_3)_2CH_3$.

In another embodiment of this invention, there are 2 to 5 $R^{21}$ groups present in formula (I), and two of the $R^{21}$ groups are selected from the group consisting of: —$SF_5$, $OSF_5$ and —$Si(R^{15A})_3$, and each $R^{15A}$ is the same or different alkyl group.

In another embodiment of this invention, there are 2 to 5 $R^{21}$ groups present in formula (I), and two of the $R^{21}$ groups are selected from the group consisting of: —$SF_5$, —$OSF_5$, —$Si(CH_3)_3$, —$Si(CH_3)_2phenyl$, and —$Si(CH_2CH_3)_2CH_3$.

In another embodiment of this invention, there are 2 to 5 $R^{21}$ groups present in formula (I), and two of the $R^{21}$ groups are selected from the group consisting of: —$SF_5$, —$OSF_5$ and —$Si(CH_3)_3$.

In another embodiment of this invention, there are 1 to 5 $R^{21}$ groups present in formula (I), and at feast one (e.g., 1 to 2) $R^{21}$ is selected from the group consisting of: —$SF_5$ and —$Si(R^{15A})_3$, wherein each $R^{15A}$ is independently selected.

In another embodiment of this invention, there are 1 to 5 $R^{21}$ groups present in formula (I), and at least one $R^{21}$ is selected from the group consisting of: —$SF_5$ and —$Si(R^{15A})_3$), and each $R^{15A}$ is the same or different alkyl group.

In another embodiment of this invention, there are 1 to 5 $R^{21}$ groups present in formula (I), and at least one $R^{21}$ is selected from the group consisting of: —$SF_5$ and —$Si(CH_3)_3$.

In another embodiment of this invention, there are 1 to 5 $R^{21}$ groups present in formula (I), and one of the $R^{21}$ groups is selected from the group consisting of: —$SF_5$ and —$Si(R^{15A})_3$.

In another embodiment of this invention, there are 1 to 5 $R^{21}$ groups present in formula (I), and one of the $R^{21}$ groups is selected from the group consisting of: —$SF_5$ and —$Si(R^{15A})_3$, and each $R^{15A}$ is the same or different alkyl group.

In another embodiment of this invention, there are 1 to 5 $R^{21}$ groups present in formula (I), and one of the $R^{21}$ groups is selected from the group consisting of: —$SF_5$ and —$Si(CH_3)_3$.

In another embodiment of this invention, there are 2 to 5 $R^{21}$ groups present in formula (I), and two of the $R^{21}$ groups are selected from the group consisting of: —$SF_5$ and —$Si(R^{15A})_3$, wherein each $R^{15A}$ is independently selected.

In another embodiment of this invention, there are 2 to 5 $R^{21}$ groups present in formula (I), and two of the $R^{21}$ groups are selected from the group consisting of: —$SF_5$ and —$Si(R^{15A})_3$, and each $R^{15A}$ is the same or different alkyl group.

In another embodiment of this invention, there are 2 to 5 $R^{21}$ groups present formula (I), and two of the $R^{21}$ groups are selected from the group consisting of: —$SF_5$ and —$Si(CH_3)_3$.

In another embodiment of this invention, there are 1 to 5 $R^{21}$ groups present in formula (I), and one of the $R^{21}$ groups is —$SF_5$.

In another embodiment of this invention, there are 2 to 5 $R^{21}$ groups present in formula (I), and two of the $R^{21}$ groups are —$SF_5$.

In another embodiment of this invention, there are 1 to 5 $R^{21}$ groups present in formula (I), and one of the $R^{21}$ groups is —$OSF_5$.

In another embodiment of this invention, there are 2 to 5 $R^{21}$ groups present in formula (I), and two of the $R^{21}$ groups are —$OSF_5$.

In another embodiment of this invention, there are 1 to 5 $R^{21}$ groups present in formula (I), and one of the $R^{21}$ groups is —$Si(R^{15A})_3$.

In another embodiment of this invention, there are 1 to 5 $R^{21}$ groups present in formula (I), and one of the $R^{21}$ groups is —$Si(R^{15A})_3$, wherein each $R^{15A}$ is independently selected from the group consisting of alkyl and aryl (e.g., phenyl). Examples of said —$Si(R^{15A})_3$ moiety include, for example, —$Si(CH_3)_3$, —$Si(CH_3)_2phenyl$, and —$Si(CH_2CH_3)_2CH_3$.

In another embodiment of this invention, there are 1 to 5 $R^{21}$ groups present in formula (I), and one of the $R^{21}$ groups is —$Si(R^{15A})_3$ and each $R^{15A}$ is the same or different alkyl group.

In another embodiment of this invention, there are 1 to 5 $R^{21}$ groups present in formula (I), and one of the $R^{21}$ groups is —$Si(CH_3)_3$.

In another embodiment of this invention, there are 1 to 5 $R^{21}$ groups present in formula (I), and one of the $R^{21}$ groups is —$Si(CH_3)_2phenyl$.

In another embodiment of this invention, there are 1 to 5 $R^{21}$ groups present in formula (I), and one of the $R^{21}$ groups is —$Si(CH_2CH_3)_2CH_3$.

In another embodiment of this invention, there are 2 to 5 $R^{21}$ groups present in formula (I), and two of the $R^{21}$ groups are the same or different —$Si(R^{15A})_3$, wherein each $R^{15A}$ is independently selected.

In another embodiment of this invention, there are 2 to 5 $R^{21}$ groups present in formula (I), and two of the $R^{21}$ groups are the same or different —$Si(R^{15A})_3$, wherein each $R^{15A}$ is independently selected from the group consisting of alkyl and aryl (e.g., phenyl). Examples of said —$Si(R^{15})_3$ moiety include, for example, —$Si(CH_3)_3$, —$Si(CH_3)_2phenyl$, and —$Si(CH_2CH_3)_2CH_3$.

In another embodiment of this invention, there are 2 to 5 $R^{21}$ groups present in formula (I), and two of the $R^{21}$ groups are the same or different —$Si(R^{15A})_3$ and each $R^{15A}$ is the same or different alkyl group.

In another embodiment of this invention, there are 2 to 5 $R^{21}$ groups present in formula (I), and two of the $R^{21}$ groups are —$Si(CH_3)_3$.

In another embodiment of this invention, there are 2 to 5 $R^{21}$ groups present in formula (I), and two of the $R^{21}$ groups are —$Si(CH_3)_2phenyl$.

In another embodiment of this invention, there are 2 to 5 $R^{21}$ groups present in formula (I), and two of the $R^{21}$ groups are —$Si(CH_2CH_3)_2CH_3$.

In another embodiment of this invention there is at least one $R^{21}$ group present that is selected from the group consisting of: halo (e.g., F and Cl), alkyl substituted with 1 to 3 halos (e.g., alkyl substituted with 1 to 3 F, such as methyl substituted with 1 to 3 F, such as —$CF_3$), —$CN$, —$SF_5$, —$OSF_5$, and —$Si(R^{15A})_3$ (such as for example, —$Si(CH_3)_3$, —$Si(CH_3)_2phenyl$, and —$Si(CH_2CH_3)_2CH_3$), and when there is more than one $R^{21}$ group, each $R^{21}$ group is independently selected.

In another embodiment of this invention there is at least one $R^{21}$ group present that is selected from the group consisting of: halo (e.g., F and Cl), alkyl substituted with 1 to 3 halos (e.g., alkyl substituted with 1 to 3 F, such as methyl substituted with 1 to 3 F, such as —$CF_3$), —$SF_5$, —$OSF_5$, and —$Si(R^{15A})_3$ (such as for example, —$Si(CH_3)_3$, —$Si(CH_3)_2phenyl$, and —$Si(CH_2CH_3)_2CH_3$), and when there is more than one $R^{21}$ group, each $R^{21}$ group is independently selected.

In another embodiment of this invention, there is at least one $R^{21}$ group present that is selected from the group consisting of: $-SF_5$, $-OSF_5$ and $-Si(R^{15A})_3$, wherein each $R^{15}$ is independently selected, and when there is more than one $R^{21}$ group, each $R^{21}$ group is independently selected.

In another embodiment of this invention, there is at least one $R^{21}$ group present that is selected from the group consisting of: $-SF_5$, $-OSF_5$, and $-Si(R^{15A})_3$, wherein each $R^{15A}$ is independently selected from the group consisting of alkyl and aryl (e.g., phenyl). Examples of said $-Si(R^{15A})_3$ moiety include, for example, $-Si(CH_3)_3$, $-Si(CH_3)_2$phenyl, and $-Si(CH_2CH_3)_2CH_3$, and when there is more than one $R^{21}$ group, each $R^{21}$ is independently selected, In another embodiment of this invention, there is at least one $R^{21}$ group present that is selected from the group consisting of: $-SF_5$ and $-Si(R^{15A})_3$, wherein each $R^{15A}$ is independently selected from the group consisting of alkyl and aryl (e.g., phenyl). Examples of said $-Si(R^{15A})_3$ moiety include, for example, $-Si(CH_3)_3$, $-Si(CH_3)_2$phenyl, and $-Si(CH_2CH_3)_2CH_3$, and when there is more than one $R^{21}$ group, each $R^{21}$ group is independently selected.

In another embodiment of this invention, there is at least one $R^{21}$ group present that is selected from the group consisting of: $-SF_5$ and $-Si(R^{15A})_3$, and each $R^{15A}$ is the same or different alkyl group, and when there is more than one $R^{21}$ group, each $R^{21}$ group is independently selected.

In another embodiment of this invention, there is at least one $R^{21}$ group present that is selected from the group consisting of: $-SF_5$, $-OSF_5$, $-Si(CH_3)_3$, $-Si(CH_3)_2$phenyl, and $-Si(CH_2CH_3)_2CH_3$, and when there is more than one $R^{21}$ group, each $R^{21}$ group is independently selected.

In another embodiment of this invention, there is at least one $R^{21}$ group present that is selected from the group consisting of: $-SF_5$, $-OSF_5$ and $-Si(CH_3)_3$, and when there is more than one $R^{21}$ group, each $R^{21}$ group is independently selected.

In another embodiment of this invention, one $R^{21}$ group that is present is selected from the group consisting of: $-SF_5$, $-OSF_5$ and $-Si(R^{15A})_3$, wherein each $R^{15A}$ is independently selected.

In another embodiment of this invention, one $R^{21}$ group that is present is selected from the group consisting of: $-SF_5$, $-OSF_5$, and $-Si(R^{15A})_3$, wherein each $R^{15A}$ is independently selected from the group consisting of alkyl and aryl (e.g., phenyl). Examples of said $-Si(R^{15A})_3$ moiety include, for example, $-Si(CH_3)_3$, $-Si(CH_3)_2$phenyl, and $-Si(CH_2CH_3)_2CH_3$.

In another embodiment of this invention, one $R^{21}$ group that is present is selected from the group consisting of: $-SF_5$ and $-Si(R^{15A})_3$, wherein each $R^{15A}$ is independently selected from the group consisting of alkyl and aryl (e.g., phenyl). Examples of said $-Si(R^{15})_3$ moiety include, for example, $-Si(CH_3)_3$, $-Si(CH_3)_2$phenyl, and $-Si(CH_2CH_3)_2CH_3$.

In another embodiment of this invention, one $R^{21}$ group that is present is selected from the group consisting of: $-SF_5$ and $-Si(R^{15A})_3$, and each $R^{15A}$ is the same or different alkyl group.

In another embodiment of this invention, one $R^{21}$ group that is present is selected from the group consisting of: $-SF_5$, $-OSF_5$, $-Si(CH_3)_2$phenyl, and $-Si(CH_2CH_3)_2CH_3$, In another embodiment of this invention, one $R^{21}$ group that is present is selected from the group consisting of: $-SF_5$, $-OSF_5$ and $-Si(CH_3)_3$.

In another embodiment of this invention, two $R^{21}$ groups that are present are independently selected from the group consisting of: $-SF_5$, $-OSF_5$, and $-Si(R^{15A})_3$, wherein each $R^{15A}$ is independently selected from the group consisting of alkyl and aryl (e.g., phenyl). Examples of said $-Si(R^{15A})_3$ moiety include, for example, $-Si(CH_3)_3$, $-Si(CH_3)_2$phenyl, and $-Si(CH_2CH_3)_2CH_3$.

In another embodiment of this invention, two $R^{21}$ groups that are present are independently selected from the group consisting of: $-SF_5$ and $-Si(R^{15A})_3$, wherein each $R^{15A}$ is independently selected from the group consisting of alkyl and aryl (e.g., phenyl). Examples of said $-Si(R^{15})_3$ moiety include, for example, $-Si(CH_3)_3$, $-Si(CH_3)_2$phenyl, and $-Si(CH_2CH_3)_2CH_3$.

In another embodiment of this invention, two $R^{21}$ groups that are present are independently selected from the group consisting of: $-SF_5$, $-OSF_5$, $-Si(CH_3)_3$, $-Si(CH_3)_2$phenyl, and $-Si(CH_2CH_3)_2CH_3$.

In another embodiment of this invention, two $R^{21}$ groups that are present are independently selected from the group consisting of: $-SF_5$, $-Si(CH_3)_3$, $-Si(CH_3)_2$phenyl, and $-Si(CH_2CH_3)_2CH_3$.

In another embodiment of this invention, two $R^{21}$ groups that are present are independently selected from the group consisting of: $-SF_5$ and $-Si(CH_3)_3$.

In another embodiment of this invention, one $R^{21}$ group that is present is $-SF_5$.

In another embodiment of this invention, two $R^{21}$ groups that are present are $-SF_5$.

In another embodiment of this invention, one $R^{21}$ group that is present is $-OSF_5$.

In another embodiment of this invention, two $R^{21}$ groups that are present are $-OSF_5$.

In another embodiment of this invention, one $R^{21}$ group that is present is $-Si(R^{15A})_3$.

In another embodiment of this invention, two $R^{21}$ groups that are present are $-Si(R^{15A})_3$.

In another embodiment of this invention, one $R^{21}$ group that is present is $-Si(R^{15A})_3$, wherein each $R^{15A}$ is independently selected from the group consisting of alkyl and aryl (e.g., phenyl). Examples of said $-Si(R^{15A})_3$ moiety include, for example, $-Si(CH_3)_3$, $-Si(CH_3)_2$phenyl, and $-Si(CH_2CH_3)_2CH_3$.

In another embodiment of this invention, two $R^{21}$ groups that are present are $Si(R^{15A})_3$, wherein each $R^{15A}$ is independently selected from the group consisting of alkyl and aryl (e.g., phenyl). Examples of said $-Si(R^{15A})_3$ moiety include, for example, $-Si(CH_3)_3$, $-Si(CH_3)_2$phenyl, and $-Si(CH_2CH_3)_2CH_3$.

In another embodiment of this invention, one $R^2$ group that is present is $-Si(R^{15A})_3$, and each $R^{15A}$ is the same or different alkyl group.

In another embodiment of this invention, two $R^{21}$ groups that are present are $-Si(R^{15A})_3$, and each $R^{15A}$ is the same or different alkyl group.

In another embodiment of this invention, one $R^{21}$ group that is present is $-Si(CH_3)_3$.

In another embodiment of this invention, there are two $-Si(CH_3)_3R^{21}$ groups present.

In another embodiment of this invention, one $R^{21}$ group that is present is $-S(CH_2CH_3)_2CH_3$.

In another embodiment of this invention, there are two $-Si(CH_2CH_3)_2CH_3R^{21}$ groups present.

In another embodiment of this invention, one $R^{21}$ group that is present is $-Si(CH_3)_2$phenyl.

In another embodiment of this invention, there are two $-Si(CH_3)_2$phenyl $R^{21}$ groups present.

In another embodiment of this invention $R^6$ is H.

In another embodiment $R^6$ is —C(O)O$R^{15}$ (i.e. alkyl(methyl) substituted with the $R^{21}$ group =O, and the $R^{21}$ group —O$R^{15}$).

In another embodiment $R^6$ is —C(O)O$R^{15}$ alkyl(methyl) substituted with the $R^{21}$ group =O, and the $R^{21}$ group —O$R^{15}$), wherein $R^{15}$ is alkyl.

In another embodiment $R^6$ is —C(O)OCH$_3$.

In another embodiment $R^6$ is alkyl substituted with the $R^{21}$ substituent =O.

In another embodiment $R^6$ is —CH=O (i.e. alkyl(methyl) substituted with the $R^{21}$ group =O).

In another embodiment $R^6$ is alkenyl substituted $R^{21}$ substituent —S(O)$_2R^{15A}$.

In another embodiment $R^6$ is alkenyl substituted with the $R^{21}$ substituent —S(O)$_2R^{15A}$, wherein $R^{15A}$ is alkyl.

In another embodiment $R^6$ is alkenyl substituted with the $R^{21}$ substituent —S(O)$_2R^{15A}$, wherein $R^{15A}$ is methyl.

In another embodiment $R^6$ is —CH=CH—S(O)$_2R^{15A}$ wherein said $R^{15A}$ is alkyl.

In another embodiment $R^6$ is —CH=CH—S(O)$_2$CH$_3$.

In another embodiment $R^6$ is alkyl substituted with the $R^{21}$ substituent —N$R^{15}R^{16}$.

In another embodiment $R^6$ is alkyl substituted with the $R^{21}$ substituent —N$R^{15}R^{16}$ wherein $R^{15}$ and $R^{16}$ are independently selected from the group consisting of H and alkyl.

In another embodiment $R^6$ is alkyl substituted with the $R^{21}$ substituent —N$R^{15}R^{16}$ wherein $R^{15}$ and $R^{16}$ are.

In another embodiment $R^6$ is —CH$_2$NH$_2$.

In another example $R^6$ is -heterocycloakylfusedaryl substituted with 1 or 2 independently selected $R^{21}$ groups, such as, for example, -heterocycloakylfusedaryl substituted with two independently selected $R^{21}$ groups. In one example $R^6$ is heterocycloalkylfusedaryl substituted with two =O$R^{21}$ groups in another example $R^6$ is:

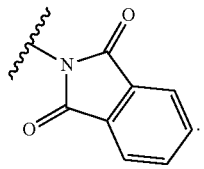 [SMILES: *N1C(=O)c2ccccc2C1=O]

In another embodiment of this invention $R^6$ is alkyl. In one example $R^6$ is methyl. In another example $R^6$ is ethyl.

In another embodiment of this invention $R^6$ is alkyl substituted with $R^{21}$ groups.

In another embodiment $R^6$ is alkyl substituted with one $R^{21}$ group. In one example $R^6$ is alkyl substituted with —O$R^{15}$ (e.g., —OH). In another example $R^6$ is alkyl substituted with —S(O)$_2R^{15A}$. In another example $R^6$ is alkyl substituted with —S(O)$_2R^{15A}$ wherein $R^{15A}$ is alkyl (e.g., methyl, ethyl or propyl). In another example $R^6$ is alkyl substituted with —S(O)$_2R^{15A}$ wherein $R^{15A}$ is ($R^{18}$)$_q$-alkyl-, in another example $R^6$ is alkyl substituted with —S(O)$_2R^{15A}$ wherein $R^{15A}$ is ($R^{18}$)$_q$-alkyl-, and wherein $R^{18}$ is selected from the group consisting of: halo and cycloalkyl.

Examples of $R^6$ include, for example, H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl.

In another embodiment of this invention $R^7$ is aryl (e.g., phenyl).

In another embodiment of this invention $R^7$ is aryl (e.g., phenyl) substituted with 1 to 3 independently selected $R^{21}$ groups.

In another embodiment of this invention $R^7$ is aryl (e.g., phenyl) substituted with at least one $R^{21}$ group selected from the group consisting of: halo (e.g., F, Cl, Br and I), alkyl substituted with 1 to 3 halos (e.g., alkyl substituted with 1 to 3 F, such as methyl substituted with 1 to 3 F, such as —CF$_3$), —CN, —SF$_5$, —OSF$_5$, and —Si($R^{15A}$)$_3$ (such as for example, —Si(CH$_3$)$_3$, —Si(CH$_3$)$_2$phenyl, and —Si(CH$_2$CH$_3$)$_2$CH$_3$), and when there is more than one $R^{21}$ group present each $R^{21}$ group is independently selected.

In another embodiment of this invention $R^7$ is aryl (e.g., phenyl) substituted with at least one $R^{21}$ group selected from the group consisting of: halo (e.g., F and Cl), alkyl substituted with 1 to 3 halos (e.g., alkyl substituted with 1 to 3 F, such as methyl substituted with 1 to 3 F, such as —CF$_3$), —CN, —SF$_5$, —OSF$_5$, and —Si($R^{15A}$)$_3$ (such as for example, —Si(CH$_3$)$_3$, —Si(CH$_3$)$_2$phenyl, and —Si(CH$_2$CH$_3$)$_2$CH$_3$), and when there is more than one $R^{21}$ group present each $R^{21}$ group is independently selected.

In another embodiment of this invention $R^7$ is aryl (e.g., phenyl) substituted with 1 to 3 $R^{21}$ groups independently selected from the group consisting of: halo (e.g., F, Cl, Br and I), alkyl substituted with 1 to 3 halos (e.g., alkyl substituted with 1 to 3 F, such as methyl substituted with 1 to 3 F, such as —CF$_3$), —CN, —SF$_5$, —OSF$_5$, and —Si($R^{15A}$)$_3$ (such as for example, —Si(CH$_3$)$_3$, —Si(CH$_3$)$_2$phenyl, and —Si(CH$_2$CH$_3$)$_2$CH$_3$).

In another embodiment of this invention $R^7$ is aryl (e.g., phenyl) substituted with 1 to 3 $R^{21}$ groups independently selected from the group consisting of: halo (e.g., F, Cl, and Br), alkyl substituted with 1 to 3 halos (e.g., alkyl substituted with 1 to 3 F, such as methyl substituted with 1 to 3 F, such as —CF$_3$), —CN, —SF$_5$, —OSF$_5$, and —Si($R^{15A}$)$_3$ (such as for example, —Si(CH$_3$)$_3$, —Si(CH$_3$)$_2$phenyl, and —Si(CH$_2$CH$_3$)$_2$CH$_3$).

In another embodiment of this invention $R^7$ is aryl (e.g., phenyl) substituted with to 3 $R^{21}$ groups independently selected from the croup consisting of: halo (e.g., F and Cl), alkyl substituted with 1 to 3 halos alkyl substituted with 1 to 3 F, such as methyl substituted with 1 to 3 F, such as —CF$_3$), —CN, —SF$_5$, —OSF$_5$, and —Si($R^{15}$)$_3$ (such as for example, —Si(CH$_3$)$_3$, —Si(CH$_3$)$_2$phenyl, and —Si(CH$_2$CH$_3$)$_2$CH$_3$, In another embodiment of this invention $R^7$ is -arylfusedheteroaryl (e.g., -phenylfusedheteroaryl).

In another embodiment of this invention $R^7$ is -arylfusedheterocycloalkyl (e.g., -phenylfusedheterocycloalkyl), such as, for example,

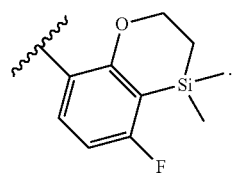

31d

In another embodiment of this invention $R^7$ is aryl (e.g., phenyl) substituted with 1 to 3 independently selected $R^{21}$ groups, and wherein said $R^{21}$ groups are the same or different halo.

In another embodiment of this invention $R^7$ is aryl (e.g., phenyl) substituted with 1 to 2 independently selected $R^{21}$ groups.

In another embodiment of this invention $R^7$ is aryl (e.g., phenyl) substituted with 1 to 2 independently selected $R^{21}$ groups, and wherein said $R^{21}$ groups are the same or different halo.

In another embodiment of this invention $R^7$ is aryl (e.g., phenyl) substituted with 1 to 2 $R^{21}$ groups, and said $R^{21}$ groups are independently selected from the group consisting of F, Br, Cl, and I. In one example there is one $R^{21}$ group and said $R^{21}$ group is F. In another example there are two $R^{21}$ groups and each $R^{21}$ is F. In another example there are two $R^{21}$ groups and one $R^{21}$ is F and the other $R^{21}$ is Br.

In another embodiment of this invention $R^7$ is aryl (e.g., phenyl) substituted with 1 to 2 $R^{21}$ groups, and said $R^{21}$ groups are independently selected from the group consisting of F, Br, and Cl. In one example there is one $R^{21}$ group and said $R^{21}$ group is F. In another example there are two $R^{21}$ groups and each $R^{21}$ is F. In another example there are two $R^{21}$ groups and one $R^{21}$ is F and the other $R^{21}$ is Br.

In another embodiment of this invention $R^7$ is aryl (e.g., phenyl) substituted with 1 to 2 $R^{21}$ groups, and said $R^{21}$ groups are independently selected from the group consisting of F and Cl. In one example there is one $R^{21}$ group and said $R^{21}$ group is F. In another example there are two $R^{21}$ groups and each $R^{21}$ is F.

In another embodiment of this invention $R^7$ is aryl (e.g., phenyl) substituted with 1 $R^{21}$ group.

In another embodiment of this invention $R^7$ is aryl (e.g., phenyl) substituted with 1 $R^{21}$ group, and wherein said $R^{21}$ group is halo.

In another embodiment of this invention $R^7$ is aryl (e.g., phenyl) substituted with 1 $R^{21}$ group, and said $R^{21}$ group is F.

In another embodiment of this invention $R^7$ is aryl (e.g., phenyl) substituted with 2 $R^{21}$ groups.

In another embodiment of this invention $R^7$ is aryl (e.g., phenyl) substituted with 2 $R^{21}$ groups, and wherein said $R^{21}$ groups are the same or different halos.

In another embodiment of this invention $R^7$ is aryl (e.g., phenyl) substituted with 2 $R^{21}$ groups, and said $R^{21}$ groups are independently selected from the group consisting of F, Cl, and Br. In one example both $R^{21}$ groups are F. In another example, one $R^{21}$ group is F and the other $R^{21}$ group is Cl. In another example, one $R^{21}$ group is F and the other $R^{21}$ group is Br.

In another embodiment of this invention $R^7$ is aryl (e.g., phenyl) substituted with 2 $R^{21}$ groups, and said $R^{21}$ groups are independently selected from the group consisting of F and Cl. In one example both $R^{21}$ groups are F. In another example, one $R^{21}$ group is F and the other $R^{21}$ group is Cl.

In another embodiment of this invention $R^7$ is aryl (e.g., phenyl) substituted with 3 $R^{21}$ groups.

In another embodiment of this invention $R^7$ is aryl (e.g., phenyl) substituted with 3 $R^{21}$ groups, and wherein said $R^{21}$ groups are the same or different halos.

In another embodiment of this invention $R^7$ is aryl (e.g., phenyl) substituted with $R^{21}$ groups, and said $R^{21}$ groups are selected from the group consisting of F and Cl. In one example the $R^{21}$ groups are F. In another example two $R^{21}$ groups are F and one $R^{21}$ group is Cl.

In another embodiment of this invention $R^7$ is phenyl.

In another embodiment of this invention $R^7$ is phenyl substituted with 1 to 3 independently selected $R^{21}$ groups.

In another embodiment of this invention $R^7$ is phenyl substituted with at least one $R^{21}$ group selected from the group consisting of: halo (e.g., F, Cl, Br and I), alkyl substituted with 1 to 3 halos (e.g. alkyl substituted with 1 to 3 F, such as methyl substituted with 1 to 3 F, such as —CF$_3$), —CN, —SF$_5$, —OSF$_5$, and —Si(R$^{15A}$)$_3$ (such as for example, —Si(CH$_3$)$_3$, —Si(CH$_3$)$_2$phenyl, and —Si(CH$_2$CH$_3$)$_2$CH$_3$), and when there is more than one $R^{21}$ group present each $R^{21}$ group is independently selected.

In another embodiment of this invention $R^7$ is phenyl substituted with at least one $R^{21}$ group selected from the group consisting of: halo (e.g., F, Cl, and Br), alkyl substituted with 1 to 3 halos (e.g., alkyl substituted with 1 to 3 F, such as methyl substituted with 1 to 3 F, such as —CF$_3$), —CN, —SF$_5$, —OSF$_5$, and —Si(R$^{15A}$)$_3$ (such as for example, —Si(CH$_3$)$_3$, —Si(CH$_3$)$_2$phenyl, and —Si(CH$_2$CH$_3$)$_2$CH$_3$), and when there is more than one $R^{21}$ group present each $R^{21}$ group is independently selected.

In another embodiment of this invention $R^7$ is phenyl substituted with at least one $R^{21}$ group selected from the group consisting of: halo (e.g., F and Cl), alkyl substituted with 1 to 3 halos (e.g., alkyl substituted with 1 to 3 F, such as methyl substituted with 1 to 3 F, such as —CF$_3$), —CN, —SF$_5$, —OSF$_5$, and —Si(R$^{15A}$)$_3$ (such as for example, —Si(CH$_3$)$_3$, —Si(CH$_3$)$_2$phenyl, and —Si(CH$_2$CH$_3$)$_2$CH$_3$), and when there is more than one $R^{21}$ group present each $R^{21}$ group is independently selected.

In another embodiment of this invention $R^7$ is phenyl substituted with 1 to 3 $R^{21}$ groups independently selected from the group consisting of: halo (e.g., F, Cl, Br and I), alkyl substituted with 1 to 3 halos (e.g., alkyl substituted with 1 to 3 F, such as methyl substituted with 1 to 3 F, such as —CF$_3$), —CN, —SF$_5$, —OSF$_5$, and —Si(R$^{15A}$)$_3$ (such as for example, —Si(CH$_3$)$_3$, —Si(CH$_3$)$_2$phenyl, and —Si(CH$_2$CH$_3$)$_2$CH$_3$).

In another embodiment of this invention $R^7$ is phenyl substituted with 1 to 3 $R^{21}$ groups independently selected from the group consisting of: halo (e.g., F, Cl, and Br), alkyl substituted with 1 to 3 halos (e.g., alkyl substituted with 1 to 3 F, such as methyl substituted with 1 to 3 F, such as —CF$_3$), —CN, —SF$_5$, —OSF$_5$, and —Si(R$^{15A}$)$_3$ (such as for example, —Si(CH$_3$)$_3$, —Si(CH$_3$)$_2$phenyl, and —Si(CH$_2$CH$_3$)$_2$CH$_3$).

In another embodiment of this invention $R^7$ is phenyl substituted with 1 to 3 $R^{21}$ groups independently selected from the group consisting of: halo (e.g., F and Cl), alkyl substituted with 1 to 3 halos (e.g., alkyl substituted with 1 to 3 F, such as methyl substituted with 1 to 3 F, such as —CF$_3$), —CN, —SF$_5$, —OSF$_5$, and —Si(R$^{15A}$)$_3$ (such as for example, —Si(CH$_3$)$_3$, —Si(CH$_3$)$_2$phenyl, and —Si(CH$_2$CH$_3$)$_2$CH$_3$).

In another embodiment of this invention $R^7$ is -arylfusedheteroaryl (e.g., -phenylfusedheteroaryl) substituted with at least one $R^{21}$ group selected from the group consisting of: halo (e.g., F, Cl, Br and I), alkyl substituted with 1 to 3 halos (e.g., alkyl substituted with 1 to 3 F, such as methyl substituted with 1 to 3 F, such as —CF$_3$), —CN, —SF$_5$, —OSF$_5$, and —Si(R$^{15A}$)$_3$ (such as for example, —Si(CH$_3$)$_3$, —Si(CH$_3$)$_2$phenyl, and —Si(CH$_2$CH$_3$)$_2$CH$_3$), and when there is more than one $R^{21}$ group present each $R^{21}$ group is independently selected.

In another embodiment of this invention $R^7$ is -arylfusedheteroaryl (e.g., -phenylfusedheteroaryl) substituted with at least one $R^{21}$ group selected from the group consisting of: halo (e.g., F, Cl, and Br), alkyl substituted with 1 to 3 halos (e.g., alkyl substituted with 1 to 3 F, such as methyl substituted with 1 to 3 F, such as —CF$_3$), —CN, —SF$_5$, —OSF$_5$, and —Si(R$^{15A}$)$_3$ (such as for example, —Si(CH$_3$)$_3$, —Si(CH$_3$)$_2$phenyl, and —Si(CH$_2$CH$_3$)$_2$CH$_3$), and when there is more than one $R^{21}$ group present each $R^{21}$ group is independently selected.

In another embodiment of this invention $R^7$ is -arylfusedheteroaryl (e.g., -phenylfusedheteroaryl) substituted with at least one $R^{21}$ group selected from the group consisting of:

halo (e.g., F and Cl), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$), and when there is more than one $R^{21}$ group present each $R^{21}$ group is independently selected.

In another embodiment of this invention $R^7$ is -phenyl-fusedheteroaryl substituted with at least one $R^{21}$ group selected from the group consisting of: halo (e.g., F, Cl, Br and I), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$), and when there is more than one $R^{21}$ group present each $R^{21}$ group is independently selected.

In another embodiment of this invention $R^7$ is -phenyl-fusedheteroaryl substituted with at least one $R^{21}$ group selected from the group consisting of: halo (e.g., F, Cl, and Br), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$), and when there is more than one $R^{21}$ group present each $R^{21}$ group is independently selected.

In another embodiment of this invention $R^7$ is -phenyl-fusedheteroaryl substituted with at least one $R^{21}$ group selected from the group consisting of: halo (e.g., F, and Cl), alkyl substituted with 1 to 3 halos (e.g., alkyl substituted with 1 to 3 F. such as methyl substituted with 1 to 3 F. such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$), and when there is more than one $R^{21}$ group present each $R^{21}$ group is independently selected.

In another embodiment of this invention $R^7$ is -phenyl-fusedheteroaryl.

In another embodiment of this invention $R^7$ is -arylfused-heterocycloalkyl (e.g., -phenylfusedheterocycloalkyl) substituted with at least one $R^{21}$ group selected from the group consisting of: halo (e.g., F, Cl, Br and I), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$), and when there is more than one $R^{21}$ group present each $R^{21}$ group is independently selected.

In another embodiment of this invention $R^7$ is -arylfused-heterocycloalkyl (e.g., -phenylfusedheterocycloalkyl) substituted with at least one $R^{21}$ group selected from the group consisting of: halo (e.g., F, Cl, and Br), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$), and when there is more than one $R^{21}$ group present each $R^{21}$ group is independently selected.

In another embodiment of this invention $R^7$ is -arylfused-heterocycloalkyl (e.g., -phenylfusedheterocycloalkyl) substituted with at least one $R^{21}$ group selected from the group consisting of: halo (e.g., F and Cl), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$), and when there is more than one $R^{21}$ group present each $R^{21}$ group is independently selected.

In another embodiment of this invention $R^7$ is -phenyl-fusedheterocycloalkyl substituted with at least one $R^{21}$ group selected from the group consisting of: halo (e.g., F, Cl, Br and I), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$), and when there is more than one $R^{21}$ group present each $R^{21}$ group is independently selected.

In another embodiment of this invention $R^7$ is -phenyl-fusedheterocycloalkyl substituted with at least one $R^{21}$ group selected from the group consisting of: halo (e.g., F, Cl, and Br), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$), and when there is more than one $R^{21}$ group present each $R^{21}$ group is independently selected.

In another embodiment of this invention $R^7$ is -phenyl-fusedheterocycloalkyl substituted with at least one $R^{21}$ group selected from the group consisting of: halo (e.g., F and Cl), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$), and when there is more than one $R^{21}$ group present each $R^{21}$ group is independently selected.

In another embodiment of this invention $R^7$ is -phenyl-fusedheterocycloalkyl, such as, for example,

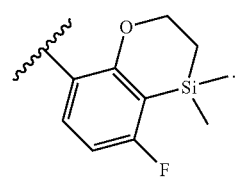

31d

In another embodiment of this invention $R^7$ is phenyl substituted with 1 to 3 independently selected $R^{21}$ groups, and wherein said $R^{21}$ groups are the same or different halo.

In another embodiment of this invention $R^7$ is phenyl substituted with 1 to 2 independently selected $R^{21}$ groups.

In another embodiment of this invention $R^7$ is phenyl substituted with 1 to 2 independently selected $R^{21}$ groups, and wherein said $R^{21}$ groups are the same or different halo.

In another embodiment of this invention $R^7$ is phenyl substituted with 1 to 2 $R^{21}$ groups, and said $R^{21}$ groups are independently selected from the group consisting of F, Br, and Cl. In one example there is one $R^{21}$ group and said $R^{21}$ group is F. In another example there are two $R^{21}$ groups and each $R^{21}$ is F. In another example there are two $R^{21}$ groups and one $R^{21}$ is F and the other $R^{21}$ is Br.

In another embodiment of this invention $R^7$ is phenyl substituted with 1 to 2 $R^{21}$ groups, and said $R^{21}$ groups are independently selected from the group consisting of F and Cl. In one example there is one $R^{21}$ group and said $R^{21}$ group is F. In another example there are two $R^{21}$ groups and each $R^{21}$ is F.

In another embodiment of this invention $R^7$ is phenyl substituted with 1 $R^{21}$ group.

In another embodiment of this invention $R^7$ is phenyl substituted with 1 $R^{21}$ group, and wherein said $R^{21}$ group is halo.

In another embodiment of this invention $R^7$ is phenyl substituted with 1 $R^{21}$ group, and said $R^{21}$ group is F.

In another embodiment of this invention $R^7$ is phenyl substituted with 2 $R^{21}$ groups.

In another embodiment of this invention $R^7$ is phenyl substituted with 2 $R^{21}$ groups, and wherein said $R^{21}$ groups are the same or different halos.

In another embodiment of this invention $R^7$ is phenyl substituted with 2 $R^{21}$ groups, and said $R^{21}$ groups are independently selected from the group consisting of F, Cl, and Br. In one example both $R^{21}$ groups are F. In another example, one $R^{21}$ group is F and the other $R^{21}$ group is Cl. In another example, one $R^{21}$ group is F and the other $R^{21}$ group is Br.

In another embodiment of this invention $R^7$ is phenyl substituted with 2 $R^{21}$ groups, and said $R^{21}$ groups are independently selected from the group consisting of F and Cl. In one example both $R^{21}$ groups are F. In another example, one $R^{21}$ group is F and the other $R^{21}$ group is Cl.

In another embodiment of this invention $R^7$ is phenyl substituted with 3 $R^{21}$ groups.

In another embodiment of this invention $R^7$ is phenyl substituted with 3 $R^{21}$ groups, and wherein said $R^{21}$ groups are the same or different halos.

In another embodiment of this invention $R^7$ is phenyl substituted with 3 $R^{21}$ groups, and said $R^{21}$ groups are selected from the group consisting of F and Cl, in one example the $R^{21}$ groups are F.

In another embodiment of this invention $R^7$ is heteroaryl (e.g., pyridyl, thienyl, oxazolyl, and thiazolyl).

In another embodiment of this invention $R^7$ is heteroaryl pyridyl, thienyl, oxazolyl, and thiazolyl) substituted with 1 to 3 independently selected $R^{21}$ groups.

In another embodiment of this invention $R^7$ is heteroaryl pyridyl, thienyl, oxazolyl, and thiazolyl) substituted with 1 to 3 $R^{21}$ groups independently selected from the group consisting of: halo (e.g., F, Cl, Br and I), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$).

In another embodiment of this invention $R^7$ is heteroaryl (e.g., pyridyl, thienyl, oxazolyl, and thiazolyl) substituted with 1 to 3 $R^{21}$ groups independently selected from the group consisting of: halo (e.g., F, Cl, and Br), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$).

In another embodiment of this invention $R^7$ is heteroaryl (e.g., pyridyl, thienyl, oxazolyl, and thiazolyl) substituted with 1 to 3 $R^{21}$ groups independently selected from the group consisting of: halo (e.g., F and Cl), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$).

In another embodiment of this invention $R^7$ is heteroaryl (e.g., pyridyl, thienyl, oxazolyl, and thiazolyl) substituted with 1 to 3 independently selected $R^{21}$ groups, and wherein said $R^{21}$ groups are the same or different halo.

In another embodiment of this invention $R^7$ is heteroaryl (e.g., pyridyl, thienyl, oxazolyl, and thiazolyl) substituted with 1 to 2 independently selected $R^{21}$ groups.

In another embodiment of this invention $R^7$ is heteroaryl (e.g., pyridyl, thienyl, oxazolyl, and thiazolyl) substituted with 1 to 2 independently selected $R^{21}$ groups, and wherein said $R^{21}$ groups are the same or different halo.

In another embodiment of this invention $R^7$ is heteroaryl (e.g., pyridyl, thienyl, oxazolyl, and thiazolyl) substituted with 1 to 2 $R^{21}$ groups, and said $R^{21}$ groups are independently selected from the group consisting of F and Cl. In one example each $R^{21}$ is F.

In another embodiment of this invention $R^7$ is heteroaryl (e.g., pyridyl, thienyl, oxazolyl, and thiazolyl) substituted with 1 $R^{21}$ group.

In another embodiment of this invention $R^7$ is heteroaryl (e.g., pyridyl, thienyl, oxazolyl, and thiazolyl) substituted with 1 $R^{21}$ group, and wherein said $R^{21}$ group is halo.

In another embodiment of this invention $R^7$ is heteroaryl (e.g., pyridyl, thienyl, oxazolyl, and thiazolyl) substituted with 1 $R^{21}$ group, and said $R^{21}$ group is F.

In another embodiment of this invention $R^7$ is heteroaryl (e.g., pyridyl, thienyl, oxazolyl, and thiazolyl) substituted with 2 $R^{21}$ groups.

In another embodiment of this invention $R^7$ is heteroaryl (e.g., pyridyl, thienyl, oxazolyl, and thiazolyl) substituted with 2 $R^{21}$ groups, and wherein said $R^{21}$ groups are the same or different halos.

In another embodiment of this invention $R^7$ is heteroaryl (e.g., pyridyl, thienyl, oxazolyl, and thiazolyl) substituted with 2 $R^{21}$ groups, and said $R^{21}$ groups are independently selected from the group consisting of F and Cl. In one example both $R^{21}$ groups are F. In another example, one $R^{21}$ group is F and the other $R^{21}$ group is Cl.

In another embodiment of this invention $R^7$ is heteroaryl (e.g., pyridyl, thienyl, oxazolyl, and thiazolyl) substituted with 3 $R^{21}$ groups.

In another embodiment of this invention $R^7$ is heteroaryl (e.g., pyridyl, thienyl, oxazolyl, and thiazolyl) substituted with 3 $R^{21}$ groups, and wherein said $R^{21}$ groups are the same or different halos.

In another embodiment of this invention $R^7$ is heteroaryl (e.g., pyridyl, thienyl, oxazolyl, and thiazolyl) substituted with 3 $R^{21}$ groups, and said $R^{21}$ groups are selected from the group consisting of F and Cl. In one example the $R^{21}$ groups are F.

In another embodiment of this invention $R^7$ is pyridyl.

In another embodiment of this invention $R^7$ is pyridyl substituted with 1 to 3 independently selected $R^{21}$ groups.

In another embodiment of this invention $R^7$ is pyridyl substituted with 1 to 3 $R^{21}$ groups independently selected from the group consisting of: halo (e.g., F, Cl, Br and I), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$).

In another embodiment of this invention $R^7$ is pyridyl substituted with 1 to 3 $R^{21}$ groups independently selected from the group consisting of: halo (e.g., F, Cl, and Br), alkyl substituted with 1 to 3 hates (e.g. alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$).

In another embodiment of this invention $R^7$ is pyridyl substituted with 1 to 3 $R^{21}$ groups independently selected from the group consisting of: halo (e.g., F and Cl), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$).

In another embodiment of this invention $R^7$ is pyridyl substituted with 1 to 3 independently selected $R^{21}$ groups, and wherein said $R^{21}$ groups are the same or different halo.

In another embodiment of this invention $R^7$ is pyridyl substituted with 1 to 2 independently selected $R^{21}$ groups.

In another embodiment of this invention $R^7$ is pyridyl substituted with 1 to 2 independently selected $R^{21}$ groups, and wherein said $R^{21}$ groups are the same or different halo.

In another embodiment of this invention $R^7$ is pyridyl substituted with 1 to 2 $R^{21}$ groups, and said $R^{21}$ groups are independently selected from the group consisting of F and Cl. In one example each $R^{21}$ is F.

In another embodiment of this invention $R^7$ is pyridyl substituted with 1 $R^{21}$ group.

In another embodiment of this invention $R^7$ is pyridyl substituted with 1 $R^{21}$ group, and wherein said $R^{21}$ group is halo.

In another embodiment of this invention $R^7$ is pyridyl substituted with 1 $R^{21}$ group, and said $R^{21}$ group is F.

In another embodiment of this invention $R^7$ is pyridyl substituted with 2 $R^{21}$ groups.

In another embodiment of this invention $R^7$ is pyridyl substituted with 2 $R^{21}$ groups, and wherein said $R^{21}$ groups are the same or different halos.

In another embodiment of this invention $R^7$ is pyridyl substituted with 2 $R^{21}$ groups, and said $R^{21}$ groups are independently selected from the group consisting of F and Cl. In one example both $R^{21}$ groups are F. In another example, one $R^{21}$ group is F and the other $R^{21}$ group is Cl.

In another embodiment of this invention $R^7$ is pyridyl substituted with 3 $R^{21}$ groups.

In another embodiment of this invention $R^7$ is pyridyl substituted with 3 $R^{21}$ groups, and wherein said $R^{21}$ groups are the same or different halos.

In another embodiment of this invention $R^7$ is pyridyl substituted with 3 $R^{21}$ groups, and said $R^{21}$ groups are selected from the group consisting of F and Cl. In one example the $R^{21}$ groups are F.

In another embodiment of this invention $R^7$ is thienyl.

In another embodiment of this invention $R^7$ is thienyl substituted with 1 to 3 independently selected $R^{21}$ groups.

In another embodiment of this invention $R^7$ is thienyl substituted with 1 to 3 $R^{21}$ groups independently selected from the group consisting of: halo (e.g., F, Cl, Br and I), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$).

In another embodiment of this invention $R^7$ is thienyl substituted with 1 to 3 $R^{21}$ groups independently selected from the group consisting of: halo (e.g., F, Cl, and Br), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$).

In another embodiment of this invention $R^7$ is thienyl substituted with 1 to 3 $R^{21}$ groups independently selected from the group consisting of: halo (e.g., F and Cl), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$).

In another embodiment of this invention $R^7$ is thienyl substituted with 1 to 3 independently selected $R^{21}$ groups, and wherein said $R^{21}$ groups are the same or different halo.

In another embodiment of this invention $R^7$ is thienyl substituted with 1 to 2 independently selected $R^{21}$ groups.

In another embodiment of this invention $R^7$ is thienyl substituted with 1 to 2 independently selected $R^{21}$ groups, and wherein said $R^{21}$ groups are the same or different halo.

In another embodiment of this invention $R^7$ is thienyl substituted with 1 to 2 $R^{21}$ groups, and said $R^{21}$ groups are independently selected from the group consisting of F and Cl. In one example each $R^{21}$ is F.

In another embodiment of this invention $R^7$ is thienyl substituted with 1 $R^{21}$ group.

In another embodiment of this invention $R^7$ is thienyl substituted with 1 $R^{21}$ group, and wherein said $R^{21}$ group is halo.

In another embodiment of this invention $R^7$ is thienyl substituted with 1 $R^{21}$ group, and said $R^{21}$ group is F.

In another embodiment of this invention $R^7$ is thienyl substituted with 2 $R^{21}$ groups.

In another embodiment of this invention $R^7$ is thienyl substituted with 2 $R^{21}$ groups, and wherein said $R^{21}$ groups are the same or different halos.

In another embodiment of this invention $R^7$ is thienyl substituted with 2 $R^{21}$ groups, and said $R^{21}$ groups are independently selected from the group consisting of F and Cl. In one example both $R^{21}$ groups are F. In another example, one $R^{21}$ group is F and the other $R^{21}$ group is Cl.

In another embodiment of this invention $R^7$ is thienyl substituted with 3 $R^{21}$ groups.

In another embodiment of this invention $R^7$ is thienyl substituted with 3 $R^{21}$ groups, and wherein said $R^{21}$ groups are the same or different halos.

In another embodiment of this invention $R^7$ is thienyl substituted with 3 $R^{21}$ groups, and said $R^{21}$ groups are selected from the group consisting of F and Cl. In one example the $R^{21}$ groups are F.

In another embodiment of this invention $R^7$ is oxazolyl.

In another embodiment of this invention $R^7$ is oxazolyl substituted with 1 to 3 independently selected $R^{21}$ groups.

In another embodiment of this invention $R^7$ is oxazolyl substituted with 1 to 3 $R^{21}$ groups independently selected from the group consisting of: halo (e.g., F, Cl, Br and I), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$).

In another embodiment of this invention $R^7$ is oxazolyl substituted with 1 to 3 $R^{21}$ groups independently selected from the group consisting of: halo (e.g., F, Cl, and Br), alkyl substituted with 1 to 3 halos (e.g., alkyl substituted with 1 to 3 F, such as methyl substituted with 1 to 3 F, such as —$CF_3$), —$SF_5$, and —$Si(R^{15A})_3$ (such as for example, —$Si(CH_3)_3$, —$Si(CH_3)_2$phenyl, and —$Si(CH_2CH_3)_2CH_3$).

In another embodiment of this invention $R^7$ is oxazolyl substituted with 1 to 3 $R^{21}$ groups independently selected from the group consisting of: halo (e.g., F and Cl), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$).

In another embodiment of this invention $R^7$ is oxazolyl substituted with 1 to 3 independently selected $R^{21}$ groups, and wherein said $R^{21}$ groups are the same or different halo.

In another embodiment of this invention $R^7$ is oxazolyl substituted with 1 to 2 independently selected $R^{21}$ groups.

In another embodiment of this invention $R^7$ is oxazolyl substituted with 1 to 2 independently selected $R^{21}$ groups, and wherein said $R^{21}$ groups are the same or different halo.

In another embodiment of this invention R⁷ is oxazolyl substituted with 1 to 2 R²¹ groups, and said R²¹ groups are independently selected from the group consisting of F and Cl. In one example each R²¹ is F.

In another embodiment of this invention R⁷ is oxazolyl substituted with 1 R²¹ group.

In another embodiment of this invention R⁷ is oxazolyl substituted with 1 R²¹ group, and wherein said R²¹ group is halo.

In another embodiment of this invention R⁷ is oxazolyl substituted with 1 R²¹ group, and said R²¹ group is F.

In another embodiment of this invention R⁷ is oxazolyl substituted with 2 R²¹ groups.

In another embodiment of this invention R⁷ is oxazolyl substituted with 2 R²¹ groups, and wherein said R²¹ groups are the same or different halos.

In another embodiment of this invention R⁷ is oxazolyl substituted with 2 R²¹ groups, and said R²¹ groups are independently selected from the group consisting of F and Cl. In one example both R²¹ groups are F. In another example, one R²¹ group is F and the other R²¹ group is Cl.

In another embodiment of this invention R⁷ is oxazolyl substituted with 3 R²¹ groups.

In another embodiment of this invention R⁷ is oxazolyl substituted with 3 R²¹ and wherein said R²¹ groups are the same or different halos.

In another embodiment of this invention R⁷ is oxazolyl substituted with 3 R²¹ groups, and said R²¹ groups are selected from the group consisting of F and Cl. In one example the R²¹ groups are F.

In another embodiment of this invention R⁷ is thiazolyl.

In another embodiment of this invention R⁷ is thiazolyl substituted with 1 to 3 independently selected R²¹ groups.

In another embodiment of this invention R⁷ is thiazolyl substituted with 1 to 3 R²¹ groups independently selected from the group consisting of: halo (e.g., F, Cl, Br and I), alkyl substituted with 1 to 3 halos (e.g., alkyl substituted with 1 to 3 F, such as methyl substituted with 1 to 3 F, such as —CF₃), —CN, —SF₅, —OSF₅, and —Si(R¹⁵ᴬ)₃ (such as for example, —Si(CH₃)₃, —Si(CH₃)₂phenyl, and —Si(CH₂CH₃)₂CH₃).

In another embodiment of this invention R⁷ is thiazolyl substituted with 1 to 3 R²¹ groups independently selected from the group consisting of: halo (e.g., F, Cl, and Br), alkyl substituted with 1 to 3 halos (e.g., alkyl substituted with 1 to 3 F, such as methyl substituted with 1 to 3 F, such as —CF₃), —CN, —SF₅, —OSF₅, and —Si(R¹⁵ᴬ)₃ (such as for example, —Si(CH₃)₃, —Si(CH₃)₂phenyl, and —Si(CH₂CH₃)₂CH₃).

In another embodiment of this invention R⁷ is thiazolyl substituted with 1 to 3 R²¹ groups independently selected from the group consisting of: halo (e.g., F and Cl), alkyl substituted with 1 to 3 halos (e.g., alkyl substituted with 1 to 3 F, such as methyl substituted with 1 to 3 F, such as —CF₃), —CN, —SF₅, —OSF₅, and —Si(R¹⁵ᴬ)₃ (such as for example, —Si(CH₃)₃, —Si(CH₃)₂phenyl, and —Si(CH₂CH₃)₂CH₃).

In another embodiment of this invention R⁷ is thiazolyl substituted with 1 to 3 independently selected R²¹ groups, and wherein said R²¹ groups are the same or different halo.

In another embodiment of this invention R⁷ is thiazolyl substituted with 1 to 2 independently selected R²¹ groups.

In another embodiment of this invention R⁷ is thiazolyl substituted with 1 to 2 independently selected R²¹ groups, and wherein said R²¹ groups are the same or different halo.

In another embodiment of this invention R⁷ is thiazolyl substituted with 1 to 2 R²¹ groups, and said R²¹ groups are independently selected from the group consisting of F and Cl. In one example each R²¹ is F.

In another embodiment of this invention R⁷ is thiazolyl substituted with 1 R²¹ group.

In another embodiment of this invention R⁷ is thiazolyl substituted with 1 R²¹ group, and wherein said R²¹ group is halo.

In another embodiment of this invention R⁷ is thiazolyl substituted with 1 R²¹ group, and said R²¹ group is F.

In another embodiment of this invention R⁷ is thiazolyl substituted with 2 R²¹ groups.

In another embodiment of this invention R⁷ is thiazolyl substituted with 2 R²¹ groups, and wherein said R²¹ groups are the same or different halos.

In another embodiment of this invention R⁷ is thiazolyl substituted with 2 R²¹ groups, and said R²¹ groups are independently selected from the group consisting of F and Cl. In one example both R²¹ groups are F. In another example, one R²¹ group is F and the other R²¹ group is Cl.

In another embodiment of this invention R⁷ is thiazolyl substituted with 3 R²¹ groups.

In another embodiment of this invention R⁷ is thiazolyl substituted with 3 R²¹ groups, and wherein said R²¹ groups are the same or different halos.

In another embodiment of this invention R⁷ is thiazolyl substituted with 3 R²¹ groups, and said R²¹ groups are selected from the group consisting of F and Cl. In one example the R²¹ groups are F.

In another embodiment of this invention R⁷ is selected from the group consisting of:

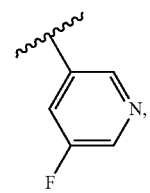

1d

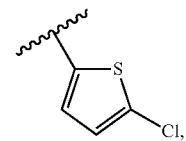

2d

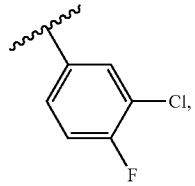

3d

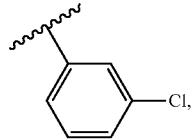

4d

5d 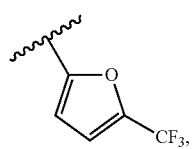
6d 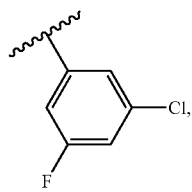
7d 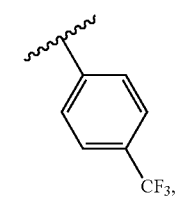
8d 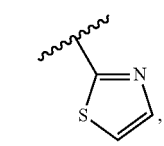
9d 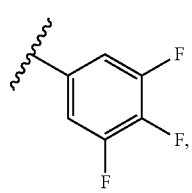
10d 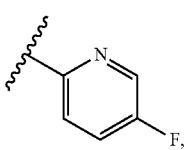
11d 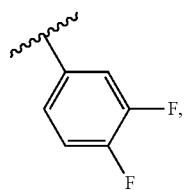
12d 
13d 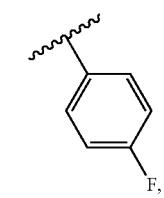
14d 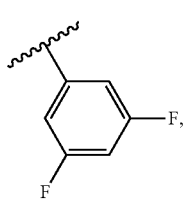
15d 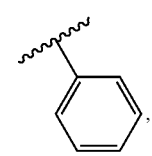
16d 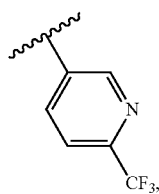
17d 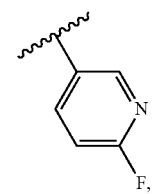
18d 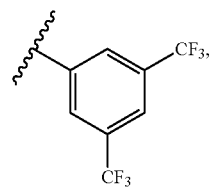
19d 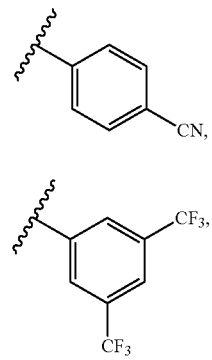
20d 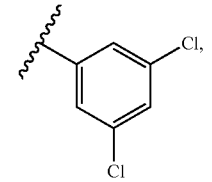
21d 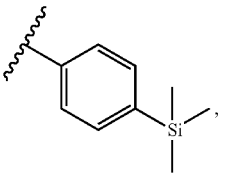

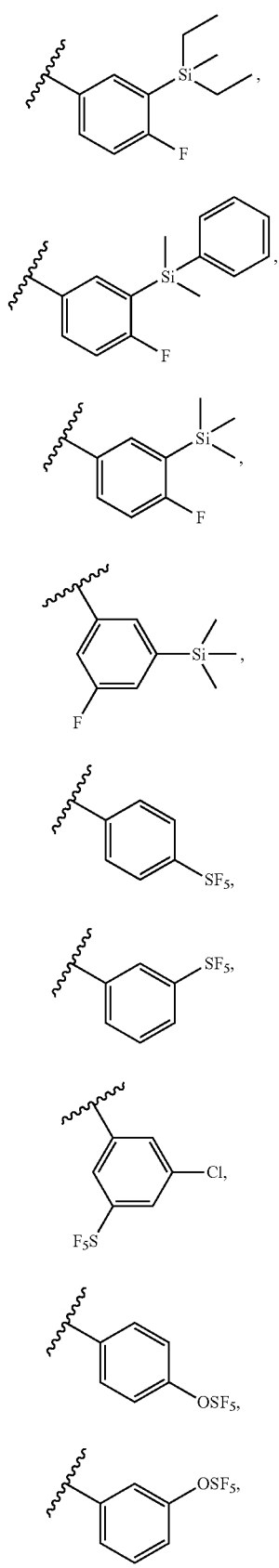

In another embodiment of this invention $R^7$ is 1d. In another embodiment of this invention $R^7$ is 2d. In another embodiment of this invention $R^7$ is 3d. In another embodiment of this invention $R^7$ is 4d. In another embodiment of this invention $R^7$ is 5d. In another embodiment of this invention $R^7$ is 6d. In another embodiment of this invention $R^7$ is 7d. In another embodiment of this invention $R^7$ is 8d. In another embodiment of this invention $R^7$ is 9d. In another embodiment of this invention $R^7$ is 10d. In another embodiment of this invention $R^7$ is 11d. In another embodiment of this invention $R^7$ is 12d. In another embodiment of this invention $R^7$ is p-F-phenyl (i.e. 13d). In another embodiment of this invention $R^7$ is 14d. In another embodiment of this invention $R^7$ is 15d. In another embodiment of this invention $R^7$ is 16d. In another embodiment of this invention $R^7$ is 17d. In another embodiment of this invention $R^7$ is 18d. In another embodiment of this invention $R^7$ is 19d. In another embodiment of this invention $R^7$ is 20d. In another embodiment of this invention $R^7$ is 21d. In another embodiment of this invention $R^7$ is 22d. In another embodiment of this invention $R^7$ is 23d. In another embodiment of this invention $R^7$ is 24d. In another embodiment of this invention $R^7$ is 25d. In another embodiment of this invention $R^7$ is 26d. In another embodiment of this invention $R^7$ is 27d. In another embodiment of this invention $R^7$ is 28d. In another embodiment of this invention $R^7$ is 29d. In another embodiment of this invention $R^7$ is 30d. In another embodiment of this invention $R^7$ is 31d. In another embodiment of this invention $R^7$ is 32d. In another embodiment of this invention $R^7$ is 33d. In another embodiment of this invention $R^7$ is 34d. In another embodiment of this invention $R^7$ is 35d.

In another embodiment of this invention $R^6$ and $R^7$ are taken together with the carbon atom to which they are bound to form a spiro ring.

In another embodiment of this invention $R^6$ and $R^7$ taken together with the carbon atom to which they are bound, form a cycloalkyl ring.

In another embodiment of this invention $R^6$ and $R^7$ taken together with the carbon atom to which they are bound, form a cycloalkenyl ring, said cycloalkenyl ring comprising one double bond.

In another embodiment of this invention $R^6$ and $R^7$ taken together with the carbon atom to which they are bound, form a cycloalkenyl ring, said cycloalkenyl ring comprising two double bonds.

In another embodiment of this invention $R^6$ and $R^7$ taken together with the carbon atom to which they are bound, form a heterocycloalkyl ring.

In another embodiment of this invention $R^6$ and $R^7$ taken together with the carbon atom to which they are bound, form a heterocycloalkenyl ring, said heterocycloalkenyl ring comprising one double bond.

In another embodiment of this invention $R^6$ and $R^7$ taken together with the carbon atom to which they are bound, form a heterocycloalkenyl ring, said heterocycloalkenyl ring comprising two double bonds.

In another embodiment of this invention $R^6$ and $R^7$ taken together with the carbon atom to which they are bound, form a cycloalkyl ring fused to an aryl ring (e.g., phenyl).

In another embodiment of this invention $R^6$ and $R^7$ taken together with the carbon atom to which they are bound, form a cycloalkenyl ring fused to an aryl ring (e.g., phenyl), said cycloalkenyl ring comprising one double bond.

In another embodiment of this invention $R^6$ and $R^7$ taken together with the carbon atom to which they are bound, form a cycloalkenyl ring fused to an aryl ring (e.g., phenyl), said cycloalkenyl ring comprising two double bonds.

In another embodiment of this invention $R^6$ and $R^7$ taken together with the carbon atom to which they are bound, form a heterocycloalkyl ring fused to an aryl ring (e.g., phenyl).

In another embodiment of this invention $R^6$ and $R^7$ taken together with the carbon atom to which they are bound, form a heterocycloalkenyl ring fused to an aryl ring (e.g., phenyl), said heterocycloalkenyl ring comprising one double bond.

In another embodiment of this invention $R^6$ and $R^7$ taken together with the carbon atom to which they are bound, form a heterocycloalkenyl ring fused to an aryl ring (e.g., phenyl), said heterocycloalkenyl ring comprising two double bonds.

In another embodiment of this invention $R^6$ and $R^7$ taken together with the carbon atom to which they are bound, form a cycloalkyl ring fused to a heteroaryl ring.

In another embodiment of this invention $R^6$ and $R^7$ taken together with the carbon atom to which they are bound, form a cycloalkenyl ring fused to a heteroaryl ring, said cycloalkenyl ring comprising one double bond.

In another embodiment of this invention $R^6$ and $R^7$ taken together with the carbon atom to which they are bound, form a cycloalkenyl ring fused to a heteroaryl ring, said cycloalkenyl ring comprising two double bonds.

In another embodiment of this invention $R^6$ and $R^7$ taken together with the carbon atom to which they are bound, form a heterocycloalkyl ring fused to a heteroaryl ring.

In another embodiment of this invention $R^6$ and $R^7$ taken together with the carbon atom to which they are bound, form a heterocycloalkenyl ring fused to a heteroaryl ring, said heterocycloalkenyl ring comprising one double bond.

In another embodiment of this invention $R^6$ and $R^7$ taken together with the carbon atom to which they are bound, form a heterocycloalkenyl ring fused to a heteroaryl ring, said heterocycloalkenyl ring comprising two double bonds.

Other embodiments of this invention are directed to any one of the embodiments above wherein $R^6$ and $R^7$ are taken together to form a ring wherein said ring is optionally substituted with 1 to 4 independently selected $R^{21}$ groups, and when said ring is a fused ring then each ring of the fused ring is optionally substituted with 1 to 4 independently selected $R^{21}$ groups. Other embodiments of this invention are directed to any one of the embodiments above wherein $R^6$ and $R^7$ are taken together to form a ring wherein said ring is optionally substituted with 1 to 4 independently selected $R^{21}$ groups, and when said ring is a fused ring then each ring of the fused ring is optionally substituted with 1 to 3 independently selected $R^{21}$ groups, and wherein said $R^{21}$ groups are independently selected from the group consisting of: halo (e.g., F and Cl), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$). Other embodiments of this invention are directed to any one of the embodiments above wherein $R^6$ and $R^7$ are taken together to form a ring wherein said ring is optionally substituted with 1 to 3 independently selected $R^{21}$ groups, and when said ring is a fused ring then each ring of the fused ring is optionally substituted with 1 to 3 independently selected $R^{21}$ groups. Other embodiments of this invention are directed to any one of the embodiments above wherein $R^6$ and $R^7$ are taken together to form a ring wherein said ring is optionally substituted with 1 to 3 independently selected $R^{21}$ groups, and when said ring is a fused ring then each ring of the fused ring is optionally substituted with 1 to 3 independently selected $R^{21}$ groups, and wherein said $R^{21}$ groups are independently selected from the group consisting of: halo (e.g., F and Cl), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$).

In another embodiment of this invention $R^6$ and $R^7$ taken together with the carbon atom to which they are bound, form an unsubstituted heterocycloalkyl ring fused to an unsubstituted aryl ring (e.g., phenyl). In another embodiment the aryl (e.g., phenyl) moiety is substituted with 1 to 3 $R^{21}$ moieties. In another embodiment the aryl (e.g., phenyl) moiety is substituted with 1 to 3 $R^{21}$ groups are independently selected from the group consisting of: halo (e.g., F and Cl), alkyl substituted with 1 to 3 halos (e.g., alkyl substituted with 1 to 3 F, such as methyl substituted with 1 to 3 F, such as —$CF_3$), —CN, —$SF_5$, —$OSF_5$, and —$Si(R^{15A})_3$ (such as for example, —$Si(CH_3)_3$, —$Si(CH_3)_2$phenyl, and —$Si(CH_2CH_3)_2CH_3$). In another embodiment the aryl (e.g., phenyl) moiety is substituted with 1 to 3 independently selected halos (e.g., wherein the halos are selected from the group consisting of F and Cl). In another embodiment the aryl (e.g., phenyl) moiety is substituted with 1 to 3 F. In another embodiment the aryl (e.g., phenyl) is substituted with 1 to 2 F. In another embodiment the aryl (e.g., phenyl) is substituted with 2 F. In another embodiment the aryl (e.g., phenyl) moiety is substituted with 1. In another embodiment the heterocycloalkyl moiety comprises N and said N is unsubstituted (i.e., the heterocycloalkyl ring has a NH in the ring), and the aryl moiety (e.g., phenyl) is as described in any one of the embodiments described in this paragraph. In another embodiment the heterocycloalkyl moiety comprises N and said N is substituted (i.e., the heterocycloalkyl ring has a substituted N in the ring), and the aryl moiety (e.g., phenyl) is as described in any one of the embodiments described in this paragraph. In another embodiment the heterocycloalkyl moiety comprises N and said N is substituted with alkyl, such as, methyl (i.e., the heterocycloalkyl ring has an alkyl substituted N in the ring), and the aryl moiety (e.g., phenyl) is as described in any one of the embodiments described in this paragraph.

In another embodiment of this invention $R^6$ and $R^7$ taken together with the carbon atom to which they are bound, form an unsubstituted heterocycloalkyl ring fused to an unsubstituted heteroaryl ring. In another embodiment the heteroaryl pyridyl) moiety is substituted with 1 to 3 $R^{21}$ moieties. In another embodiment the heteroaryl pyridyl) moiety is substituted with 1 to 3 $R^{21}$ groups are independently selected from the group consisting of: halo (e.g., F and Cl), alkyl substituted with 1 to 3 halos (e.g., alkyl substituted with 1 to 3 F, such as methyl substituted with 1 to 3 F, such as —CF$_3$), —CN, —SF$_5$, —OSF$_5$, and —Si(R$^{15A}$)$_3$ (such as for example, —Si(CH$_3$)$_3$, —Si(CH$_3$)$_2$phenyl, and —Si(CH$_2$CH$_3$)$_2$CH$_3$). In another embodiment the heteroaryl (e.g., pyridyl) moiety is substituted with 1 to 3 independently selected halos (e.g., wherein the halos are selected from the group consisting of F and Cl). In another embodiment the heteroaryl (e.g., pyridyl) moiety is substituted with 1 to 3 F. In another embodiment the heteroaryl (e.g., pyridyl) is substituted with 1 to 2 F. In another embodiment the heteroaryl (e.g., pyridyl) is substituted with 2 F. In another embodiment the heteroaryl (e.g., pyridyl) moiety is substituted with 1. In another embodiment the heterocycloalkyl moiety comprises N and said N is unsubstituted (i.e., the heterocycloalkyl ring has a NH in the ring), and the heteroaryl moiety (e.g., pyridyl) is as described in any one of the embodiments described in this paragraph. In another embodiment the heterocycloalkyl moiety comprises N and said N is substituted (i.e., the heterocycloalkyl ring has a substituted N in the ring), and the heteroaryl moiety (e.g., pyridyl) is as described in any one of the embodiments described in this paragraph. In another embodiment the heterocycloalkyl moiety comprises N and said N is substituted with alkyl, such as, methyl (i.e., the heterocycloalkyl ring has an alkyl substituted N in the ring), and the heteroaryl moiety (e.g., pyridyl) is as described in any one of the embodiments described in this paragraph.

In another embodiment of this invention $R^6$ and $R^7$ taken together with the carbon atom to which they are bound, form a fused ring selected from the group consisting of:

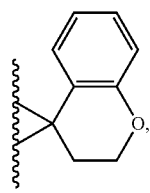

1e

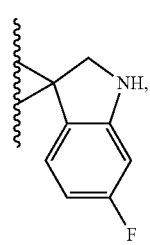

2e

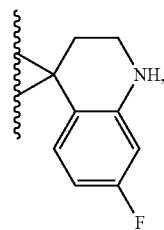

3e

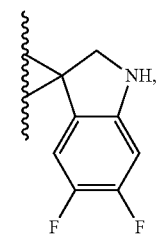

4e

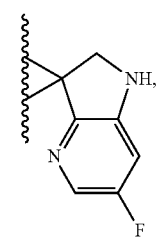

5e

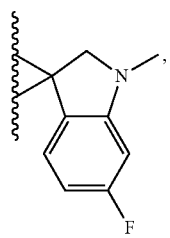

6e

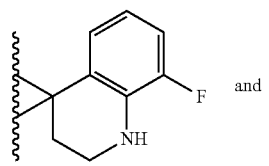

7e and

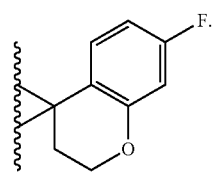

8e

In another embodiment $R^6$ and $R^7$ are taken together with the carbon atom to which they are bound to form 1e. In another embodiment $R^6$ and $R^7$ are taken together with the carbon atom to which they are bound to form 2e. In another embodiment $R^6$ and $R^7$ are taken together with the carbon atom to which they are bound to form 3e. In another embodiment $R^6$ and $R^7$ are taken together with the carbon atom to which they are bound to form 4e. In another embodiment $R^6$ and $R^7$ are taken together with the carbon atom to which they are bound to form 5e. In another embodiment $R^6$ and $R^7$ are taken together with the carbon atom to which they are bound to form 6e. In another embodiment $R^6$ and $R^7$ are taken together with the carbon atom to which they are bound to form 7e. In another embodiment R⁶ and R⁷ are taken together with the carbon atom to which they are bound to form 8e.

In another embodiment of this invention Ring (A) is a cycloalkyl ring.

In another embodiment of this invention Ring (A) is a cyclopropyl ring.

In another embodiment of this invention Ring (A) is a cycloalkenyl ring, said cycloalkenyl ring comprising one double bond.

In another embodiment of this invention Ring (A) is a cycloalkenyl ring, said cycloalkenyl ring comprising two double bonds.

In another embodiment of this invention Ring (A) is a heterocycloalkyl ring.

In another embodiment of this invention Ring (A) is a heterocycloalkenyl ring, said heterocycloalkenyl ring comprising one double bond.

In another embodiment of this invention Ring (A) is a heterocycloalkenyl ring, said heterocycloalkenyl ring comprising two double bonds.

In another embodiment of this invention Ring (A) is a heterocycloalkyl ring fused to an aryl ring (e.g., phenyl).

In another embodiment of this invention Ring (A) is a cycloalkyl ring fused to an aryl ring (e.g., phenyl).

In another embodiment of this invention Ring (A) is a cycloalkyl ring fused to a heteroaryl ring (e.g., pyridyl and oxazolyl).

In another embodiment of this invention Ring (A) is selected from the group consisting of:

1a

2a

3a

4a

5a

6a

7a 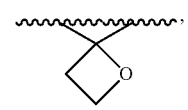

8a 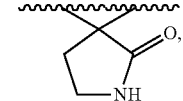

9a 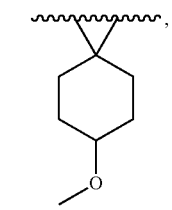

10a 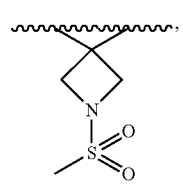

11a 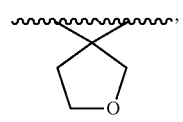

12a 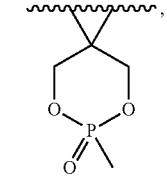

13a 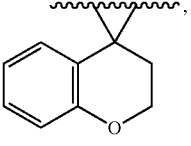

14a 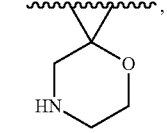

15a 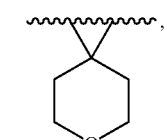

16a 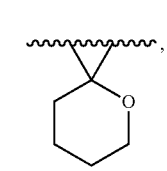

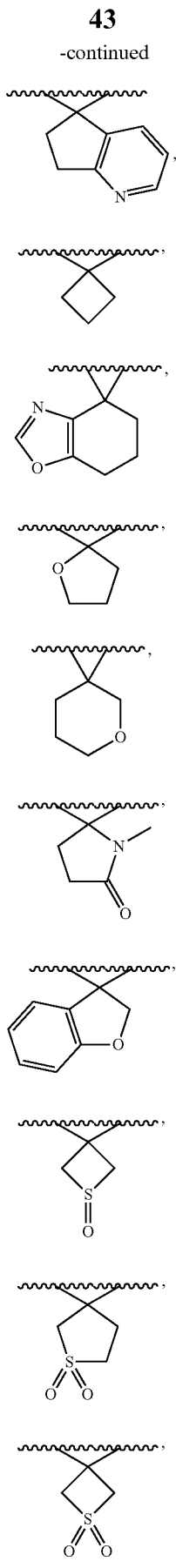
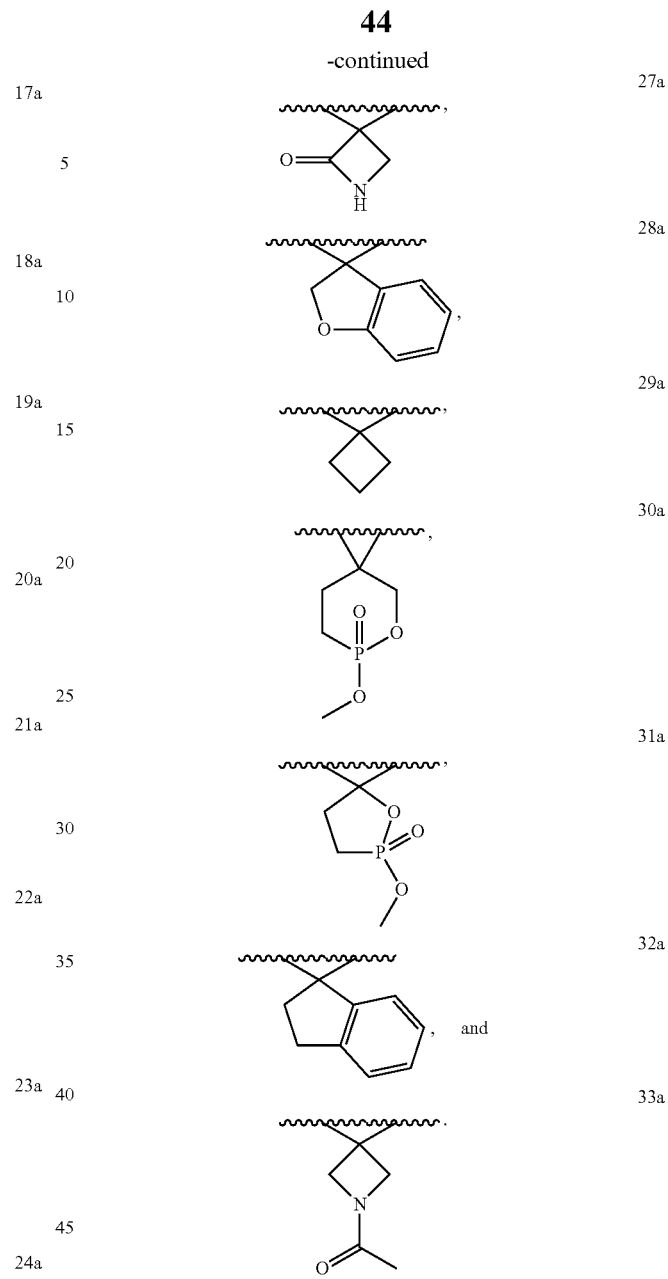

In another embodiment of this invention Ring (A) is 1a. In another embodiment of this invention Ring (A) is 2a. In another embodiment of this invention Ring (A) is 3a. In another embodiment of this invention Ring (A) is 4a. In another embodiment of this invention Ring (A) is 5a. In another embodiment of this invention Ring (A) is 6a. In another embodiment of this invention Ring (A) is 7a. In another embodiment of this invention Ring (A) is 8a. In another embodiment of this invention Ring (A) is 9a. In another embodiment of this invention Ring (A) is 10a. In another embodiment of this invention Ring (A) is 11a. In another embodiment of this invention Ring (A) is 12a. In another embodiment of this invention Ring (A) is 13a. In another embodiment of this invention Ring (A) is 14a. In another embodiment of this invention Ring (A) is 15a. In another embodiment of this invention Ring (A) is 16a. In another embodiment of this invention Ring (A) is 17a. In another embodiment of this invention Ring (A) is 18a. In another embodiment of this invention Ring (A) is 19a. In another embodiment of this invention Ring (A) is 20a. In another embodiment of this invention Ring (A) is 21a. In another embodiment of this invention Ring (A) is 22a. In another embodiment of this invention Ring (A) is 23a. In another embodiment of this invention Ring (A) is 24a. In another embodiment of this invention Ring (A) is 25a. In another embodiment of this invention Ring (A) is 26a. In another embodiment of this invention Ring (A) is 27a. In another embodiment of this invention Ring (A) is 28a. In another embodiment of this invention Ring (A) is 29a. In another embodiment of this invention Ring (A) is 30a. In another embodiment of this invention Ring (A) is 31a. In another embodiment of this invention Ring (A) is 32a. In another embodiment of this invention Ring (A) is 33a.

In another embodiment of this invention $R^8$ is H.

In another embodiment of this invention $R^8$ is alkyl,

In another embodiment of this invention $R^8$ is methyl.

In another embodiment of this invention optional Bond 1 is present.

In another embodiment of this invention the optional Bond 1 is present and $R^8$ is H.

In another embodiment of this invention the optional Bond 1 is present and $R^8$ is alkyl.

In another embodiment of this invention the optional Bond 1 is present and $R^8$ is methyl.

In another embodiment of this invention the optional Bond 1 is absent.

In another embodiment of this invention optional Bond 1 is absent, and optional Bonds 2 and 3 are present, and $R^{8A}$ and $R^{8B}$ are each independently selected from the group consisting of H and alkyl.

In another embodiment of this invention optional Bond 1 is absent, and optional Bonds 2 and 3 are present, and $R^{8A}$ and $R^{8B}$ are each H.

In another embodiment of this invention the optional Bond 1 is absent and $R^8$ is H.

In another embodiment of this invention the optional Bond 1 is absent, optional Bonds 2 and 3 are present, $R^{8A}$ and $R^{8B}$ are each independently selected from the group consisting of H and alkyl, and $R^8$ is H.

In another embodiment of this invention the optional Bond 1 is absent, optional Bonds 2 and 3 are present, $R^{8A}$ and $R^{8B}$ are each H, and $R^8$ is H.

In another embodiment of this invention the optional Bond 1 is absent and $R^8$ is alkyl.

In another embodiment of this invention the optional Bond 1 is absent, optional Bonds 2 and 3 are present, $R^{8A}$ and $R^{8B}$ are each independently selected from the group consisting of H and alkyl, and $R^8$ is alkyl.

In another embodiment of this invention the optional Bond 1 is absent, optional Bonds 2 and 3 are present, $R^{8A}$ and $R^{8B}$ are each H, and $R^8$ is alkyl.

In another embodiment of this invention the optional Bond 1 is absent and $R^8$ is methyl.

In another embodiment of this invention the optional Bond 1 is absent, optional Bonds 2 and 3 are present, $R^{8A}$ and $R^{8B}$ are each independently selected from the group consisting of H and alkyl, and $R^8$ is methyl.

In another embodiment of this invention the optional Bond 1 is absent, optional Bonds 2 and 3 are present, $R^{8A}$ and $R^{8B}$ each H, and $R^8$ is methyl.

In another embodiment of this invention the optional Bond 1 is absent, and $R^{8A}$ and $R^{8B}$, taken together with the carbon atoms to which they are bound, form a cycloalkyl ring.

In another embodiment of this invention the optional Bond 1 is absent, and $R^{8A}$ and $R^{8B}$, taken together with the carbon atoms to which they are bound, form a cycloalkyl ring, and $R^8$ is H.

In another embodiment of this invention the optional Bond 1 is absent, and $R^{8A}$ and $R^{8B}$, taken together with the carbon atoms to which they are bound, form a cycloalkyl ring, and $R^8$ is alkyl.

In another embodiment of this invention the optional Bond 1 is absent, and $R^{8A}$ and $R^{8B}$, taken together with the carbon atoms to which they are bound, form a cycloalkyl ring, and $R^8$ is methyl.

In another embodiment of this invention the optional Bond 1 is absent, and $R^{8A}$ and $R^{8B}$, taken together with the carbon atoms to which they are bound, form a 3 to 6 membered cycloalkyl ring.

In another embodiment of this invention the optional Bond 1 is absent, and $R^{8A}$ and $R^{8B}$, taken together with the carbon atoms to which they are bound, form a 3 to 6 membered cycloalkyl ring, and $R^8$ is H.

In another embodiment of this invention the optional Bond 1 is absent, and $R^{8A}$ and $R^{8B}$, taken together with the carbon atoms to which they are bound, form a 3 to 6 membered cycloalkyl ring, and $R^8$ is alkyl.

In another embodiment of this invention the optional Bond 1 is absent, and $R^{8A}$ and $R^{8B}$, taken together with the carbon atoms to which they are bound, form a 3 to 6 membered cycloalkyl ring, and $R^8$ is methyl.

In another embodiment of this invention the optional Bond 1 is absent, and $R^{8A}$ and $R^{8B}$, taken together with the carbon atoms to which they are bound, form a C5 to C8 cycloalkenyl ring (and in one example a C5 cycloalkenyl ring, and in another example a C8 cycloalkenyl ring), said cycloalkenyl ring comprising one double bond, provided that said double bond is not to the carbon to which $R^8$ is bound.

In another embodiment of this invention the optional Bond 1 is absent, and $R^{8A}$ and $R^{8B}$, taken together with the carbon atoms to which they are bound, form a C5 to C8 cycloalkenyl ring (and in one example a C5 cycloalkenyl ring, and in another example a C6 cycloalkenyl ring), said cycloalkenyl ring comprising one double bond, provided that said double bond is not to the carbon to which $R^8$ is bound, and $R^8$ is H.

In another embodiment of this invention the optional Bond 1 is absent, and $R^{8A}$ and $R^{8B}$, taken together with the carbon atoms to which they are bound, form a C5 to C8 cycloalkenyl ring (and in one example a C5 cycloalkenyl ring, and in another example a C6 cycloalkenyl ring), said cycloalkenyl ring comprising one double bond, provided that said double bond is not to the carbon to which $R^8$ is bound, and $R^8$ is alkyl.

In another embodiment of this invention the optional Bond 1 is absent, and $R^{8A}$ and $R^{8B}$, taken together with the carbon atoms to which they are bound, form a C5 to C8 cycloalkenyl ring (and in one example a C5 cycloalkenyl ring, and in another example a C6 cycloalkenyl ring), said cycloalkenyl ring comprising one double bond, provided that said double bond is not to the carbon to which $R^8$ is bound, and $R^8$ is methyl.

In another embodiment of this invention the optional Bond 1 is absent, and $R^{8A}$ and $R^{8B}$, taken together with the carbon atoms to which they are bound, form a C5 to C8 cycloalkenyl ring (and in one example a C5 cycloalkenyl ring, and in another example a C6 cycloalkenyl ring), said cycloalkenyl ring comprising two double bonds, provided that there is no double bond bound to the carbon to which $R^8$ is bound.

In another embodiment of this invention the optional Bond 1 is absent, and $R^{8A}$ and $R^{8B}$, taken together with the carbon atoms to which they are bound, form a C5 to C8 cycloalkenyl ring (and in one example a C5 cycloalkenyl ring, and in another example a C6 cycloalkenyl ring), said cycloalkenyl ring comprising two double bonds, provided that there is no double bond bound to the carbon to which $R^8$ is bound, and $R^8$ is H.

In another embodiment of this invention the optional Bond 1 is absent, and $R^{8A}$ and $R^{8B}$, taken together with the carbon atoms to which they are bound, form a C5 to C8 cycloalkenyl ring (and in one example a C5 cycloalkenyl ring, and in another example a C6 cycloalkenyl ring), said cycloalkenyl ring comprising two double bonds, provided that there is no double bond bound to the carbon to which $R^8$ is bound, and $R^8$ is alkyl.

In another embodiment of this invention the optional Bond 1 is absent, and $R^{8A}$ and $R^{8B}$, taken together with the carbon atoms to which they are bound, form a C5 to C8 cycloalkenyl ring (and in one example a C5 cycloalkenyl ring, and in another example a C6 cycloalkenyl ring), said cycloalkenyl ring comprising two double bonds, provided that there is no double bond bound to the carbon to which $R^8$ is bound, and $R^8$ is methyl.

In another embodiment of this invention the optional Bond 1 is absent, and $R^{8A}$ and $R^{8B}$, taken together with the carbon atoms to which they are bound, form a heterocycloalkyl ring.

In another embodiment of this invention the optional Bond 1 is absent, and $R^{8A}$ and $R^{8B}$, taken together with the carbon atoms to which they are bound, form a heterocycloalkyl ring, and $R^8$ is H.

In another embodiment of this invention the optional Bond 1 is absent, and $R^{8A}$ and $R^{8B}$, taken together with the carbon atoms to which they are bound, form a heterocycloalkyl ring, and $R^8$ is alkyl.

In another embodiment of this invention the optional Bond 1 is absent, and $R^{8A}$ and $R^{8B}$, taken together with the carbon atoms to which they are bound, form a heterocycloalkyl ring, and $R^8$ is methyl.

In another embodiment of this invention the optional Bond 1 is absent, and $R^{8A}$ and $R^{8B}$, taken together with the carbon atoms to which they are bound, form a C5 to C8 heterocycloalkenyl ring (and in one example a C5 heterocycloalkenyl ring, and in another example a C6 heterocycloalkenyl ring), said heterocycloalkenyl ring comprising one double bond, provided that said double bond is not to the carbon to which $R^8$ is bound.

In another embodiment of this invention the optional Bond 1 is absent, and $R^{8A}$ and $R^{8B}$, taken together with the carbon atoms to which they are bound, form a C5 to C8 heterocycloalkenyl ring (and in one example a C5 heterocycloalkenyl ring, and in another example a C6 heterocycloalkenyl ring), said heterocycloalkenyl ring comprising one double bond, provided that said double bond is not to the carbon to which $R^8$ is bound, and $R^8$ is H.

In another embodiment of this invention the optional Bond 1 is absent and $R^{8A}$ and $R^{8B}$, taken together with the carbon atoms to which they are bound, form a C5 to C8 heterocycloalkenyl ring (and in one example a C5 heterocycloalkenyl ring, and in another example a C6 heterocycloalkenyl ring), said heterocycloalkenyl ring comprising one double bond, provided that said double bond is not to the carbon to which $R^8$ is bound, and $R^8$ is alkyl.

In another embodiment of this invention the optional Bond 1 is absent, and $R^{8A}$ and $R^{8B}$, taken together with the carbon atoms to which they are bound, form a C5 to C8 heterocycloalkenyl ring (and in one example a C5 heterocycloalkenyl ring, and in another example a C6 heterocycloalkenyl ring), said heterocycloalkenyl ring comprising one double bond, provided that said double bond is not to the carbon to which $R^8$ is bound, and $R^8$ is methyl.

In another embodiment of this invention the optional Bond 1 is absent, and $R^{8A}$ and $R^{8B}$, taken together with the carbon atoms to which they are bound, form a C5 to C8 heterocycloalkenyl (and in one example a C5 heterocycloalkenyl ring, and in another example a C6 heterocycloalkenyl ring), said heterocycloalkenyl ring comprising two double bonds, provided that there is no double bond bound to the carbon to which $R^8$ is bound.

In another embodiment of this invention the optional Bond 1 is absent, and $R^{8A}$ and $R^{8B}$, taken together with the carbon atoms to which they are bound, form a C5 to C8 heterocycloalkenyl (and in one example a C5 heterocycloalkenyl ring, and in another example a C6 heterocycloalkenyl ring), said heterocycloalkenyl ring comprising two double bonds, provided that there is no double bond bound to the carbon to which $R^8$ is bound, and $R^8$ is H.

In another embodiment of this invention the optional Bond 1 is absent, and $R^{8A}$ and $R^{8B}$, taken together with the carbon atoms to which they are bound, form a C5 to C8 heterocycloalkenyl ring (and in one example a C5 heterocycloalkenyl ring, and in another example a C6 heterocycloalkenyl ring), said heterocycloalkenyl ring comprising two double bonds, provided that there is no double bond bound to the carbon to which $R^8$ is bound, and $R^8$ is alkyl.

In another embodiment of this invention the optional Bond 1 is absent, and $R^{8A}$ and $R^{8B}$, taken together with the carbon atoms to which they are bound, form a C5 to C8 heterocycloalkenyl ring (and in one example a C5 heterocycloalkenyl ring, and in another example a C6 heterocycloalkenyl ring), said heterocycloalkenyl ring comprising two double bonds, provided that there is no double bond bound to the carbon to which $R^8$ is bound, and $R^8$ is methyl.

Other embodiments of the invention are directed to any one of the embodiments directed to the cycloalkyl, cycloalkenyl, heterocycloalkyl, or heterocycloalkenyl rings when formed $R^{8A}$ and $R^{8B}$ are taken together with the carbon atoms to which they are bound wherein said rings are optionally substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$ and —P(O)(OR$^{15}$)(OR$^{16}$).

Other embodiments of the invention are directed to any one of the embodiments directed to the cycloalkyl, cycloalkenyl, heterocycloalkyl, or heterocycloalkenyl rings when formed $R^{8A}$ and $R^{8B}$ are taken together with the carbon atoms to which they are bound wherein said rings are substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$).

In another embodiment of this invention the optional Bond 1 is absent, and $R^{8A}$ and $R^{8B}$, taken together with the carbon atoms to which they are bound, form a cycloalkyl ring, wherein said cycloalkyl ring is a cyclopropyl ring, and said cyclopropyl ring is optionally substituted.

In another embodiment of this invention the optional Bond 1 is absent, and $R^{8A}$ and $R^{8B}$, taken together with the carbon atoms to which they are bound, form a cycloalkyl ring, wherein said cycloalkyl ring is a cyclopropyl ring, and said cyclopropyl ring is optionally substituted, and $R^8$ is H.

In another embodiment of this invention the optional Bond 1 is absent, and $R^{8A}$ and $R^{8B}$, taken together with the carbon atoms to which they are bound, form a cycloalkyl ring, wherein said cycloalkyl ring is a cyclopropyl ring, and said cyclopropyl ring is optionally substituted, and $R^8$ is alkyl.

In another embodiment of this invention the optional Bond 1 is absent, and $R^{8A}$ and $R^{8B}$, taken together with the carbon atoms to which they are bound, form a cycloalkyl ring, wherein said cycloalkyl ring is a cyclopropyl ring, and said cyclopropyl ring is optionally substituted, and $R^8$ is methyl.

In another embodiment of this invention the optional Bond 1 is absent, and $R^{8A}$ and $R^{8B}$, taken together with the carbon atoms to which they are bound, form a cycloalkyl rind, wherein said cycloalkyl ring is a cyclohexyl ring, and said cyclohexyl ring is optionally substituted.

In another embodiment of this invention the optional Bond 1 is absent, and $R^{8A}$ and $R^{8B}$, taken together with the carbon atoms to which they are bound, form a cycloalkyl ring, wherein said cycloalkyl ring is a cyclohexyl ring, and said cyclopropyl ring is optionally substituted, and $R^8$ is H.

In another embodiment of this invention the optional Bond 1 is absent, and $R^{8A}$ and $R^{8B}$, taken together with the carbon atoms to which they are bound, form a cycloalkyl ring, wherein said cycloalkyl ring is a cyclohexyl ring, and said cyclohexyl ring is optionally substituted, and $R^8$ is alkyl.

In another embodiment of this invention the optional Bond 1 is absent, and $R^{8A}$ and $R^{8B}$, taken together with the carbon atoms to which they are bound, form a cycloalkyl ring, wherein said cycloalkyl ring is a cyclohexyl ring, and said cyclohexyl ring is optionally substituted, and $R^8$ is methyl.

In another embodiment of this invention $R^{10}$ is aryl.

In another embodiment of this invention $R^{15}$ is aryl substituted with 1 to 3 independently selected $R^{21}$ groups.

In another embodiment of this invention $R^{10}$ is aryl substituted with 1 to 3 $R^{21}$ groups independently selected from the group consisting of halo (e.g., F, Br and Cl) and —$OR^{15}$ (e.g., —O-alkyl, such as —$OCH_3$).

In another embodiment of this invention $R^{10}$ is aryl substituted with 1 $R^{21}$ group.

In another embodiment of this invention $R^{10}$ is aryl substituted with 1 $R^{21}$ group wherein said $R^{21}$ group is halo.

In another embodiment of this invention $R^{10}$ is aryl substituted with 1 $R^{21}$ group wherein said $R^{21}$ group is halo, and said halo is F.

In another embodiment of this invention $R^{15}$ is aryl substituted with 1 $R^{21}$ group, wherein said $R^{21}$ group is —$OR^{15}$.

In another embodiment of this invention $R^{15}$ is aryl substituted with 1 $R^{21}$ group, wherein said $R^{21}$ group is —$OR^{15}$, and wherein said $R^{15}$ is alkyl (e.g., methyl, ethyl and propyl).

In another embodiment of this invention $R^{10}$ is phenyl.

In another embodiment of this invention $R^{10}$ is phenyl substituted with 1 to 3 independently selected $R^{21}$ groups.

In another embodiment of this invention $R^{10}$ is phenyl substituted with 1 to 3 $R^{21}$ groups independently selected from the group consisting of halo (e.g., F, Br and Cl) and —$OR^{15}$ (e.g., —O-alkyl, such as —$OCH_3$). In one example $R^{10}$ is:

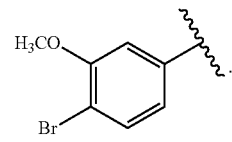 [SMILES: *c1ccc(Br)c(OC)c1]

In another embodiment of this invention $R^{10}$ is phenyl substituted with 1 $R^{21}$ group.

In another embodiment of this invention $R^{10}$ is phenyl substituted with 1 $R^{21}$ group wherein said $R^{21}$ group is halo.

In another embodiment of this invention $R^{10}$ is phenyl substituted with 1 $R^{21}$ group wherein said $R^{21}$ group is halo, and said halo is F.

In another embodiment of this invention $R^{10}$ is phenyl substituted with 1 $R^{21}$ group, wherein said $R^{21}$ group is —$OR^{15}$.

In another embodiment of this invention $R^{10}$ is phenyl substituted with 1 $R^{21}$ group, wherein said $R^{21}$ group is —$OR^{15}$, and wherein said $R^{15}$ is alkyl (e.g., methyl, ethyl, and propyl).

In another embodiment of this invention $R^{10}$ is heteroaryl.

In another embodiment of this invention $R^{10}$ is heteroaryl substituted with 1 to 3 independently selected $R^{21}$ groups.

In another embodiment of this invention $R^{10}$ is selected from the group consisting of:

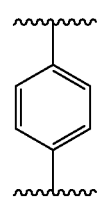

1f

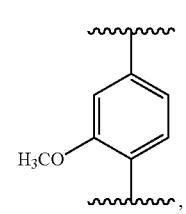

2f

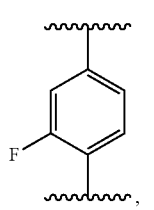

3f

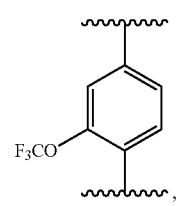

4f

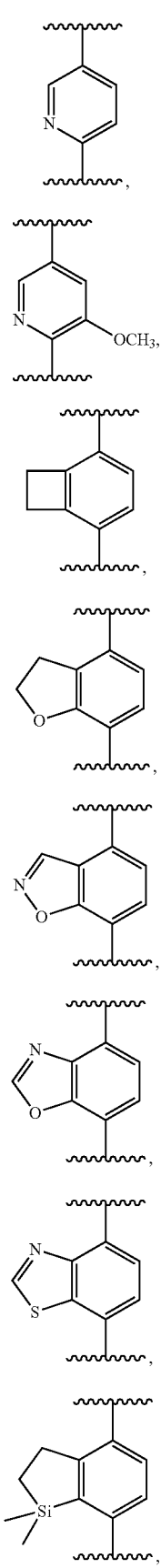

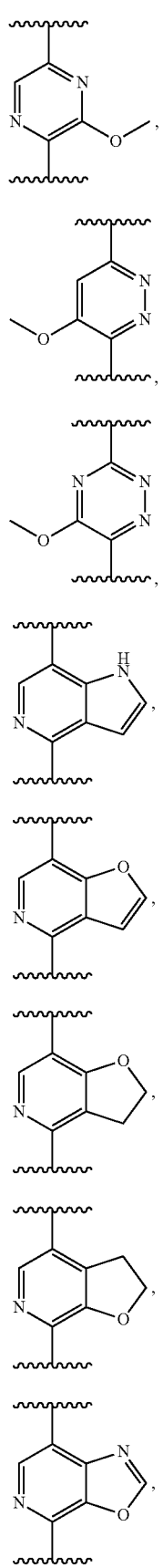
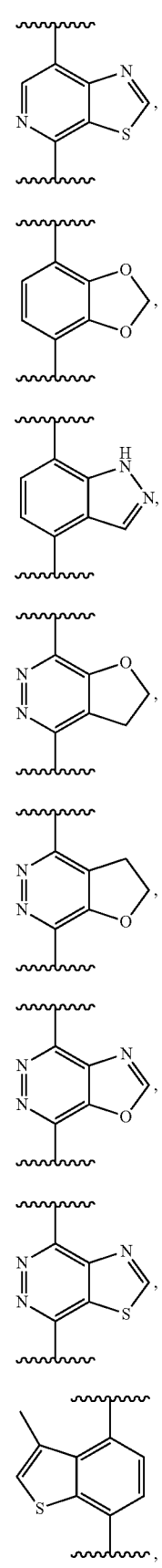

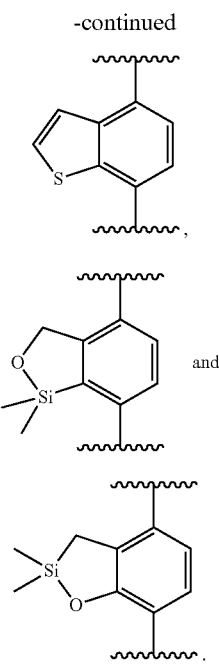

In another embodiment of this invention $R^{10}$ is 1f. In another embodiment of this invention $R^{10}$ is 2f. In another embodiment of this invention $R^{10}$ is 3f. In another embodiment of this invention $R^{10}$ is 4f. In another embodiment of this invention $R^{10}$ is 5f. In another embodiment of this invention $R^{10}$ is 6f. In another embodiment of this invention $R^{10}$ is 7f. In another embodiment of this invention $R^{10}$ is 8f. In another embodiment of this invention $R^{10}$ is 9f. In another embodiment of this invention $R^{10}$ is 10f. In another embodiment of this invention $R^{10}$ is 11f. In another embodiment of this invention $R^{10}$ is 12f. In another embodiment of this invention $R^{10}$ is 13f. In another embodiment of this invention $R^{10}$ is 14f. In another embodiment of this invention $R^{10}$ is 15f. In another embodiment of this invention $R^{10}$ is 16f. In another embodiment of this invention $R^{10}$ is 17f. In another embodiment of this invention $R^{10}$ is 18f. In another embodiment of this invention $R^{10}$ is 19f. In another embodiment of this invention $R^{10}$ is 20f. In another embodiment of this invention $R^{10}$ is 21f. In another embodiment of this invention $R^{10}$ is 22f. In another embodiment of this invention $R^{10}$ is 23f. In another embodiment of this invention $R^{10}$ is 24f. In another embodiment of this invention $R^{10}$ is 25f. In another embodiment of this invention $R^{10}$ is 26f. In another embodiment of this invention $R^{10}$ is 27f. In another embodiment of this invention $R^{10}$ is 28f. In another embodiment of this invention $R^{10}$ is 29f. In another embodiment of this invention $R^{10}$ is 30f. In another embodiment of this invention $R^{10}$ is 31f. In another embodiment of this invention $R^{10}$ is 32f. In another embodiment of this invention $R^{10}$ is 33f, in another embodiment of this invention $R^{10}$ is 34f. In another embodiment of this invention $R^{10}$ is 35f. In another embodiment of this invention $R^{10}$ is 36f. In another embodiment of this invention $R^{10}$ is 37f. In another embodiment of this invention $R^{10}$ is 38f. In another embodiment of this invention $R^{10}$ is 39f.

In another embodiment of this invention $R^9$ is selected from the group consisting of alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl-, wherein independently each of said alkyl-, alkenyl- and alkynyl-, aryl-, arylalkyl-, alkylaryl-, cycloalkyl-, cycloalkylalkyl-, heteroaryl-, heteroarylalkyl-, heterocyclyl- and heterocyclylalkyl- is optionally substituted with 1 to 3 independently selected $R^{21}$ groups.

In another embodiment of this invention $R^9$ is H.

In another embodiment of this invention $R^9$ is heteroaryl.

In another embodiment of this invention $R^9$ is heteroaryl substituted with 1 to 3 independently selected $R^{21}$ groups.

In another embodiment of this invention $R^9$ is heteroaryl substituted with 1 to 3 $R^{21}$ groups independently selected from the group consisting of: alkyl (e.g., methyl and ethyl), halo (e.g., Cl and F, and in one example Cl), and —$OR^{15}$.

In another embodiment of this invention $R^9$ is heteroaryl substituted with 1 to 3 $R^{21}$ groups independently selected from the group consisting of: alkyl (e.g., methyl and ethyl), halo (e.g., Cl and F, and in one example Cl), and —$OR^{15}$, wherein $R^{15}$ is alkyl (e.g., methyl).

In another embodiment of this invention $R^9$ is heteroaryl substituted with 1 to 2 $R^{21}$ groups independently selected from the group consisting of: alkyl (e.g., methyl and ethyl), halo (e.g., Cl and F, and in one example Cl), and —$OR^{15}$ In another embodiment of this invention $R^9$ is heteroaryl substituted with 1 to 2 $R^{21}$ groups independently selected from the group consisting of: alkyl (e.g., methyl and ethyl), halo (e.g., Cl and F, and in one example Cl), and —$OR^{15}$, wherein $R^{15}$ is alkyl (e.g., methyl).

In another embodiment of this invention $R^9$ is heteroaryl substituted with 1 $R^{21}$ group.

In another embodiment of this invention $R^9$ is heteroaryl substituted with 1 $R^{21}$ group selected from the group consisting of: alkyl (e.g., methyl and ethyl), halo (e.g., Cl and F, and in one example Cl), and —$OR^{15}$.

In another embodiment of this invention $R^9$ is heteroaryl substituted with 1 $R^{21}$ group selected from the group consisting of: alkyl (e.g., methyl and ethyl), halo (e.g., Cl and F, and in one example Cl), and —$OR^{15}$, wherein $R^{15}$ is alkyl (e.g., methyl).

In another embodiment of this invention $R^9$ is heteroaryl substituted with 1 to 3 independently selected $R^{21}$ groups, wherein said $R^{21}$ groups are the same or different alkyl group.

In another embodiment of this invention $R^9$ is heteroaryl substituted with 1 $R^{21}$ group, wherein said $R^{21}$ group is alkyl (e.g., methyl).

In another embodiment of this invention $R^9$ is imidazolyl.

In another embodiment of this invention $R^9$ is the imidazolyl:

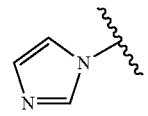

imidazol-1-yl

In another embodiment of this invention $R^9$ is imidazolyl substituted with 1 to 3 independently selected $R^{21}$ groups.

In another embodiment of this invention $R^9$ is imidazolyl substituted with 1 to 3 $R^{21}$ groups independently selected from the group consisting of: alkyl (e.g., methyl and ethyl), halo (e.g., Cl and F, and in one example Cl), and —$OR^{15}$.

In another embodiment of this invention $R^5$ is imidazolyl substituted with 1 to 3 $R^{21}$ groups independently selected from the group consisting of: alkyl (e.g., methyl and ethyl), halo (e.g., Cl and F, and in one example Cl), and —$OR^{15}$, wherein $R^{15}$ is alkyl (e.g., methyl).

In another embodiment of this invention $R^9$ is imidazolyl substituted with 1 to 2 $R^{21}$ groups independently selected from the group consisting of: alkyl (e.g., methyl and ethyl), halo (e.g., Cl and F, and in one example Cl), and —$OR^{15}$.

In another embodiment of this invention $R^9$ is imidazolyl substituted with 1 to 2 $R^{21}$ groups independently selected from the group consisting of: alkyl (e.g., methyl and ethyl), halo (e.g., Cl and F, and in one example Cl), and —$OR^{15}$, wherein $R^{15}$ is alkyl (e.g., methyl).

In another embodiment of this invention $R^9$ is imidazolyl substituted with 1 group:

In another embodiment of this invention $R^9$ is imidazolyl substituted with 1 $R^{21}$ group selected from the group consisting of: alkyl (e.g., methyl and ethyl), halo (e.g., Cl and F, and in one example Cl), and —$OR^{15}$.

In another embodiment of this invention $R^9$ is imidazolyl substituted with 1 $R^{21}$ group selected from the group consisting of: alkyl (e.g., methyl and ethyl), halo (e.g., Cl and F, and in one example Cl), and —$OR^{15}$, wherein $R^{15}$ is alkyl (e.g., methyl).

In another embodiment of this invention $R^9$ is imidazolyl substituted with 1 to 3 independently selected $R^{21}$ groups, wherein said $R^{21}$ groups are the same or different alkyl group.

In another embodiment of this invention $R^9$ is imidazolyl substituted with 1 $R^{21}$ group, wherein said $R^{21}$ group is alkyl (e.g., methyl).

In another embodiment of this invention $R^9$ is selected from the group consisting of:

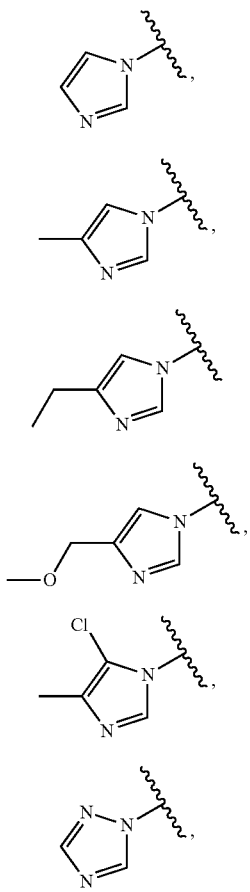

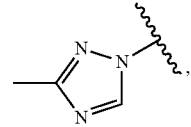

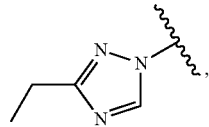

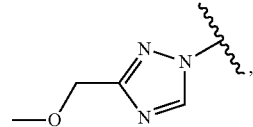

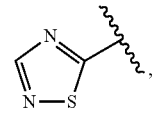

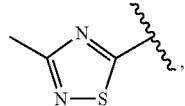

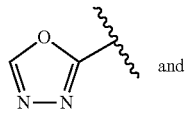

In another embodiment of this invention $R^9$ is 1g. In another embodiment of this invention $R^9$ is:

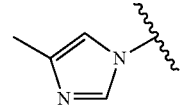

4-methyl-imidazol-1-yl (i.e. 2g). In another embodiment of this invention $R^9$ is 3g. In another embodiment of this invention $R^9$ is 4g. In another embodiment of this invention $R^9$ is 5g. In another embodiment of this invention $R^9$ is 6g. In another embodiment of this invention $R^9$ is 7g. In another embodiment of this invention $R^9$ is 8g. In another embodiment of this invention $R^9$ is 9g. In another embodiment of this invention $R^9$ is 10g. In another embodiment of this invention $R^9$ is 11g. In another embodiment of this invention $R^9$ is 12g. In another embodiment of this invention $R^9$ is 13g.

In another embodiment of the invention:
$R^{10}$ is selected from the group consisting of: (1) heteroaryl and (2) heteroaryl substituted with 1 to 3 independently selected $R^{21}$ groups; and
$R^9$ is selected from the group consisting of: (1) heteroaryl (e.g., imidazolyl, such as, for example imidazol-1-yl), (2) heteroaryl (e.g., imidazolyl, such as, for example imidazol-1-yl) substituted with 1 to 3 independently selected $R^{21}$ groups, (3) heteroaryl (e.g., imidazolyl, such as, for example imidazol-1-yl) substituted with 1 $R^{21}$ group, (4) heteroaryl (e.g., imidazolyl, such as, for example imidazol-1-yl) substituted with 1 to 3 independently selected $R^{21}$ groups, wherein said $R^{21}$ groups are the same or different alkyl group, and (5) heteroaryl (e.g., imidazolyl, such as, for example imidazol-1-yl) substituted with 1 $R^{21}$ group, wherein said $R^{21}$ group is alkyl (e.g., methyl).

In another embodiment of this invention $R^{10}$ is selected from the group consisting of 1f to 39f, and $R^9$ is selected from the group consisting of 1g to 13g.

In another embodiment of this invention $R^{10}$ is selected from the group consisting of 1f to 39f, and $R^9$ is 2g.

In another embodiment of this invention $R^{10}$ is selected from the group consisting of 1f to 39f, and $R^9$ is H.

In another embodiment of this invention the $R^{10}$—$R^9$— moiety is selected from the group consisting of:

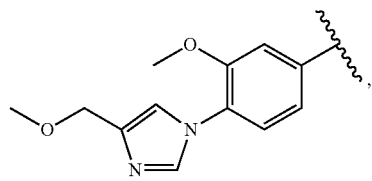

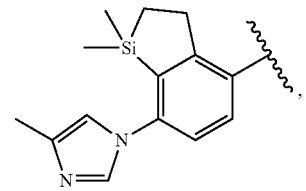

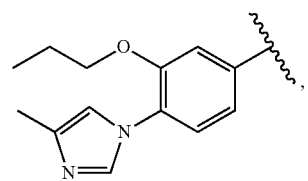

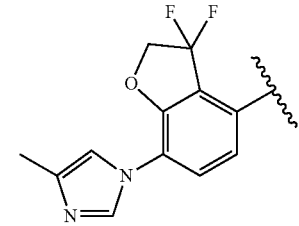

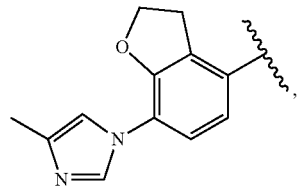

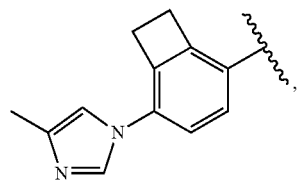

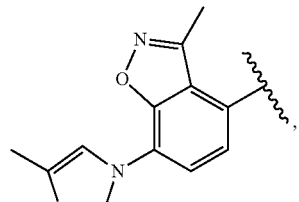

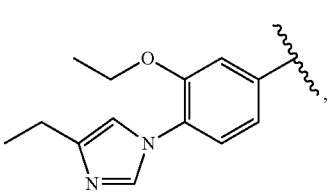

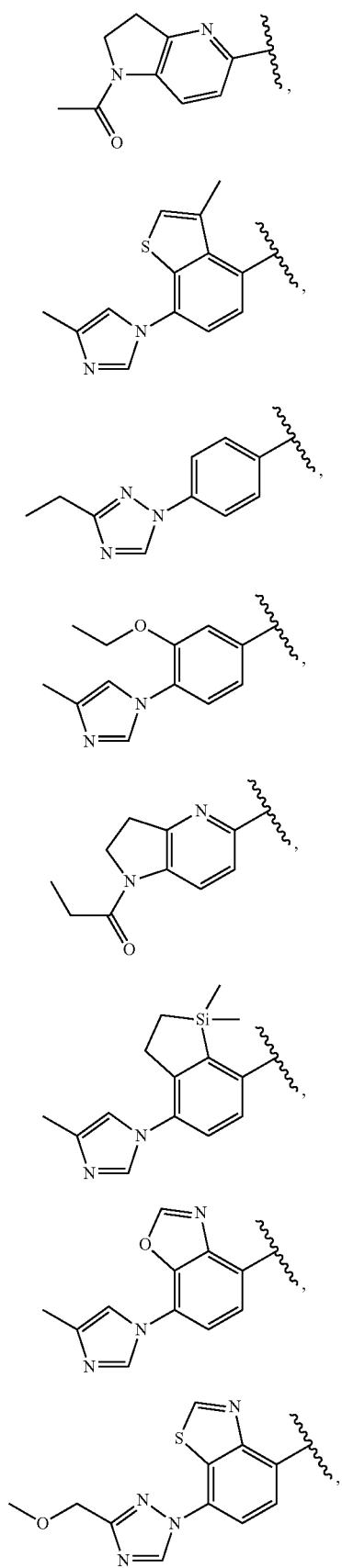
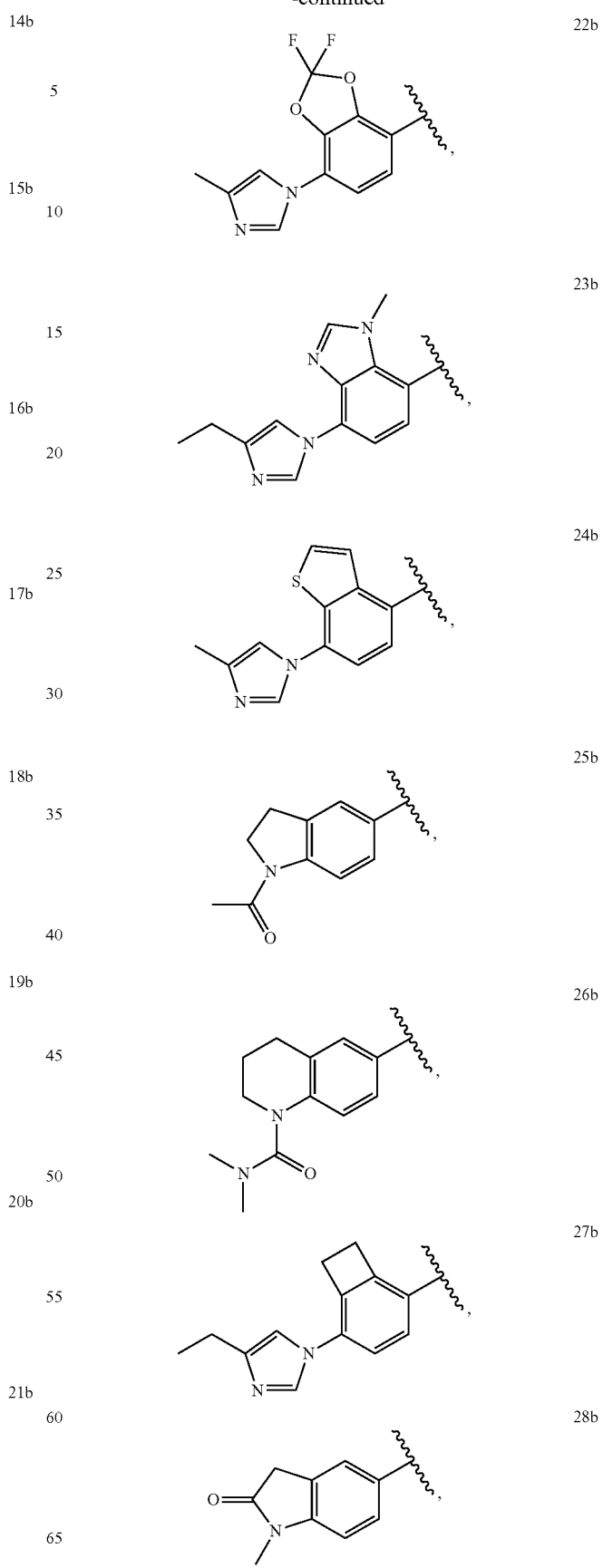

-continued
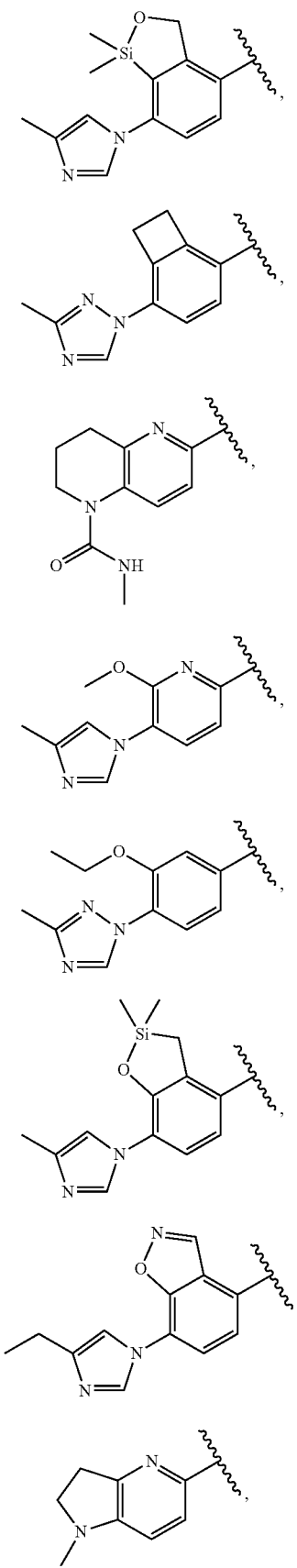
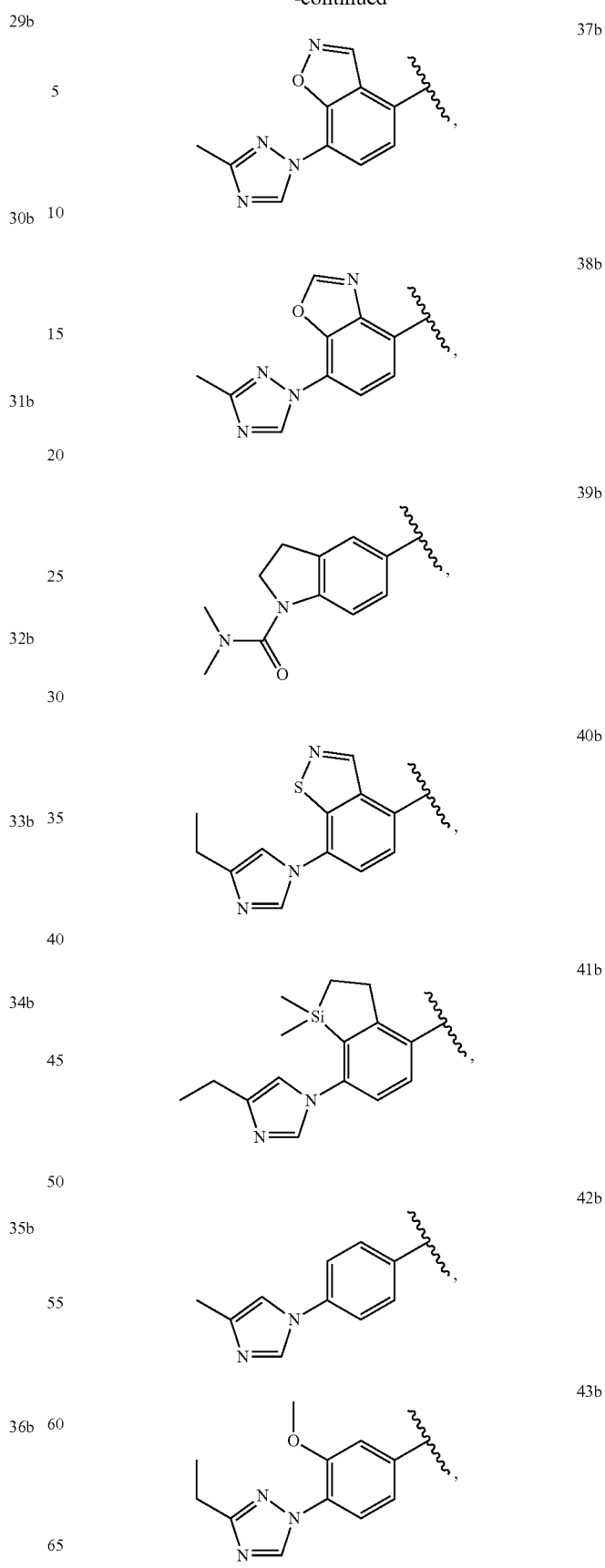

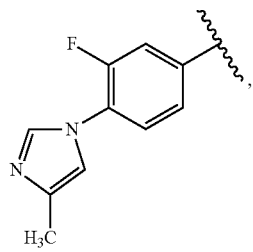

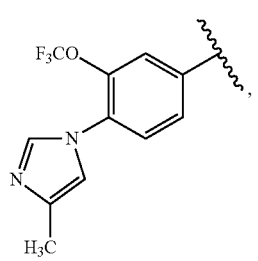

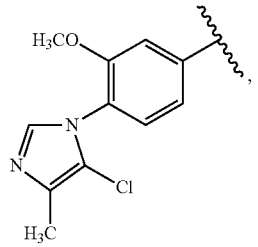

and

In another embodiment the $R^{10}$—$R^9$— moiety is 1b. In another embodiment the $R^{10}$—$R^9$— moiety is 2b. In another embodiment the $R^{10}$—$R^9$— moiety is 3b. In another embodiment the $R^{10}$—$R^9$— moiety is 4b. In another embodiment the $R^{10}$—$R^9$— moiety is 5b. In another embodiment the $R^{10}$—$R^9$— moiety is 6b. In another embodiment the $R^{10}$—$R^9$— moiety is 7b. In another embodiment the $R^{10}$—$R^9$— moiety is 8b. In another embodiment the $R^{10}$—$R^9$— moiety is 9b. In another embodiment the $R^{10}$—$R^9$— moiety is 10b. In another embodiment the $R^{10}$—$R^9$— moiety is 11b. In another embodiment the $R^{10}$—$R^9$— moiety is 12b. In another embodiment the $R^{10}$—$R^9$— moiety is 13b. In another embodiment the $R^{10}$—$R^9$— moiety is 14b. In another embodiment the $R^{10}$—$R^9$— moiety is 15b. In another embodiment the $R^{10}$—$R^9$— moiety is 16b. In another embodiment the $R^{10}$—$R^9$— moiety is 17b. In another embodiment the $R^{10}$—$R^9$— moiety is 18b. In another embodiment the $R^{10}$—$R^9$— moiety is 19b. In another embodiment the $R^{10}$—$R^9$— moiety is 20b. In another embodiment the $R^{10}$—$R^9$— moiety is 21b. In another embodiment the $R^{10}$—$R^9$— moiety is 22b. In another embodiment the $R^{10}$—$R^9$— moiety is 23b. In another embodiment the $R^{10}$—$R^9$— moiety is 24b. In another embodiment the $R^{10}$—$R^9$— moiety is 25b. In another embodiment the $R^{10}$—$R^9$— moiety is 26b. In another embodiment the $R^{10}$—$R^9$— moiety is 27b. In another embodiment the $R^{10}$—$R^9$— moiety is 28b. In another embodiment the $R^{10}$—$R^9$— moiety is 29b. In another embodiment the $R^{10}$—$R^9$— moiety is 30b. In another embodiment the $R^{10}$—$R^9$— moiety is 31b. In another embodiment the $R^{10}$—$R^9$— moiety is 32b. In another embodiment the $R^{10}$—$R^9$— moiety is 33b, in another embodiment the $R^{10}$—$R^9$— moiety is 34b. In another embodiment the $R^{10}$—$R^9$— moiety is 35b. In another embodiment the $R^{10}$—$R^9$— moiety is 36b. In another embodiment the $R^{10}$—$R^9$— moiety is 37b. In another embodiment the $R^{10}$—$R^9$— moiety is 38b. In another embodiment the $R^{10}$—$R^9$— moiety is 39b. In another embodiment the $R^{10}$—$R^9$— moiety is 40b, in another embodiment the $R^{10}$—$R^9$— moiety is 41b. In another embodiment the $R^{10}$—$R^9$— moiety is 42b. In another embodiment the $R^{10}$—$R^9$— moiety is 43b. In another embodiment the $R^{10}$—$R^9$— moiety is 44b. In another embodiment the $R^{10}$—$R^9$— moiety is 45b. In another embodiment the $R^{10}$—$R^9$— moiety is 46b. In another embodiment the $R^{10}$—$R^9$— moiety is 47b. In another embodiment the $R^{10}$—$R^9$— moiety is 48b. In another embodiment the $R^{10}$—$R^9$— moiety is 49b. In another embodiment the $R^{10}$—$R^9$— moiety is 50b.

In another embodiment of this invention Ring (A) is selected from the group consisting of: 1a to 33a, the $R^{10}$—$R^9$— moiety is selected from the group consisting of: 1b to 50b, and $R^7$ is selected from the group consisting of: 1d to 35d.

In another embodiment of this invention Ring (A) is selected from the group consisting of: 1a to 33a, the $R^{10}$—$R^9$— moiety is selected from the group consisting of: 1b to 50b, and $R^6$ and $R^7$ taken together form a moiety selected from the group consisting of: 1e to 7f.

In another embodiment of this invention Ring (A) is selected from the group consisting of: 1a to 33a, the $R^{10}$—$R^9$— moiety is selected from the group consisting of: 1b to 50b, $R^6$ is selected from the group consisting of H, alkyl, alkyl substituted with —$OR^{15}$, —$C(O)OR^{15}$, alkyl substituted with =O (e.g., —CH=O), alkenyl substituted with —$S(O)_2R^{15}$, alkyl substituted with —$NR^{15}R^{16}$, -heterocycloalkyl-fusedaryl substituted with 1 or 2 independently selected $R^{21}$ groups, and alkyl substituted with —$S(O)_2R^{15}$, and $R^7$ is selected from the group consisting of: 1d to 35d.

In another embodiment of this invention Ring (A) is selected from the group consisting of: 1a to 33a, the $R^{10}$—$R^9$— moiety is selected from the group consisting of: 1b to 50b, $R^6$ is selected from the group consisting of H, alkyl, alkyl substituted with —$OR^{15}$, and alkyl substituted with —$S(O)_2R^{15}$, and $R^7$ is selected from the group consisting of: 1d to 35d.

In another embodiment of this invention Ring (A) is selected from the group consisting of: 1a to 33a, the $R^{10}$—$R^9$— moiety is selected from the group consisting of: 1b to 50b, $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, —$(CH_2)S(O)_2CH_2$cyclopropyl, —$C(O)OCH_3$, —CH=O, —CH=CH—$S(O)_2CH_3$, —$CH_2NH_2$, and

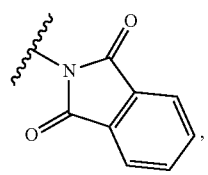 [SMILES: *N1C(=O)c2ccccc2C1=O]

and $R^7$ is selected from the group consisting of: 1d to 35d.

In another embodiment of this invention Ring (A) is selected from the group consisting of: 1a to 33a, the $R^{10}$—$R^9$— moiety is selected from the group consisting of: 1b to 50b, $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2$cyclopropyl, and $R^7$ is selected from the group consisting of: 1d to 35d.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is O, W is a bond, X is —$CH_2$—, Y is —$CH_2$—, m is 1 and n is 1.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$CH_2$—, W is O, X is —$CH_2$—, Y is —$CH_2$—, m is 1 and n is 1.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is O, W is a bond, X is —$CH_2$—, Y is O, m is 1 and n is 1.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$CH_2$—, W is NH, X is —$CH_2$—, Y is —$CH_2$—, m is 1 and n is 1.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, C is —C(O)—, W is NH, X is —$CH_2$—Y is —$CH_2$—, m is 1 and n is 1.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$CF_2$—, W is a bond, X is —$CH_2$—, Y is O, m is 1 and n is 1.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$CF_2$—, W is a bond, X is —$S(O)_2$—, Y is —$CH_2$—, m is 1 and n is 1.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$C(R^3)_2$— (e.g., —$CH_2$—), W is —$NR^2$— (e.g., —NH— or —Nalkyl-), X is —$CH_2$—, Y is —$CH_2$—, m is 1 and n is 1.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$C(R^3)_2$— (e.g., —$CH_2$—), W is —$NR^2$— (e.g., —NH— or —Nalkyl-), X is —$CH_2$—, Y is O, m is 1 and n is 1.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$C(R^3)_2$— (e.g., —$CH_2$—), W is O, X is —$CH_2$—, Y is O, m is 1 and n is 1.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is O, W is a bond, X is —$CH_2$—, Y is —$CH_2$—, m is 1, n is 1, and optional bond 1 is present.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$CH_2$—, W is O, X is —$CH_2$—, Y is —$CH_2$—, m is 1, n is 1, and optional bond 1 is present.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is O, W is a bond, X is —$CH_2$—, Y is O, m is 1, n is 1, and optional bond 1 is present.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —CH$_2$—, W is NH, X is —CH$_2$—, Y is —CH$_2$—, m is 1, n is 1, and optional bond 1 is present.

In another embodiment of this invention Ring (A) is selected from the group consisting of: 1a to 33a, the R$^{10}$—R$^9$— moiety is selected from the group consisting of: 1b to 50b, R$^7$ is selected from the group consisting of: 1d to 35d, U is N, G is —C(O)—W is NH, X is —CH$_2$—, Y is —CH$_2$ m is 1, n is 1, and optional bond 1 is present, In another embodiment of this invention Ring (A) is selected from the group consisting of: 1a to 33a, the R$^{10}$—R$^9$— moiety is selected from the group consisting of: 1b to 50b, R$^7$ is selected from the group consisting of: 1d to 35d, U is N, G is —CF$_2$—, W is a bond, X is —CH$_2$—, Y is O, m is 1, n is 1, and optional bond 1 is present.

In another embodiment of this invention Ring (A) is selected from the group consisting of: 1a to 33a, the R$^{10}$—R$^9$— moiety is selected from the group consisting of: 1b to 50b, R$^7$ is selected from the group consisting of: 1d to 35d, U is N, G is —CF$_2$—, W is a bond, X is —S(O)$_2$—, Y is —CH$_2$—, m is 1, n is 1, and optional bond 1 is present.

In another embodiment of this invention Ring (A) is selected from the group consisting of: 1a to 33a, the R$^{10}$—R$^9$— moiety is selected from the group consisting of: 1b to 50b, R$^7$ is selected from the group consisting of: 1d to 35d, U is N, G is —C(R$^3$)$_2$— (e.g., —CH$_2$—), W is —NR$^2$— (e.g., —NH— or —Nalkyl-), X is —CH$_2$—, Y is —CH$_2$—, m is 1, n is 1, and optional bond 1 is present.

In another embodiment of this invention Ring (A) is selected from the group consisting of: 1a to 33a, the R$^{10}$—R$^9$— moiety is selected from the group consisting of: 1b to 50b, R$^7$ is selected from the group consisting of: 1d to 35d, U is N, G is —C(R$^3$)$_2$— (e.g., —CH$_2$—), W is —NR$^2$— (e.g., —NH— or —Nalkyl-), X is —CH$_2$—, Y is O, m is 1, n is 1, and optional bond 1 is present.

In another embodiment of this invention Ring (A) is selected from the group consisting of: 1a to 33a, the R$^{10}$—R$^9$— moiety is selected from the group consisting of: 1b to 50b, R$^7$ is selected from the group consisting of: 1d to 35d, U is N, G is —C(R$^3$)$_2$— (e.g., —CH$_2$—), W is O, X is —CH$_2$—, Y is O, m is 1, n is 1, and optional bond 1 is present.

In another embodiment of this invention Ring (A) is selected from the group consisting of: 1a to 33a, the R$^{10}$—R$^9$— moiety is selected from the group consisting of: 1b to 50b, R$^7$ is selected from the group consisting of: 1d to 35d, U is N, G is O, W is a bond, X is —CH$_2$—, Y is —CH$_2$—, m is 1, n is 1, optional bond 1 is present, and R$^8$ is H.

In another embodiment of this invention Ring (A) is selected from the group consisting of: 1a to 33a, the R$^{10}$—R$^9$— moiety is selected from the group consisting of: 1b to 50b, R$^7$ is selected from the group consisting of: 1d to 35d, U is N, G is —CH$_2$—, W is O, X is —CH$_2$—, Y is —CH$_2$—, m is 1, n is 1, optional bond 1 is present, and R$^8$ is H.

In another embodiment of this invention Ring (A) is selected from the group consisting of: 1a to 33a, the R$^{10}$—R$^9$— moiety is selected from the group consisting of: 1b to 50b, R$^7$ is selected from the group consisting of: 1d to 35d, U is N, G is O, W is a bond, X is —CH$_2$—, Y is O, m is 1, n is 1, optional bond 1 is present, and R$^8$ is H.

In another embodiment of this invention Ring (A) is selected from the group consisting of: 1a to 33a, the R$^{10}$—R$^9$— moiety is selected from the group consisting of: 1b to 50b, R$^7$ is selected from the group consisting of: 1d to 35d, U is N, G is —CH$_2$—, W is NH, X is —CH$_2$—, Y is —CH$_2$—, m is 1, n is 1, optional bond 1 is present, and R$^8$ is H.

In another embodiment of this invention Ring (A) is selected from the group consisting of: 1a to 33a, the R$^{10}$—R$^9$— moiety is selected from the group consisting of: 1b to 50b, R$^7$ is selected from the group consisting of: 1d to 35d, U is N, G is —C(O)—, W is NH, X is —CH$_2$—, Y is —CH$_2$ m is 1, n is 1, optional bond 1 is present, and R$^8$ is H.

In another embodiment of this invention Ring (A) is selected from the group consisting of: 1a to 33a, the R$^{10}$—R$^9$— moiety is selected from the group consisting of: 1b to 50b, R$^7$ is selected from the group consisting of: 1d to 35d, U is N, G is —CF$_2$—, W is a bond, X is —CH$_2$—, Y is O, m is 1, n is 1, optional bond 1 is present, and R$^8$ is H.

In another embodiment of this invention Ring (A) is selected from the group consisting of: 1a to 33a, the R$^{10}$—R$^9$ moiety is selected from the group consisting of: 1b to 50b, R$^7$ is selected from the group consisting of: 1d to 35d, U is N, G is —CF$_2$—, W is a bond, X is —S(O)$_2$—, Y is —CH$_2$—, m is 1, n is 1, and optional bond 1 is present.

In another embodiment of this invention Ring (A) is selected from the group consisting of: 1a to 33a, the R$^{10}$—R$^9$— moiety is selected from the group consisting of: 1b to 50b, R$^7$ is selected from the group consisting of: 1d to 35d, U is N, G is —C(R$^3$)$_2$— (e.g., —CH$_2$—), W is —NR$^2$— (e.g., —NH— or —Nalkyl-), X is —CH$_2$—, Y is —CH$_2$—, m is 1, n is 1, optional bond 1 is present, and R$^8$ is H.

In another embodiment of this invention Ring (A) is selected from the group consisting of: 1a to 33a, the R$^{10}$—R$^9$— moiety is selected from the group consisting of: 1b to 50b, R$^7$ is selected from the group consisting of: 1d to 35d, U is N, G is —C(R$^3$)$_2$— (e.g., —CH$_2$—), W is —NR$^2$— (e.g., —NH— or —Nalkyl-), X is —CH$_2$—, Y is O, m is 1, n is 1, optional bond 1 is present, and R$^8$ is H.

In another embodiment of this invention Ring (A) is selected from the group consisting of: 1a to 33a, the R$^{10}$—R$^9$— moiety is selected from the group consisting of: 1b to 50b, R$^7$ is selected from the group consisting of: 1d to 35d, U is N, G is —C(R$^3$)$_2$— (e.g., —CH$_2$—), W is O, X is —CH$_2$—, Y is O, m is 1, n is 1, optional bond 1 is present, and R$^8$ is H.

In another embodiment of this invention Ring (A) is selected from the group consisting of: 1a to 33a, the R$^{10}$—R$^9$— moiety is selected from the group consisting of: 1b to 50b, R$^7$ is selected from the group consisting of: 1d to 35d, U is N, G is O, W is a bond, X is —CH$_2$—, Y is —CH$_2$—, m is 1, n is 1, and R$^6$ is selected from the group consisting of: H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$ CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl.

In another embodiment of this invention Ring (A) is selected from the group consisting of: 1a to 33a, the R$^{10}$—R$^9$— moiety is selected from the group consisting of: 1b to 50b, R$^7$ is selected from the group consisting of: 1d to 35d, U is N, G is —CH$_2$—, W is O, X is —CH$_2$—, Y is —CH$_2$—, m is 1, n is 1, and R$^6$ is selected from the group consisting of: H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$ CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl.

In another embodiment of this invention Ring (A) is selected from the group consisting of: 1a to 33a, the R$^{10}$—R$^9$— moiety is selected from the group consisting of: 1b to 50b, R$^7$ is selected from the group consisting of: 1d to 35d, U is N, G is O, W is a bond, X is —CH$_2$—, Y is O, m is 1, n is 1, and R$^6$ is selected from the group consisting of: H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$CH_2$—, W is NH, X is —$CH_2$—, Y is —$CH_2$—, m is 1, n is 1, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —C(O)—, W is NH, X is —$CH_2$—, Y is —$CH_2$—, m is 1, n is 1, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$CF_2$—, W is a bond, X is —$CH_2$—, Y is O, m is 1, n is 1, and $R^6$ is selected from the group consisting of: H, methyl, ethyl, —$CH_2OH$, —$CH(OH)CH_3$, —$(CH_2)_2S(O)_2CH_3$, $CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$CF_2$—, W is a bond, X is —$S(O)_2$—, Y is —$CH_2$—, m is 1, n is 1, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: is to 33a, the $R^{10}$—$R^9$— moiety is selected from the group consisting of: 1b to 50b, $R^7$ is selected from the group consisting of: 1d to 35d, U is N, G is —$C(R^3)_2$—, (e.g., —$CH_2$—), W is —$NR^2$— (e.g., —NH— or —Nalkyl-), X is —$CH_2$—, Y is —$CH_2$—, m is 1, n is 1, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$C(R^3)_2$—, (e.g., —$CH_2$—), W is —$NR^2$— (e.g., —NH— or —Nalkyl-), X is —$CH_2$—, Y is O, m is 1, n is 1, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$C(R^3)_2$— (e.g., —$CH_2$—), W is O, X is —$CH_2$—, Y is O, m is 1, n is 1, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is O, W is a bond, X is —$CH_2$—, Y is —$CH_2$—, m is 1, n is 1, optional bond 1 is present, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$CH_2$—, W is O, X is —$CH_2$—, Y is —$CH_2$—, m is 1, n is 1, optional bond 1 is present, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is O, W is a bond, X is —$CH_2$—, Y is O, m is 1, n is 1, optional bond 1 is present, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$CH_2$—, W is NH, X is —$CH_2$—, Y is —$CH_2$—, m is 1, n is 1, optional bond 1 is present, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —C(O)—, W is NH, X is —$CH_2$—, Y is —$CH_2$— m is 1, n is 1, optional bond 1 is present, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$CF_2$—, W is a bond, X is —$CH_2$—, Y is O, m is 1, n is 1, optional bond 1 is present, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$, In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$CF_2$—, W is a bond, X is —$S(O)_2$—, Y is —$CH_2$—, m is 1, n is 1, optional bond 1 is present, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$C(R^3)_2$— (e.g., —$CH_2$—), W is —$NR^2$— (e.g., —NH— or —Nalkyl-), X is —$CH_2$—, Y is —$CH_2$—, m is 1, n is 1, optional bond 1 is present, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$C(R^3)_2$— (e.g., —$CH_2$—), W is —$NR^2$— (e.g., —NH— or —Nalkyl-), X is —$CH_2$—, Y is O, m is 1, n is 1, optional bond 1 is present, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$C(R^3)_2$— (e.g., —$CH_2$—), W is O, X is —$CH_2$—, Y is O, m is 1, n is 1, optional bond 1 is present, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is O, W is a bond, X is —$CH_2$—, Y is —$CH_2$—, m is 1, n is 1, optional bond 1 is present, $R^8$ is H, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$CH_2$—, W is O, X is —$CH_2$—, Y is —$CH_2$—, m is 1, n is 1, optional bond 1 is present, $R^8$ is H, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is O, W is a bond, X is —$CH_2$—, Y is O, m is 1, n is 1, optional bond 1 is present, $R^8$ is H, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$CH_2$—, W is NH, X is —$CH_2$—, Y is —$CH_2$—, m is 1, n is 1, optional bond 1 is present, $R^8$ is H, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —C(O)—, W is NH, X is —$CH_2$—, Y is —$CH_2$ m is 1, n is 1, optional bond 1 is present, $R^8$ is H, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$CF_2$—, W is a bond, X is —$CH_2$—, Y is O, m is 1, n is 1, optional bond 1 is present, $R^8$ is H, and $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$.

In another embodiment of this invention Ring (A) is selected from the group consisting of: 1a to 33a, the $R^{10}$—$R^9$— moiety is selected from the group consisting of: 1b to 50b, $R^7$ is selected from the group consisting of: 1d to 35d, U is N, G is —$CF_2$—, W is a bond, X is —$S(O)_2$—, Y is —$CH_2$—, m is 1, n is 1, optional bond 1 is present, $R^3$ is H, and $R^6$ is selected from the group consisting of: H, methyl, ethyl, —$CH_2OH$, $CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl.

In another embodiment of this invention Ring (A) is selected from the group consisting of: 1a to 33a, the R$^{10}$—R$^9$— moiety is selected from the group consisting of: 1b to 50b, R$^7$ is selected from the group consisting of: 1d to 35d, U is N, G is —C(R$^3$)$_2$— (e.g., —CH$_2$—), W is —NR$^2$— (e.g., —NH— or —Nalkyl-), X is —CH$_2$—, Y is —CH$_2$—, m is 1, n is 1, optional bond 1 is present, R$^8$ is H, and R$^6$ is selected from the group consisting of: H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl.

In another embodiment of this invention Ring (A) is selected from the group consisting of: 1a to 33a, the R$^{10}$—R$^9$— moiety is selected from the group consisting of: b to 50b, R$^7$ is selected from the group consisting of: 1d to 35d, U is N, G is —C(R$^3$)$_2$— (e.g., —CH$_2$—), W is —NR$^2$— (e.g., —NH— or —Nalkyl-), X is —CH$_2$—, Y is O, m is 1, n is 1, optional bond 1 is present, R$^8$ is H, and R$^6$ is selected from the group consisting of: H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl.

In another embodiment of this invention Ring (A) is selected from the group consisting of: 1a to 33a, the R$^{10}$—R$^9$— moiety is selected from the group consisting of: 1b to 50b, R$^7$ is selected from the group consisting of: 1d to 35d, U is N, G is —C(R$^3$)$_2$— (e.g., —CH$_2$—), W is O, X is —CH$_2$—, Y is O, m is 1, n is 1, optional bond 1 is present, R$^8$ is H, and R$^3$ is selected from the group consisting of: H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl.

In another embodiment of this invention Ring (A) is selected from the group consisting of: 1a to 33a, the R$^{10}$—R$^9$— moiety is selected from the group consisting of: 1b to 50b, and R$^6$ and R$^7$ taken together form a moiety selected from the group consisting of: 1e to 8e.

In another embodiment of this invention Ring (A) is selected from the group consisting of: 1a to 33a, the R$^{10}$—R$^9$— moiety is selected from the group consisting of: 1b to 50b, R$^6$ and R$^7$ taken together form a moiety selected from the group consisting of: 1e to 8e, U is N, G is O, W is a bond, X is —CH$_2$—, Y is —CH$_2$—, m is 1 and n is 1.

In another embodiment of this invention Ring (A) is selected from the group consisting of: 1a to 33a, the R$^{10}$—R$^9$— moiety is selected from the group consisting of: 1b to 50b, R$^6$ and R$^7$ taken together form a moiety selected from the group consisting of: 1e to 8e, U is N, G is —CH$_2$—, W is O, X is —CH$_2$—, Y is —CH$_2$—, m is 1 and n is 1.

In another embodiment of this invention Ring (A) is selected from the group consisting of: 1a to 33a, the R$^{10}$—R$^9$— moiety is selected from the group consisting of: 1b to 50b, R$^6$ and R$^7$ taken together form a moiety selected from the group consisting of: 1e to 8e, U is N, G is O, W is a bond, X is —CH$_2$—, Y is O, m is 1 and n is 1.

In another embodiment of this invention Ring (A) is selected from the group consisting of: 1a to 33a, the R$^{10}$—R$^9$— moiety is selected from the group consisting of: 1b to 50b, R$^6$ and R$^7$ taken together form a moiety selected from the group consisting of: 1e to 8e, U is N, G is —CH$_2$—, W is NH, X is —CH$_2$—, Y is —CH$_2$—, m is 1 and n is 1.

In another embodiment of this invention Ring (A) is selected from the group consisting of: 1a to 33a, the R$^{10}$—R$^9$— moiety is selected from the group consisting of: 1b to 50b, R$^6$ and R$^7$ taken together form a moiety selected from the group consisting of: 1e to 8e, Li is N, G is —C(O)—, W is NH, X is —CH$_2$—, Y is —CH$_2$—, m is 1 and n is 1.

In another embodiment of this invention Ring (A) is selected from the group consisting of: 1a to 33a, the R$^{10}$—R$^9$— moiety is selected from the group consisting of: 1b to 50b, R$^6$ and R$^7$ taken together form a moiety selected from the group consisting of: 1e to 8e, U is N, G is —CF$_2$—, W is a bond, X is —CH$_2$—, Y is O, m is 1 and n is 1.

In another embodiment of this invention Ring (A) is selected from the group consisting of: 1a to 33a, the R$^{10}$—R$^9$— moiety is selected from the group consisting of: 1b to 50b, R$^6$ and R$^7$ taken together form a moiety selected from the group consisting of: 1e to 8e, U is N, G is —CF$_2$—, W is a bond, X is —S(O)$_2$—, Y is —CH$_2$—, m is 1 and n is 1.

In another embodiment of this invention Ring (A) is selected from the group consisting of: 1a to 33a, the R$^{10}$—R$^9$— moiety is selected from the group consisting of: 1b to 50b, R$^6$ and R$^7$ taken together form a moiety selected from the group consisting of: 1e to 8e, U is N, G is —C(R$^3$)$_2$— (e.g., —CH$_2$—), W is —NR$^2$— (e.g., —NH— or —Nalkyl-), X is —CH$_2$—, Y is —CH$_2$—, m is 1 and n is 1.

In another embodiment of this invention Ring (A) is selected from the group consisting of: 1a to 33a, the R$^{10}$—R$^9$— moiety is selected from the group consisting of: 1b to 50b, R$^6$ and R$^7$ taken together form a moiety selected from the group consisting of: 1e to 8e, U is N, G is —C(R$^3$)$_2$— (e.g., —CH$_2$—), W is —NR$^2$— (e.g., —NH— or —Nalkyl-), X is —CH$_2$—, Y is O, m is 1 and n is 1.

In another embodiment of this invention Ring (A) is selected from the group consisting of: 1a to 33a, the R$^{10}$—R$^9$— moiety is selected from the group consisting of: 1b to 50b, R$^6$ and R$^7$ taken together form a moiety selected from the group consisting of: 1e to 8e, U is N, G is —C(R$^3$)$_2$— (e.g., —CH$_2$—), W is O, X is —CH$_2$—, Y is O, m is 1 and n is 1.

In another embodiment of this invention Ring (A) is selected from the group consisting of: 1a to 33a, the R$^{10}$—R$^9$— moiety is selected from the group consisting of: 1b to 50b, R$^6$ and R$^7$ taken together form a moiety selected from the group consisting of: 1e to 8e, U is N, G is O, W is a bond, X is —CH$_2$—, Y is —CH$_2$—, m is 1, n is 1, and optional bond 1 is present.

In another embodiment of this invention Ring (A) is selected from the group consisting of: 1a to 33a, the R$^{10}$—R$^9$— moiety is selected from the group consisting of: 1b to 50b, R$^6$ and R$^7$ taken together form a moiety selected from the group consisting of: 1e to 8e, U is N, G is —CH$_2$—, W is O, X is —CH$_2$—, Y is —CH$_2$—, m is 1, n is 1, and optional bond 1 is present.

In another embodiment of this invention Ring (A) is selected from the group consisting of: 1a to 33a, the R$^{10}$—R$^9$— moiety is selected from the group consisting of: 1b to 50b, R$^6$ and R$^7$ taken together form a moiety selected from the group consisting of: 1e to 8e, U is N, G is O, W is a bond, X is —CH$_2$—, Y is O, m is 1, n is 1, and optional bond 1 is present, In another embodiment of this invention Ring (A) is selected from the group consisting of: 1a to 33a, the R$^{10}$—R$^9$— moiety is selected from the group consisting of: 1b to 50b, R$^6$ and R$^7$ taken together form a moiety selected from the group consisting of: 1e to 8e, U is N, G is —CH$_2$—, W is NH, X is —CH$_2$—, Y is —CH$_2$—, m is 1, n is 1, and optional bond 1 is present.

In another embodiment of this invention Ring (A) is selected from the group consisting of: 1a to 33a, the $R^{10}$—$R^9$— moiety is selected from the group consisting of: 1b to 50b, $R^6$ and $R^7$ taken together form a moiety selected from the group consisting of: 1e to 8e, U is N, G is —C(O)—, W is NH, X is —CH$_2$—, Y is —CH$_2$ m is 1, n is 1, and optional bond 1 is present.

In another embodiment of this invention Ring (A) is selected from the group consisting of: 1a to 33a, the $R^{10}$—$R^9$— moiety is selected from the group consisting of: 1b to 50b, $R^6$ and $R^7$ taken together form a moiety selected from the group consisting of: 1e to 8e, U is N, G is —CF$_2$—, W is a bond, X is —CH$_2$—, Y is O, m is 1, n is 1, and optional bond 1 is present.

In another embodiment of this invention Ring (A) is selected from the group consisting of: 1a to 33a, the $R^{10}$—$R^9$— moiety is selected from the group consisting of: 1b to 50b, $R^6$ and $R^7$ taken together form a moiety selected from the group consisting of: 1e to 8e, U is N, G is —CF$_2$—, W is a bond, X is —S(O)$_2$—, Y is —CH$_2$—, m is 1, n is 1, and optional bond 1 is present.

In another embodiment of this invention Ring (A) is selected from the group consisting of: 1a to 33a, the $R^{10}$—$R^9$— moiety is selected from the group consisting of: 1b to 50b, $R^6$ and $R^7$ taken together form a moiety selected from the group consisting of: 1e to 8e, U is N, G is —C($R^3$)$_2$— (e.g., —CH$_2$—), W is —NR$^2$— (e.g., —NH— or —Nalkyl-), X is —CH$_2$—, Y is —CH$_2$—, m is 1, n is 1, and optional bond 1 is present.

In another embodiment of this invention Ring (A) is selected from the group consisting of: 1a to 33a, the $R^{10}$—$R^9$— moiety is selected from the group consisting of: 1b to 50b, $R^6$ and $R^7$ taken together form a moiety selected from the group consisting of: 1e to 8e, U is N, G is —C($R^3$)$_2$— (e.g., —CH$_2$—), W is —NR$^2$— (e.g., —NH— or —Nalkyl-), X is —CH$_2$—, Y is O, m is 1, n is 1, and optional bond 1 is present.

In another embodiment of this invention Ring (A) is selected from the group consisting of: 1a to 33a, the $R^{10}$—$R^9$— moiety is selected from the group consisting of: 1b to 50b, $R^6$ and $R^7$ taken together form a moiety selected from the group consisting of: 1e to 8e, U is N, O is —C($R^3$)$_2$— (e.g., —CH$_2$—), W is O, X is —CH$_2$—, Y is O, m is 1, n is 1, and optional bond 1 is present.

In another embodiment of this invention Ring (A) is selected from the group consisting of: 1a to 33a, the $R^{10}$—$R^9$— moiety is selected from the group consisting of: 1b to 50b, $R^6$ and $R^7$ taken together form a moiety selected from the group consisting of: 1e to 8e, U is N, G is O, W is a bond, X is —CH$_2$—, Y is —CH$_2$—, m is 1, n is 1, optional bond 1 is present, and $R^8$ is H.

In another embodiment of this invention Ring (A) is selected from the group consisting of: 1a to 33a, the $R^{10}$—$R^9$— moiety is selected from the group consisting of: 1b to 50b, $R^6$ and $R^7$ taken together form a moiety selected from the group consisting of: 1e to 8e, U is N, G is —CH$_2$—, W is O, X is —CH$_2$—, Y is —CH$_2$—, m is 1, n is 1, optional bond 1 is present, and $R^8$ is H.

In another embodiment of this invention Ring (A) is selected from the group consisting of: 1a to 33a, the $R^{10}$—$R^9$— moiety is selected from the group consisting of: 1b to 50b, $R^6$ and $R^7$ taken together form a moiety selected from the group consisting of: 1e to 8e, U is N, G is O, W is a bond, X is —CH$_2$—, Y is O, m is 1, n is 1, optional bond 1 is present, and $R^8$ is H.

In another embodiment of this invention Ring (A) is selected from the group consisting of: 1a to 33a, the $R^{10}$—$R^9$— moiety is selected from the group consisting of: 1b to 50b, $R^6$ and $R^7$ taken together form a moiety selected from the group consisting of: 1e to 8e, U is N, G is —CH$_2$—, W is NH, X is —CH$_2$—, Y is —CH$_2$—, m is 1, n is 1, optional bond 1 is present, and $R^8$ is H.

In another embodiment of this invention Ring (A) is selected from the group consisting of: 1a to 33a, the $R^{10}$—$R^9$— moiety is selected from the group consisting of: 1b to 50b, $R^6$ and $R^7$ taken together form a moiety selected from the group consisting of: 1e to 8e, U is N, G is —C(O)—, W is NH, X is —CH$_2$—, Y is —CH$_2$ m is 1, n is 1, optional bond 1 is present, and $R^3$ is H.

In another embodiment of this invention Ring (A) is selected from the group consisting of: 1a to 33a, the $R^{10}$—$R^9$— moiety is selected from the group consisting of: 1b to 50b, $R^6$ and $R^7$ taken together form a moiety selected from the group consisting of: 1e to 8e, U is N, G is —CF$_2$—, W is a bond, X is —CH$_2$—, Y is O, m is 1, n is 1, optional bond 1 is present, and $R^8$ is H.

In another embodiment of this invention Ring (A) is selected from the group consisting of: 1a to 33a, the $R^{10}$—$R^9$— moiety is selected from the group consisting of: 1b to 50b, $R^6$ and $R^7$ taken together form a moiety selected from the group consisting of: 1e to 8e, U is N, G is —CF$_2$—, W is a bond, X is —S(O)$_2$—, Y is —CH$_2$—, m is 1, n is 1, and optional bond 1 is present.

In another embodiment of this invention Ring (A) is selected from the group consisting of: 1a to 33a, the $R^{10}$—$R^9$— moiety is selected from the group consisting of: 1b to 50b, $R^6$ and $R^7$ taken together form a moiety selected from the group consisting of: 1e to 8e, U is N, G is —C($R^3$)$_2$— (e.g., —CH$_2$—), W is —NR$^2$— (e.g., —NH— or —Nalkyl-), X is —CH$_2$—, Y is —CH$_2$—, m is 1, n is 1, optional bond 1 is present, and $R^8$ is H.

In another embodiment of this invention Ring (A) is selected from the group consisting of: 1a to 33a, the $R^{10}$—$R^9$— moiety is selected from the group consisting of: 1b to 50b, $R^6$ and $R^7$ taken together form a moiety selected from the group consisting of: 1e to 8e, U is N, G is —C($R^3$)$_2$— (e.g., —CH$_2$—), W is —NR$^2$— (e.g., —NH— or —Nalkyl-), X is —CH$_2$—, Y is O, m is 1, n is 1, optional bond 1 is present, and $R^8$ is H.

In another embodiment of this invention Ring (A) is selected from the group consisting of: 1a to 33a, the $R^{10}$—$R^9$— moiety is selected from the group consisting of: 1b to 50b, $R^6$ and $R^7$ taken together form a moiety selected from the group consisting of: 1e to 8e, U is N, G is —C($R^3$)$_2$— (e.g., —CH$_2$—), W is O, X is —CH$_2$—, Y is O, m is 1, n is 1, optional bond 1 is present, and $R^8$ is H.

In another embodiment of this invention, optional Bond 1 is present.

In another embodiment of this invention, optional Bond 1 is absent and optional Bonds 2 and 3 are present along with moieties $R^{8A}$ and $R^{8B}$ In another embodiment of this invention, optional Bond 1 is absent, and optional Bonds 2 and 3 are present and moieties $R^{8A}$ and $R^{8B}$ taken together, along with the carbon atoms to which they are bound, form a ring selected from the group consisting of: cycloalkyl, cycloalkenyl, heterocycloalkyl, and heterocycloalkenyl, wherein:
  (i) said cycloalkyl ring is a 3 to 8 carbon membered ring (and in one example a said ring is cyclopropyl, and in another example said ring is cyclohexyl), and
  (ii) said cycloalkenyl ring is a 5 to 8 carbon membered ring comprising one or two double bonds (and in one example one double bond, and in another example two double bonds), provided that $R^8$ is absent when there is a double bond to the carbon to which $R^{10}$ is bound, and provided that there is no double bond to the carbon common to Ring (B) and said cycloalkenyl ring, and (iii) said heterocycloalkyl ring is a 4 to 8 membered ring comprising 1 to 3 ring members selected from the group consisting of: O, S, $NR^2$, C(O), S(O), and $S(O)_2$, and wherein the remaining ring members are carbon, and (iv) said heterocycloalkenyl ring is a 5 to 8 membered ring comprising one or two double bonds (and in one example one double bond, and in another example two double bonds), and comprising 1 to 3 ring members selected from the group consisting of: O, S, $NR^2$, C(O), S(O), and $S(O)_2$, and wherein the remaining ring members are carbon, provided that $R^8$ is absent when there is a double bond to the carbon to which $R^{16}$ is bound, and provided that there is no double bond to the carbon common to Ring (B) and said heterocycloalkenyl ring, and (v) said cycloalkyl, cycloalkenyl, heterocycloalkyl, or heterocycloalkenyl ring is optionally substituted with 1 to 3 substituents selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —$OR^{15}$ (e.g., —$CH_3$), —C(O)$R^{15}$, —C(O)O$R^{15}$, —C(O)N($R^{15}$)($R^{16}$), —S(O)N($R^{15}$)($R^{16}$), —S(O)$_2$N($R^{15}$)($R^{16}$), —C(=NO$R^{15}$)$R^{16}$, and —P(O)(O$R^{15}$)(O$R^{16}$).

In another embodiment of this invention, optional Bond 1 is absent, and optional Bonds 2 and 3 are present and moieties $R^{8A}$ and $R^{8B}$ taken together, along with the carbon atoms to which they are bound, form a ring selected from the group consisting of: cycloalkyl, cycloalkenyl, heterocycloalkyl, and heterocycloalkenyl, wherein:

(i) said cycloalkyl ring is a 3 to 8 carbon membered ring (and in one example a said ring is cyclopropyl, and in another example said ring is cyclohexyl), and (ii) said cycloalkenyl ring is a 5 to 8 carbon membered ring comprising one or two double bonds (and in one example one double bond, and in another example two double bonds), provided that $R^8$ is absent when there is a double bond to the carbon to which $R^{10}$ is bound, and provided that there is no double bond to the carbon common to Ring (B) and said cycloalkenyl ring, and (iii) said heterocycloalkyl ring is a 4 to 8 membered ring comprising 1 to 3 ring members selected from the group consisting of: O, S, $NR^2$, C(O), S(O), and $S(O)_2$, and wherein the remaining ring members are carbon, and (iv) said heterocycloalkenyl ring is a 5 to 8 membered ring comprising one or two double bonds (and in one example one double bond, and in another example two double bonds), and comprising 1 to 3 ring members selected from the group consisting of: O, S, $NR^2$, C(O), S(O), and $S(O)_2$, and wherein the remaining ring members are carbon, provided that $R^8$ is absent when there is a double bond to the carbon to which $R^{10}$ is bound, and provided that there is no double bond to the carbon common to Ring (B) and said heterocycloalkenyl ring.

In another embodiment of this invention, optional Bond 1 is absent and optional Bonds 2 and 3 are present and moieties $R^{8A}$ and $R^{8B}$ taken together, along with the carbon atoms to which they are bound, form an unsubstituted cycloalkyl ring (e.g., cyclopropyl, and in another example cyclohexyl).

In another embodiment of this invention, optional Bond 1 is absent, and optional Bonds 2 and 3 are present and moieties $R^{8A}$ and $R^{8B}$ taken together, along with the carbon atoms to which they are bound, form a substituted cycloalkyl ring (e.g., a substituted cyclopropyl, and in another example substituted cyclohexyl) substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —$OR^{15}$ (e.g., —$CH_3$), —C(O)$R^{15}$, —C(O)O$R^{15}$, —C(O)N($R^{15}$)($R^{16}$), —S(O)N($R^{15}$)($R^{16}$), —S(O)$_2$N($R^{15}$)($R^{16}$), —C(=NO$R^{15}$)$R^{16}$, and —P(O)(O$R^{15}$)(O$R^{16}$).

In another embodiment of this invention, optional Bond 1 is absent and optional Bonds 2 and 3 are present along with moieties $R^{8A}$ and $R^{8B}$, Ring (A) is selected from the group consisting of: 1a to 33a, the $R^{10}$—$R^9$— moiety is selected from the group consisting of: 1b to 50b, and $R^7$ is selected from the group consisting of: 1d to 35d.

In another embodiment of this invention, Ring (A) is selected from the group consisting of: 1a to 33a, the $R^{10}$—$R^9$— moiety is selected from the group consisting of: 1b to 50b, $R^7$ is selected from the group consisting of: 1d to 35d, optional Bond 1 is absent, and optional Bonds 2 and 3 are present and moieties $R^{8A}$ and $R^{8B}$ taken together, along with the carbon atoms to which they are bound, form a ring selected from the group consisting of: cycloalkyl, cycloalkenyl, heterocycloalkyl, and heterocycloalkenyl, wherein:

(i) said cycloalkyl ring is a 3 to 8 carbon membered ring (and in one example a said ring is cyclopropyl, and in another example said ring is cyclohexyl), and (ii) said cycloalkenyl ring is a 5 to 8 carbon membered ring comprising one or two double bonds (and in one example one double bond, and in another example two double bonds), provided that $R^8$ is absent when there is a double bond to the carbon to which $R^{10}$ is bound, and provided that there is no double bond to the carbon common to Ring (B) and said cycloalkenyl ring, and (iii) said heterocycloalkyl ring is a 4 to 8 membered ring comprising 1 to 3 ring members selected from the group consisting of: O, S, $NR^2$, C(O), S(O), and $S(O)_2$, and wherein the remaining ring members are carbon, and (iv) said heterocycloalkenyl ring is a 5 to 8 membered ring comprising one or two double bonds (and in one example one double bond, and in another example two double bonds), and comprising 1 to 3 ring members selected from the group consisting of: O, S, $NR^2$, C(O), S(O), and $S(O)_2$, and wherein the remaining ring members are carbon, provided that $R^8$ is absent when there is a double bond to the carbon to which $R^{10}$ is bound, and provided that there is no double bond to the carbon common to Ring (B) and said heterocycloalkenyl ring, and (v) said cycloalkyl, cycloalkenyl, heterocycloalkyl, or heterocycloalkenyl ring is optionally substituted with 1 to 3 substituents selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —$OR^{15}$ (e.g., —$CH_3$), —C(O)$R^{15}$, —C(O)O$R^{15}$, —C(O)N($R^{15}$)($R^{16}$), —S(O)N($R^{15}$)($R^{16}$), —S(O)$_2$N($R^{15}$)($R^{16}$), —C(=NO$R^{15}$)$R^{16}$, and —P(O)(O$R^{15}$)(O$R^{16}$).

In another embodiment of this invention, Ring (A) is selected from the group consisting of: 1a to 33a, the $R^{10}$—$R^9$— moiety is selected from the group consisting of: 1b to 50b, $R^7$ is selected from the group consisting of: 1d to 35d, optional Bond 1 is absent, and optional Bonds 2 and 3 are present and moieties $R^{8A}$ and $R^{8B}$ taken together, along with the carbon atoms to which they are bound, form a ring selected from the group consisting of: cycloalkyl, cycloalkenyl, heterocycloalkyl, and heterocycloalkenyl, wherein:

(i) said cycloalkyl ring is a 3 to 8 carbon membered ring (and in one example a said ring is cyclopropyl, and in another example said ring is cyclohexyl), and (ii) said cycloalkenyl ring is a 5 to 8 carbon membered ring comprising one or two double bonds (and in one example one double bond, and in another example two double bonds), provided that $R^8$ is absent when there is a double bond to the carbon to which $R^{10}$ is bound, and provided that there is no double bond to the carbon common to Ring (B) and said cycloalkenyl ring, and (iii) said heterocycloalkyl ring is a 4 to 8 membered ring comprising 1 to 3 ring members selected from the group consisting of: O, S, $NR^2$, C(O), S(O), and $S(O)_2$, and wherein the remaining ring members are carbon, and (iv) said heterocycloalkenyl ring is a 5 to 8 membered ring comprising one or two double bonds (and in one example one double bond, and in another example two double bonds), and comprising 1 to 3 ring members selected from the group consisting of: O, S, $NR^2$, C(O), S(O), and $S(O)_2$, and wherein the remaining ring members are carbon, provided that $R^8$ is absent when there is a double bond to the carbon to which $R^{10}$ is bound, and provided that there is no double bond to the carbon common to Ring (B) and said heterocycloalkenyl ring.

In another embodiment of this invention, Ring (A) is selected from the group consisting of: 1a to 33a, the $R^{10}$—$R^9$— moiety is selected from the group consisting of: 1b to 50b, and $R^7$ is selected from the group consisting of: 1d to 35d, optional Bond 1 is absent and optional Bonds 2 and 3 are present and moieties $R^{8A}$ and $R^{8B}$ taken together, along with the carbon atoms to which they are bound, form an unsubstituted cycloalkyl ring (e.g., cyclopropyl, and in another example cyclohexyl).

In another embodiment of this invention, Ring (A) is selected from the group consisting of: 1a to 33a, the $R^{10}$—$R^9$— moiety is selected from the group consisting of: 1b to 50b, $R^7$ is selected from the group consisting of: 1d to 35d, optional Bond 1 is absent, and optional Bonds 2 and 3 are present and moieties $R^{8A}$ and $R^{8B}$ taken together, along with the carbon atoms to which they are bound, form a substituted cycloalkyl ring (e.g., a substituted cyclopropyl, and in another example substituted cyclohexyl) substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —$OR^{15}$ (e.g., —$CH_3$), —$C(O)R^{15}$, —$C(O)OR^{15}$, —$C(O)N(R^{15})(R^{16})$, —$S(O)N(R^{15})(R^{16})$, —$S(O)_2N(R^{15})(R^{16})$, —C(=$NOR^{15}$)$R^{16}$, and —$P(O)(OR^{15})(OR^{16})$.

In another embodiment of this invention, optional Bond 1 is absent and optional Bonds 2 and 3 are present along with moieties $R^{8A}$ and $R^{8B}$, Ring (A) is selected from the group consisting of: is to 33a, the $R^{10}$—$R^9$— moiety is selected from the group consisting of: 1b to 50b, $R^6$ is selected from the group consisting of H, alkyl, alkyl substituted with —$OR^{15}$, and alkyl substituted with —$S(O)_2R^{15A}$ and $R^7$ is selected from the group consisting of: 1d to 35d.

In another embodiment of this invention, Ring (A) is selected from the group consisting of: 1a to 33a, the $R^{10}$—$R^9$— moiety is selected from the group consisting of: 1b to 50b, $R^6$ is selected from the group consisting of H, alkyl, alkyl substituted with —$OR^{15}$, and alkyl substituted with —$S(O)_2R^{15A}$, $R^7$ is selected from the group consisting of: 1d to 35d, optional Bond 1 is absent, and optional Bonds 2 and 3 are present and moieties $R^{8A}$ and $R^{8B}$ taken together, along with the carbon atoms to which they are bound, form a ring selected from the group consisting of: cycloalkyl, cycloalkenyl, heterocycloalkyl, and heterocycloalkenyl, wherein:

(i) said cycloalkyl ring is a 3 to 8 carbon membered ring (and in one example a said ring is cyclopropyl, and in another example said ring is cyclohexyl), and (ii) said cycloalkenyl ring is a 5 to 8 carbon membered ring comprising one or two double bonds (and in one example one double bond, and in another example two double bonds), provided that $R^8$ is absent when there is a double bond to the carbon to which $R^{10}$ is bound, and provided that there is no double bond to the carbon common to Ring (B) and said cycloalkenyl ring, and (iii) said heterocycloalkyl ring is a 4 to 8 membered ring comprising 1 to 3 ring members selected from the group consisting of: O, S, $NR^2$, C(O), S(O), and $S(O)_2$, and wherein the remaining ring members are carbon, and (iv) said heterocycloalkenyl ring is a 5 to 8 membered ring comprising one or two double bonds (and in one example one double bond, and in another example two double bonds), and comprising 1 to 3 ring members selected from the group consisting of: O, S, $NR^2$, C(O), S(O), and $S(O)_2$, and wherein the remaining ring members are carbon, provided that $R^8$ is absent when there is a double bond to the carbon to which $R^1$ is bound, and provided that there is no double bond to the carbon common to Ring (B) and said heterocycloalkenyl ring, and (v) said cycloalkyl, cycloalkenyl, heterocycloalkyl, or heterocycloalkenyl ring is optionally substituted with 1 to 3 substituents selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —$OR^{15}$ (e.g., —$CH_3$), —$C(O)R^{15}$, —$C(O)OR^{16}$, —$C(O)N(R^{15})(R^{16})$, —$S(O)N(R^{15})(R^{16})$, $S(O)_2N(R^{15})(R^{16})$, —C(=$NOR^{15}$)$R^{16}$, and —$P(O)(OR^{15})(OR^{16})$.

In another embodiment of this invention, Ring (A) is selected from the group consisting of: 1a to 33a, the $R^{10}$—$R^9$— moiety is selected from the group consisting of: 1b to 50b, $R^6$ is selected from the group consisting of H, alkyl, alkyl substituted with —$OR^{15}$, and alkyl substituted with —$S(O)_2R^{15A}$, $R^7$ is selected from the group consisting of: 1d to 35d, optional Bond 1 is absent, and optional Bonds 2 and 3 are present and moieties $R^{8A}$ and $R^{8B}$ taken together, along with the carbon atoms to which they are bound, form a ring selected from the group consisting of: cycloalkyl, cycloalkenyl, heterocycloalkyl, and heterocycloalkenyl, wherein:

(i) said cycloalkyl ring is a 3 to 8 carbon membered ring (and in one example a said ring is cyclopropyl, and in another example said ring is cyclohexyl), and (ii) said cycloalkenyl ring is a 5 to 8 carbon membered ring comprising one or two double bonds (and in one example one double bond, and in another example two double bonds), provided that $R^8$ is absent when there is a double bond to the carbon to which $R^{10}$ is bound, and provided that there is no double bond to the carbon common to Ring (B) and said cycloalkenyl ring, and (iii) said heterocycloalkyl ring is a 4 to 8 membered ring comprising 1 to 3 ring members selected from the group consisting of: O, S, $NR^2$, C(O), S(O), and $S(O)_2$, and wherein the remaining ring members are carbon, and (iv) said heterocycloalkenyl ring is a 5 to 8 membered ring comprising one or two double bonds (and in one example one double bond, and in another example two double bonds), and comprising 1 to 3 ring members selected from the group consisting of: O, S, $NR^2$, C(O), S(O), and $S(O)_2$, and wherein the remaining ring members are carbon, provided that $R^8$ is absent when there is a double bond to the carbon to which $R^{10}$ is bound, and provided that there is no double bond to the carbon common to Ring (B) and said heterocycloalkenyl ring.

In another embodiment of this invention. Ring (A) is selected from the group consisting of: 1a to 33a, the $R^{10}$—$R^9$— moiety is selected from the group consisting of: 1b to 50b, $R^6$ is selected from the group consisting of H, alkyl, alkyl substituted with —$OR^{15}$, and alkyl substituted with —$S(O)_2$ $R^{15A}$, $R^7$ is selected from the group consisting of: 1d to 35d, optional Bond 1 is absent and optional Bonds 2 and 3 are present and moieties $R^{8A}$ and $R^{8B}$ taken together, along with the carbon atoms to which they are bound, form an unsubstituted cycloalkyl ring (e.g., cyclopropyl, and in another example cyclohexyl).

In another embodiment of this invention, Ring (A) is selected from the group consisting of: 1a to 33a, the $R^{10}$—$R^9$ moiety is selected from the group consisting of: 1b to 50b, $R^6$ is selected from the group consisting of H, alkyl, alkyl substituted with —$OR^{15}$, and alkyl substituted with —$S(O)_2$ $R^{15A}$, $R^7$ is selected from the group consisting of: 1d to 35d, optional Bond 1 is absent, and optional Bonds 2 and 3 are present and moieties $R^{8A}$ and $R^{8B}$ taken together, along with the carbon atoms to which they are bound, form a substituted cycloalkyl ring (e.g., a substituted cyclopropyl, and in another example substituted cyclohexyl) substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —$OR^{15}$ (e.g., —$CH_3$), —$C(O)R^{15}$, —$C(O)OR^{15}$, —$C(O)N(R^{15})(R^{16})$, —$S(O)N(R^{15})(R^{16})$, —$S(O)_2N(R^{15})(R^{16})$, —$C(=NOR^{15})R^{16}$, and —$P(O)(OR^{15})(OR^{16})$.

In another embodiment of this invention, optional Bond 1 is absent and optional Bonds 2 and 3 are present along with moieties $R^{8A}$ and $R^{8B}$, Ring (A) is selected from the group consisting of: 1a to 33a, the $R^{10}$—$R^9$— moiety is selected from the group consisting of: 1b to 50b, $R^6$ and $R^7$ taken together form a moiety selected from the group consisting of: 1e to 8e.

In another embodiment of this invention, Ring (A) is selected from the group consisting of: 1a to 33a, the $R^{10}$—$R^9$— moiety is selected from the group consisting of: 1b to 50b, $R^6$ and $R^7$ taken together form a moiety selected from the group consisting of: 1e to 8e, optional Bond 1 is absent, and optional Bonds 2 and 3 are present and moieties $R^{8A}$ and $R^{8B}$ taken together, along with the carbon atoms to which they are bound, form a ring selected from the group consisting of: cycloalkyl, cycloalkenyl, heterocycloalkyl, and heterocycloalkenyl, wherein:
 (i) said cycloalkyl ring is a 3 to 8 carbon membered ring (and in one example a said ring is cyclopropyl, and in another example said ring is cyclohexyl), and
 (ii) said cycloalkenyl ring is a 5 to 8 carbon membered ring comprising one or two double bonds (and in one example one double bond, and in another example two double bonds), provided that $R^8$ is absent when there is a double bond to the carbon to which $R^{10}$ is bound, and provided that there is no double bond to the carbon common to Ring (B) and said cycloalkenyl ring, and
 (iii) said heterocycloalkyl ring is a 4 to 8 membered ring comprising 1 to 3 ring members selected from the group consisting of: O, S, $NR^2$, C(O), S(O), and $S(O)_2$, and wherein the remaining ring members are carbon, and
 (iv) said heterocycloalkenyl ring is a 5 to 8 membered ring comprising one or two double bonds (and in one example one double bond, and in another example two double bonds), and comprising 1 to 3 ring members selected from the group consisting of: O, S, $NR^2$, C(O), S(O), and $S(O)_2$, and wherein the remaining ring members are carbon, provided that $R^8$ is absent when there is a double bond to the carbon to which $R^{10}$ is bound, and provided that there is no double bond to the carbon common to Ring (B) and said heterocycloalkenyl ring, and
 (v) said cycloalkyl, cycloalkenyl, heterocycloalkyl, or heterocycloalkenyl ring is optionally substituted with 1 to 3 substituents selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —$OR^{15}$ (e.g., —$CH_3$), —$C(O)R^{15}$, —$C(O)OR^{15}$, —$C(O)N(R^{15})(R^{16})$, —$S(O)N(R^{15})(R^{16})$, —$S(O)_2N(R^{15})(R^{16})$, —$C(=NOR^{15})R^{16}$, and —$P(O)(OR^{15})(OR^{16})$.

In another embodiment of this invention, Ring (A) is selected from the group consisting of: 1a to 33a, the $R^{10}$—$R^9$— moiety is selected from the group consisting of: 1b to 50b, $R^6$ and $R^7$ taken together form a moiety selected from the group consisting of: 1e to 8e, optional Bond 1 is absent and optional Bonds 2 and 3 are present and moieties $R^{8A}$ and $R^{8B}$ taken together, along with the carbon atoms to which they are bound, form a ring selected from the group consisting of: cycloalkyl, cycloalkenyl, heterocycloalkyl, and heterocycloalkenyl, wherein:
 (i) said cycloalkyl ring is a 3 to 8 carbon membered ring (and in one example a said ring is cyclopropyl, and in another example said ring is cyclohexyl), and
 (ii) said cycloalkenyl ring is a 5 to 8 carbon membered ring comprising one or two double bonds (and in one example one double bond, and in another example two double bonds), provided that $R^8$ is absent when there is a double bond to the carbon to which $R^{10}$ is bound, and provided that there is no double bond to the carbon common to Ring (B) and said cycloalkenyl ring, and
 (iii) said heterocycloalkyl ring is a 4 to 8 membered ring comprising 1 to 3 ring members selected from the group consisting of: O, S, $NR^2$, C(O), S(O), and $S(O)_2$, and wherein the remaining ring members are carbon, and
 (iv) said heterocycloalkenyl ring is a 5 to 8 membered ring comprising one or two double bonds (and in one example one double bond, and in another example two double bonds), and comprising 1 to 3 ring members selected from the group consisting of: O, S, $NR^2$, C(O), S(O), and $S(O)_2$, and wherein the remaining ring members are carbon, provided that $R^8$ is absent when there is a double bond to the carbon to which $R^{10}$ is bound, and provided that there is no double bond to the carbon common to Ring (B) and said heterocycloalkenyl ring.

In another embodiment of this invention, Ring (A) is selected from the group consisting of: 1a to 33a, the $R^{10}$—$R^9$— moiety is selected from the group consisting of: 1b to 50b, $R^6$ and $R^7$ taken together form a moiety selected from the group consisting of: 1e to 8e, optional Bond 1 is absent and optional Bonds 2 and 3 are present and moieties $R^{8A}$ and $R^{8B}$ taken together, along with the carbon atoms to which they are bound, form an unsubstituted cycloalkyl ring (e.g., cyclopropyl, and in another example cyclohexyl).

In another embodiment of this invention, Ring (A) is selected from the group consisting of: 1a to 33a, the $R^{10}$—$R^9$— moiety is selected from the group consisting of: 1b to 50b, $R^6$ and $R^7$ taken together form a moiety selected from the group consisting of: 1e to 8e, optional Bond 1 is absent, and optional Bonds 2 and 3 are present and moieties $R^{8A}$ and $R^{8B}$ taken together, along with the carbon atoms to which they are bound, form a substituted cycloalkyl ring (e.g., a substituted cyclopropyl, and in another example substituted cyclohexyl) substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —$OR^{15}$ (e.g., —$CH_3$), —$C(O)R^{15}$, —$C(O)OR^{15}$, —$C(O)N(R^{15})(R^{16})$, —$S(O)N(R^{15})(R^{16})$, —$S(O)_2N(R^{15})(R^{16})$, —$C(=NOR^{15})R^{16}$, and —$P(O)(OR^{15})(OR^{16})$.

In another embodiment of this invention, optional Bond 1 is absent and optional Bonds 2 and 3 are present along with moieties $R^{8A}$ and $R^{8B}$, Ring (A) is selected from the group consisting of: 1a to 33a, the $R^{10}$—$R^9$— moiety is selected from the group consisting of: 1b to 50b, $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$, and $R^7$ is selected from the group consisting of: 1d to 35d.

In another embodiment of this invention, Ring (A) is selected from the group consisting of: 1a to 33a, the $R^{10}$—$R^9$— moiety is selected from the group consisting of: 1b to 50b, $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$, $R^7$ is selected from the group consisting of: 1d to 35d, optional Bond 1 is absent, and optional Bonds 2 and 3 are present and moieties $R^{8A}$ and $R^{8B}$ taken together, along with the carbon atoms to which they are bound, form a ring selected from the group consisting of: cycloalkyl, cycloalkenyl, heterocycloalkyl, and heterocycloalkenyl, wherein:
  (i) said cycloalkyl ring is a 3 to 8 carbon membered ring (and in one example a said ring is cyclopropyl, and in another example said ring is cyclohexyl), and
  (ii) said cycloalkenyl ring is a 5 to 8 carbon membered ring comprising one or two double bonds (and in one example one double bond, and in another example two double bonds), provided that $R^8$ is absent when there is a double bond to the carbon to which $R^{10}$ is bound, and provided that there is no double bond to the carbon common to Ring (B) and said cycloalkenyl ring, and
  (iii) said heterocycloalkyl ring is a 4 to 8 membered ring comprising 1 to 3 ring members selected from the group consisting of: O, S, $NR^2$, C(O), S(O), and $S(O)_2$, and wherein the remaining ring members are carbon, and
  (iv) said heterocycloalkenyl ring is a 5 to 8 membered ring comprising one or two double bonds (and in one example one double bond, and in another example two double bonds), and comprising 1 to 3 ring members selected from the group consisting of: O, S, $NR^2$, C(O), S(O), and $S(O)_2$, and wherein the remaining ring members are carbon, provided that $R^8$ is absent when there is a double bond to the carbon to which $R^{10}$ is bound, and provided that there is no double bond to the carbon common to Ring (B) and said heterocycloalkenyl ring, and
  (v) said cycloalkyl, cycloalkenyl, heterocycloalkyl, or heterocycloalkenyl ring is optionally substituted with 1 to 3 substituents selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —$OR^{15}$ (e.g., —$CH_3$), —$C(O)R^{15}$, —$C(O)OR^{15}$, —$C(O)N(R^{15})(R^{16})$, —$S(O)N(R^{15})(R^{16})$, —$S(O)_2N(R^{15})(R^{16})$, —$C(=NOR^{15})R^{16}$, and —$P(O)(OR^{15})(OR^{16})$.

In another embodiment of this invention, Ring (A) is selected from the group consisting of: 1a to 33a, the $R^{10}$—$R^9$— moiety is selected from the group consisting of: 1b to 50b, $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$, $R^7$ is selected from the group consisting of: 1d to 35d, optional Bond 1 is absent, and optional Bonds 2 and 3 are present and moieties $R^{8A}$ and $R^{8B}$ taken together, along with the carbon atoms to which they are bound, form a ring selected from the group consisting of: cycloalkyl, cycloalkenyl, heterocycloalkyl, and heterocycloalkenyl, wherein:
  (i) said cycloalkyl ring is a 3 to 8 carbon membered ring (and in one example a said ring is cyclopropyl, and in another example said ring is cyclohexyl), and
  (ii) said cycloalkenyl ring is a 5 to 8 carbon membered ring comprising one or two double bonds (and in one example one double bond, and in another example two double bonds), provided that $R^8$ is absent when there is a double bond to the carbon to which $R^{10}$ is bound, and provided that there is no double bond to the carbon common to Ring (B) and said cycloalkenyl ring, and
  (iii) said heterocycloalkyl ring is a 4 to 8 membered ring comprising 1 to 3 ring members selected from the group consisting of: O, S, $NR^2$, C(O), S(O), and $S(O)_2$, and wherein the remaining ring members are carbon, and
  (iv) said heterocycloalkenyl ring is a 5 to 8 membered ring comprising one or two double bonds (and in one example one double bond, and in another example two double bonds), and comprising 1 to 3 ring members selected from the group consisting of: O, S, $NR^2$, C(O), S(O), and $S(O)_2$, and wherein the remaining ring members are carbon, provided that $R^8$ is absent when there is a double bond to the carbon to which $R^{10}$ is bound, and provided that there is no double bond to the carbon common to Ring (B) and said heterocycloalkenyl ring.

In another embodiment of this invention, Ring (A) is selected from the group consisting of: 1a to 33a, the $R^{10}$—$R^9$— moiety is selected from the group consisting of: 1b to 50b, $R^6$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$, $R^7$ is selected from the group consisting of: d to 35d, optional Bond 1 is absent and optional Bonds 2 and 3 are present and moieties $R^{8A}$ and $R^{8B}$ taken together, along with the carbon atoms to which they are bound, form an unsubstituted cycloalkyl ring (e.g., cyclopropyl, and in another example cyclohexyl).

In another embodiment of this invention, Ring (A) is selected from the group consisting of: 1a to 33a, the $R^{10}$—$R^9$— moiety is selected from the group consisting of: 1b to 50b, $R^b$ is selected from the group consisting of: H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$, $R^7$ is selected from the group consisting of: 1d to 35d, optional Bond 1 is absent, and optional Bonds 2 and 3 are present and moieties $R^{8A}$ and $R^{8B}$ taken together, along with the carbon atoms to which they are bound, form a substituted cycloalkyl ring (e.g., a substituted cyclopropyl, and in another example substituted cyclohexyl) substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$).

In another embodiment of this invention, optional Bond 1 is absent and optional Bonds 2 and 3 are present along with moieties R$^{8A}$ and R$^{8B}$, Ring (A) is selected from the group consisting of: 1a to 33a, the R$^{10}$—R$^9$— moiety is selected from the group consisting of: 1b to 50b, R$^6$ is selected from the group consisting of: H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, R$^7$ is selected from the group consisting of: 1d to 35d, and (a) U is N, G is O, W is a bond, X is —CH$_2$—, Y is —CH$_2$—, m is 1 and n is 1, or
(b) U is N, G is —CH$_2$—, W is O, X is —CH$_2$—. Y is —CH$_2$—, m is 1 and n is 1, or
(c) U is N, G is O, W is a bond, X is —CH$_2$—, Y is O, m is 1 and n is 1, or
(d) U is N, G is —CH$_2$—, W is NH, X is —CH$_2$—, Y is —CH$_2$—, m is 1 and n is 1, or
(e) U is N, G is —C(O)—, W is NH, X is —CH$_2$—, Y is —CH$_2$—, m is 1 and n is 1, or
(f) U is N, G is —CF$_2$—, W is a bond, X is —CH$_2$—, Y is O, m is 1 and n is 1, or
(g) U is N, G is —CF$_2$—, W is a bond, X is —S(O)$_2$—, Y is —CH$_2$—, m is 1 and n is 1, or
(h) U is N, G is —C(R$^3$)$_2$— (e.g., —CH$_2$—), W is —NR$^2$— (e.g., —NH— or —Nalkyl-), X is —CH$_2$—, Y is —CH$_2$—, m is 1 and n is 1, or
(i) U is N, G is —C(R$^3$)$_2$— (e.g., —CH$_2$—), W is —NR$^2$— (e.g., —NH— or —Nalkyl-), X is —CH$_2$—, Y is O, m is 1 and n is 1, or
(j) U is N, G is —C(R$^3$)$_2$— (e.g., —CH$_2$—), W is O, X is —CH$_2$—, Y is O, m is 1 and n is 1.

In another embodiment of this invention, Ring (A) is selected from the group consisting of: 1a to 33a, the R$^{10}$—R$^9$— moiety is selected from the group consisting of: 1b to 50b, R$^6$ is selected from the group consisting of: H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, R$^7$ is selected from the group consisting of: 1d to 35d, optional Bond 1 is absent, and optional Bonds 2 and 3 are present and moieties R$^{8A}$ and R$^{8B}$ taken together, along with the carbon atoms to which they are bound, form a ring selected from the group consisting of: cycloalkyl, cycloalkenyl, heterocycloalkyl, and heterocycloalkenyl, and (a) U is N, G is O, W is a bond, X is —CH$_2$—, Y is —CH$_2$—, m is 1 and n is 1, or
(b) U is N, G is —CH$_2$—, W is O, X is —CH$_2$—, Y is —CH$_2$—, m is 1 and n is 1, or
(c) U is N, G is O, W is a bond, X is —CH$_2$—, Y is O, m is 1 and n is 1, or
(d) U is N, G is —CH$_2$—, W is NH, X is —CH$_2$—, Y is —CH$_2$—, m is 1 and n is 1, or
(e) U is N, G is —C(O)—, W is NH, X is —CH$_2$—, Y is —CH$_2$—, m is 1 and n is 1, or
(f) U is N, G is —CF$_2$—, W is a bond, X is —CH$_2$—, Y is O, m is 1 and n is 1, or
(g) U is N, G is —CF$_2$—, W is a bond, X is —S(O)$_2$—, Y is —CH$_2$—, m is 1 and n is 1, or
(h) U is N, G is —C(R$^3$)$_2$— (e.g., —CH$_2$—), W is —NR$^2$— (e.g., —NH— or —Nalkyl-), X is —CH$_2$—, Y is —CH$_2$—, m is 1 and n is 1, or
(i) U is N, G is —C(R$^3$)$_2$— (e.g., —CH$_2$—), W is —NR$^2$— (e.g., —NH— or —Nalkyl-), X is —CH$_2$—, Y is O, m is 1 and n is 1, or
(j) U is N, G is —C(R$^3$)$_2$— (e.g., —CH$_2$—), W is O, X is —CH$_2$—, Y is O, m is 1 and n is 1, and wherein:
(i) said cycloalkyl ring is a 3 to 8 carbon membered ring (and in one example a said ring is cyclopropyl, and in another example said ring is cyclohexyl), and
(ii) said cycloalkenyl ring is a 5 to 8 carbon membered ring comprising one or two double bonds (and in one example one double bond, and in another example two double bonds), provided that R$^8$ is absent when there is a double bond to the carbon to which R$^{10}$ is bound, and provided that there is no double bond to the carbon common to Ring (B) and said cycloalkenyl ring, and
(iii) said heterocycloalkyl ring is a 4 to 8 membered ring comprising 1 to 3 ring members selected from the group consisting of: O, S, NR$^2$, C(O), S(O), and S(O)$_2$, and wherein the remaining ring members are carbon, and
(iv) said heterocycloalkenyl ring is a 5 to 8 membered ring comprising one or two double bonds (and in one example one double bond, and in another example two double bonds), and comprising 1 to 3 ring members selected from the group consisting of: O, S, NR$^2$, C(O), S(O), and S(O)$_2$, and wherein the remaining ring members are carbon, provided that R$^8$ is absent when there is a double bond to the carbon to which R$^{10}$ is bound, and provided that there is no double bond to the carbon common to Ring (B) and said heterocycloalkenyl ring, and
(v) said cycloalkyl, cycloalkenyl, heterocycloalkyl, or heterocycloalkenyl ring is optionally substituted with 1 to 3 substituents selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$).

In another embodiment of this invention, Ring (A) is selected from the group consisting of: 1a to 33a, the R$^{10}$—R$^9$— moiety is selected from the group consisting of: 1b to 50b, R$^6$ is selected from the group consisting of: H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, R$^7$ is selected from the group consisting of: 1d to 35d, optional Bond 1 is absent, and optional Bonds 2 and 3 are present and moieties R$^{8A}$ and R$^{8B}$ taken together, along with the carbon atoms to which they are bound, form a ring selected from the group consisting of: cycloalkyl, cycloalkenyl, heterocycloalkyl, and heterocycloalkenyl, and (a) U is N, G is O, W is a bond, X is —CH$_2$—, Y is —CH$_2$—, m is 1 and n is 1, or
(b) U is N, G is —CH$_2$—, W is O, X is —CH$_2$—, Y is —CH$_2$—, m is 1 and n is 1, or
(c) U is N, G is O, W is a bond, X is —CH$_2$—, Y is O, m is 1 and n is 1, or
(d) U is N, G is —CH$_2$—, W is NH, X is —CH$_2$—, Y is —CH$_2$—, m is 1 and n is 1, or (e) U is N, G is —C(O)—, W is NH, X is —CH$_2$—, Y is —CH$_2$—, m is 1 and n is 1, or
(f) U is N, G is —CF$_2$—, W is a bond, X is —CH$_2$—, Y is O, m is 1 and n is 1, or
(g) U is N, G is —CF$_2$—, W is a bond, X is —S(O)$_2$—, Y is —CH$_2$—, m is 1 and n is 1, or
(h) U is N, G is —C(R$^3$)$_2$— (e.g., —CH$_2$—), W is —NR$^2$— (e.g., —NH— or —Nalkyl-), X is —CH$_2$—, Y is —CH$_2$—, m is 1 and n is 1, or
(i) U is N, G is —C(R$^3$)$_2$— (e.g., —CH$_2$—), W is —NR$^2$— (e.g., —NH— or —Nalkyl-), X is —CH$_2$—, Y is O, m is 1 and n is 1, or
(j) U is N, G is —C(R$^3$)$_2$— (e.g., —CH$_2$—), W is O, X is —CH$_2$—, Y is O, m is 1 and n is 1, and wherein:
(i) said cycloalkyl ring is a 3 to 8 carbon membered ring (and in one example a said ring is cyclopropyl, and in another example said ring is cyclohexyl), and
(ii) said cycloalkenyl ring is a 5 to 8 carbon membered ring comprising one or two double bonds (and in one example one double bond, and in another example two double bonds), provided that R$^8$ is absent when there is a double bond to the carbon to which R$^{10}$ is bound, and provided that there is no double bond to the carbon common to Ring (B) and said cycloalkenyl ring, and
(iii) said heterocycloalkyl ring is a 4 to 8 membered ring comprising 1 to 3 ring members selected from the group consisting of: O, S, NR$^2$, C(O), S(O), and S(O)$_2$, and wherein the remaining ring members are carbon, and
(iv) said heterocycloalkenyl ring is a 5 to 8 membered ring comprising one or two double bonds (and in one example one double bond, and in another example two double bonds), and comprising 1 to 3 ring members selected from the group consisting of O, S, NR$^2$, C(O), S(O), and S(O)$_2$, and wherein the remaining ring members are carbon, provided that R$^8$ is absent when there is a double bond to the carbon to which R$^{10}$ is bound, and provided that there is no double bond to the carbon common to Ring (B) and said heterocycloalkenyl ring.

In another embodiment of this invention, Ring (A) is selected from the group consisting of: 1a to 33a, the R$^{10}$—R$^9$— moiety is selected from the group consisting of: 1b to 50b, R$^6$ is selected from the group consisting of: H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, R$^7$ is selected from the group consisting of: 1d to 35d, optional Bond 1 is absent and optional Bonds 2 and 3 are present and moieties R$^{8A}$ and R$^{8B}$ taken together, along with the carbon atoms to which they are bound, form an unsubstituted cycloalkyl ring (e.g., cyclopropyl, and in another example cyclohexyl), and
(a) U is N, G is O, W is a bond, X is —CH$_2$—, Y is —CH$_2$—, m is 1 and n is 1, or
(b) U is N, G is —CH$_2$—, W is O, X is —CH$_2$—, Y is —CH$_2$—, m is 1 and n is 1, or
(c) U is N, G is O, W is a bond, X is —CH$_2$—, Y is O, m is 1 and n is 1, or
(d) U is N, G is —CH$_2$—, W is NH, X is —CH$_2$—, Y is —CH$_2$—, m is 1 and n is 1, or
(e) U is N, G is —C(O)—, W is NH, X is —CH$_2$—, Y is —CH$_2$—, m is 1 and n is 1, or
(f) U is N, G is —CF$_2$—, W is a bond, X is —CH$_2$—, Y is O, m is 1 and n is 1, or
(g) U is N, G is —CF$_2$—, W is a bond, X is —S(O)$_2$—, Y is —CH$_2$—, m is 1 and n is 1, or
(h) U is N, G is —C(R$^3$)$_2$— (e.g., —CH$_2$—), W is —NR$^2$— (e.g., —NH— or —Nalkyl-), X is —CH$_2$—, Y is —CH$_2$—, m is 1 and n is 1, or
(i) U is N, G is —C(R$^3$)$_2$— (e.g., —CH$_2$—), W is —NR$^2$— (e.g., —NH— or —Nalkyl-), X is —CH$_2$—, Y is O, m is 1 and n is 1, or
(j) U is N, G is —C(R$^3$)$_2$— (e.g., —CH$_2$—) W is O, X is —CH$_2$—, Y is O, m is 1 and n is 1.

In another embodiment of this invention, Ring (A) is selected from the group consisting of: 1a to 33a, the R$^{10}$—R$^9$— moiety is selected from the group consisting of: 1b to 50b, R$^6$ is selected from the group consisting of: H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, R$^7$ is selected from the group consisting of: 1d to 35d, optional Bond 1 is absent, and optional Bonds 2 and 3 are present and moieties R$^{8A}$ and R$^{8B}$ taken together, along with the carbon atoms to which they are bound, form a substituted cycloalkyl ring (e.g., a substituted cyclopropyl, and in another example substituted cyclohexyl) substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$).

In another embodiment of this invention, optional Bond 1 is absent and optional Bonds 2 and 3 are present along with moieties R$^{8A}$ and R$^{8B}$, Ring (A) is selected from the group consisting of: 1a to 33a, the R$^{10}$—R$^9$— moiety is selected from the group consisting of: 1b to 50b, R$^6$ and R$^7$ taken together form a moiety selected from the group consisting of: 1e to 8e, and
(a) U is N, G is O, W is a bond, X is —CH$_2$—, Y is —CH$_2$—, m is 1 and n is 1, or
(b) U is N, G is —CH$_2$—, W is O, X is —CH$_2$—, Y is —CH$_2$—, m is 1 and n is 1, or
(c) U is N, G is O, W is a bond, X is —CH$_2$—, Y is O, m is 1 and n is 1, or
(d) U is N, G is —CH$_2$—, W is NH, X is —CH$_2$—, Y is —CH$_2$—, m is 1 and n is 1, or
(e) U is N, G is —C(O)—, W is NH, X is —CH$_2$—, Y is —CH$_2$—, m is 1 and n is 1, or
(f) U is N, G is —CF$_2$—, W is a bond, X is —CH$_2$—, Y is O, m is 1 and n is 1, or
(g) U is N, G is —CF$_2$—, W is a bond, X is —S(O)$_2$—, Y is —CH$_2$—, m is 1 and n is 1, or
(h) U is N, G is —C(R$^3$)$_2$— (e.g., —CH$_2$—), W is —NR$^2$— (e.g., —NH— or —Nalkyl-), X is —CH$_2$—, Y is —CH$_2$—, m is 1 and n is 1, or
(i) U is N, G is —C(R$^3$)$_2$— (e.g., —CH$_2$—), W is —NR$^2$— (e.g., —NH— or —Nalkyl-), X is —CH$_2$—, Y is O, m is 1 and n is 1, or
(j) U is N, G is —C(R$^3$)$_2$— (e.g., —CH$_2$—), W is O, X is —CH$_2$—, Y is O, m is 1 and n is 1.

In another embodiment of this invention, Ring (A) is selected from the group consisting of: 1a to 33a, the R$^{10}$—R$^9$— moiety is selected from the group consisting of: 1b to 50b, R$^6$ and R$^7$ taken together form a moiety selected from the group consisting of: 1e to 8e, optional Bond 1 is absent, and optional Bonds 2 and 3 are present and moieties R$^{8A}$ and R$^{8B}$ taken together, along with the carbon atoms to which they are bound, form a ring selected from the group consisting of: cycloalkyl, cycloalkenyl, heterocycloalkyl, and heterocycloalkenyl, and (a) U is N, G is O, W is a bond, X is —$CH_2$—, Y is —$CH_2$—, m is 1 and n is 1, or
(b) U is N, G is —$CH_2$—, W is O, X is —$CH_2$—, Y is —$CH_2$—, m is 1 and n is 1, or
(c) U is N, G is O, W is a bond, X is —$CH_2$—, Y is O, m is 1 and n is 1, or
(d) U is N, G is —$CH_2$—, W is NH, X is —$CH_2$—, Y is —$CH_2$—, m is 1 and n is 1, or
(e) U is N, G is —C(O)—, W is NH, X is —$CH_2$—, Y is —$CH_2$—, m is 1 and n is 1, or
(f) U is N, G is —$CF_2$—, W is a bond, X is —$CH_2$—, Y is O, m is 1 and n is 1, or
(g) U is N, G is —$CF_2$—, W is a bond, X is —$S(O)_2$—, Y is —$CH_2$—, m is 1 and n is 1, or
(h) U is N, G is —$C(R)_2$— (e.g., —$CH_2$—), W is —$NR^2$— (e.g., —NH— or —Nalkyl-), X is —$CH_2$—, Y is —$CH_2$—, m is 1 and n is 1, or
(i) U is N, G is —$C(R^3)_2$— (e.g., —$CH_2$—), W is —$NR^2$— (e.g., —NH— or —Nalkyl-), X is —$CH_2$—, Y is O, m is 1 and n is 1, or
(j) U is N, G is —$C(R^3)_2$— (e.g., —$CH_2$—), W is O, X is —$CH_2$—, Y is O, m is 1 and n is 1, and wherein:
(i) said cycloalkyl ring is a 3 to 8 carbon membered ring (and in one example a said ring is cyclopropyl, and in another example said ring is cyclohexyl), and
(ii) said cycloalkenyl ring is a 5 to 8 carbon membered ring comprising one or two double bonds (and in one example one double bond, and in another example two double bonds), provided that $R^8$ is absent when there is a double bond to the carbon to which $R^{10}$ is bound, and provided that there is no double bond to the carbon common to Ring (B) and said cycloalkenyl ring, and
(iii) said heterocycloalkyl ring is a 4 to 8 membered ring comprising 1 to 3 ring members selected from the group consisting of: O, S, $NR^2$, C(O), S(O), and $S(O)_2$, and wherein the remaining ring members are carbon, and
(iv) said heterocycloalkenyl ring is a 5 to 8 membered ring comprising one or two double bonds (and in one example one double bond, and in another example two double bonds), and comprising 1 to 3 ring members selected from the group consisting of: O, S, $NR^2$, C(O), S(O), and $S(O)_2$, and wherein the remaining ring members are carbon, provided that $R^8$ is absent when there is a double bond to the carbon to which $R^{10}$ is bound, and provided that there is no double bond to the carbon common to Ring (B) and said heterocycloalkenyl ring, and
(v) said cycloalkyl, cycloalkenyl, heterocycloalkyl, or heterocycloalkenyl ring is optionally substituted with 1 to 3 substituents selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —$OR^{15}$ (e.g., —$CH_3$), —$C(O)R^{15}$, —$C(O)OR^{15}$, —$C(O)N(R^{15})(R^{16})$, —$S(O)N(R^{15})(R^{16})$, $S(O)_2N(R^{15})(R^{16})$, —C(=$NOR^{15})R^{16}$, and —$P(O)(OR^{15})(OR^{16})$.

In another embodiment of this invention, Ring (A) is selected from the group consisting of: 1a to 33a, the $R^{18}$—$R^9$— moiety is selected from the group consisting of: 1b to 50b, $R^6$ and $R^7$ taken together form a moiety selected from the group consisting of: 1e to 8e, optional Bond 1 is absent, and optional Bonds 2 and 3 are present and moieties $R^{8A}$ and $R^{8B}$ taken together, along with the carbon atoms to which they are bound, form a ring selected from the group consisting of: cycloalkyl, cycloalkenyl, heterocycloalkyl, and heterocycloalkenyl, and (a) U is N, G is O, W is a bond, X is —$CH_2$—, Y is —$CH_2$—, m is 1 and n is 1, or
(b) U is N, G is —$CH_2$—, W is O, X is —$CH_2$—, Y is —$CH_2$—, m is 1 and n is 1, or
(c) U is N, G is O, W is a bond, X is —$CH_2$—, Y is O, m is 1 and n is 1, or
(d) U is N, G is —$CH_2$—, W is NH, X is —$CH_2$—, Y is m is 1 and n is 1, or
(e) U is N, G is —C(O)—, W is NH, X is —$CH_2$—, Y is —$CH_2$—, m is 1 and n is 1, or
(f) U is N, G is —$CF_2$—, W is a bond, X is —$CH_2$—, Y is O, m is 1 and n is 1, or
(g) U is N, G is —$CF_2$—, W is a bond, X is —$S(O)_2$—, Y is —$CH_2$—, m is 1 and n is 1, or
(h) U is N, G is —$C(R^3)_2$— (e.g., —$CH_2$—), W is —$NR^2$— (e.g., —NH— or —Nalkyl-), X is —$CH_2$—, Y is —$CH_2$—, m is 1 and n is 1, or
(i) U is N, G is —$C(R^3)_2$— (e.g., —$CH_2$—), W is —$NR^2$— (e.g., —NH— or —Nalkyl-), X is —$CH_2$—, Y is O, m is 1 and n is 1, or
(j) U is N, G is —$C(R^3)_2$— (e.g., —$CH_2$—), W is O, X is —$CH_2$—, Y is O, m is 1 and n is 1, and wherein:
(i) said cycloalkyl ring is a 3 to 8 carbon membered ring (and in one example a said ring is cyclopropyl, and in another example said ring is cyclohexyl), and
(ii) said cycloalkenyl ring is a 5 to 8 carbon membered ring comprising one or two double bonds (and in one example one double bond, and in another example two double bonds), provided that $R^8$ is absent when there is a double bond to the carbon to which $R^{10}$ is bound, and provided that there is no double bond to the carbon common to Ring (B) and said cycloalkenyl ring, and
(iii) said heterocycloalkyl ring is a 4 to 8 membered ring comprising 1 to 3 ring members selected from the group consisting of: O, S, $NR^2$, C(O), S(O), and $S(O)_2$, and wherein the remaining ring members are carbon, and
(iv) said heterocycloalkenyl ring is a 5 to 8 membered ring comprising one or two double bonds (and in one example one double bond, and in another example two double bonds), and comprising 1 to 3 ring members selected from the group consisting of: O, S, $NR^2$, C(O), S(O), and $S(O)_2$, and wherein the remaining ring members are carbon, provided that $R^8$ is absent when there is a double bond to the carbon to which $R^{10}$ is bound, and provided that there is no double bond to the carbon common to Ring (B) and said heterocycloalkenyl ring.

In another embodiment of this invention, Ring (A) is selected from the group consisting of: 1a to 33a, the $R^{10}$—$R^9$— moiety is selected from the group consisting of: 1b to 50b, $R^5$ and $R^7$ taken together form a moiety selected from the group consisting of: 1e to 8e, optional Bond 1 is absent and optional Bonds 2 and 3 are present and moieties $R^{8A}$ and $R^{8B}$ taken together, along with the carbon atoms to which they are bound, form an unsubstituted cycloalkyl ring (e.g., cyclopropyl, and in another example cyclohexyl), and (a) U is N, G is O, W is a bond, X is —$CH_2$—, Y is —$CH_2$—, m is 1 and n is 1, or
(b) U is N, G is —$CH_2$—, W is O, X is —$CH_2$—, Y is —$CH_2$—, m is 1 and n is 1, or
(c) U is N, G is O, W is a bond, X is —$CH_2$—, Y is O, m is 1 and n is 1, or
(d) U is N, G is —$CH_2$—, W is NH, X is —$CH_2$—, Y is —$CH_2$—, m is 1 and n is 1, or (e) U is N, G is —C(O)—, W is NH, X is —CH$_2$—, Y is —CH$_2$—, m is 1 and n is 1, or (f) U is N, G is —CF$_2$—, W is a bond, X is —CH$_2$—, Y is O, m is 1 and n is 1, or (g) U is N, G is —CF$_2$—, W is a bond, X is —S(O)$_2$—, Y is —CH$_2$—, m is 1 and n is 1, or (h) U is N, G is —C(R$^3$)$_2$— (e.g., —CH$_2$—), W is —NR$^2$— (e.g., —NH— or —Nalkyl-), X is —CH$_2$—, Y is —CH$_2$—, m is 1 and n is 1, or (i) U is N, G is —C(R$^3$)— (e.g., —CH$_2$—), W is —NR$^2$— (e.g., —NH— or —Nalkyl-), X is —CH$_2$—, Y is O, m is 1 and n is 1, or (j) U is N, G is —C(R$^3$)$_2$— (e.g., —CH$_2$—), W is O, X is —CH$_2$—, Y is O, m is 1 and n is 1.

In another embodiment of this invention, Ring (A) is selected from the group consisting of: 1a to 33a, the R$^{10}$—R$^9$— moiety is selected from the group consisting of: 1b to 50b, R$^6$ and R$^7$ taken together form a moiety selected from the group consisting of: 1e to 8e, optional Bond 1 is absent, and optional Bonds 2 and 3 are present and moieties R$^{8A}$ and R$^{8B}$ taken together, along with the carbon atoms to which they are bound, form a substituted cycloalkyl ring (e.g., a substituted cyclopropyl, and in another example substituted cyclohexyl) substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$), and (a) U is N, G is O, W is a bond, X is —CH$_2$—, Y is —CH$_2$—, m is 1 and n is 1, or (b) U is N, G is —CH$_2$—, W is O, X is —CH$_2$—, Y is —CH$_2$—, m is 1 and n is 1, or (c) U is N, G is O, W is a bond, X is —CH$_2$—, Y is O, m is 1 and n is 1, or (d) U is N, G is —CH$_2$—, W is NH, X is —CH$_2$—, Y is —CH$_2$—, m is 1 and n is 1, or (e) U is N, G is —C(O)—, W is NH, X is —CH$_2$—, Y is —CH$_2$—, m is 1 and n is 1, or (f) U is N, G is —CF$_2$—, W is a bond, X is —CH$_2$—, Y is O, m is 1 and n is 1, or (g) U is N, G is —CF$_2$—, W is a bond, X is —S(O)$_2$—, Y is —CH$_2$—, m is 1 and n is 1, or (h) U is N, G is —C(R$^3$)$_2$— (e.g., —CH$_2$—), W is —NR$^2$— (e.g., —NH— or —Nalkyl-), X is —CH$_2$—, Y is —CH$_2$—, m is 1 and n is 1, or (i) U is N, G is —C(R$^3$)$_2$— (e.g., —CH$_2$—), W is —NR$^2$— (e.g., —NH— or —Nalkyl-), X is —CH$_2$—, Y is O, m is 1 and n is 1, or (j) U is N, G is —C(R$^3$)$_2$— (e.g., —CH$_2$—), W is O, X is —CH$_2$—, Y is O, m is 1 and n is 1.

In another embodiment of this invention: Ring (A) is cycloalkyl (e.g., cyclopropyl); U is N; G is —O—; W is a bond; optional Bond 1 is present; R$^8$ is H; R$^6$ is H; R$^7$ is selected from the group consisting of: (1) phenyl and (2) phenyl substituted with 1 to 3 independently selected R$^{21}$ groups, and wherein said R$^{21}$ groups are the same or different halo: R$^{10}$ is selected from the group consisting of: (1) phenyl and (2) phenyl substituted with 1 to 3 independently selected R$^{21}$ groups; and R$^9$ is selected from the group consisting of: (1) imidazolyl (e.g., imidazol-1-yl), and (2) imidazolyl (e.g., imidazol-1-yl) substituted with 1 to 3 independently selected R$^{21}$ groups.

In another embodiment of this invention: Ring (A) is cycloalkyl (e.g., cyclopropyl); U is N; G is —O—; W is a bond; optional Bond 1 is present; R$^8$ is H; R$^6$ is H; R$^7$ is selected from the group consisting of: (1) phenyl, (2) phenyl substituted with 1 to 2 independently selected R$^{21}$ groups and wherein said R$^{21}$ groups are the same or different halo (e.g., each R$^{21}$ is F), and (3) phenyl substituted with 1 R$^{21}$ group, and said R$^{21}$ group is halo (e.g., F); R$^{10}$ is selected from the group consisting of: (1) phenyl and (2) phenyl substituted with 1 R$^{21}$ group (e.g., R$^{21}$ is —OR$^{15}$, and in another example R$^{21}$ is —OR$^{15}$ wherein R$^{15}$ is alkyl (such as methyl), and in another example R$^{21}$ is halo (such as F)); and R$^9$ is selected from the group consisting of: (1) imidazolyl (e.g., imidazol-1-yl), (2) imidazolyl (e.g., imidazol-1-yl) substituted with 1 R$^{21}$ group, and (3) imidazolyl (e.g., imidazol-1-yl) substituted with 1 R$^{21}$ group wherein said R$^{21}$ group is alkyl (e.g., methyl).

In another embodiment of this invention: Ring (A) is cycloalkyl (e.g., cyclopropyl); U is N; G is —O—; W is a bond; optional Bond 1 is present; m is 1; n is 1 R$^8$ is H; R$^6$ is H; R$^7$ is selected from the group consisting of: (1) phenyl; and (2) phenyl substituted with 1 to 3 independently selected R$^{21}$ groups, and wherein said R$^{21}$ groups are the same or different halo; R$^{10}$ is selected from the group consisting of: (1) phenyl; and (2) phenyl substituted with 1 to 3 independently selected R$^{21}$ groups; and R$^9$ is selected from the group consisting of: (1) imidazolyl (e.g., imidazol-1-yl), and (2) imidazolyl (e.g., imidazol-1-yl) substituted with 1 to 3 independently selected R$^{21}$ groups.

In another embodiment of this invention: Ring (A) is cycloalkyl (e.g., cyclopropyl); U is N; G is —O—; W is a bond; optional Bond 1 is present; m is 1; n is 1 R$^8$ is H; R$^6$ is H; R$^7$ is selected from the group consisting of: (1) phenyl, (2) phenyl substituted with 1 to 2 independently selected R$^{21}$ groups and wherein said R$^2$/groups are the same or different halo (e.g., each R$^{21}$ is F), and (3) phenyl substituted with 1 R$^{21}$ group, and said R$^{21}$ group is halo (e.g., F); R$^{10}$ is selected from the group consisting of: (1) phenyl and (2) phenyl substituted with 1 R$^{21}$ group (e.g., R$^{21}$ is —OR$^{15}$, and in another example R$^{21}$ is —OR$^{15}$ wherein R$^{15}$ is alkyl (such as methyl), and in another example R$^{21}$ is halo (such as F)); and R$^9$ is selected from the group consisting of: (1) imidazolyl (e.g., imidazol-1-yl), (2) imidazolyl (e.g., imidazol-1-yl) substituted with 1 R$^{21}$ group, and (3) imidazolyl (e.g., imidazol-1-yl) substituted with 1 R$^{21}$ group wherein said R$^{21}$ group is alkyl (e.g., methyl).

In another embodiment of this invention: Ring (A) is cycloalkyl (e.g., cyclopropyl); U is N; G is —O—; W is a bond; optional Bond 1 is present; X is —C(R$^3$)$_2$— (wherein each R$^3$ is independently selected), and, for example, X is —CH$_2$—; Y is —C(R$^3$)$_2$— (wherein each R$^3$ is independently selected), and, for example, Y is —CH$_2$—; R$^8$ is H; R$^6$ is H; R$^7$ is selected from the group consisting of: (1) phenyl and (2) phenyl substituted with 1 to 3 independently selected R$^{21}$ groups, and wherein said R$^{21}$ groups are the same or different halo; R$^{10}$ is selected from the group consisting of: (1) phenyl and (2) phenyl substituted with 1 to 3 independently selected R$^{21}$ groups; and R$^9$ is selected from the group consisting of: (1) imidazolyl (e.g., imidazol-1-yl), and (2) imidazolyl (e.g., imidazol-1-yl) substituted with 1 to 3 independently selected R$^{21}$ groups.

In another embodiment of this invention: Ring (A) is cycloalkyl (e.g., cyclopropyl); U is N; G is —O—; W is a bond; optional Bond 1 is present; X is —C(R$^3$)$_2$— (wherein each R$^3$ is independently selected), and, for example, X is —CH$_2$—; Y is —C(R$^3$)$_2$— (wherein each R$^3$ is independently selected), and, for example, Y is —CH$_2$—R$^8$ is H; R$^6$ is H; R$^7$ is selected from the group consisting of: (1) phenyl, (2) phenyl substituted with 1 to 2 independently selected $R^2$/ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —O—; W is a bond; optional Bond 1 is present; X is —$C(R^3)_2$— (wherein each $R^3$ is independently selected), and, for example, X is —$CH_2$—; Y is —$C(R^3)_2$— (wherein each $R^3$ is independently selected), and, for example, Y is is 1; n is 1; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{15}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —O—; W is a bond; optional Bond 1 is present; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; m is 1; n is 1; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F); and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group; and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —O—; W is a bond; optional Bond 1 is present; $R^6$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —O—; W is a bond; optional Bond 1 is present; $R^8$ is alkyl (e.g., methyl); $R^6$ is H; $R^7$ is selected from the group consisting of: (1) phenyl; (2) phenyl substituted with 1 to 2 independently selected $R^{21}$ groups, and wherein said $R^{21}$ groups are the same or different halo (e.g., each $R^{21}$ is F); and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —O—; W is a bond; optional Bond 1 is present; m is 1; n is 1; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —O—; W is a bond; optional Bond 1 is present; m is 1; n is 1; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —O—; W is a bond; optional Bond 1 is present; X is —$C(R^3)_2$— (wherein each $R^3$ is independently selected), and, for example, X is —$CH_2$—; Y is —$C(R^3)$— (wherein each $R^3$ is independently selected), and, for example, Y is —$CH_2$—; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —O—; W is a bond; optional Bond 1 is present; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —O—; W is a bond; optional Bond 1 is present; X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; is 1; n is 1; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —O—; W is a bond; optional Bond 1 is present; X is —C($R^3$)$_2$— (wherein each $R^3$ is independently selected), and, for example, X is Y is —C($R^3$)$_2$— (wherein each $R^3$ is independently selected), and, for example, Y is —CH$_2$—; m is 1; n is 1; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —O—; W is a bond; optional Bond 1 is absent; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —O—; W is a bond; optional Bond 1 is absent; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —O—; W is a bond; optional Bond 1 is absent; m is 1; n is 1; $R^8$ is H; $R^6$ is H; $R^7$ is selected from the group consisting of: (1) phenyl; and (2) phenyl substituted with 1 to 3 independently selected $R^{21}$ groups, and wherein said $R^{21}$ groups are the same or different halo; $R^{10}$ is selected from the group consisting of: (1) phenyl; and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —O—; W is a bond; optional Bond 1 is absent; m is 1; n is 1; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —O—; W is a bond; optional Bond 1 is absent; X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl imidazol-1-yl) substituted with 1 to 3 independently selected $R^{21}$ groups.

In another embodiment of this invention: Ring (A) is cycloalkyl (e.g., cyclopropyl); U is N; G is —O—; W is a bond; optional Bond 1 is absent; X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —O—; W is a bond; optional Bond 1 is absent; X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; m is 1; n is 1; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —O—; W is a bond; optional Bond 1 is absent; X is —C($R^3$)$_2$— (wherein each $R^3$ is independently selected), and, for example, X is —CH$_2$—Y is —C($R^3$)$_2$— (wherein each $R^3$ is independently selected), and, for example, Y is —CH$_2$—; is 1; n is 1; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F); and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g. $R^{21}$ is —O$R^{15}$, and in another example $R^{21}$ is —O$R^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group; and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N, G is —O—; W is a bond; optional Bond 1 is absent; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —O—; W is a bond; optional Bond 1 is absent; $R^8$ is alkyl (e.g., methyl); $R^6$ is H; is selected from the group consisting of: (1) phenyl; (2) phenyl substituted with 1 to 2 independently selected $R^{21}$ groups, and wherein said $R^{21}$ groups are the same or different halo (e.g., each $R^{21}$ is F); and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —O$R^{15}$, and in another example $R^{21}$ is —O$R^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —O—; W is a bond; optional Bond 1 is absent; m is 1; n is 1; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —O—; W is a bond; optional Bond 1 is absent; m is 1; n is 1; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —O$R^{15}$, and in another example $R^{21}$ is —O$R^{18}$ wherein $R^{18}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —O—; W is a bond; optional Bond 1 is absent; X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —O—; W is a bond; optional Bond 1 is absent; X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —O$R^{15}$, and in another example $R^{21}$ is —O$R^{15}$ wherein $R^{/8}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —O—, W is a bond; optional Bond 1 is absent; X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; m is 1; n is 1; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —O—; W is a bond; optional Bond 1 is absent; X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; m is 1; n is 1; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{16}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —O—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); $R^a$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl imidazol-1-yl), and (2) imidazolyl (e.g., imidazol-1-yl) substituted with 1 to 3 independently selected $R^{21}$ groups.

In another embodiment of this invention: Ring (A) is cycloalkyl cyclopropyl); U is N; G is —O—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —O—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); m is 1; n is 1; $R^8$ is H; $R^6$ is H; $R^7$ is selected from the group consisting of: (1) phenyl; and (2) phenyl substituted with 1 to 3 independently selected $R^{21}$ groups, and wherein said $R^{21}$ groups are the same or different halo; $R^{18}$ is selected from the group consisting of: (1) phenyl; and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —O—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); m is 1; n is 1; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —O—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —O—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{16}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention; Ring (A) is cycloalkyl (e.g., cyclopropyl); U is N; G is —O—: W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; m is 1; n is 1; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —O—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is Y is —C($R^3$)$_2$— (wherein each $R^3$ is independently selected), and, for example, Y is —CH$_2$—; m is 1; n is 1; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F); and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl imidazol-1-yl) substituted with 1 $R^{21}$ group; and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —O—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —O—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); $R^8$ is alkyl (e.g., methyl); $R^6$ is H; $R^7$ is selected from the group consisting of: (1) phenyl; (2) phenyl substituted with 1 to 2 independently selected $R^{21}$ groups, and wherein said $R^{21}$ groups are the same or different halo (e.g., each $R^{21}$ is F); and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —O—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); m is 1; n is 1; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —O—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); m is 1; n is 1; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —O—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1)

imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —O—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; $R^8$ is alkyl (e.g., methyl); $R^6$ is H; $R^7$ is selected from the group consisting of: (1) phenyl, (2) phenyl substituted with 1 to 2 independently selected $R^{21}$ groups, and wherein said $R^{21}$ groups are the same or different halo (e.g. each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —O—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; m is 1; n is 1; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —O—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is Y is —C($R^3$)$_2$— (wherein each $R^3$ is independently selected), and, for example, Y is —CH$_2$—; m is 1; n is 1; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is present; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl); and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C(O)—; W is a bond; optional Bond 1 is present; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^6$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is present; m is 1; n is 1; $R^8$ is H; $R^6$ is H; $R^7$ is selected from the group consisting of: (1) phenyl; and (2) phenyl substituted with 1 to 3 independently selected $R^{21}$ groups, and wherein said $R^{21}$ groups are the same or different halo; $R^{10}$ is selected from the group consisting of: (1) phenyl; and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C(O)—; W is a bond; optional Bond 1 is present; m is 1; 1; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is present; X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C(O)—; W is a bond; optional Bond 1 is present; X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^5$ is selected from the group consisting of: (1) imidazolyl imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is present; X is —C($R^3$)$_2$— (wherein each $R^3$ is independently selected), and, for example, X is —CH$_2$—; is —C($R^3$)$_2$— (wherein each $R^3$ is independently selected), and, for example, Y is —CH$_2$—; m is 1; n is 1; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C(O)—; W is a bond; optional Bond 1 is present; X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; m is 1; n is 1; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F); and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group; and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is present; $R^8$ is alkyl (e.g., methyl); $R^6$ is H; $R^7$ is selected from the group consisting of: (1) phenyl; (2) phenyl substituted with 1 to 2 independently selected $R^{21}$ groups, and wherein said $R^{21}$ groups are the same or different halo (e.g., each $R^{21}$ is F); and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is present; m is 1; n is 1; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C(O)—; W is a bond; optional Bond 1 is present; m is 1; n is 1; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is present; X is —C($R^3$)$_2$— (wherein each $R^3$ is independently selected), and, for example, X is —CH$_2$—; Y is —C($R^3$)— (wherein each $R^3$ is independently selected), and, for example, Y is —CH$_2$—; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C(O)—; W is a bond; optional Bond 1 is present; X is —C(R$^3$)$_2$— (wherein each R$^3$ is independently selected), and, for example, X is —CH$_2$—; Y is —C(R$^3$)$_2$— (wherein each R$^3$ is independently selected), and, for example, Y is —CH$_2$—; R$^8$ is alkyl (e.g., methyl); R$^6$ is H; R$^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein R$^{15}$ is alkyl (such as methyl), and in another example $R^{21}$ is halo (such as F)); and R$^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is present; X is —C(R$^3$)$_2$— (wherein each R$^3$ is independently selected), and, for example, X is —CH$_2$—; Y is —C(R$^3$)$_2$— (wherein each R$^3$ is independently selected), and, for example, Y is —OH$_2$—; m is 1; n is 1; R$^8$ is alkyl (e.g., methyl); R$^6$ is H; R$^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and R$^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C(O)—; W is a bond; optional Bond 1 is present; X is —C(R$^3$)$_2$— (wherein each R$^3$ is independently selected), and, for example, X is —CH$_2$—; Y is —C(R$^3$)$_2$— (wherein each R$^3$ is independently selected), and, for example, Y is —CH$_2$—; m is 1; n is 1; R$^8$ is alkyl (e.g., methyl); R$^6$ is H; R$^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein R$^{15}$ is alkyl (such as methyl), and in another example $R^{21}$ is halo (such as F)); and R$^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is absent; R$^8$ is H; R$^8$ is H; R$^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and R$^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl cycloalkyl (e.g., cyclopropyl); U is N; G is —C(O)—; W is a bond; optional Bond 1 is absent; R$^a$ is H; R$^6$ is H; R$^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{16}$ wherein R$^{15}$ is alkyl (such as methyl), and in another example $R^{21}$ is halo (such as F)); and R$^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is absent; m is 1; n is 1; R$^8$ is H; R$^6$ is H; R$^7$ is selected from the group consisting of: (1) phenyl; and (2) phenyl substituted with 1 to 3 independently selected $R^{21}$ groups, and wherein said $R^{21}$ groups are the same or different halo; $R^{10}$ is selected from the group consisting of: (1) phenyl; and (2) phenyl substituted with 1 to 3 independently selected $R^{21}$ groups; and R$^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C(O)—; W is a bond; optional Bond 1 is absent; m is 1; n is 1; R$^6$ is H; R$^6$ is H; R$^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein R$^{15}$ is alkyl (such as methyl), and in another example $R^{21}$ is halo (such as F)); and R$^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is absent; X is —C(R$^3$)$_2$— (wherein each R$^3$ is independently selected), and, for example, X is —CH—; Y is —C(R$^3$)$_2$— (wherein each R$^3$ is independently selected), and, for example, Y is —CH$_2$—; R$^8$ is H; R$^6$ is H; R$^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and R$^9$ is selected from the group consisting of (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C(O)—; W is a bond; optional Bond 1 is absent; X is —C(R$^3$)$_2$— (wherein each $R^3$ is independently selected), and, for example, X is —$CH_2$—; Y is —$C(R^3)_2$— (wherein each $R^3$ is independently selected), and, for example, Y is —$CH_2$—; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is absent; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; m is 1; n is 1 $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C(O)—; W is a bond; optional Bond 1 is absent; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; m is 1; n is 1 $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F); and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group; and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is absent; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C(O)—; W is a bond; optional Bond 1 is absent; $R^8$ is alkyl (e.g., methyl); $R^6$ is H; $R^7$ is selected from the group consisting of: (1) phenyl, (2) phenyl substituted with 1 to 2 independently selected $R^{21}$ groups, and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl cyclopropyl); U is N; G is —C(O)—; W is a bond; optional Bond 1 is absent; m is 1; n is 1; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C(O)—; W is a bond; optional Bond 1 is absent; m is 1; n is 1; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is absent; X is —$C(R^3)_2$— (wherein each $R^3$ is independently selected), and, for example, X is —$CH_2$—; is —$C(R^3)_2$— (wherein each $R^3$ is independently selected), and, for example, Y is —$CH_2$—; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C(O)—; W is a bond; optional Bond 1 is absent; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is absent; X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; m is 1; n is 1; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C(O)—; W is a bond; optional Bond 1 is absent; X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; m is 1; n is 1; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C(O)—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl cyclopropyl); U is N; G is —C(O): W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); m is 1; n is 1; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C(O)—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{\prime 8}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; m is 1; n is 1; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C(O)—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; m is 1; n is 1; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F); and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^2$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group; and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C(O)—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); $R^8$ is alkyl (e.g., methyl); $R^6$ is H; $R^7$ is selected from the group consisting of: (1) phenyl; (2) phenyl substituted with 1 to 2 independently selected $R^{21}$ groups, and wherein said $R^{21}$ groups are the same or different halo (e.g., each $R^{21}$ is F); and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); m is 1; n is 1; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C(O)—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); m is 1; n is 1; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{18}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C(O)—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; $R^8$ is alkyl (e.g., methyl); $R^6$ is H; $R^7$ is selected from the group consisting of: (1) phenyl, (2) phenyl substituted with 1 to 2 independently selected $R^{21}$ groups, and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —O$R^{15}$, and in another example $R^{21}$ is —O$R^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C(O)—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; m is 1; n is 1; $R^5$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C(O)—; W is a bond; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; m is 1; n is 1; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —O$R^{15}$, and in another example $R^{21}$ is —O$R^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C($R^3$)$_2$— (wherein each $R^5$ is independently selected); W is —O—; optional Bond 1 is present; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is present; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —O$R^{15}$, and in another example $R^{21}$ is —O$R^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is present; m is 1; n is 1; $R^8$ is H; $R^6$ is H; $R^7$ is selected from the group consisting of: (1) phenyl; and (2) phenyl substituted with 1 to 3 independently selected $R^{21}$ groups, and wherein said $R^{21}$ groups are the same or different halo; $R^{10}$ is selected from the group consisting of: (1) phenyl; and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is present; m is 1; n is 1; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{16}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —$C(R^3)_2$— (wherein each $R^3$ is independently selected); W is —O—; optional Bond 1 is present; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$C(R^3)_2$— (wherein each $R^3$ is independently selected); W is —O—; optional Bond 1 is present; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; $R^8$ is H; $R^6$ is H; $R^7$ is selected from the group consisting of: (1) phenyl and (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —$C(R^3)_2$— (wherein each $R^3$ is independently selected); W is —O—; optional Bond 1 is present; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; m is 1; n is 1; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$C(R^3)_2$— (wherein each $R^3$ is independently selected); W is —O—; optional Bond 1 is present; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; m is 1; n is 1; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F); and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —$C(R^3)_2$— (wherein each $R^3$ is independently selected); W is —O—; optional Bond 1 is present; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$C(R^3)_2$— (wherein each $R^3$ is independently selected); W is —O—; optional Bond 1 is present; $R^6$ is alkyl (e.g., methyl); $R^6$ is H; $R^7$ is selected from the group consisting of: (1) phenyl; (2) phenyl substituted with 1 to 2 independently selected $R^{21}$ groups, and wherein said $R^{21}$ groups are the same or different halo (e.g., each $R^{21}$ is F); and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —$C(R^3)_2$— (wherein each $R^3$ is independently selected); W is —O—; optional Bond 1 is present; m is 1; n is 1; $R^6$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$C(R^3)_2$—

(wherein each $R^3$ is independently selected); W is —O—; optional Bond 1 is present; is 1; n is 1; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{16}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is present; X is —C($R^3$)$_2$— (wherein each $R^3$ is independently selected), and, for example, X is —CH$_2$—; Y is —C($R^3$)— (wherein each $R^3$ is independently selected), and, for example, Y is —CH$_2$—; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is present; X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH—; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is present; X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; m is 1; n is 1; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is present; X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; m is 1; n is 1; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is absent; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is absent; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{16}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is absent; m is 1; n is 1; $R^8$ is H; $R^6$ is H; $R^7$ is selected from the group consisting of: (1) phenyl; and (2) phenyl substituted with 1 to 3 independently selected $R^{21}$ groups, and wherein said $R^{21}$ groups are the same or different halo; $R^{10}$ is selected from the group consisting of: (1) phenyl; and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is absent; m is 1; n is 1; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —O$R^{15}$, and in another example $R^{21}$ is —O$R^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is absent; X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is absent; X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —O$R^{15}$, and in another example $R^{21}$ is —O$R^{15}$ wherein $R^{15}$ is alkyl (such as methyl), and in another example $R^{21}$ is halo (such as F)); and $R^3$ is selected from the group consisting of: (1) imidazolyl (e.g., imidazol-1-yl), (2) imidazolyl imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is absent; X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; m is 1; n is 1; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is absent; X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; m is 1; n is 1; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F); and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —O$R^{15}$, and in another example $R^{21}$ is —O$R^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C($R^3$)$_9$— (wherein each $R^3$ is independently selected); W is —O—; optional Bond 1 is absent; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{2'}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is absent; $R^8$ is alkyl (e.g., methyl); $R^6$ is H; $R^7$ is selected from the group consisting of: (1) phenyl; (2) phenyl substituted with 1 to 2 independently selected $R^{21}$ groups, and wherein said $R^{21}$ groups are the same or different halo (e.g., each $R^{21}$ is F); and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —O$R^{15}$, and in another example $R^{21}$ is —O$R^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is absent; m is 1; n is 1; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$C(R)_2$— (wherein $R^3$ is independently selected); W is —O—; optional Bond 1 is absent; m is 1; n is 1; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^2$ is —$OR^{15}$; and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —$C(R^3)_2$— (wherein each $R^3$ is independently selected); W is —O—; optional Bond 1 is absent; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$C(R^3)_2$— (wherein each $R^3$ is independently selected); W is —O—; optional Bond 1 is absent; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{16}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —$C(R^3)_2$— (wherein each $R^3$ is independently selected); W is —O—; optional Bond 1 is absent; X is —$C(R^3)_2$— (wherein each $R^8$ is independently selected), and, for example, X is —$CH_2$—; Y is —$C(R^3)_2$— (wherein each $R^3$ is independently selected), and, for example, Y is —$CH_2$—; m is 1; n is 1; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$C(R^3)_2$— (wherein each $R^3$ is independently selected); W is —O—; optional Bond 1 is absent; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; m is 1; n is 1; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —$C(R^3)_2$— (wherein each $R^3$ is independently selected); W is —O—; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$C(R^3)_2$— (wherein each $R^3$ is independently selected); W is —O—; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —$C(R^3)_2$— (wherein each $R^3$ is independently selected); W is —O—;

optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); m is 1; n is 1; $R^8$ is H; $R^6$ is H; $R^7$ is selected from the group consisting of: (1) phenyl; and (2) phenyl substituted with 1 to 3 independently selected $R^{21}$ groups, and wherein said $R^{21}$ groups are the same or different halo; $R^{18}$ is selected from the group consisting of: (1) phenyl; and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); m is 1; n is 1; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl cyclopropyl); U is N; G is —C($R^3$)$_2$— (wherein each $R^3$ is independently selected); W is —O—; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—, m is 1; n is 1; $R^8$ is H; $R^6$ is 1-1; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F); and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —OR$^{15}$, and in another example $R^{21}$ is —OR$^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group; and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is absent, and optional Bonds 2 and 3 are present and moieties $R^{6A}$ and $R^{8B}$ taken together, along with the carbon atoms to which they are bound, form an unsubstituted cycloalkyl ring (e.g., cyclopropyl); $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); $R^8$ is alkyl (e.g., methyl); $R^6$ is H; $R^7$ is selected from the group consisting of: (1) phenyl; (2) phenyl substituted with 1 to 2 independently selected $R^{21}$ groups, and wherein said $R^{21}$ groups are the same or different halo (e.g., each $R^{21}$ is F); and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —O$R^{15}$, and in another example $R^{21}$ is —O$R^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); m is 1; n is 1; $R^8$ is alkyl methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); m is 1; n is 1; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —O$R^{15}$, and in another example $R^{21}$ is —O$R^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; $R^8$ is alkyl (e.g., methyl); $R^6$ is H; $R^7$ is selected from the group consisting of: (1) phenyl, (2) phenyl substituted with 1 to 2 independently selected $R^{21}$ groups, and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —O$R^{15}$, and in another example $R^{21}$ is —O$R^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —C($R^3$)$_2$— (wherein each $R^3$ is independently selected); W is —O—; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; m is 1; n is 1; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl cyclopropyl); U is N; G is —C($R^3$)$_2$— (wherein each $R^3$ is independently selected); W is —O—; optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —C($R^3$)$_2$— (wherein each $R^3$ is independently selected), and, for example, X is —CH$_2$—; Y is —C($R^3$)$_2$— (wherein each $R^3$ is independently selected), and, for example, Y is —CH$_2$—; m is 1; n is 1; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is present; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is present; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is present; m is 1; n is 1; $R^8$ is H; $R^6$ is H; $R^7$ is selected from the group consisting of: (1) phenyl; and (2) phenyl substituted with 1 to 3 independently selected $R^{21}$ groups, and wherein said $R^{21}$ groups are the same or different halo; $R^{10}$ is selected from the group consisting of: (1) phenyl; and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is present; m is 1; n is 1; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is present; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is present; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is present; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; m is 1; n is 1; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is present; X is —$C(R^3)_2$— (wherein each $R^3$ is independently selected), and, for example, X is —$CH_2$—; Y is —$C(R^3)_2$— (wherein each $R^3$ is independently selected), and, for example, Y is —CH$_2$e m is 1; n is 1; R$^8$ is H; R$^6$ is H; R$^7$ is selected from the group consisting of: (1) phenyl, (2) phenyl substituted with 1 to 2 independently selected R$^{21}$ groups and wherein said R$^{21}$ groups are the same or different halo (e.g., each R$^{21}$ is F); and (3) phenyl substituted with 1 R$^{21}$ group, and said R$^{21}$ group is halo (e.g., F); R$^{10}$ is selected from the group consisting of: (1) phenyl and (2) phenyl substituted with 1 R$^{21}$ group (e.g., R$^{21}$ is —OR$^{15}$, and in another example R$^{21}$ is —OR$^{15}$ wherein R$^{15}$ is alkyl (such as methyl), and in another example R$^{21}$ is halo (such as F)); and R$^9$ is selected from the group consisting of: (1) imidazolyl (e.g., imidazol-1-yl), (2) imidazolyl (e.g., imidazol-1-yl) substituted with 1 R$^{21}$ group; and (3) imidazolyl (e.g., imidazol-1-yl) substituted with 1 R$^{21}$ group wherein said R$^{21}$ group is alkyl (e.g., methyl).

In another embodiment of this invention: Ring (A) is cycloalkyl (e.g., cyclopropyl); U is N; G is —CF$_2$—; W is —C(R$^3$)$_2$— (wherein each R$^3$ is independently selected); optional Bond 1 is present; R$^8$ is alkyl (e.g., methyl); R$^6$ is H; R$^7$ is selected from the group consisting of: (1) phenyl and (2) phenyl substituted with 1 to 3 independently selected R$^{21}$ groups, and wherein said R$^{21}$ groups are the same or different halo; R$^{10}$ is selected from the group consisting of: (1) phenyl and (2) phenyl substituted with 1 to 3 independently selected R$^{21}$ groups; and R$^9$ is selected from the group consisting of: (1) imidazolyl (e.g., imidazol-1-yl), and (2) imidazolyl (e.g., imidazol-1-yl) substituted with 1 to 3 independently selected R$^{21}$ groups.

In another embodiment of this invention: Ring (A) is cycloalkyl (e.g., cyclopropyl); U is N; G is —CF$_2$—; W is —C(R$^3$)$_2$— (wherein each R$^3$ is independently selected); optional Bond 1 is present; R$^8$ is alkyl (e.g., methyl); R$^6$ is H; R$^7$ is selected from the group consisting of: (1) phenyl; (2) phenyl substituted with 1 to 2 independently selected R$^{21}$ groups, and wherein said R$^{21}$ groups are the same or different halo (e.g., each R$^{21}$ is F); and (3) phenyl substituted with 1 R$^{21}$ group, and said R$^{21}$ group is halo (e.g., F); R$^{10}$ is selected from the group consisting of: (1) phenyl and (2) phenyl substituted with 1 R$^{21}$ group (e.g., R$^{21}$ is —OR$^{16}$, and in another example R$^{21}$ is —OR$^{15}$ wherein R$^{15}$ is alkyl (such as methyl), and in another example R$^{21}$ is halo (such as F)); and R$^9$ is selected from the group consisting of: (1) imidazolyl (e.g., imidazol-1-yl), (2) imidazolyl (e.g., imidazol-1-yl) substituted with 1 R$^{21}$ group, and (3) imidazolyl (e.g., imidazol-1-yl) substituted with 1 R$^{21}$ group wherein said R$^{21}$ group is alkyl (e.g., methyl).

In another embodiment of this invention: Ring (A) is cycloalkyl (e.g., cyclopropyl); U is N; G is —CF$_2$—; W is —C(R$^3$)$_2$— (wherein each R$^3$ is independently selected); optional Bond 1 is present; m is 1; n is 1; R$^8$ is alkyl (e.g., methyl); R$^6$ is H; R$^7$ is selected from the group consisting of: (1) phenyl and (2) phenyl substituted with 1 to 3 independently selected R$^{21}$ groups, and wherein said R$^{21}$ groups are the same or different halo; R$^{10}$ is selected from the group consisting of: (1) phenyl and (2) phenyl substituted with 1 to 3 independently selected R$^{21}$ groups; and R$^9$ is selected from the group consisting of: (1) imidazolyl (e.g., imidazol-1-yl), and (2) imidazolyl (e.g., imidazol-1-yl) substituted with 1 to 3 independently selected R$^{21}$ groups.

In another embodiment of this invention: Ring (A) is cycloalkyl (e.g., cyclopropyl); U is N; G is —CF$_2$—; W is —C(R$^3$)$_2$— (wherein each R$^3$ is independently selected); optional Bond 1 is present; m is 1; n is 1; R$^8$ is alkyl (e.g., methyl); R$^6$ is H; R$^7$ is selected from the group consisting of: (1) phenyl, (2) phenyl substituted with 1 to 2 independently selected R$^{21}$ groups and wherein said R$^{21}$ groups are the same or different halo (e.g., each R$^{21}$ is F), and (3) phenyl substituted with 1 R$^{21}$ group, and said R$^{21}$ group is halo (e.g., F); R$^{10}$ is selected from the group consisting of: (1) phenyl and (2) phenyl substituted with 1 R$^{21}$ group (e.g., R$^{21}$ is —OR$^{15}$, and in another example R$^{21}$ is —OR$^{15}$ wherein R$^{15}$ is alkyl (such as methyl), and in another example R$^{21}$ is halo (such as F)); and R$^9$ is selected from the group consisting of: (1) imidazolyl (e.g., imidazol-1-yl), (2) imidazolyl (e.g., imidazol-1-yl) substituted with 1 R$^{21}$ group, and (3) imidazolyl (e.g., imidazol-1-yl) substituted with 1 R$^{21}$ group wherein said R$^{21}$ group is alkyl (e.g., methyl).

In another embodiment of this invention: Ring (A) is cycloalkyl (e.g., cyclopropyl); U is N; G is —CF$_2$—; W is —C(R$^2$)$_2$— (wherein each R$^3$ is independently selected); optional Bond 1 is present; X is —C(R$^3$)$_2$— (wherein each R$^3$ is independently selected), and, for example, X is —CH$_2$—; Y is —C(R$^3$)$_2$— (wherein each R$^3$ is independently selected), and, for example, Y is —CH$_2$—; R$^8$ is alkyl (e.g., methyl); R$^6$ is H; R$^7$ is selected from the group consisting of: (1) phenyl, (2) phenyl substituted with 1 to 2 independently selected R$^{21}$ groups and wherein said R$^{21}$ groups are the same or different halo (e.g., each R$^{21}$ is F), and (3) phenyl substituted with 1 R$^{21}$ group, and said R$^{21}$ group is halo (e.g., F); R$^{10}$ is selected from the group consisting of: (1) phenyl and (2) phenyl substituted with 1 R$^{21}$ group (e.g., R$^{21}$ is —OR$^{15}$, and in another example R$^{21}$ is —OR$^{15}$ wherein R$^{15}$ is alkyl (such as methyl), and in another example R$^{21}$ is halo (such as F)); and R$^9$ is selected from the group consisting of: (1) imidazolyl (e.g., imidazol-1-yl), (2) imidazolyl (e.g., imidazol-1-yl) substituted with 1 R$^{21}$ group, and (3) imidazolyl (e.g., imidazol-1-yl) substituted with 1 R$^{21}$ group wherein said R$^{21}$ group is alkyl (e.g., methyl).

In another embodiment of this invention: Ring (A) is cycloalkyl cyclopropyl); U is N; G is —CF$_2$—; W is —C(R$^3$)$_2$— (wherein each R$^3$ is independently selected); optional Bond 1 is present; X is —C(R$^3$)$_2$— (wherein each R$^3$ is independently selected), and, for example, X is —CH$_2$—; Y is —C(R$^3$)$_2$— (wherein each R$^3$ is independently selected), and, for example, Y is —CH$_2$—; m is 1; n is 1; R$^8$ is alkyl (e.g., methyl); R$^6$ is H; R$^7$ is selected from the group consisting of: (1) phenyl and (2) phenyl substituted with 1 to 3 independently selected R$^{21}$ groups, and wherein said R$^{21}$ groups are the same or different halo; R$^{10}$ is selected from the group consisting of: (1) phenyl and (2) phenyl substituted with 1 to 3 independently selected R$^{21}$ groups; and R$^9$ is selected from the group consisting of: (1) imidazolyl (e.g., imidazol-1-yl), and (2) imidazolyl (e.g., imidazol-1-yl) substituted with 1 to 3 independently selected R$^{21}$ groups.

In another embodiment of his invention: Ring (A) is cycloalkyl (e.g., cyclopropyl); U is N; G is —CF$_2$—; W is —C(R$^3$)$_2$— (wherein each R$^3$ is independently selected); optional Bond 1 is present; X is —C(R$^3$)$_2$— (wherein each R$^3$ is independently selected), and, for example, X is —$CH_2$—; Y is —$C(R^3)_2$— (wherein each $R^3$ is independently selected), and, for example, Y is —$CH_2$—; m is 1; n is 1; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is absent; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl cycloalkyl (e.g., cyclopropyl); U is N; G is —$CF_2$—; W is —$C(R^3)_2$— (wherein each $R^3$ is independently selected); optional Bond 1 is absent; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is absent; m is 1; n is 1; $R^8$ is H; $R^6$ is H; $R^7$ is selected from the group consisting of: (1) phenyl; and (2) phenyl substituted with 1 to 3 independently selected $R^{21}$ groups, and wherein said $R^{21}$ groups are the same or different halo; $R^{10}$ is selected from the group consisting of: (1) phenyl; and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is absent; m is 1; n is 1; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is W is —$C(R^3)_2$— (wherein each $R^3$ is independently selected); optional Bond 1 is absent; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is absent; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is absent; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; m is 1; n is 1; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is absent; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; m is 1; n is 1; $R^8$ is H; $R^8$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F); and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^5$ is selected from the group consisting of: (1) imidazolyl (e.g., imidazol-1-yl), (2) imidazolyl (e.g., imidazol-1-yl) substituted with 1 $R^{21}$ group; and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is absent; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is absent; $R^8$ is alkyl (e.g., methyl); $R^6$ is H; $R^7$ is selected from the group consisting of: (1) phenyl; (2) phenyl substituted with 1 to 2 independently selected $R^{21}$ groups, and wherein said $R^{21}$ groups are the same or different halo (e.g., each $R^{21}$ is F); and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is absent; m is 1; n is 1; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is absent; m is 1; n is 1; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl imidazol-1-yl) substituted with 1 $R^{21}$ group, and (3) imidazolyl imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is absent; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$CH_2$—; W is —$C(R^3)_2$— (wherein each $R^3$ is independently selected); optional Bond 1 is absent; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo F); $R^9$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazoiyl (e.g., substituted with 1 $R^{21}$ group wherein said $R^{21}$ group is alkyl (e.g., methyl), In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is absent; X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; m is 1; n is 1; $R^6$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$CF_2$—; W is —$C(R^3)_2$— (wherein each $R^3$ is independently selected);

optional Bond 1 is absent; X is —C(R$^3$)$_2$— (wherein each R$^3$ is independently selected), and, for example, X is —CH$_2$—; Y is —C(R$^3$)$_2$— (wherein each R$^3$ is independently selected), and, for example, Y is —CH$_2$—; m is 1; n is 1; R$^8$ is alkyl (e.g., methyl); R$^6$ is H; R$^7$ is selected from the group consisting of: (1) phenyl, (2) phenyl substituted with 1 to 2 independently selected R$^{21}$ groups and wherein said R$^{21}$ groups are the same or different halo (e.g., each R$^{21}$ is F), and (3) phenyl substituted with 1 R$^{21}$ group, and said R$^{21}$ group is halo (e.g., F); R$^{13}$ is selected from the group consisting of: (1) phenyl and (2) phenyl substituted with 1 R$^{21}$ group (e.g., R$^{21}$ is —OR$^{15}$, and in another example R$^{21}$ is —OR$^{15}$ wherein R$^{15}$ is alkyl (such as methyl), and in another example R$^{21}$ is halo (such as F)); and R$^9$ is selected from the group consisting of: (1) imidazolyl (e.g., imidazol-1-yl), (2) imidazolyl (e.g., imidazol-1-yl) substituted with 1 R$^{21}$ group, and (3) imidazolyl (e.g., imidazol-1-yl) substituted with 1 R$^{21}$ group wherein said R$^{21}$ group is alkyl (e.g., methyl).

In another embodiment of this invention: Ring (A) is cycloalkyl (e.g., cyclopropyl); U is N; G is —CF$_2$—; W is —C(R$^3$)$_2$— (wherein each R$^3$ is independently selected); optional Bond 1 is absent, and optional Bonds 2 and 3 are present and moieties R$^{8A}$ and R$^{8B}$ taken together, along with the carbon atoms to which they are bound, form an unsubstituted cycloalkyl ring (e.g., cyclopropyl); R$^8$ is H; R$^6$ is H; R$^7$ is selected from the group consisting of: (1) phenyl and (2) phenyl substituted with 1 to 3 independently selected R$^{21}$ groups, and wherein said R$^{21}$ groups are the same or different halo; R$^{10}$ is selected from the group consisting of: (1) phenyl and (2) phenyl substituted with 1 to 3 independently selected R$^{21}$ groups; and R$^9$ is selected from the group consisting of: (1) imidazolyl imidazol-1-yl), and (2) imidazolyl (e.g., imidazol-1-yl) substituted with 1 to 3 independently selected R$^{21}$ groups.

In another embodiment of this invention: Ring (A) is cycloalkyl (e.g., cyclopropyl); U is N; G is W is —C(R$^3$)$_2$— (wherein each R$^3$ is independently selected); optional Bond 1 is absent, and optional Bonds 2 and 3 are present and moieties R$^{8A}$ and R$^{8B}$ taken together, along with the carbon atoms to which they are bound, form an unsubstituted cycloalkyl ring (e.g., cyclopropyl); R$^8$ is H; R$^6$ is H; R$^7$ is selected from the group consisting of: (1) phenyl, (2) phenyl substituted with 1 to 2 independently selected R$^{21}$ groups and wherein said R$^{21}$ groups are the same or different halo (e.g., each R$^{21}$ is F), and (3) phenyl substituted with 1 R$^{21}$ group, and said R$^{21}$ group is halo (e.g., F); R$^{10}$ is selected from the group consisting of: (1) phenyl and (2) phenyl substituted with 1 R$^{21}$ group (e.g., R$^{21}$ is —OR$^{15}$, and in another example R$^{21}$ is —OR$^{15}$ wherein R$^{15}$ is alkyl (such as methyl), and in another example R$^{21}$ is halo (such as F)); and R$^9$ is selected from the group consisting of: (1) imidazolyl (e.g., imidazol-1-yl), (2) imidazolyl (e.g., imidazol-1-yl) substituted with 1 R$^{21}$ group, and (3) imidazolyl (e.g., imidazol-1-yl) substituted with 1 R$^{21}$ group wherein said R$^{21}$ group is alkyl (e.g., methyl).

In another embodiment of this invention: Ring (A) is cycloalkyl (e.g., cyclopropyl); U is N; G is —CF$_2$—; W is —C(R$^3$)$_2$— (wherein each R$^3$ is independently selected); optional Bond 1 is absent, and optional Bonds 2 and 3 are present and moieties R$^{8A}$ and R$^{8B}$ taken together, along with the carbon atoms to which they are bound, form an unsubstituted cycloalkyl ring (e.g., cyclopropyl); m is 1; n is 1; R$^8$ is H; R$^6$ is H; R$^7$ is selected from the group consisting of: (1) phenyl; and (2) phenyl substituted with 1 to 3 independently selected R$^{21}$ groups, and wherein said R$^{21}$ groups are the same or different halo; R$^{10}$ is selected from the group consisting of: (1) phenyl; and (2) phenyl substituted with 1 to 3 independently selected R$^{21}$ groups; and R$^9$ is selected from the group consisting of: (1) imidazolyl (e.g., imidazol-1-yl), and (2) imidazolyl (e.g., imidazol-1-yl) substituted with 1 to 3 independently selected R$^{21}$ groups.

In another embodiment of this invention: Ring (A) is cycloalkyl (e.g., cyclopropyl); U is N; G is —CF$_3$—; W is —C(R$^3$)$_2$— (wherein each R$^3$ is independently selected); optional Bond 1 is absent, and optional Bonds 2 and 3 are present and moieties R$^{8A}$ and R$^{8B}$ taken together, along with the carbon atoms to which they are bound, form an unsubstituted cycloalkyl ring (e.g., cyclopropyl); m is 1; n is 1; R$^5$ is H; R$^6$ is H; R$^7$ is selected from the group consisting of (1) phenyl, (2) phenyl substituted with 1 to 2 independently selected R$^{21}$ groups and wherein said R$^{21}$ groups are the same or different halo (e.g., each R$^{21}$ is F), and (3) phenyl substituted with 1 R$^{21}$ group, and said R$^{21}$ group is halo (e.g., F); R$^{10}$ is selected from the group consisting of: (1) phenyl and (2) phenyl substituted with 1 R$^{21}$ group (e.g., R$^{21}$ is —OR$^{15}$, and in another example R$^{21}$ is —OR$^{15}$ wherein R$^{15}$ is alkyl (such as methyl), and in another example R$^{21}$ is halo (such as F)); and R$^9$ is selected from the group consisting of: (1) imidazolyl (e.g., imidazol-1-yl), (2) imidazolyl (e.g., imidazol-1-yl) substituted with 1 R$^{21}$ group, and (3) imidazolyl (e.g., imidazol-1-yl) substituted with 1 R$^{21}$ group wherein said R$^{21}$ group is alkyl (e.g., methyl).

In another embodiment of this invention: Ring (A) is cycloalkyl (e.g., cyclopropyl); U is N; G is —CF$_2$—; W is —C(R$^3$)$_2$— (wherein each R$^3$ is independently selected); optional Bond 1 is absent, and optional Bonds 2 and 3 are present and moieties R$^{8A}$ and R$^{8B}$ taken together, along with the carbon atoms to which they are bound, form an unsubstituted cycloalkyl ring (e.g., cyclopropyl); X is —C(R$^3$)$_2$— (wherein each R$^3$ is independently selected), and, for example, X is —CH$_2$—; Y is —C(R$^3$)$_2$— (wherein each R$^3$ is independently selected), and, for example, Y is —CH$_2$—; R$^8$ is H; R$^6$ is H; R$^7$ is selected from the group consisting of: (1) phenyl and (2) phenyl substituted with 1 to 3 independently selected R$^{21}$ groups, and wherein said R$^{21}$ groups are the same or different halo; R$^{10}$ is selected from the group consisting of: (1) phenyl and (2) phenyl substituted with 1 to 3 independently selected R$^{21}$ groups; and R$^9$ is selected from the group consisting of: (1) imidazoyl (e.g., imidazol-1-yl), and (2) imidazolyl (e.g., imidazol-1-yl) substituted with 1 to 3 independently selected R$^{21}$ groups.

In another embodiment of this invention: Ring (A) is cycloalkyl (e.g., cyclopropyl); U is N; G is —CF$_2$—; W is —C(R$^3$)$_2$— (wherein each R$^3$ is independently selected); optional Bond 1 is absent, and optional Bonds 2 and 3 are present and moieties R$^{8A}$ and R$^{8B}$ taken together, along with the carbon atoms to which they are bound, form an unsubstituted cycloalkyl ring (e.g., cyclopropyl); X is —C(R$^3$)$_2$— (wherein each R$^3$ is independently selected), and, for example, X is —CH$_2$—; Y is —C(R$^3$)$_2$— (wherein each R$^3$ is independently selected), and, for example, Y is —CH$_2$—; R$^8$ is H; R$^6$ is H; R$^7$ is selected from the group consisting of: (1) phenyl, (2) phenyl substituted with 1 to 2 independently selected R$^{21}$ groups and wherein said R$^{21}$ groups are the same or different halo (e.g., each R$^{21}$ is F), and (3) phenyl substituted with 1 R$^{21}$ group, and said R$^{21}$ group is halo (e.g., F); R$^{10}$ is selected from the group consisting of: (1) phenyl and (2) phenyl substituted with 1 R$^{21}$ group (e.g., R$^{21}$ is —OR$^{15}$, and in another example R$^{21}$ is —OR$^{15}$ wherein R$^{15}$ is alkyl (such as methyl), and in another example R$^{21}$ is halo (such as F)); and R$^9$ is selected from the group consisting of: (1) imidazolyl (e.g., imidazol-1-yl), (2) imidazolyl (e.g., imidazol-1-yl) substituted with 1 R$^{21}$ group, and (3) imidazolyl (e.g., imidazol-1-yl) substituted with 1 R$^{21}$ group wherein said R$^{21}$ group is alkyl (e.g., methyl).

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; m is 1; n is 1; $R^8$ is H; $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (I) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; m is 1; is 1; $R^8$ is H; $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F); and (3) phenyl substituted with 1 $R^{21}$ group, and said $R^{21}$ group is halo (e.g.; F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{13}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group; and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g. cyclopropyl); U is N; G is —$CF_2$—; W is —$C(R^3)_2$— (wherein each $R^3$ is independently selected); optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); $R^8$ is alkyl (e.g., methyl); $R^6$ is H; $R^7$ is selected from the group consisting of: (1) phenyl; (2) phenyl substituted with 1 to 2 independently selected $R^{21}$ groups, and wherein said $R^{21}$ groups are the same or different halo (e.g., each $R^{21}$ is F); and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl cyclopropyl); U is N; G is —$CF_2$—, W is —$C(R^3)_2$— (wherein each $R^3$ is independently selected); optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); m is 1; n is 1; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); m is 1; n is 1; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —$C(R^3)_2$— (wherein each $R^3$ is independently selected), and, for example, X is —$CH_2$—; Y is —$C(R)_2$— (wherein each $R^3$ is independently selected), and, for example, Y is —$CH_2$—; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl imidazol-1-yl) substituted with 1 to 3 independently selected $R^{21}$ groups.

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; $R^8$ is alkyl (e.g., methyl); $R^6$ is H; $R^7$ is selected from the group consisting of: (1) phenyl, (2) phenyl substituted with 1 to 2 independently selected $R^{21}$ groups, and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; m is 1; n is 1; $R^8$ is alkyl (e.g., methyl); $R^6$ is H; $R^7$ is selected from the group consisting of: (1) phenyl and (2) phenyl substituted with 1 to 3 independently selected $R^{21}$ groups, and wherein said $R^{21}$ groups are the same or different halo; $R^{10}$ is selected from the group consisting of: (1) phenyl and (2) phenyl substituted with 1 to 3 independently selected $R^{21}$ groups; and $R^9$ is selected from the group consisting of: (1) imidazolyl (e.g., imidazol-1-yl), and (2) imidazolyl (e.g., imidazol-1-yl) substituted with 1 to 3 independently selected $R^{21}$ groups.

In another embodiment of this invention: Ring (A) is cycloalkyl (e.g., cyclopropyl); U is N; G is —$CF_2$—; W is —$C(R^3)_2$— (wherein each $R^3$ is independently selected); optional Bond 1 is absent, and optional Bonds 2 and 3 are present and moieties $R^{8A}$ and $R^{8B}$ taken together, along with the carbon atoms to which they are bound, form an unsubstituted cycloalkyl ring (e.g., cyclopropyl); X is —$C(R^3)_2$— (wherein each $R^3$ is independently selected), and, for example, X is —$CH_2$—; Y is —$C(R^3)_2$— (wherein each $R^3$ is independently selected), and, for example, Y is —$CH_2$—; m is 1; n is 1; $R^8$ is alkyl (e.g., methyl); $R^6$ is H; $R^7$ is selected from the group consisting of: (1) phenyl, (2) phenyl substituted with 1 to 2 independently selected $R^{21}$ groups and wherein said $R^{21}$ groups are the same or different halo (e.g., each $R^{21}$ is F), and (3) phenyl substituted with 1 $R^{21}$ group, and said $R^{21}$ group is halo (e.g., F); $R^{10}$ is selected from the group consisting of: (1) phenyl and (2) phenyl substituted with 1 $R^{21}$ group (e.g., $R^{21}$ is —$OR^{15}$, and in another example $R^{21}$ is —$OR^{15}$ wherein $R^{15}$ is alkyl (such as methyl), and in another example $R^{21}$ is halo (such as F)); and $R^9$ is selected from the group consisting of: (1) imidazolyl (e.g., imidazol-1-yl), (2) imidazolyl (e.g., imidazol-1-yl) substituted with 1 $R^{21}$ group, and (3) imidazolyl (e.g., imidazol-1-yl) substituted with 1 $R^{21}$ group wherein said $R^{21}$ group is alkyl (e.g., methyl).

One example of the —$R^{10}$—$R^9$ moiety for any of the embodiments described above is:

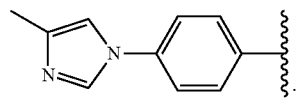 [SMILES: *c1ccc(-n2cnc(C)c2)cc1]

Another example of the —$R^{10}$—$R^9$ moiety for any of the embodiments described above is:

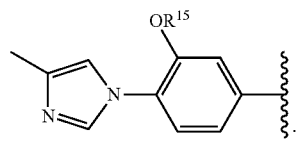

Another example of the moiety for any of the embodiments described above is:

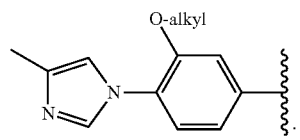

Another example of the —$R^{10}$—$R^9$ moiety for any of the embodiments described above is:

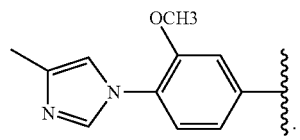 [SMILES: *c1ccc(-n2cnc(C)c2)c(OC)c1]

Another example of the moiety for any of the embodiments described above is:

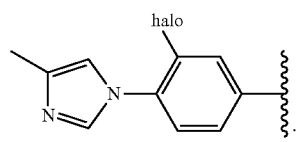

Another example of the —$R^{10}$—$R^9$ moiety for any of the embodiments described above is:

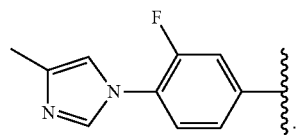 [SMILES: *c1ccc(-n2cnc(C)c2)c(F)c1]

Thus, one embodiment of this invention is directed to compounds of formula (I) having the formula:

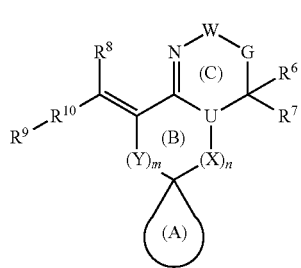
(IA)

wherein all substituents are as defined for formula (I) or any one of the embodiments of formula (I) described above.

Another embodiment of this invention is directed to compounds of formula (I) having the formula:

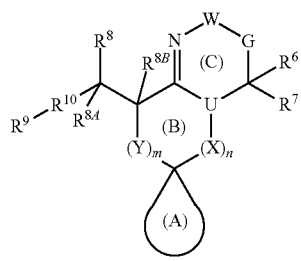
(IB)

wherein all substituents are as defined for formula (I) or any one of the embodiments of formula (I) described above. In one embodiment $R^{8A}$ and $R^{8B}$ in formula (IB) are each H. In another embodiment $R^{8A}$ and $R^{8B}$ in formula (IB) are taken together along with the carbon atoms to which they are bound to form a ring. In another embodiment $R^{8A}$ and $R^{8B}$ in formula (IB) are taken together along with the carbon atoms to which they are bound to form an unsubstituted cycloalkyl ring. In another embodiment $R^{8A}$ and $R^{8B}$ in formula (IB) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$). In another embodiment $R^{8A}$ and $R^{8B}$ in formula (IB) are taken together along with the carbon atoms to which they are bound to form a cyclopropyl ring thus making the compound of formula (IB) a compound of the formula (IB.1):

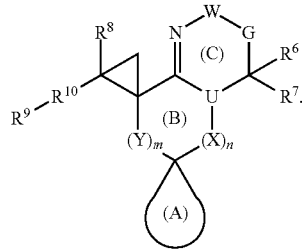
(IB.1)

Another embodiment of this invention is directed to compounds of formula (I) having the formula:

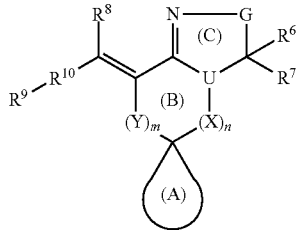
(IC)

wherein all substituents are as defined for formula (I) or any one of the embodiments of formula (I) described above.

Another embodiment of this invention is directed to compounds of formula (I) having the formula:

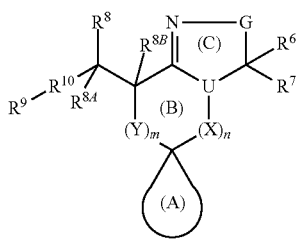
(ID)

wherein all substituents are as defined for formula (I) or any one of the embodiments of formula (I) described above. In one embodiment, $R^{8A}$ and $R^{8B}$ in formula (ID) are each H. In another embodiment $R^{8A}$ and $R^{8B}$ in formula (ID) are taken together along with the carbon atoms to which they are bound to form a ring. In another embodiment $R^{8A}$ and $R^{8B}$ in formula (ID) are taken together along with the carbon atoms to which they are bound to form an unsubstituted cycloalkyl ring. In another embodiment $R^{8A}$ and $R^{8B}$ in formula (ID) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$). In another embodiment $R^{8A}$ and $R^{8B}$ formula (ID) are taken together along with the carbon atoms to which they are bound to form a cyclopropyl ring thus making the compound of formula (ID) a compound of the formula (ID.1):

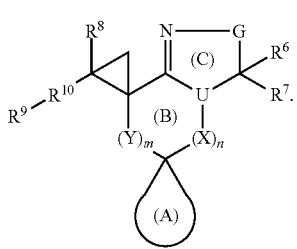
(ID.1)

In another embodiment $R^{8A}$ and $R^{8B}$ in formula (ID) are taken together along with the carbon atoms to which they are bound to form a substituted cyclohexyl ring thus making the compound of formula (ID) a compound of the formula (ID.2):

(ID.2)

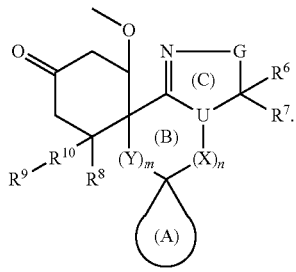

In another embodiment $R^{8A}$ and $R^{8B}$ in formula (ID) are taken together along with the carbon atoms to which they are bound to form a substituted cyclohexyl ring thus making the compound of formula (ID) a compound of the formula (ID.3):

(ID.3)

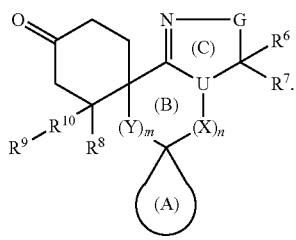

Another embodiment of this invention is directed to compounds of formula (I) having the formula:

(IE)

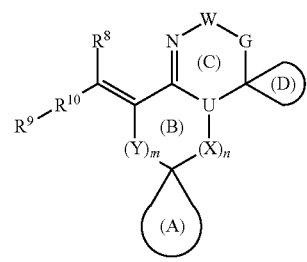

wherein all substituents are as defined for formula (I) or any one of the embodiments of formula (I) described above, and wherein Ring (D) is the ring formed by taking $R^6$ and $R^7$ together with the carbon atom to which they are bound.

Another embodiment of this invention is directed to compounds of formula (I) having the formula:

(IF)

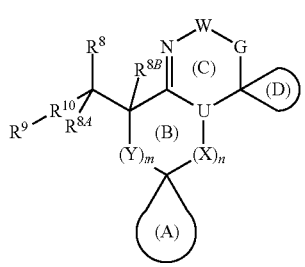

wherein all substituents are as defined for formula (I) or any one of the embodiments of formula (I) described above, and wherein Ring (D) is the ring formed by taking $R^6$ and $R^7$ together with the carbon atom to which they are bound. In one embodiment, $R^{8A}$ and $R^{8B}$ in formula (IF) are each H. In another embodiment $R^{8A}$ and $R^{8B}$ in formula (IF) are taken together along with the carbon atoms to which they are bound to form a ring. In another embodiment $R^{8A}$ and $R^{8B}$ in formula (IF) are taken together along with the carbon atoms to which they are bound to form an unsubstituted cycloalkyl ring. In another embodiment $R^{8A}$ and $R^{8B}$ in formula (IF) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$). In another embodiment $R^{8A}$ and $R^{8B}$ in formula (IF) are taken together along with the carbon atoms to which they are bound to form a cyclopropyl ring thus making the compound of formula (IF) a compound of the formula (IF.1):

(IF.1)

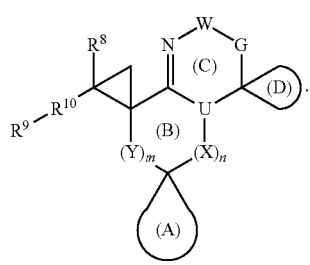

Another embodiment of this invention is directed to compounds of formula (I) having the formula:

(IG)

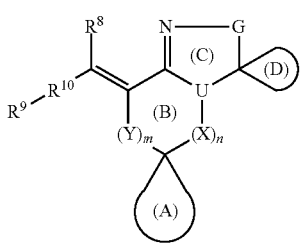

wherein all substituents are as defined for formula (I) or any one of the embodiments of formula (I) described above, and wherein Ring (D) is the ring formed by taking $R^6$ and $R^7$ together with the carbon atom to which they are bound.

Another embodiment of this invention is directed to compounds of formula (I) having the formula:

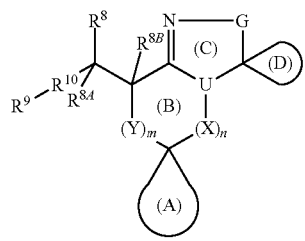

(IH)

wherein all substituents are as defined for formula (I) or any one of the embodiments of formula (I) described above, and wherein Ring (D) is the ring formed by taking $R^6$ and $R^7$ together with the carbon atom to which they are bound. In one embodiment, $R^{8A}$ and $R^{8B}$ in formula (IH) are each H. In another embodiment $R^{8A}$ and $R^{8B}$ in formula (IH) are taken together along with the carbon atoms to which they are bound to form a rind, in another embodiment $R^{8A}$ and $R^{8B}$ formula (IH) are taken together along with the carbon atoms to which they are bound to form an unsubstituted cycloalkyl ring. In another embodiment $R^{8A}$ and $R^{8B}$ formula (IH) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$). In another embodiment $R^{8A}$ and $R^{8B}$ in formula (IH) are taken together along with the carbon atoms to which they are bound to form a cyclopropyl ring thus making the compound of formula (IH) a compound of the formula (IH.1):

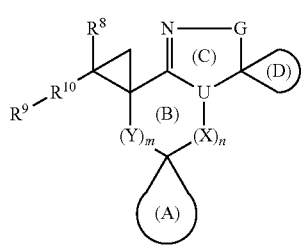

(IH.1)

Another embodiment of this invention is directed to compounds of formula (I) having the formula:

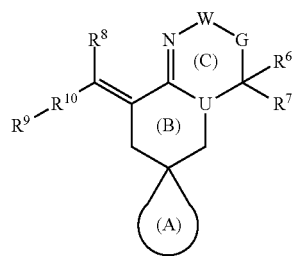

(II)

wherein all substituents are as defined for formula (I) or any one of the embodiments of formula (I) described above.

Another embodiment of this invention is directed to compounds of formula (I) having the formula:

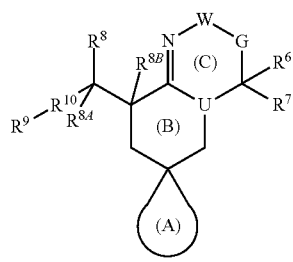

(IJ)

wherein all substituents are as defined for formula (I) or any one of the embodiments of formula (I) described above. In one embodiment, $R^{8A}$ and $R^{8B}$ in formula (IJ) are each H. In another embodiment $R^{8A}$ and $R^{8B}$ in formula (IJ) are taken together along with the carbon atoms to which they are bound to form a ring. In another embodiment $R^{8A}$ and $R^{8B}$ in formula (IJ) are taken together along with the carbon atoms to which they are bound to form an unsubstituted cycloalkyl ring. In another embodiment $R^{8A}$ and $R^{8B}$ in formula (IJ) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$). In another embodiment $R^{8A}$ and $R^{8B}$ in formula (IJ) are taken together along with the carbon atoms to which they are bound to form a cyclopropyl ring thus making the compound of formula (IJ) a compound of the formula (IJ.1):

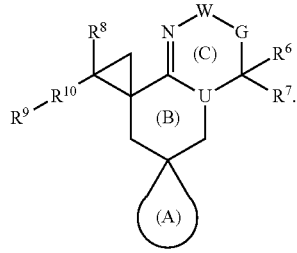

(IJ-1)

Another embodiment of this invention is directed to compounds of formula (I) having the formula:

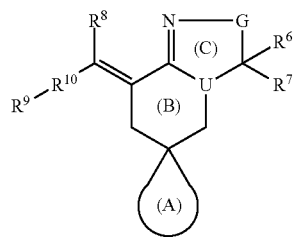

(IK)

wherein all substituents are as defined for formula (I) or any one of the embodiments of formula (I) described above.

Another embodiment of this invention is directed to compounds of formula (I) having the formula:

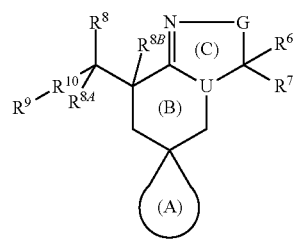

(IL)

wherein all substituents are as defined for formula (I) or any one of the embodiments of formula (I) described above. In one embodiment, $R^{8A}$ and $R^{8B}$ in formula (IL) are each H. In another embodiment $R^{8A}$ and $R^{8B}$ in formula (IL) are taken together along with the carbon atoms to which they are bound to form a ring. In another embodiment $R^{8A}$ and $R^{8B}$ in formula (IL) are taken together along with the carbon atoms to which they are bound to form an unsubstituted cycloalkyl ring. In another embodiment $R^{8A}$ and $R^{8B}$ in formula (IL) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$). In another embodiment $R^{8A}$ and $R^{8B}$ in formula (IL) are taken together along with the carbon atoms to which they are bound to form a cyclopropyl ring thus making the compound of formula (IL) a compound of the formula (IL.1):

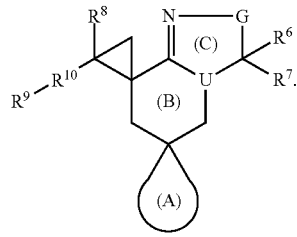

(IL.1)

Another embodiment of this invention is directed to compounds of formula (I) having the formula:

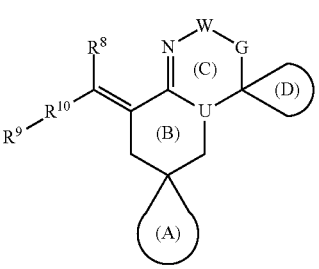

(IM)

wherein all substituents are as defined for formula (I) or any one of the embodiments of formula (I) described above, and wherein Ring (D) is the ring formed by taking $R^6$ and $R^7$ together with the carbon atom to which they are bound.

Another embodiment of this invention is directed to compounds of formula (I) having the formula:

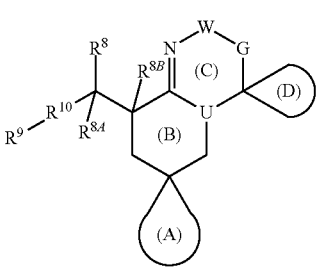

(IN)

wherein all substituents are as defined for formula (I) or any one of the embodiments of formula (I) described above, and wherein Ring (D) is the ring formed by taking $R^6$ and $R^7$ together with the carbon atom to which they are bound. In one embodiment, $R^{8A}$ and $R^{8B}$ in formula (IN) are each H. In another embodiment $R^{8A}$ and $R^{8B}$ in formula (IN) are taken together along with the carbon atoms to which they are bound to form a ring. In another embodiment $R^{8A}$ and $R^{8B}$ in formula (IN) are taken together along with the carbon atoms to which they are bound to form an unsubstituted cycloalkyl ring. In another embodiment $R^{8A}$ and $R^{8B}$ in formula (IN) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$). In another embodiment R$^{8A}$ and R$^{8B}$ in formula (IN) are taken together along with the carbon atoms to which they are bound to form a cyclopropyl ring thus making the compound of formula (IN) a compound of the formula (IN.1):

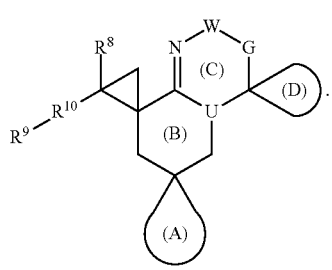

(IN.1)

Another embodiment of this invention is directed to compounds of formula (I) having the formula:

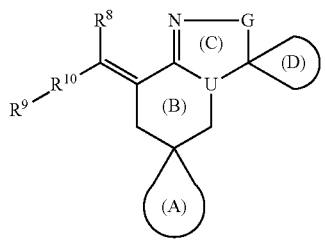

(IO)

wherein all substituents are as defined for formula (I) or any one of the embodiments of formula (I) described above, and wherein Ring (D) is the ring formed by taking R$^6$ and R$^7$ together with the carbon atom to which they are bound.

Another embodiment of this invention is directed to compounds of formula (I) having the formula:

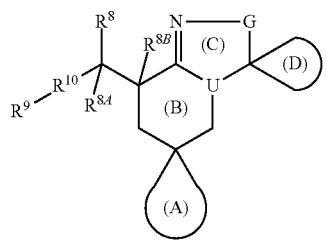

(IP)

wherein all substituents are as defined for formula (I) or any one of the embodiments of formula (I) described above, and wherein Ring (D) is the ring formed by taking R$^6$ and R$^7$ together with the carbon atom to which they are bound. In one embodiment. R$^{8A}$ and R$^{8B}$ in formula (IP) are each H. In another embodiment R$^{8A}$ and R$^{8B}$ formula (IP) are taken together along with the carbon atoms to which they are bound to form a ring. In another embodiment R$^{8A}$ and R$^{8B}$ in formula (IP) are taken together along with the carbon atoms to which they are bound to form an unsubstituted cycloalkyl ring. In another embodiment R$^{8A}$ and R$^{8B}$ in formula (IP) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$). In another embodiment R$^{8A}$ and R$^{8B}$ in formula (IP) are taken together along with the carbon atoms to which they are bound to form a cyclopropyl ring thus making the compound of formula (IP) a compound of the formula (IP.1):

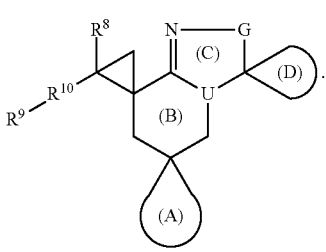

(IP.1)

Another embodiment of this invention is directed to compounds of formula (I) having the formula:

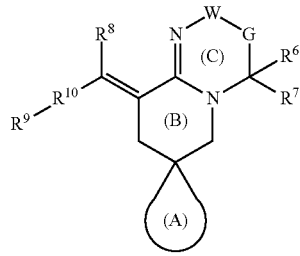

(IQ)

wherein all substituents are as defined for formula (I) or any one of the embodiments of formula (I) described above.

Another embodiment of this invention is directed to compounds of formula (I) having the formula:

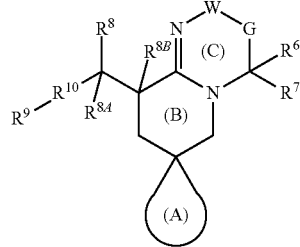

(IR)

wherein all substituents are as defined for formula (I) or any one of the embodiments of formula (I) described above. In one embodiment, R$^{8A}$ and R$^{8B}$ in formula (IR) are each H. In another embodiment R$^{8A}$ and R$^{8B}$ in formula (IR) are taken together along with the carbon atoms to which they are bound to form a ring. In another embodiment R$^{8A}$ and R$^{8B}$ in formula (IR) are taken together along with the carbon atoms to which they are bound to form an unsubstituted cycloalkyl ring. In another embodiment R$^{8A}$ and R$^{8B}$ in formula (IR) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$). In another embodiment R$^{8A}$ and R$^{8B}$ in formula (IR) are taken together along with the carbon atoms to which they are bound to form a cyclopropyl ring thus making the compound of formula (IR) a compound of the formula (IR.1):

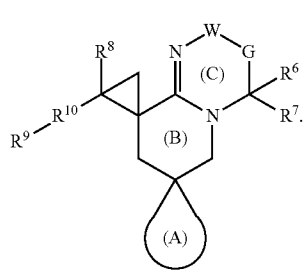

(IR.1)

Another embodiment of this invention is directed to compounds of formula (I) having the formula:

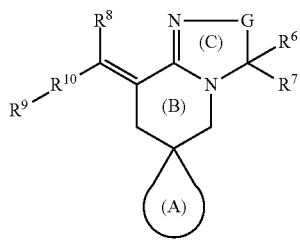

(IS)

wherein all substituents are as defined for formula (I) or any one of the embodiments of formula (I) described above.

Another embodiment of this invention is directed to compounds of formula (I) having the formula:

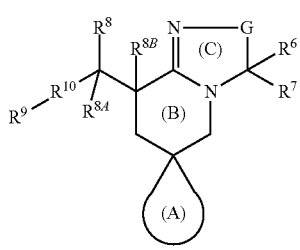

(IT)

wherein all substituents are as defined for formula (I) or any one of the embodiments of formula (I) described above. In one embodiment, R$^{8A}$ and R$^{8B}$ in formula (IT) are each H. In another embodiment R$^{8A}$ and R$^{8B}$ in formula (IT) are taken together along with the carbon atoms to which they are bound to form a ring. In another embodiment R$^{8A}$ and R$^{8B}$ in formula (IT) are taken together along with the carbon atoms to which they are bound to form an unsubstituted cycloalkyl ring. In another embodiment R$^{8A}$ and R$^{8B}$ in formula (IT) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$). In another embodiment R$^{8A}$ and R$^{8B}$ in formula (IT) are taken together along with the carbon atoms to which they are bound to form a cyclopropyl ring thus making the compound of formula (IT) a compound of the formula (IT.1):

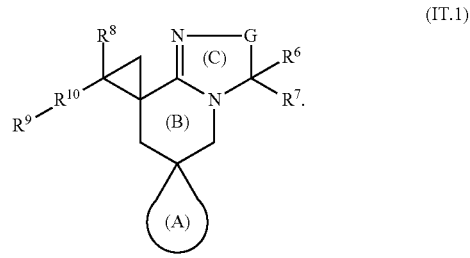

(IT.1)

Another embodiment of this invention is directed to compounds of formula (I) having the formula:

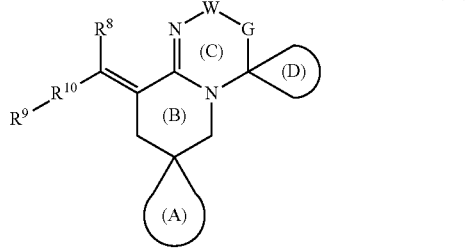

(IU)

wherein all substituents are as defined for formula (I) or any one of the embodiments of formula (I) described above, and wherein Ring (D) is the ring formed by taking R$^6$ and R$^7$ together with the carbon atom to which they are bound.

Another embodiment of this invention is directed to compounds of formula (I) having the formula:

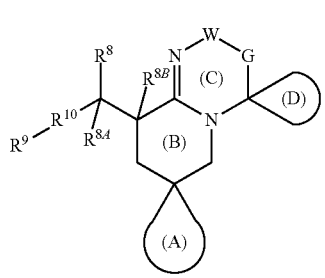

(IV)

wherein all substituents are as defined for formula (I) or any one of the embodiments of formula (I) described above, and wherein Ring (D) is the ring formed by taking R$^6$ and R$^7$ together with the carbon atom to which they are bound. In one embodiment, R$^{8A}$ and R$^{8B}$ in formula (IV) are each H. In another embodiment $R^{8A}$ and $R^{8B}$ in formula (IV) are taken together along with the carbon atoms to which they are bound to form a ring. In another embodiment $R^{8A}$ and $R^{8B}$ in formula (IV) are taken together along with the carbon atoms to which they are bound to form an unsubstituted cycloalkyl ring. In another embodiment $R^{8A}$ and $R^{8B}$ in formula (IV) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, awl, arylalkyl, heteroaryl, heteroarylalkyl, —CN, halo, =O, —OR$^{15}$ (e.g., —CH$_3$), —C(O)R$^{15}$, —C(O)OR$^{16}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$). In another embodiment $R^{8A}$ and $R^{8B}$ in formula (IV) are taken together along with the carbon atoms to which they are bound to form a cyclopropyl ring thus making the compound of formula (IV) a compound of the formula (IV.1):

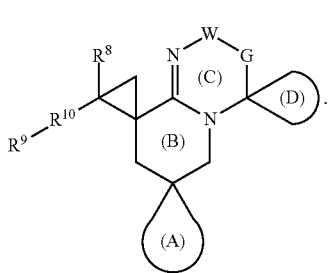

(IV.1)

Another embodiment of this invention is directed to compounds of formula (I) having the formula:

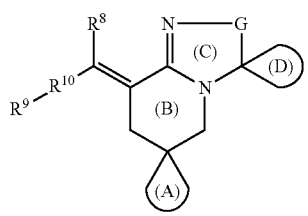

(IW)

wherein all substituents are as defined for formula (I) or any one of the embodiments of formula (I) described above, and wherein Ring (D) is the ring formed by taking $R^6$ and $R^7$ together with the carbon atom to which they are bound.

Another embodiment of this invention is directed to compounds of formula (I) having the formula:

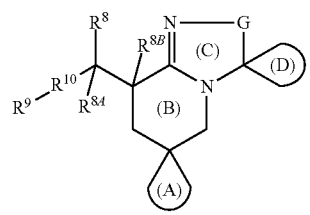

(IX)

wherein all substituents are as defined for formula (I) or any one of the embodiments of formula (I) described above, and wherein Ring (D) is the ring formed by taking $R^6$ and $R^7$ together with the carbon atom to which they are bound. In one embodiment, $R^{8A}$ and $R^{8B}$ in formula (IX) are each H. In another embodiment $R^{8A}$ and $R^{8B}$ in formula (IX) are taken together along with the carbon atoms to which they are bound to form a ring. In another embodiment $R^{8A}$ and $R^{8B}$ in formula (IX) are taken together along with the carbon atoms to which they are bound to form an unsubstituted cycloalkyl ring. In another embodiment $R^{8A}$ and $R^{8B}$ in formula (IX) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$—N(R$^{15}$)(R$^{16}$), —C(=NOR$^{15}$)R$^{16}$, and —P(O)(OR$^{15}$)(OR$^{16}$). In another embodiment $R^{8A}$ and $R^{8B}$ in formula (IX) are taken together along with the carbon atoms to which they are bound to form a cyclopropyl ring thus making the compound of formula (IX) a compound of the formula (IX.1):

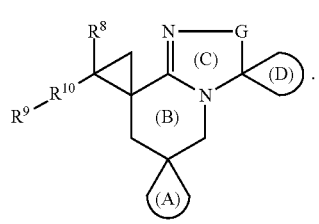

(IX.1)

Another embodiment of this invention is directed to compounds of formula (I) having the formula:

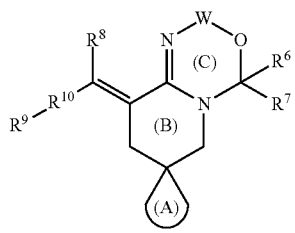

(IY)

wherein all substituents are as defined for formula (I) or any one of the embodiments of formula (I) described above.

Another embodiment of this invention is directed to compounds of formula (I) having the formula:

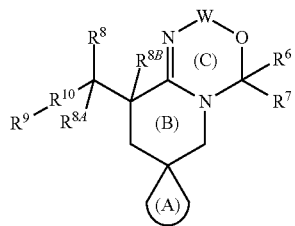

(IZ)

wherein all substituents are as defined for formula (I) or any one of the embodiments of formula (I) described above. In one embodiment, $R^{8A}$ and $R^{8B}$ in formula (IZ) are each H. In another embodiment $R^{8A}$ and $R^{8B}$ in formula (IZ) are taken together along with the carbon atoms to which they are bound to form a ring. In another embodiment $R^{8A}$ and $R^{8B}$ in formula (IZ) are taken together along with the carbon atoms to which they are bound to form an unsubstituted cycloalkyl ring. In another embodiment $R^{8A}$ and $R^{8B}$ in formula (IZ) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —$OR^{15}$ (e.g., —$CH_3$), —$C(O)R^{15}$, —$C(O)OR^{15}$, —$C(O)N(R^{15})(R^{16})$, —$S(O)N(R^{15})(R^{16})$, —$S(O)_2N(R^{15})(R^{16})$, —$C(=NOR^{15})R^{16}$, and —$P(O)(OR^{15})(OR^{16})$. In another embodiment $R^{8A}$ and $R^{8B}$ in formula (IZ) are taken together along with the carbon atoms to which they are bound to form a cyclopropyl ring thus making the compound of formula (IZ) a compound of the formula (IZ.1):

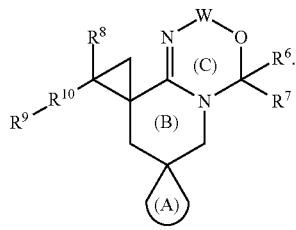

(IZ.1)

Another embodiment of this invention is directed to compounds of formula (I) having the formula:

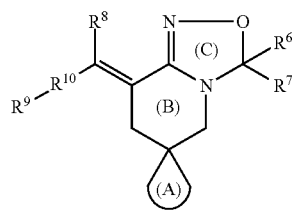

(IAA)

wherein all substituents are as defined for formula (I) or any one of the embodiments of formula (I) described above.

Another embodiment of this invention is directed to compounds of formula (I) having the formula:

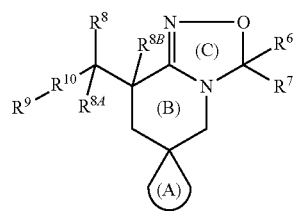

(IAB)

wherein all substituents are as defined for formula (I) or any one of the embodiments of formula (I) described above. In one embodiment, $R^{8A}$ and $R^{8B}$ in formula (IAB) are each H. In another embodiment $R^{8A}$ and $R^{8B}$ in formula (JAB) are taken together along with the carbon atoms to which they are bound to form a ring. In another embodiment $R^{8A}$ and $R^{8B}$ in formula (IAB) are taken together along with the carbon atoms to which they are bound to form an unsubstituted cycloalkyl ring. In another embodiment $R^{8A}$ and $R^{8B}$ in formula (IAB) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —$OR^{15}$ (e.g., —$CH_3$), —$C(O)R^{15}$, —$C(O)OR^{15}$, —$C(O)N(R^{15})(R^{16})$, —$S(O)N(R^{15})(R^{16})$, —$S(O)_2N(R^{15})(R^{16})$, —$C(=NOR^{15})R^{16}$ and —$P(O)(OR^{15})(OR^{16})$. In another embodiment $R^{8A}$ and $R^{8B}$ in formula (IAB) are taken together along with the carbon atoms to which they are bound to form a cyclopropyl ring thus making the compound of formula (IAB) a compound of the formula (IAB.1):

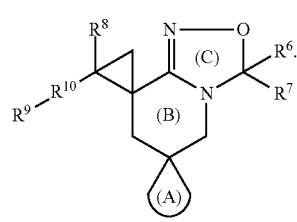

(IAB.1)

Another embodiment of this invention is directed to compounds of formula (I) having the formula:

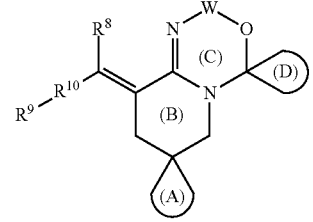

(IAC)

wherein all substituents are as defined for formula (I) or any one of the embodiments of formula (I) described above, and wherein Ring (D) is the ring formed by taking $R^6$ and $R^7$ together with the carbon atom to which they are bound.

Another embodiment of this invention is directed to compounds of formula (I) having the formula:

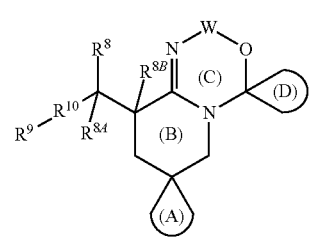

(IAD)

wherein all substituents are as defined for formula (I) or any one of the embodiments of formula (I) described above, and wherein Ring (D) is the ring formed by taking $R^6$ and $R^7$ together with the carbon atom to which they are bound. In one embodiment, $R^{8A}$ and $R^{8B}$ in formula (IAD) are each H. In another embodiment $R^{8A}$ and $R^{8B}$ in formula (IAD) are taken together along with the carbon atoms to which they are bound to form a ring. In another embodiment $R^{8A}$ and $R^{8B}$ in formula (IAD) are taken together along with the carbon atoms to which they are bound to form an unsubstituted cycloalkyl ring. In another embodiment $R^{8A}$ and $R^{8B}$ in formula (IAD) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —$OR^{15}$ (e.g., —$CH_3$), —$C(O)R^{15}$, —$C(O)OR^{15}$, —$C(O)N(R^{15})(R^{16})$, —$S(O)N(R^{15})(R^{16})$, —$S(O)_2N(R^{15})(R^{16})$, —$C(=NOR^{15})R^{16}$, and —$P(O)(OR^{15})(OR^{16})$. In another embodiment $R^{8A}$ and $R^{8B}$ in formula (IAD) are taken together along with the carbon atoms to which they are bound to form a cyclopropyl ring thus making the compound of formula (IAD) a compound of the formula (IAD.1):

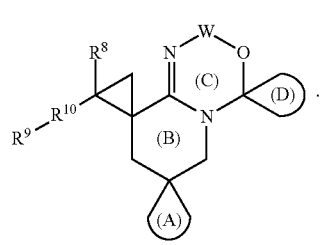

(IAD.1)

Another embodiment of this invention is directed to compounds of formula (I) having the formula:

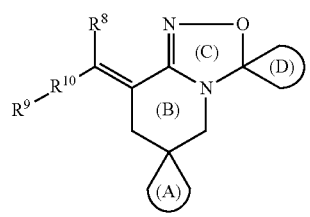

(IAE)

wherein all substituents are as defined for formula (I) or any one of the embodiments of formula (I) described above, and wherein Ring (D) is the ring formed by taking $R^6$ and $R^7$ together with the carbon atom to which they are bound.

Another embodiment of this invention is directed to compounds of formula (I) having the formula:

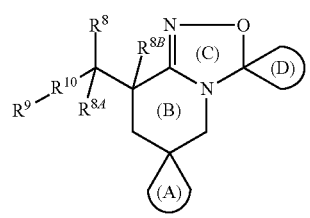

(IAF)

wherein all substituents are as defined for formula (I) or any one of the embodiments of formula (I) described above, and wherein Ring (D) is the ring formed by taking $R^6$ and $R^7$ together with the carbon atom to which they are bound. In one embodiment, $R^{8A}$ and $R^{8B}$ in formula (IAF) are each H. In another embodiment $R^{8A}$ and $R^{8B}$ in formula (IAF) are taken together along with the carbon atoms to which they are bound to form a ring. In another embodiment $R^{8A}$ and $R^{8B}$ in formula (IAF) are taken together along with the carbon atoms to which they are bound to form an unsubstituted cycloalkyl ring. In another embodiment $R^{8A}$ and $R^{8B}$ in formula (IAF) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —$OR^{15}$ (e.g., —$CH_3$), —$C(O)R^{15}$, —$C(O)OR^{15}$, —$C(O)N(R^{15})(R^{16})$, —$S(O)N(R^{15})(R^{16})$, —$S(O)_2N(R^{15})(R^{16})$, —$C(=NOR^{15})R^{16}$, and —$P(O)(OR^{15})(OR^{16})$. In another embodiment $R^{8A}$ and $R^{8B}$ in formula (IAF) are taken together along with the carbon atoms to which they are bound to form a cyclopropyl ring thus making the compound of formula (IAF) a compound of the formula (IAF.1):

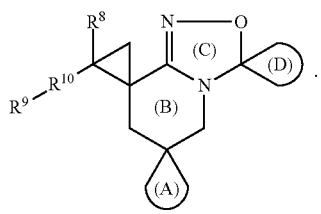

(IAF.1)

Another embodiment of this invention is directed to compounds of formula (I) having the formula:

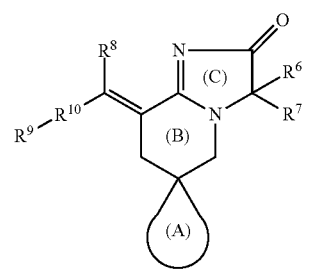

(IAG)

wherein all substituents are as defined for formula (I) or any one of the embodiments of formula (I) described above.

Another embodiment of this invention is directed to compounds of formula (I) having the formula:

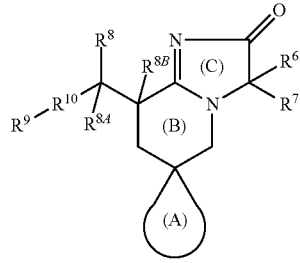

(IAH)

wherein all substituents are as defined for formula (I) or any one of the embodiments of formula (I) described above. In one embodiment, $R^{8A}$ and $R^{8B}$ in formula (IAH) are each H. In another embodiment $R^{8A}$ and $R^{8B}$ in formula (IAH) are taken together along with the carbon atoms to which they are bound to form a ring. In another embodiment $R^{8A}$ and $R^{8B}$ in formula (IAH) are taken together along with the carbon atoms to which they are bound to form an unsubstituted cycloalkyl ring, in another embodiment $R^{8A}$ and $R^{8B}$ in formula (IAH) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —$OR^{15}$ (e.g., —$CH_3$), —C(O)$R^{15}$, —C(O)O$R^{15}$, —C(O)N($R^{15}$)($R^{16}$), —S(O)N($R^{15}$)($R^{16}$), —S(O)$_2$N($R^{15}$)($R^{16}$), —C(=NO$R^{15}$)$R^{16}$, and —P(O)(O$R^{15}$)(O$R^{16}$). In another embodiment $R^{8A}$ and $R^{8B}$ in formula (IAH) are taken together along with the carbon atoms to which they are bound to form a cyclopropyl ring thus making the compound of formula (IAH) a compound of the formula (IAH.1):

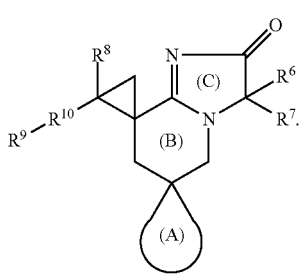

(IAH.1)

Another embodiment of this invention is directed to compounds of formula (I) having the formula:

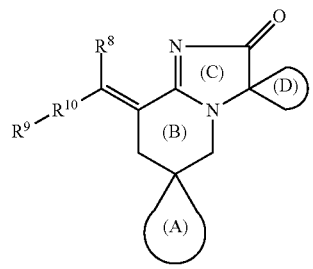

(IAI)

wherein all substituents are as defined for formula (I) or any one of the embodiments of formula (I) described above, and wherein Ring (D) is the ring formed by taking $R^6$ and $R^7$ together with the carbon atom to which they are bound.

Another embodiment of this invention is directed to compounds of formula (I) having the formula:

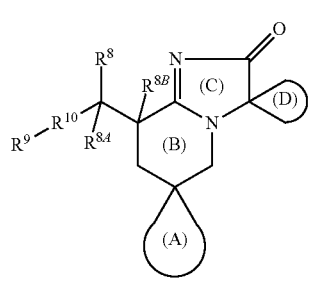

(IAJ)

wherein all substituents are as defined for formula (I) or any one of the embodiments of formula (I) described above, and wherein Ring (D) is the ring formed by taking $R^6$ and $R^7$ together with the carbon atom to which they are bound. In one embodiment, $R^{8A}$ and $R^{8B}$ formula (IAJ) are each H. In another embodiment $R^{8A}$ and $R^{8B}$ in formula (IAJ) are taken together along with the carbon atoms to which they are bound to form a ring. In another embodiment $R^{8A}$ and $R^{8B}$ in formula (IAJ) are taken together along with the carbon atoms to which they are bound to form an unsubstituted cycloalkyl ring. In another embodiment $R^{8A}$ and $R^{8B}$ in formula (IAJ) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —$OR^{15}$ (e.g., —$CH_3$), —C(O)$R^{15}$, —C(O)O$R^{15}$, —C(O)N($R^{15}$)($R^{16}$), —S(O)N($R^{15}$)($R^{16}$), —S(O)$_2$N($R^{15}$)($R^{16}$), —C(=NO$R^{15}$)$R^{16}$, and —P(O)(O$R^{15}$)(O$R^{16}$). In another embodiment $R^{8A}$ and $R^{8B}$ in formula (IAJ) are taken together along with the carbon atoms to which they are bound to form a cyclopropyl ring thus making the compound of formula (IAJ) a compound of the formula (IAJ.1):

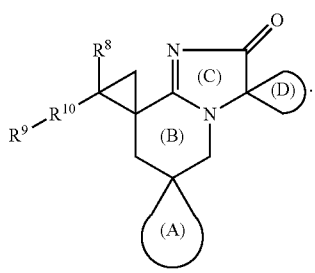

(IAJ.1)

Another embodiment of this invention is directed to compounds of formula (I) having the formula:

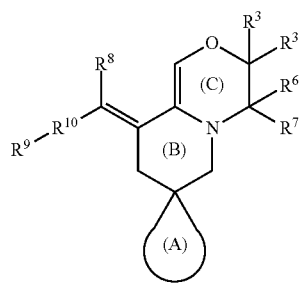

(IAK)

wherein all substituents are as defined for formula (I) or any one of the embodiments of formula (I) described above.

Another embodiment of this invention is directed to compounds of formula (I) having the formula:

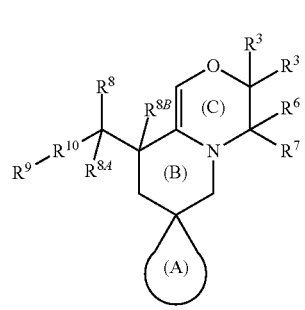

(IAL)

wherein all substituents are as defined for formula (I) or any one of the embodiments of formula (I) described above. In one embodiment, $R^{8A}$ and $R^{8B}$ in formula (IAL) are each H. In another embodiment $R^{8A}$ and $R^{8B}$ in formula (IAL) are taken together along with the carbon atoms to which they are bound to form a ring. In another embodiment $R^{8A}$ and $R^{8B}$ in formula (IAL) are taken together along with the carbon atoms to which they are bound to form an unsubstituted cycloalkyl ring. In another embodiment $R^{8A}$ and $R^{8B}$ in formula (IAL) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$) R$^{16}$, and —P(O)(OR$^{15}$)(OR$^{16}$). In another embodiment R$^{8A}$ and R$^{8B}$ in formula (IAL) are taken together along with the carbon atoms to which they are bound to form a cyclopropyl ring thus making the compound of formula (IAL) a compound of the formula (IAL.1):

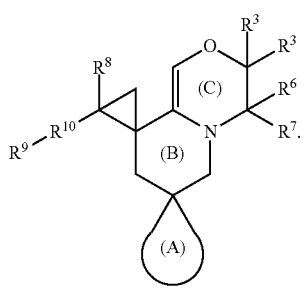

(IAL.1)

Another embodiment of this invention directed to compounds of formula (I) having the formula:

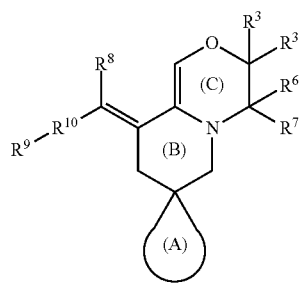

(IAM)

wherein all substituents are as defined for formula (I) or any one of the embodiments of formula (I) described above, and wherein Ring (D) is the ring formed by taking R$^6$ and R$^7$ together with the carbon atom to which they are bound.

Another embodiment of this invention is directed to compounds of formula (I) having the formula:

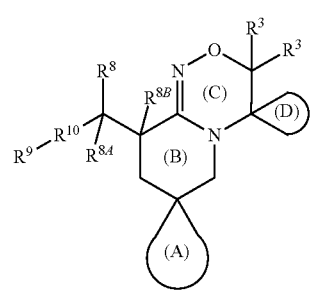

(IAN)

wherein all substituents are as defined for formula (I) or any one of the embodiments of formula (I) described above, and wherein Ring (D) is the ring formed by taking R$^6$ and R$^7$ together with the carbon atom to which they are bound. In one embodiment, R$^{8A}$ and R$^{8B}$ in formula (IAN) are each H. In another embodiment R$^{8A}$ and R$^{8B}$ in formula (IAN) are taken together along with the carbon atoms to which they are bound to form a ring. In another embodiment R$^{8A}$ and R$^{8B}$ in formula (IAN) are taken together along with the carbon atoms to which they are bound to form an unsubstituted cycloalkyl ring, in another embodiment $R^{8A}$ and $R^{8B}$ in formula (IAN) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —$OR^{15}$ (e.g., —$CH_3$), —$C(O)R^{15}$, —$C(O)OR^{15}$, —$C(O)N(R^{15})(R^{16})$, —$S(O)N(R^{15})(R^{16})$, —$S(O)_2N(R^{15})(R^{16})$, —$C(=NOR^{15})R^{16}$, and —$P(O)(OR^{15})(OR^{16})$. In another embodiment $R^{8A}$ and $R^{8B}$ in formula (IAN) are taken together along with the carbon atoms to which they are bound to form a cyclopropyl ring thus making the compound of formula (IAN) a compound of the formula (IAN.1):

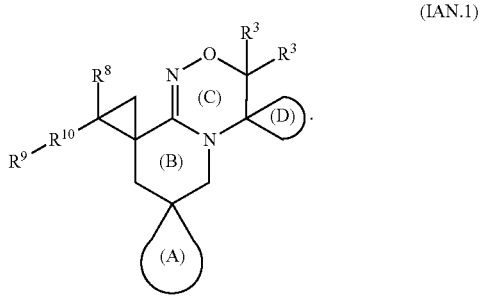

(IAN.1)

Another embodiment of this invention is directed to compounds of formula (I) having the formula:

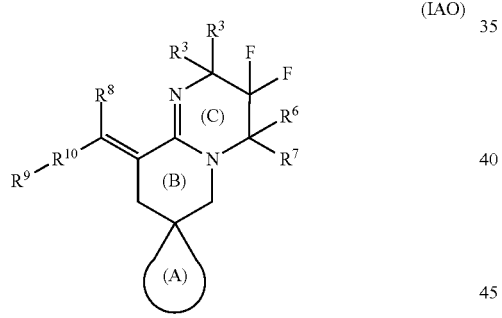

(IAO)

wherein all substituents are as defined for formula (I) or any one of the embodiments of formula (I) described above.

Another embodiment of this invention is directed to compounds of formula (I) having the formula:

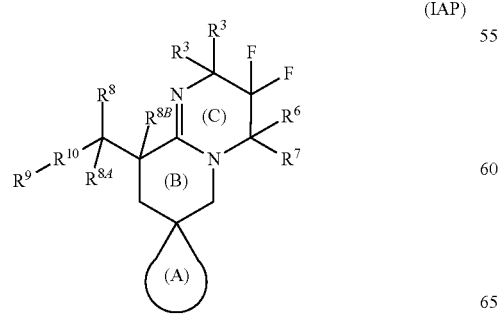

(IAP)

wherein all substituents are as defined for formula (I) or any one of the embodiments of formula (I) described above. In one embodiment, $R^{8A}$ and $R^{8B}$ in formula (IAP) are each H. In another embodiment $R^{8A}$ and $R^{8B}$ in formula (IAP) are taken together along with the carbon atoms to which they are bound to form a ring. In another embodiment $R^{8A}$ and $R^{8B}$ in formula (IAP) are taken together along with the carbon atoms to which they are bound to form an unsubstituted cycloalkyl ring. In another embodiment $R^{8A}$ and $R^{8B}$ in formula (IAP) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —$OR^{15}$ (e.g., —$CH_3$), —$C(O)R^{15}$, —$C(O)OR^{15}$, —$C(O)N(R^{15})(R^{16})$, —$S(O)N(R^{15})(R^{16})$, —$S(O)_2N(R^{15})(R^{16})$, —$C(=NOR^{15})R^{16}$, and —$P(O)(OR^{15})(OR^{16})$. In another embodiment $R^{8A}$ and $R^{8B}$ in formula (IAP) are taken together along with the carbon atoms to which they are bound to form a cyclopropyl ring thus making the compound of formula (IAP) a compound of the formula (IAP.1):

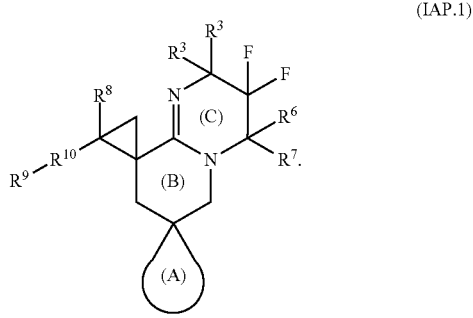

(IAP.1)

Another embodiment of this invention is directed to compounds of formula (I) having the formula:

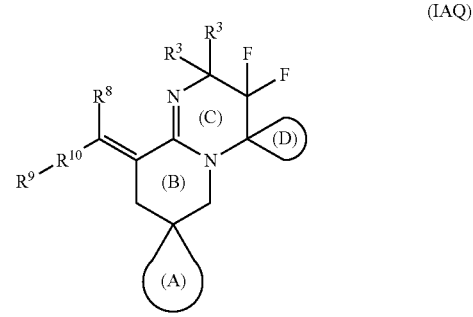

(IAQ)

wherein all substituents are as defined for formula (I) or any one of the embodiments of formula (I) described above, and wherein Ring (D) is the ring formed by taking $R^6$ and $R^7$ together with the carbon atom to which they are bound.

Another embodiment of this invention is directed to compounds of formula (I) having the formula:

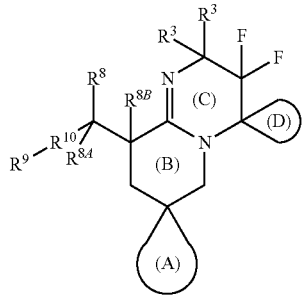

(IAR)

wherein all substituents are as defined for formula (I) or any one of the embodiments of formula (I) described above, and wherein Ring (D) is the ring formed by taking $R^6$ and $R^7$ together with the carbon atom to which they are bound. In one embodiment, $R^{8A}$ and $R^{8B}$ in formula (IAR) are each H. In another embodiment $R^{8A}$ and $R^{8B}$ in formula (IAR) are taken together along with the carbon atoms to which they are bound to form a ring. In another embodiment $R^{8A}$ and $R^{8B}$ in formula (IAR) are taken together along with the carbon atoms to which they are bound to form an unsubstituted cycloalkyl ring. In another embodiment $R^{8A}$ and $R^{8B}$ in formula (IAR) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(R$^{16}$). In another embodiment $R^{8A}$ and $R^{8B}$ in formula (IAR) are taken together along with the carbon atoms to which they are bound to form a cyclopropyl ring thus making the compound of formula (IAR) a compound of the formula (IAR.1):

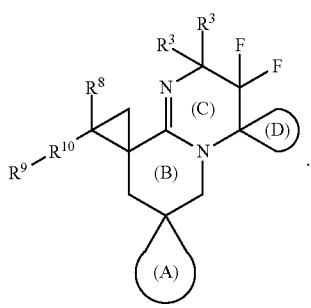

(IAR.1)

Another embodiment of this invention is directed to compounds of formula (I) having the formula:

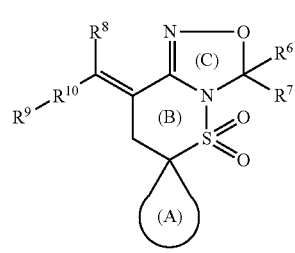

(IAS)

wherein all substituents are as defined for formula (I) or any one of the embodiments of formula (I) described above.

Another embodiment of this invention is directed to compounds of formula (I) having the formula:

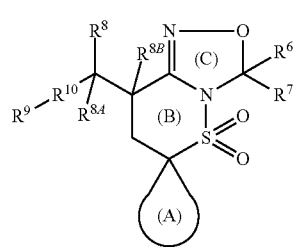

(IAT)

wherein all substituents are as defined for formula (I) or any one of the embodiments of formula (I) described above. In one embodiment, $R^{8A}$ and $R^{8B}$ in formula (IAT) are each H. In another embodiment $R^{8A}$ and $R^{8B}$ formula (IAT) are taken together along with the carbon atoms to which they are bound to form a ring. In another embodiment $R^{8A}$ and $R^{8B}$ in formula (IAT) are taken together along with the carbon atoms to which they are bound to form an unsubstituted cycloalkyl ring. In another embodiment $R^{8A}$ and $R^{8B}$ in formula (IAT) are taken together along with the carbon atoms to which they are bound to form a cycloalkyl ring substituted with 1 to 3 substituents independently selected from the group consisting of alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$). In another embodiment $R^{8A}$ and $R^{8B}$ in formula (IAH) are taken together along with the carbon atoms to which they are bound to form a cyclopropyl ring thus making the compound of formula (IAH) a compound of the formula (IAT.1):

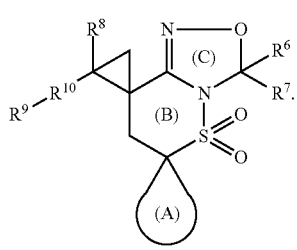

(IAT.1)

Another embodiment of this invention is directed to compounds of formula (I) having the formula:

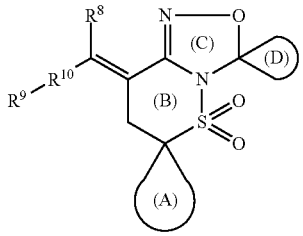
(IAU)

wherein all substituents are as defined for formula (I) or any one of the embodiments of formula (I) described above, and wherein Ring (D) is the ring formed by taking $R^6$ and $R^7$ together with the carbon atom to which they are bound.

Another embodiment of this invention is directed to compounds of formula (I) having the formula:

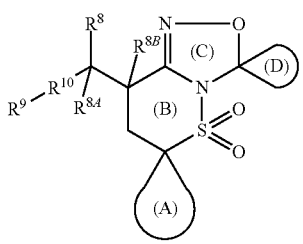
(IAV)

wherein all substituents are as defined for formula (I) or any one of the embodiments of formula (I) described above, and wherein Ring (D) is the ring formed by taking $R^6$ and $R^7$ together with the carbon atom to which they are bound. In one embodiment, $R^{8A}$ and $R^{8B}$ in formula (IAV) are each H. In another embodiment $R^{8A}$ and $R^{8B}$ in formula (IAV) are taken together along with the carbon atoms to which they are bound to form a ring. In another embodiment $R^{8A}$ and $R^{8B}$ in formula (IAV) are taken together along with the carbon atoms to which they are bound to form an unsubstituted cycloalkyl ring. In another embodiment $R^{8A}$ and $R^{8B}$ in formula (IAV) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$). In another embodiment $R^{8A}$ and $R^{8B}$ in formula (IAV) are taken together along with the carbon atoms to which they are bound to form a cyclopropyl ring thus making the compound of formula (IAV) a compound of the formula (IAV.1):

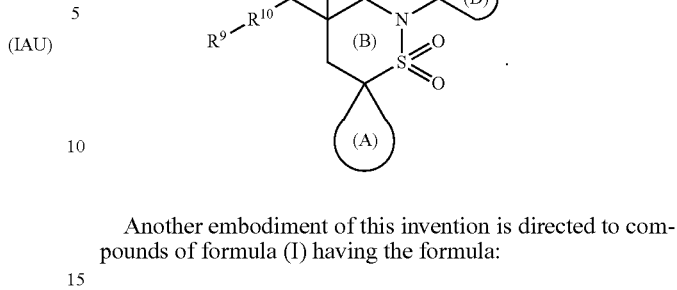
(IAV.1)

Another embodiment of this invention is directed to compounds of formula (I) having the formula:

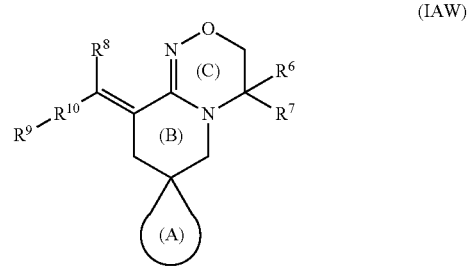
(IAW)

wherein all substituents are as defined for formula (I) or any one of the embodiments of formula (I) described above.

Another embodiment of this invention is directed to compounds of formula (I) having the formula:

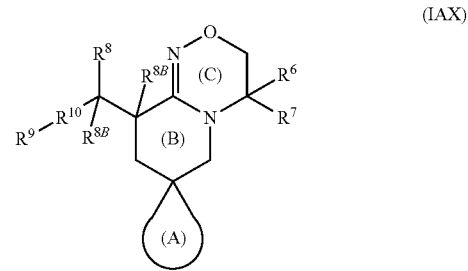
(IAX)

wherein all substituents are as defined for formula (I) or any one of the embodiments of formula (I) described above. In one embodiment, $R^{8A}$ and $R^{8B}$ in formula (IAX) are each H. In another embodiment $R^{8A}$ and $R^{8B}$ in formula (IAX) are taken together along with the carbon atoms to which they are bound to form a ring. In another embodiment $R^{8A}$ and $R^{8B}$ in formula (IAX) are taken together along with the carbon atoms to which they are bound to form an unsubstituted cycloalkyl ring. In another embodiment $R^{8A}$ and $R^{8B}$ in formula (IAX) are taken together along with the carbon atoms to which they are bound to form a cycloalkyl ring substituted with 1 to 3 substituents independently selected from the group consisting of: alkyl: alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$). In another embodiment $R^{8A}$ and $R^{8B}$ in formula (IAX) are taken together along with the carbon atoms to which they are bound to form a cyclopropyl ring thus making the compound of formula (IAX) a compound of the formula (IAX.1):

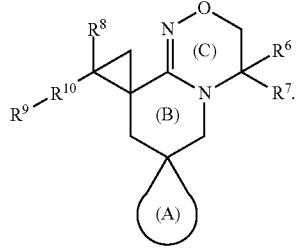

(IAX.1)

Another embodiment of this invention is directed to compounds of formula (I) having the formula:

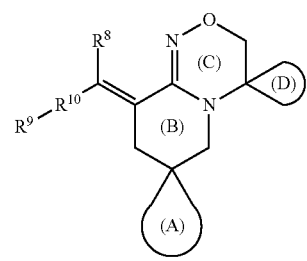

(IAY)

wherein all substituents are as defined for formula (I) or any one of the embodiments of formula (I) described above, and wherein Ring (D) is the ring formed by taking $R^6$ and $R^7$ together with the carbon atom to which they are bound.

Another embodiment of this invention is directed to compounds of formula (I) having the formula:

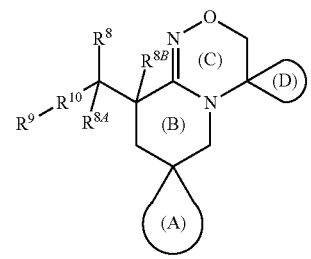

(IAZ)

wherein all substituents are as defined for formula (I) or any one of the embodiments of formula (I) described above, and wherein Ring (D) is the ring formed by taking $R^6$ and $R^7$ together with the carbon atom to which they are bound. In one embodiment, $R^{8A}$ and $R^{8B}$ in formula (IAZ) are each H. In another embodiment $R^{8A}$ and $R^{8B}$ in formula (IAZ) are taken together along with the carbon atoms to which they are bound to form a ring. In another embodiment $R^{8A}$ and $R^{8B}$ in formula (IAZ) are taken together along with the carbon atoms to which they are bound to form an unsubstituted cycloalkyl ring. In another embodiment $R^{8A}$ and $R^{8B}$ in formula (IAZ) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$). In another embodiment R$^{8A}$ and R$^{8B}$ in formula (IAZ) are taken together along with the carbon atoms to which they are bound to form a cyclopropyl ring thus making the compound of formula (IAZ) a compound of the formula (IAZ.1):

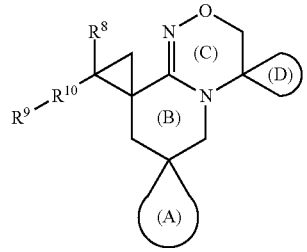

(IAZ.1)

Another embodiment of this invention is directed to compounds of formula (I) having the formula:

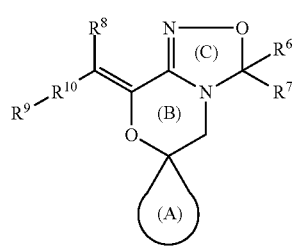

(IBA)

wherein all substituents are as defined for formula (I) or any one of the embodiments of formula (I) described above.

Another embodiment of this invention is directed to compounds of formula (I) having the formula:

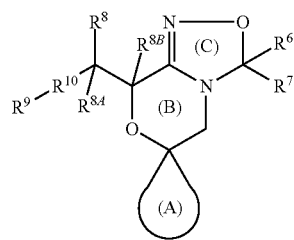

(IBB)

wherein all substituents are as defined for formula (I) or any one of the embodiments of formula (I) described above. In one embodiment, $R^{8A}$ and $R^{8B}$ in formula (IBB) are each H. In another embodiment $R^{8A}$ and $R^{8B}$ in formula (IBB) are taken together along with the carbon atoms to which they are bound to form a ring. In another embodiment $R^{8A}$ and $R^{8B}$ in formula (IBB) are taken together along with the carbon atoms to which they are bound to form an unsubstituted cycloalkyl ring. In another embodiment $R^{8A}$ and $R^{8B}$ in formula (IBB) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH₃), —C(O)R¹⁵, —C(O)OR¹⁵, —C(O)N(R¹⁵)(R¹⁶), —S(O)N(R¹⁵)(R¹⁶), —S(O)₂N(R¹⁵)(R¹⁶), —C(=NOR¹⁵)R¹⁶, and —P(O)(OR¹⁵)(OR¹⁶). In another embodiment R⁸ᴬ and R⁸ᴮ in formula (IBB) are taken together along with the carbon atoms to which they are bound to form a cyclopropyl ring thus making the compound of formula (IBB) a compound of the formula (IBB.1):

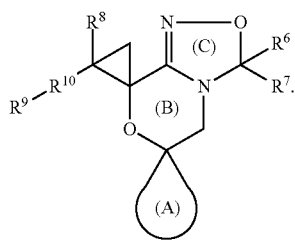

(IBB.1)

Another embodiment of this invention is directed to compounds of formula (I) having the formula:

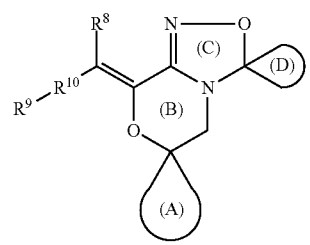

(IBC)

wherein all substituents are as defined for formula (I) or any one of the embodiments of formula (I) described above, and wherein Ring (D) is the ring formed by taking R⁶ and R⁷ together with the carbon atom to which they are bound.

Another embodiment of this invention is directed to compounds of formula (I) having the formula:

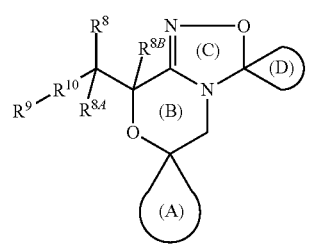

(IBD)

wherein all substituents are as defined for formula (I) or any one of the embodiments of formula (I) described above, and wherein Ring (D) is the ring formed by taking R⁶ and R⁷ together with the carbon atom to which they are bound. In one embodiment, R⁸ᴬ and R⁸ᴮ in formula (IBD) are each H. In another embodiment R⁸ᴬ and R⁸ᴮ in formula (IBDF) are taken together along with the carbon atoms to which they are bound to form a ring. In another embodiment R⁸ᴬ and R⁸ᴮ in formula (IBD) are taken together along with the carbon atoms to which they are bound to form an unsubstituted cycloalkyl ring. In another embodiment R⁸ᴬ and R⁸ᴮ in formula (IBD) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR¹⁵ (e.g., —CH₃), —C(O)R¹⁵, —C(O)OR¹⁵, —C(O)N(R¹⁵)(R¹⁶), —S(O)N(R¹⁵)(R¹⁶), —S(O)₂N(R¹⁵)(R¹⁶), —C(=NOR¹⁵)R¹⁶, and —P(O)(OR¹⁵)(OR¹⁶). In another embodiment R⁸ᴬ and R⁸ᴮ in formula (IBD) are taken together along with the carbon atoms to which they are bound to form a cyclopropyl ring thus making the compound of formula (IBD) a compound of the formula (IBD.1):

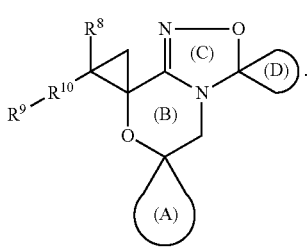

(IBD.1)

Another embodiment of this invention is directed to compounds of formula (I) having the formula:

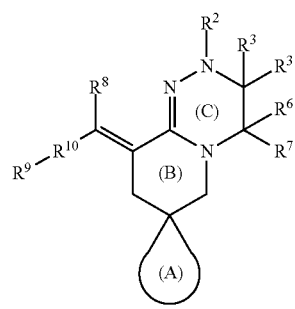

(IBE)

wherein all substituents are as defined for formula (I) or any one of the embodiments of formula (I) described above.

Another embodiment of this invention is directed to compounds of formula (I) having the formula:

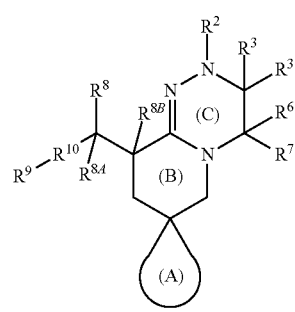

(IBF)

wherein all substituents are as defined for formula (I) or any one of the embodiments of formula (I) described above. In one embodiment, R⁸ᴬ and R⁸ᴮ. In formula (IBF) are each H. In another embodiment R⁸ᴬ and R⁸ᴮ in formula (IBF) are taken together along with the carbon atoms to which they are bound to form a ring. In another embodiment $R^{8A}$ and $R^{8B}$ in formula (IBF) are taken together along with the carbon atoms to which they are bound to form an unsubstituted cycloalkyl ring. In another embodiment $R^{8A}$ and $R^{8B}$ in formula (IBF) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$). In another embodiment $R^{8A}$ and $R^{8B}$ in formula (IBF) are taken together along with the carbon atoms to which they are bound to form a cyclopropyl ring thus making the compound of formula (IBF) a compound of the formula (IBF.1):

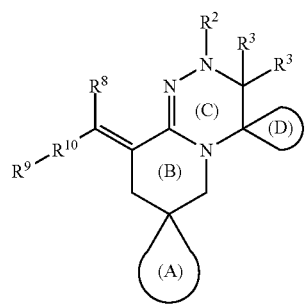

(IBF.1)

Another embodiment of this invention is directed to compounds of formula (I) having the formula:

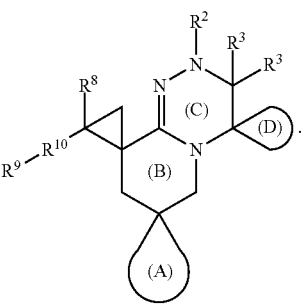

(IBG)

wherein all substituents are as defined for formula (I) or any one of the embodiments of formula (I) described above, and wherein Ring (D) is the ring formed by taking R$^6$ and R$^7$ together with the carbon atom to which they are bound.

Another embodiment of this invention is directed to compounds of formula (I) having the formula:

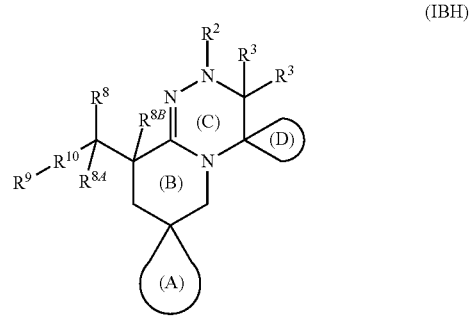

(IBH)

wherein all substituents are as defined for formula (I) or any one of the embodiments of formula (I) described above, and wherein Ring (D) is the ring formed by taking R$^6$ and R$^7$ together with the carbon atom to which they are bound. In one embodiment, $R^{8A}$ and $R^{8B}$ in formula (IBH) are each H. In another embodiment $R^{8A}$ and $R^{8B}$ in formula (IBH) are taken together along with the carbon atoms to which they are bound to form a ring. In another embodiment $R^{8A}$ and $R^{8B}$ in formula (IBH) are taken together along with the carbon atoms to which they are bound to form an unsubstituted cycloalkyl ring. In another embodiment $R^{8A}$ and $R^{8B}$ in formula (IBH) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$). In another embodiment $R^{8A}$ and $R^{8B}$ in formula (IBH) are taken together along with the carbon atoms to which they are bound to form a cyclopropyl ring thus making the compound of formula (IBH) a compound of the formula (IBH.1):

(IBH.1)

Another embodiment of this invention is directed to compounds of formula (I) having the formula:

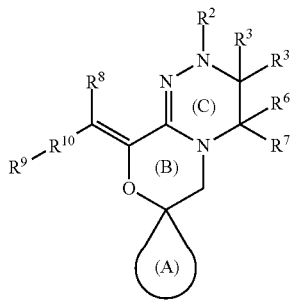
(IBI)

wherein all substituents are as defined for formula (I) or any one of the embodiments of formula (I) described above.

Another embodiment of this invention is directed to compounds of formula (I) having the formula:

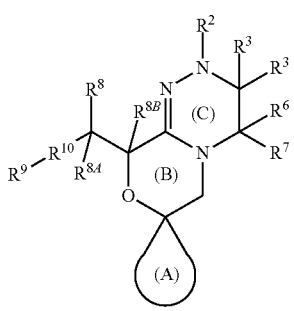
(IBJ)

wherein all substituents are as defined for formula (I) or any one of the embodiments of formula (I) described above. In one embodiment, $R^{8A}$ and $R^{8B}$ in formula (IBJ) are each H. In another embodiment $R^{8A}$ and $R^{8B}$ in formula (IBJ) are taken together along with the carbon atoms to which they are bound to form a ring. In another embodiment $R^{8A}$ and $R^{8B}$ in formula (IBJ) are taken together along with the carbon atoms to which they are bound to form en unsubstituted cycloalkyl ring. In another embodiment $R^{8A}$ and $R^{8B}$ in formula (IBJ) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$). In another embodiment $R^{8A}$ and $R^{8B}$ in formula (IBJ) are taken together along with the carbon atoms to which they are bound to form a cyclopropyl ring thus making the compound of formula (IBJ) a compound of the formula (IBJ.1):

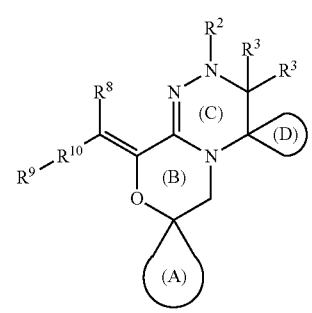
(IBJ.1)

Another embodiment of this invention is directed to compounds of formula (I) having the formula:

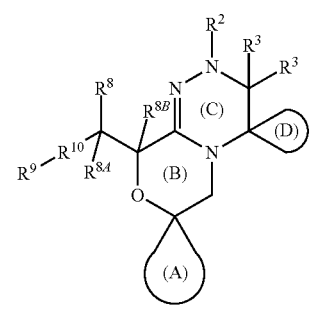
(IBK)

wherein all substituents are as defined for formula (I) or any one of the embodiments of formula (I) described above, and wherein Ring (D) is the ring formed by taking $R^6$ and $R^7$ together with the carbon atom to which they are bound.

Another embodiment of this invention is directed to compounds of formula (I) having the formula:

(IBL)

wherein all substituents are as defined for formula (I) or any one of the embodiments of formula (I) described above, and wherein Ring (D) is the ring formed by taking $R^6$ and $R^7$ together with the carbon atom to which they are bound. In one embodiment, $R^{8A}$ and $R^{8B}$ in formula (IBL) are each H. In another embodiment $R^{8A}$ and $R^{8B}$ in formula (IBL) are taken together along with the carbon atoms to which they are bound to form a ring. In another embodiment $R^{8A}$ and $R^{8B}$ in formula (IBL) are taken together along with the carbon atoms to which they are bound to form an unsubstituted cycloalkyl ring. In another embodiment $R^{8A}$ and $R^{8B}$ in formula (IBL) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$). In another embodiment R$^{8A}$ and R$^{8B}$ in formula (IBL) are taken together along with the carbon atoms to which they are bound to form a cyclopropyl ring thus making the compound of formula (IBL) a compound of the formula (IBL.1):

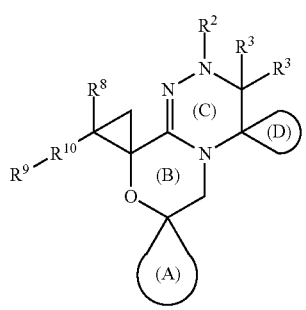

(IBL.1)

Another embodiment of this invention is directed to compounds of formula (I) having the formula:

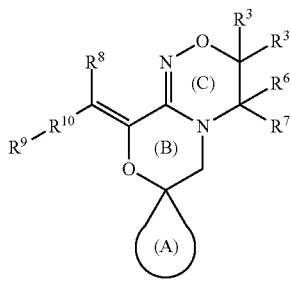

(IBM)

wherein all substituents are as defined for formula (I) or any one of the embodiments of formula (I) described above.

Another embodiment of this invention is directed to compounds of formula (I) having the formula:

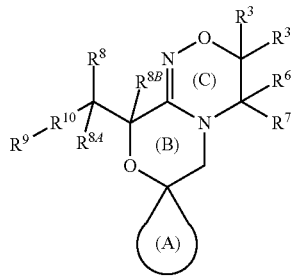

(IBN)

wherein all substituents are as defined for formula (I) or any one of the embodiments of formula (I) described above. In one embodiment, R$^{8A}$ and R$^{8B}$ in formula (IBN) are each H. In another embodiment R$^{8A}$ and R$^{8B}$ in formula (IBN) are taken together along with the carbon atoms to which they are bound to form a ring. In another embodiment R$^{8A}$ and R$^{8B}$ in formula (IBN) are taken together along with the carbon atoms to which they are bound to form an unsubstituted cycloalkyl ring. In another embodiment R$^{8A}$ and R$^{8B}$ formula (IBN) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N(R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$). In another embodiment R$^{8A}$ and R$^{8B}$ in formula (IBN) are taken together along with the carbon atoms to which they are bound to form a cyclopropyl ring thus making the compound of formula (IBN) a compound of the formula (IBN.1):

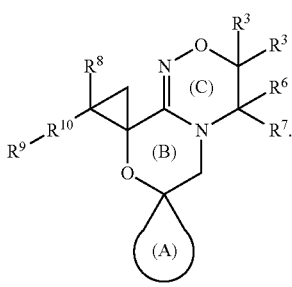

(IBN.1)

Another embodiment of this invention is directed to compounds of formula (I) having the formula:

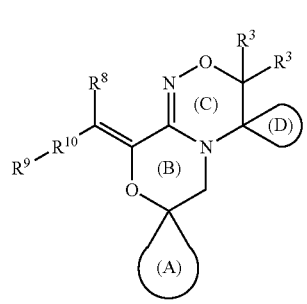

(IBO)

wherein all substituents are as defined for formula (I) or any one of the embodiments of formula (I) described above, and wherein Ring (D) is the ring formed by taking R$^6$ and R$^7$ together with the carbon atom to which they are bound.

Another embodiment of this invention is directed to compounds of formula (I) having the formula:

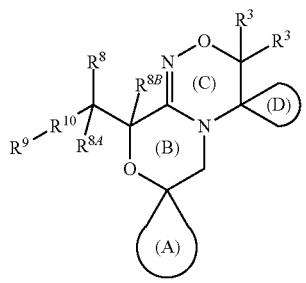

(IBP)

wherein all substituents are as defined for formula (I) or any one of the embodiments of formula (I) described above, and wherein Ring (D) is the ring formed by taking $R^6$ and $R^7$ together with the carbon atom to which they are bound. In one embodiment, $R^{8A}$ and $R^{8B}$ in formula (IBP) are each H. In another embodiment $R^{8A}$ and $R^{8B}$ in formula (IBP) are taken together along with the carbon atoms to which they are bound to form a ring. In another embodiment $R^{8A}$ and $R^{8B}$ in formula (IBP) are taken together along with the carbon atoms to which they are bound to form an unsubstituted cycloalkyl ring. In another embodiment $R^{8A}$ and $R^{8B}$ in formula (IBP) are taken together along with the carbon atoms to which they are bound to form a cycloalkyl ring substituted with 1 to 3 substituents independently selected from the group consisting of: alkyl, alkenyl, alkynyl, cycloalkyl, cycloalkylalkyl, cycloalkenyl, heterocyclyl, heterocyclylalkyl, aryl, arylalkyl, heteroaryl, heteroarylalkyl, —CN, halo, =O, —OR$^{15}$ (e.g., —CH$_3$), —C(O)R$^{15}$, —C(O)OR$^{15}$, —C(O)N(R$^{15}$)(R$^{16}$), —S(O)N (R$^{15}$)(R$^{16}$), —S(O)$_2$N(R$^{15}$)(R$^{16}$), —C(=NOR$^{15}$)R$^{16}$, and —P(O)(OR$^{15}$)(OR$^{16}$). In another embodiment $R^{8A}$ and $R^{8B}$ in formula (IBP) are taken together along with the carbon atoms to which they are bound to form a cyclopropyl ring thus making the compound of formula (IBP) a compound of the formula (IBP.1):

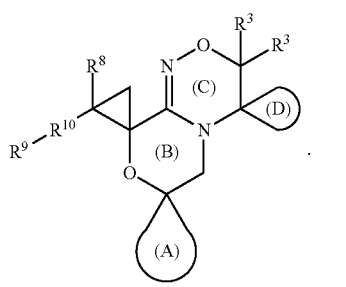

(IBP.1)

Other embodiments of this invention are directed to any one of the embodiments directed to compounds IAK, IAL, IAL.1, IAM, IAN, IAN.1, IBE, IBF, IBF.1, IBG, IBH, IBH.1, IBI, IBJ, IBJ.1, IBK, IBL, IBL.1, IBM, IBN, IBN.1, IBO, IBP, and IBP.1 wherein each $R^3$ is H.

Other embodiments of this invention are directed to any one of the embodiments directed to compounds IAO, IAP, IAP.1, IAQ, IAR, and IAR.1 wherein each $R^3$ is H.

Other embodiments of this invention are directed to any one of the embodiments directed to compounds IBE, IBF, IBF.1, IBG, IBH, IBH.1, IBI, IBJ, IBJ.1, IBK, IBL, IBL.1 wherein $R^2$ is H.

Other embodiments of this invention are directed to any one of the embodiments directed to compounds IBE, IBF, IBF.1, IBG, IBH, IBH.1, IBI, IBJ, IBJ.1, IBK, IBL, IBL.1 wherein $R^2$ is alkyl (such as, for example, methyl or ethyl).

Other embodiments of this invention are directed to any one of the embodiments directed to compounds IBE, IBF, IBF.1, IBG, IBH, IBH.1, IBI, IBJ, IBJ.1, IBK, IBL, IBL.1 wherein $R^2$ is H, and each $R^3$ is H.

Other embodiments of this invention are directed to any one of the embodiments directed to compounds IBE, IBF, IBF.1, IBG, IBH, IBH.1, IBI, IBJ, IBJ.1, IBK, IBL, IBL.1 wherein $R^2$ is alkyl (such as, for example, methyl or ethyl), and each $R^3$ is H.

Other embodiments of this invention are directed to any one of the embodiments directed to compounds IA, IB, IB.1, IC, ID, ID.1, ID.2, ID.3, II, IJ, IJ.1, IK, IL, IL.1, IQ, IR, IR.1, IS, IT, IT.1, IY, IZ, IZ.1, IAA, IAB, IAB.1, IAG, IAH, IAH.1, IAK, IAL, IAL.1, IAO, IAP, IAP.1, IAS, IAT, IAT.1, IAW, IAX, IAX.1, IBA, IBB, IBB.1, (BE, IBF, IBF.1, IBI, IBJ, IBJ.1, IBM, IBN, and IBN.1 wherein (1) Ring (A) is selected from the group consisting of 1a to 33a, (2) the $R^9$ is selected from the group consisting of 1g to 13g, (3) $R^{10}$ is selected from the group consisting of 1f to 39f, (4) $R^6$ is selected from the group consisting of H, alkyl (e.g., methyl or ethyl), alkyl substituted with —OR$^{15}$ (e.g., —OH), and alkyl substituted with —S(O)$_2$R$^{15A}$ (and in one example said $R^{15A}$ is alkyl (e.g., methyl, ethyl or propyl), and in another example said $R^{15A}$ is (R$^{18}$)$_q$-alkyl- wherein $R^{18}$ is selected from the group consisting of halo (e.g., F) and cycloalkyl (e.g., cyclopropyl)), and (5) $R^7$ is selected from the group consisting of 1d to 35d.

Other embodiments of this invention are directed to any one of the embodiments directed to compounds IA, IB, IB.1, IC, ID, ID.1, ID.2, ID.3, II, IJ, IJ.1, IK, IL, IL.1, IQ, IR, IR.1, IS, IT, IT.1, IY, IZ, IZ.1, IAA, IAB, IAB.1, IAG, IAH, IAH.1, IAK, IAL, IAL.1, IAP, IAP.1, IAS, IAT, IAT.1, IAW, IAX, IAX.1, IBA, IBB, IBB.1, IBE, IBF, IBF.1, IBI, IBJ, IBJ.1, IBM, IBN, and IBN.1 wherein (1) Ring (A) is selected from the group consisting of 1a to 33a. (2) the $R^9$ is H, (3) $R^{10}$ is selected from the group consisting of 1f to 39f, (4) $R^6$ is selected from the group consisting of H, alkyl (e.g., methyl or ethyl), alkyl substituted with —OR$^{15}$ (e.g., —OH), and alkyl substituted with —S(O)$_2$R$^{15A}$ (and in one example said is alkyl (e.g., methyl, ethyl or propyl), and in another example said $R^{15A}$ is (R$^{18}$)$_q$-alkyl- wherein $R^{18}$ is selected from the group consisting of halo (e.g., F) and cycloalkyl (e.g., cyclopropyl)), and (5) $R^7$ is selected from the group consisting of 1d to 35d.

Other embodiments of this invention are directed to any one of the embodiments directed to compounds IA, IB, IB.1, IC, ID, ID.1, ID.2, ID.3, II, IJ, IJ.1, IK, IL, IL.1, IQ, IR, IR.1, IS, IT, IT.1, IY, IZ, IZ.1, IAA, IAB, IAB.1, IAG, IAH, IAH.1, IAK, IAL, IAL.1, IAO, IAP, IAP.1, IAS, IAT, IAT.1, IAW, IAX, IAX.1, IBA, IBB, IBB.1, IBE, IBF, IBF.1, IBI, IBJ, IBJ.1, IBM, IBN, and IBN.1 wherein (1) Ring (A) is selected from the group consisting of 1a to 33a, (2) the $R^9$ is selected from the group consisting of 1g to 13g, (3) $R^{10}$ is selected from the group consisting of 1f to 39f, (4) $R^6$ is selected from the group consisting of H, methyl, ethyl, —CH$_2$OH, —CH (OH)CH$_3$, —(CH$_2$)$_2$S(O)$_2$CH$_3$, —CH(CH$_3$)CH$_2$S(O)$_2$ CH$_2$CH$_3$, —(CH$_2$)$_2$S(O)$_2$(CH$_2$)$_2$CH$_3$, —CH$_2$CH(CH$_3$)S (O)$_2$ CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, and (5) $R^7$ is selected from the group consisting of 1d to 35d.

Other embodiments of this invention are directed to any one of the embodiments directed to compounds IA, IB, IB.1, IC, ID, ID.1, ID.2, ID.3, II, IJ, IJ.1, IK, IL, IL.1, IQ, IR, IR.1, IS, IT, IT.1, IY, IZ, IZ.1, IAA, IAB, IAB.1, IAG, IAH, IAH.1, IAK, IAL, IAL.1, IAO, IAP, IAP.1, IAS, IAT, IAT.1, IAW, IAX, IAX.1, IBA, IBB, IBB.1, IBE, IBF, IBF.1, IBI, IBJ, IBJ.1, IBM, IBN, and IBN.1 wherein (1) Ring (A) is selected from the group consisting of 1a to 33a, (2) the $R^9$ is H, (3) $R^{10}$ is selected from the group consisting of 1f to 39f, (4) $R^6$ is selected from the group consisting of H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, and (5) $R^7$ is selected from the group consisting of 1d to 35d.

Other embodiments of this invention are directed to any one of the embodiments directed to compounds IA, IB, IB.1, IC, ID, ID.1, ID.2, ID.3, II, IJ, IJ.1, IK, IL, IL.1, IQ, IR, IR.1, IS, IT, IT.1, IY, IZ, IZ.1, IAA, IAB, IAB.1, IAG, IAH, IAH.1, IAK, IAL, IAL.1, IAO, IAP, IAP.1, IAS, IAT, IAT.1, IAW, IAX, IAX.1, IBA, IBB, IBB.1, IBE, IBF, IBF.1, IBI, IBJ, IBJ.1, IBM, IBN, and IBN.1 wherein (1) Ring (A) is selected from the group consisting of 1a to 33a, (2) the $R^9$—$R^{10}$— moiety is selected from the group consisting of 1b to 50b, (3) $R^6$ is selected from the group consisting of H, alkyl (e.g., methyl or ethyl), alkyl substituted with —OR$^{15}$ (e.g., —OH), and alkyl substituted with —S(O)$_2$R$^{15A}$ in one example said R$^{15A}$ is alkyl (e.g., methyl, ethyl or propyl), and in another example said R$^{15A}$ is (R$^{18}$)$_q$-alkyl- wherein R$^{18}$ is selected from the group consisting of halo (e.g., F) and cycloalkyl (e.g., cyclopropyl)), and (4) $R^7$ is selected from the group consisting of 1d to 35d.

Other embodiments of this invention are directed to any one of the embodiments directed to compounds IA, IB, IBA, IC, ID, ID.1, ID.2, ID.3, II, IJ, IJ.1, IK, IL, IL.1, IQ, IR, IR.1, IS, IT, IT.1, IY, IZ, IZ.1, IAA, IAB, IAB.1, IAG, IAH, IAH.1, IAK, IAL, IAL.1, IAO, IAP, IAP.1, IAS, IAT, IAT.1, IAW, IAX, IAX.1, IBA, IBB, IBB.1, IBE, IBF, IBF.1, IBI, IBJ, IBJ.1, IBM, IBN, and IBN.1 wherein (1) Ring (A) is selected from the group consisting of 1a to 33a, (2) the $R^9$—$R^{10}$— moiety is selected from the group consisting of 1b to 50b, (3) $R^6$ is selected from the group consisting of H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, and (4) $R^7$ is selected from the group consisting of 1d to 35d.

Other embodiments of this invention are directed to any one of the embodiments directed to compounds IA, IB, IB.1, IC, ID, ID.1, ID.2, ID.3, II, IJ, IJ.1, IK, IL, IL.1, IQ, IR, IR.1, IS, IT, IT.1, IY, IZ, IZ.1, IAA, IAB, IAB.1, IAG, IAH, IAH.1, IAK, IAL, IAL.1, IAO, IAP, IAP.1, IAS, IAT, IAT.1, IAW, IAX, IAX.1, IBA, IBB, IBB.1, IBE, IBF, IBF.1, IBI, IBJ, IBJ.1, IBM, IBN, and IBN.1 wherein (1) Ring (A) is selected from the group consisting of 1a to 33a, (2) the $R^9$—$R^{10}$— moiety is 50b, (3) $R^6$ is selected from the group consisting of H, methyl, ethyl, —CH$_2$OH, —CH(OH)CH$_3$, —(CH$_2$)$_2$S(O)$_2$ CH$_3$, —CH(CH$_3$)CH$_2$S(O)$_2$CH$_2$CH$_3$, —(CH$_2$)$_2$S(O)$_2$ (CH$_2$)$_2$CH$_3$, —CH$_2$CH(CH$_3$)S(O)$_2$CH$_3$, —(CH$_2$)$_2$S(O)$_2$ CH$_2$CH$_3$, —(CH$_2$)$_2$S(O)$_2$CF$_3$, and —(CH$_2$)S(O)$_2$ CH$_2$cyclopropyl, and (4) $R^7$ is selected from the group consisting of 1d to 35d.

Other embodiments of this invention are directed to any one of the embodiments directed to compounds IA, IB, IB.1, IC, ID, ID.1, ID.2, ID.3, II, IJ, IJ.1, IK, IL, IL.1, IQ, IR, IR.1, IS, IT, IT.1, IY, IZ, IZ.1, IAA, IAB, IAB.1, IAG, IAH, IAH.1, IAK, IAL, IAL.1, IAO, IAP, IAP.1, IAS, IAT, IAT.1, IAW, IAX, IAX.1, IBA, IBB, IBB.1, IBE, IBF, IBF.1, IBI, IBJ, IBJ.1, IBM, IBN, and IBN.1 wherein Ring (A) is 1a.

Other embodiments of this invention are directed to any one of the embodiments directed to compounds IE, IF, IF.1, IG, IH, IH.1, IM, IN, IN.1, IO, IP, IP.1, IU, IV, IV.1, IW, IX, IX.1, IAC, IAD, IAD.1, IAE, IAF, IAF.1, IAI, IAJ, IAJ.1, IAM, IAN, IAN.1, IAQ, IAR, IAR.1, IAU, IAV, IAV.1, IAY, IAZ, IAZ.1, IBC, IBD, IBD.1, IBG, IBH, IBH.1, IBK, IBL, IBL.1, IBO, IBP, and IBP.1 wherein (1) Ring (A) is selected from the group consisting of 1a to 33a, (2) the $R^9$ is selected from the group consisting of 1g to 13g, (3) $R^{10}$ is selected from the group consisting of 1f to 39f, and (4) Ring (D) is selected from the group consisting of 1e to 8e.

Other embodiments of this invention are directed to any one of the embodiments directed to compounds IE, IF, IF.1, IG, IH, IH.1, IM, IN, IN.1, IO, IP, IP.1, IU, IV, IV.1, IW, IX, IX.1, IAC, IAD, IAD.1, IAE, IAF, IAF.1, IAI, IAJ, IAJ.1, IAM, IAN, IAN.1, IAQ, IAR, IAR.1, IAU, IAV, IAV.1, IAY, IAZ, IAZ.1, IBC, IBD, IBD.1, IBG, IBH, IBH.1, IBK, IBL, IBL.1, IBO, IBP, and IBP.1 wherein (1) Ring (A) is selected from the group consisting of 1a to 33a, (2) the $R^9$ is H, (3) $R^{10}$ is selected from the group consisting of 1f to 39f, and (4) Ring (D) is selected from the group consisting of 1e to 8e.

Other embodiments of this invention are directed to any one of the embodiments directed to compounds IE, IF, IF.1, IG, IH, IH.1, IM, IN, IN.1, IO, IP, IP.1, IU, IV, IV.1, IW, IX, IX.1, IAC, IAD, IAD.1, IAE, IAF, IAF.1, IAI, IAJ, IAJ.1, IAM, IAN, IAN.1, IAQ, IAR, IAR.1, IAU, IAV, IAV.1, IAY, IAZ, IAZ.1, IBC, IBD, IBD.1, IBG, IBH, IBH.1, IBK, IBL, IBL.1, IBO, IBP, and IBP.1 wherein (1) Ring (A) is selected from the group consisting of 1a to 33a, (2) the $R^9$—$R^{10}$— moiety is selected from the group consisting of 1b to 50b, and (3) Ring (D) is selected from the group consisting of 1e to 8e.

Other embodiments of this invention are directed to any one of the embodiments directed to compounds IE, IF, IF.1, IG, IH, IH.1, IM, IN, IN.1, IO, IP, IP.1, IU, IV, IV.1, IW, IX, IX.1, IAC, IAD, IAD.1, IAE, IAF, IAF.1, IAI, IAJ, IAJ.1, IAM, IAN, IAN.1, IAQ, IAR, IAR.1, IAV, IAV.1, IAY, IAZ, IAZ.1, IBC, IBD, IBD.1, IBG, IBH, IBH.1, IBK, IBL, IBL.1, IBO, IBP, and IBP.1 wherein (1) Ring (A) is selected from the group consisting of 1a to 33a, (2) the $R^9$ moiety is 50b, and (3) Ring (D) is selected from the group consisting of 1e to 8e.

Other embodiments of this invention are directed to any one of the embodiments directed to compounds IE, IF, IF.1, IG, IH, IH.1, IM, IN, IN.1, IO, IP, IP.1, IU, IV, IV.1, IW, IX, IX.1, IAC, IAD, IAD.1, IAE, IAF, IAF.1, IAI, IAJ, IAJ.1, IAM, IAN, IAN.1, IAQ, IAR, IAR.1, IAU, IAV, IAV.1, IAY, IAZ, IAZ.1, IBC, IBD, IBD.1, IBG, IBH, IBH.1, IBK, IBL, IBL.1, IBO, IBP, and IBP.1 wherein Ring (A) is 1a.

Other embodiments of this invention are directed to any one of the embodiments directed to compounds IA, IC, II, IK, IS, IY, IAA, IAG, IAK, IAO, IAS, IAW, IBA, IBI, and IBM wherein (1) Ring (A) is selected from the group consisting of 1a to 33a, (2) the $R^9$ is selected from the group consisting of 1g to 13g, (3) $R^{10}$ is selected from the group consisting of 1f to 39f, (4) $R^6$ is selected from the group consisting of H, alkyl (e.g., methyl or ethyl), alkyl substituted with —OR$^{15}$ (e.g., —OH), and alkyl substituted with —S(O)$_2$R$^{15A}$ (and in one example said R$^{15A}$ is alkyl (e.g., methyl, ethyl or propyl), and in another example said R$^{15A}$ is (R$^{18}$)$_q$-alkyl- wherein R$^{18}$ is selected from the group consisting of halo (e.g., F) and cycloalkyl (e.g., cyclopropyl)), and (5) $R^7$ is selected from the group consisting of 1d to 35d.

Other embodiments of this invention are directed to any one of the embodiments directed to compounds IA, IC, II, IK, IS, IY, IAA, IAG, IAK, IAO, IAS, IAW, IBA, IBI, and IBM wherein (1) Ring (A) is selected from the group consisting of 1a to 33a, (2) the $R^9$ is H, (3) $R^{10}$ is selected from the group consisting of 1f to 39f, (4) $R^6$ is selected from the group consisting of H, alkyl (e.g., methyl or ethyl), alkyl substituted with —OR$^{15}$ (e.g., —OH), and alkyl substituted with —S j(O)$_2$ R$^{15A}$ (and in one example said R$^{15A}$ is alkyl (e.g., methyl, ethyl or propyl), and in another example said R$^{15A}$ is (R$^{18}$)$_q$-alkyl- wherein R$^{18}$ is selected from the group consisting of halo (e.g., F) and cycloalkyl (e.g., cyclopropyl)), and (5) R$^7$ is selected from the group consisting of 1d to 35d.

Other embodiments of this invention are directed to any one of the embodiments directed to compounds IA, IC, II, IK, IS, IY, IAA, IAG, IAK, IAO, IAS, IAW, IBA, IBI, and IBM wherein (1) Ring (A) is selected from the group consisting of 1a to 33a, (2) the R$^9$ is selected from the group consisting of 1g to 13g, (3) R$^{10}$ is selected from the group consisting of 1f to 39f, (4) R$^6$ is selected from the group consisting of H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$ CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, and (5) R$^7$ is selected from the group consisting of 1d to 35d.

Other embodiments of this invention are directed to any one of the embodiments directed to compounds IA, IC, II, IK, IS, IY, IAA, IAG, IAK, IAO, IAS, IAW, IBA, IBI, and IBM wherein (1) Ring (A) is selected from the group consisting of 1a to 33a, (2) the R$^9$ is H, (3) R$^{10}$ is selected from the group consisting of 1f to 39f, (4) R$^6$ is selected from the group consisting of H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, and (5) R$^7$ is selected from the group consisting of 1d to 35d.

Other embodiments of this invention are directed to any one of the embodiments directed to compounds IA, IC, II, IK, IS, IY, IAA, IAG, IAK, IAO, IAS, IAW, IBA, IBI, and IBM wherein (1) Ring (A) is selected from the group consisting of 1a to 33a, (2) the R$^9$—R$^{10}$— moiety is selected from the group consisting of 1b to 50b, (3) R$^6$ is selected from the group consisting of H, alkyl (e.g., methyl or ethyl), alkyl substituted with —OR$^{15}$ (e.g., —OH), and alkyl substituted with —S(O)$_2$R$^{15A}$ (and in one example said R$^{15A}$ is alkyl (e.g., methyl, ethyl or propyl), and in another example said R$^{15A}$ is (R$^{18}$)$_q$-alkyl- wherein R$^{18}$ is selected from the group consisting of halo (e.g., F) and cycloalkyl (e.g., cyclopropyl)), and (4) R$^7$ is selected from the group consisting of 1d to 35d.

Other embodiments of this invention are directed to any one of the embodiments directed to compounds IA, IC, II, IK, IS, IY, IAA, IAG, IAK, IAO, IAS, IAW, IBA, IBI, and IBM wherein (1) Ring (A) is selected from the group consisting of 1a to 33a, (2) the R$^9$—R$^{10}$— moiety is selected from the group consisting of 1b to 50b, (3) R$^6$ is selected from the group consisting of H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, and (4) R$^7$ is selected from the group consisting of 1d to 35d.

Other embodiments of this invention are directed to any one of the embodiments directed to compounds IA, IC, II, IK, IS, IY, IAA, IAG, IAK, IAO, IAS, IAW, IBA, IBI, and IBM wherein (1) Ring (A) is selected from the group consisting of 1a to 33a, (2) the R$^9$—R$^{10}$— moiety is 50b, (3) R$^6$ is selected from the group consisting of H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, and (4) R$^7$ is selected from the group consisting of 1d to 35d.

Other embodiments of this invention are directed to any one of the embodiments directed to compounds IA, IC, II, IK, IS, IY, IAA, IAG, IAK, IAO, IAS, IAW, IBA, IBI, and IBM wherein Ring (A) is 1a.

Other embodiments of this invention are directed to any one of the embodiments directed to compounds IE, IG, IM, IO, IU, IW, IAC, IAF, IAF, IAI, IAM, IAQ, IAU, IAY, IBC, IBG, IBK, and IBO wherein (1) Ring (A) is selected from the group consisting of 1a to 33a, (2) the R$^9$ is selected from the group consisting of 1g to 13g, (3) R$^{10}$ is selected from the group consisting of 1f to 39f, and (4) Ring (D) is selected from the group consisting of 1e to 8e.

Other embodiments of this invention are directed to any one of the embodiments directed to compounds IE, IG, IM, IO, IU, IW, IAC, IAE, IAF, IAI, IAM, IAQ, IAU, IAY, IBC, IBG, IBK, and IBO wherein (1) Ring (A) is selected from the group consisting of 1a to 33a, (2) the R$^9$ is H, (3) R$^{10}$ is selected from the group consisting of 1f to 39f, and (4) Ring (D) is selected from the group consisting of 1e to 8e.

Other embodiments of this invention are directed to any one of the embodiments directed to compounds IE, IG, IM, IO, IU, IW, IAC, IAE, IAF, IAI, IAM, IAQ, IAU, IAY, IBC, IBG, IBK, and IBO wherein (1) Ring (A) is selected from the group consisting of 1a to 33a, (2) the R$^9$—R$^{10}$— moiety is selected from the group consisting of 1b to 50b, and (3) Ring (D) is selected from the group consisting of 1e to 8e.

Other embodiments of this invention are directed to any one of the embodiments directed to compounds IE, IG, IM, IO, IU, IW, IAC, IAE, IAF, IAI, IAM, IAQ, IAU, IAY, IBC, IBG, IBK, and IBO wherein (1) Ring (A) is selected from the group consisting of 1a to 33a, (2) the R$^9$—R$^{10}$— moiety is 50b, and (3) Ring (D) is selected from the group consisting of 1e to 8e.

Other embodiments of this invention are directed to any one of the embodiments directed to compounds IE, IG, IM, IO, IU, IW, IAC, IAE, IAF, IAI, IAM, IAQ, IAU, IAY, IBC, IBG, IBK, and IBO wherein Ring (A) is 1a.

Other embodiments of this invention are directed to any one of the embodiments directed to compounds IB, ID, IJ, IL, IR, IT, IZ, IAB, IAH, IAL, IAP, IAT, IAX, IBB, IBF, IBJ, and IBN wherein (1) Ring (A) is selected from the group consisting of 1a to 33a, (2) the R$^9$ is selected from the group consisting of 1g to 13g, (3) R$^{10}$ is selected from the group consisting of 1f to 39f, (4) R$^6$ is selected from the group consisting of H, alkyl (e.g., methyl or ethyl), alkyl substituted with —OR$^{15}$ (e.g., —OH), and alkyl substituted with —S(O)$_2$ R$^{15A}$ (and in one example said R$^{15A}$ is alkyl (e.g., methyl, ethyl or propyl), and in another example said R$^{15A}$ is (R$^{18}$)$_q$-alkyl- wherein R$^{18}$ is selected from the group consisting of halo (e.g., F) and cycloalkyl (e.g., cyclopropyl)), and (5) R$^7$ is selected from the group consisting of 1d to 35d.

Other embodiments of this invention are directed to any one of the embodiments directed to compounds IB, ID, IJ, IL, IR, IT, IZ, IAB, IAH, IAL, IAP, IAT, IAX, IBB, IBF, IBJ, and IBN wherein (1) Ring (A) is selected from the group consisting of 1a to 33a, (2) the R$^9$ is H, (3) R$^{10}$ is selected from the group consisting of 1f to 39f, (4) R$^6$ is selected from the group consisting of H, alkyl (e.g., methyl or ethyl), alkyl substituted with —OR$^{15}$ (e.g., —OH), and alkyl substituted with —S(O)$_2$ R$^{15A}$ (and in one example said R$^{15A}$ is alkyl (e.g., methyl, ethyl or propyl), and in another example said R$^{15A}$ is (R$^{18}$)$_q$-alkyl- wherein R$^{18}$ is selected from the group consisting of halo (e.g., F) and cycloalkyl (e.g., cyclopropyl)), and (5) R$^7$ is selected from the group consisting of 1d to 35d.

Other embodiments of this invention are directed to any one of the embodiments directed to compounds IB, ID, IJ, IL, IR, IT, IZ, IAB, IAH, IAL, IAP, IAT, IAX, IBB, IBF, IBJ, and IBN wherein (1) Ring (A) is selected from the group consisting of 1a to 33a, (2) the $R^9$ is selected from the group consisting of 1g to 13g, (3) $R^{10}$ is selected from the group consisting of 1f to 39f, (4) $R^6$ is selected from the group consisting of H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$, and (5) $R^7$ is selected from the group consisting of 1d to 35d.

Other embodiments of this invention are directed to any one of the embodiments directed to compounds IB, ID, IJ, IL, IR, IT, IZ, IAB, IAH, IAL, IAP, IAT, IAX, IBB, IBF, IBJ, and IBN wherein (1) Ring (A) is selected from the group consisting of 1a to 33a, (2) the $R^9$ is H, (3) $R^{16}$ is selected from the group consisting of 1f to 39f, (4) $R^6$ is selected from the group consisting of H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$, and (5) $R^7$ is selected from the group consisting of 1d to 35d.

Other embodiments of this invention are directed to any one of the embodiments directed to compounds IB, ID, IJ, IL, IR, IT, IZ, IAB, IAH, IAL, IAP, IAT, IAX, IBB, IBF, IBJ, and IBN wherein (1) Ring (A) is selected from the group consisting of 1a to 33a, (2) the $R^9$—$R^{10}$— moiety is selected from the group consisting of 1b to 50b, (3) $R^6$ is selected from the group consisting of H, alkyl (e.g., methyl or ethyl), alkyl substituted with —$OR^{15}$ (e.g., —OH), and alkyl substituted with —$S(O)_2R^{15A}$ (and in one example said $R^{15A}$ is alkyl (e.g., methyl, ethyl or propyl), and in another example said $R^{15A}$ is $(R^{18})_q$-alkyl- wherein $R^{18}$ is selected from the group consisting of halo (e.g., F) and cycloalkyl (e.g., cyclopropyl)), and (4) $R^7$ is selected from the group consisting of 1d to 35d.

Other embodiments of this invention are directed to any one of the embodiments directed to compounds IB, ID, IJ, IL, IR, IT, IZ, IAB, IAH, IAL, IAP, IAT, IAX, IBB, IBF, IBJ, and IBN wherein (1) Ring (A) is selected from the group consisting of 1a to 33a, (2) the $R^9$—$R^{10}$— moiety is selected from the group consisting of 1b to 50b, (3) $R^6$ is selected from the group consisting of H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$, and (4) $R^7$ is selected from the group consisting of 1d to 35d Other embodiments of this invention are directed to any one of the embodiments directed to compounds IB, ID, IJ, IL, IR, IT, IZ, IAB, IAH, IAL, IAP, IAT, IAX, IBB, IBF, IBJ, and IBN wherein (1) Ring (A) is selected from the group consisting of 1a to 33a, (2) the $R^9$—$R^{10}$— moiety is 50b, (3) $R^6$ is selected from the group consisting of H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2cyclopropyl$, and (4) $R^7$ is selected from the group consisting of 1d to 35d.

Other embodiments of this invention are directed to any one of the embodiments directed to compounds IB, ID, II, IL, IR, IT, IZ, IAB, IAH, IAL, IAP, IAT, IAX, IBB, IBF, IBJ, and IBN wherein Ring (A) is 1a.

Other embodiments of this invention are directed to any one of the embodiments directed to compounds IF, IH, IN, IP, IV, IX, IAD, IAF, IAJ, IAN, IAR, IAV, IAZ, IBD, IBH, IBL, and IBP wherein (1) Ring (A) is selected from the group consisting of 1a to 33a, (2) the $R^9$ is selected from the group consisting of 1g to 13g, (3) $R^{10}$ is selected from the group consisting of 1f to 39f, and (4) Ring (D) is selected from the group consisting of 1e to 8e.

Other embodiments of this invention are directed to any one of the embodiments directed to compounds IF, IH, IN, IP, IV, IX, IAD, IAF, IN, IAN, IAR, IAV, IAZ, IBD, IBH, IBL, and IBP wherein (1) Ring (A) is selected from the group consisting of 1a to 33a, (2) the $R^9$ is H, (3) $R^{10}$ selected from the group consisting of 1f to 39f, and (4) Ring (D) is selected from the group consisting of 1e to 8e.

Other embodiments of this invention are directed to any one of the embodiments directed to compounds IF, IH, IN, IP, IV, IX, IAD, IAF, IAJ, IAN, IAR, IAV, IAZ, IBD, IBH, IBL, and IBP wherein (1) Ring (A) is selected from the group consisting of is to 33a, (2) the $R^9$—$R^{10}$— moiety is selected from the group consisting of 1b to 50b, and (3) Ring (D) is selected from the group consisting of 1e to 8e.

Other embodiments of this invention are directed to any one of the embodiments directed to compounds IF, IH, IN, IP, IV, IX, IAD, IAF, IAJ, IAN, IAR, IAV, IAZ, IBD, IBH, IBL, and IBP wherein (1) Ring (A) is selected from the group consisting of 1a to 33a, (2) the $R^9$—$R^{10}$— moiety is 50b, and (3) $R^6$ and $R^7$ taken together with the carbon atom to which they are bound form a ring selected from the group consisting of 1e to 8e.

Other embodiments of this invention are directed to any one of the embodiments directed to compounds IF, IH, IN, IP, IV, IX, IAD, IAF, IAJ, IAN, IAR, IAV, IAZ, IBD, IBH, IBL, and IBP wherein Ring (A) is 1a.

Other embodiments of this invention are directed to any one of the embodiments directed to compounds IB.1, ID.1, ID.2, ID.3, IJ.1, IL.1, IR.1, IT.1, IZ.1, IAB.1, IAH.1, IAL.1, IAP.1, IAT.1, IAX.1, IBB.1, IBF.1, IBJ.1 and IBN.1 wherein (1) Ring (A) is selected from the group consisting of 1a to 33a, (2) the $R^9$ is selected from the group consisting of 1g to 13g, (3) $R^{10}$ is selected from the group consisting of 1f to 39f, (4) $R^6$ is selected from the group consisting of H, alkyl (e.g., methyl or ethyl), alkyl substituted with —$OR^{15}$ (e.g., —OH), and alkyl substituted with —$S(O)_2R^{15A}$ (and in one example said $R^{15A}$ is alkyl (e.g., methyl, ethyl or propyl), and in another example said $R^{15A}$ is $(R^{18})_q$-alkyl- wherein $R^{18}$ is selected from the group consisting of halo (e.g., F) and cycloalkyl (e.g., cyclopropyl)), and (5) $R^7$ is selected from the group consisting of 1d to 35d.

Other embodiments of this invention are directed to any one of the embodiments directed to compounds IB.1, ID.1, ID.2, ID.3, IJ.1, IL.1, IR.1, IT.1, IZ.1, IAB.1, IAH.1, IAL.1, IAP.1, IAT.1, IAX.1, IBB.1, IBF.1, IBJ.1 and IBN.1 wherein (1) Ring (A) is selected from the group consisting of 1a to 33a, (2) the $R^9$ is H, (3) $R^{10}$ is selected from the group consisting of 1f to 39f, (4) $R^5$ is selected from the group consisting of H, alkyl (e.g., methyl or ethyl), alkyl substituted with —$OR^{15}$ (e.g., —OH), and alkyl substituted with —$S(O)_2R^{15A}$ (and in one example said $R^{15A}$ is alkyl (e.g., methyl, ethyl or propyl), and in another example said $R^{15A}$ is $(R^{18})_q$-alkyl- wherein $R^{18}$ is selected from the group consisting of halo (e.g., F) and cycloalkyl (e.g., cyclopropyl)), and (5) $R^7$ is selected from the group consisting of 1d to 35d.

Other embodiments of this invention are directed to any one of the embodiments directed to compounds IB.1, ID.1, ID.2, ID.3, IJ.1, IL.1, IR.1, IT.1, IZ.1, IAB.1, IAH.1, IAL.1, IAP.1, IAT.1, IAX.1, IBB.1, IBF.1, IBJ.1 and IBN.1 wherein (1) Ring (A) is selected from the group consisting of 1a to 33a, (2) the $R^9$ is selected from the group consisting of 1g to 13g, (3) $R^{10}$ is selected from the group consisting of 1f to 39f, (4) $R^6$ is selected from the group consisting of H, methyl, ethyl, —$CH_2OH$, —$CH(OH)CH_3$, —$(CH_2)_2S(O)_2CH_3$, —CH (CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, and (5) R$^7$ is selected from the group consisting of 1d to 35d.

Other embodiments of this invention are directed to any one of the embodiments directed to compounds IB.1, ID.1, ID.2, ID.3, IJ.1, IL.1, IR.1, IT.1, IZ.1, IAB.1, IAH.1, IAL.1, IAP.1, IAT.1, IAX.1, IBB.1, IBF.1, IBJ.1 and IBN.1 wherein (1) Ring (A) is selected from the group consisting of 1a to 33a, (2) the R$^9$ is H, (3) R$^{10}$ is selected from the group consisting of 1f to 39f, (4) R$^6$ is selected from the group consisting of H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, and (5) R$^7$ is selected from the group consisting of 1d to 35d.

Other embodiments of this invention are directed to any one of the embodiments directed to compounds IB.1, ID.1, ID.2, ID.3, IJ.1, IL.1, IR.1, IT.1, IZ.1, IAB.1, IAH.1, IAL.1, IAP.1, IAT.1, IAX.1, IBB.1, IBF.1, IBJ.1 and IBN.1 wherein (1) Ring (A) is selected from the group consisting of 1a to 33a, (2) the R$^9$—R$^{10}$— moiety is selected from the group consisting of 1b to 50b, (3) R$^6$ is selected from the group consisting of H, alkyl (e.g., methyl or ethyl), alkyl substituted with —OR$^{15}$ (e.g., —OH), and alkyl substituted with —S(O)$_2$R$^{15A}$ (and in one example said R$^{15A}$ is alkyl (e.g., methyl, ethyl or propyl), and in another example said R$^{15A}$ is (R$^{18}$)$_q$-alkyl- wherein R$^{18}$ is selected from the group consisting of halo (e.g., F) and cycloalkyl cyclopropyl)), and (4) R$^7$ is selected from the group consisting of 1d to 35d.

Other embodiments of this invention are directed to any one of the 35d embodiments directed to compounds IB.1, ID.1, ID.2, ID.3, IJ.1, IL.1, IR.1, IT.1, IZ.1, IAB.1, IAH.1, IAL.1. IAP.1, IAT.1, IAX.1, IBB.1, IBF.1, IBJ.1 and IBN.1 wherein (1) Ring (A) is selected from the group consisting of 1a to 33a, (2) the R$^9$—R$^{10}$— moiety is selected from the group consisting of 1b to 50b, (3) R$^6$ is selected from the group consisting of H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, and (4) R$^7$ is selected from the group consisting of 1d to 35d.

Other embodiments of this invention are directed to any one of the embodiments directed to compounds IB.1, ID.1, ID.2, ID.3, IJ.1, IL.1, IR.1, IT.1, IZ.1, IAB.1, IAH.1, IAL.1, IAP.1, IAT.1, IAX.1, IBB.1, IBF.1, IBJ.1 and IBN.1 wherein (1) Ring (A) is selected from the group consisting of 1a to 33a, (2) the R$^9$—R$^{10}$— moiety is 50b, (3) R$^6$ is selected from the group consisting of H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, and (4) R$^7$ is selected from the group consisting of 1d to 35d Other embodiments of this invention are directed to any one of the embodiments directed to compounds IB.1, ID.1, ID.2, ID.3, IJ.1, IL.1, IR.1, IT.1, IZ.1, IAB.1, IAH.1, IAL.1, IAP.1, IAT.1, IAX.1, IBB.1, IBF.1, IBJ.1 and IBN.1 wherein Ring (A) is 1a.

Other embodiments of this invention are directed to any one of the embodiments directed to compounds IF.1, IH.1, IN.1, IP.1, IV.1, IX.1, IAD.1, IAF.1, IAJ.1, IAN.1, IAR.1, IAV.1, IAZ.1, IBD.1, IBH.1, IBL.1, and IBP.1 wherein (1) Ring (A) is selected from the group consisting of 1a to 33a, (2) the R$^9$ is selected from the group consisting of 1g to 13g, (3) R$^{10}$ is selected from the group consisting of 1f to 39f, and (4) Ring (D) is selected from the group consisting of 1e to 8e.

Other embodiments of this invention are directed to any one of the embodiments directed to compounds IF.1, IH.1, IN.1, IP.1, IV.1, IX.1, IAD.1, IAF.1, IAJ.1, IAN.1, IAR.1, IAV.1, IAZ.1, IBD.1, IBH.1, IBL.1, and IBP.1 wherein (1) Ring (A) is selected from the group consisting of 1a to 33a, (2) the R$^9$ is H, (3) R$^{16}$ is selected from the group consisting of 1f to 39f, and (4) Ring (ID) is selected from the group consisting of 1e to 8e.

Other embodiments of this invention are directed to any one of the embodiments directed to compounds IF.1, IH.1, IN.1, IP.1, IV.1, IX.1, IAD.1, IAF.1, IAJ.1, IAN.1, IAR.1, IAV.1, IAZ.1, IBD.1, IBH.1, IBL.1, and IBP.1 wherein (1) Ring (A) is selected from the group consisting of 1a to 33a, (2) the R$^9$—R$^{10}$— moiety is selected from the group consisting of 1b to 50b, and (3) Ring (D) is selected from the group consisting of 1e to 8e.

Other embodiments of this invention are directed to any one of the embodiments directed to compounds IF.1, IH.1, IN.1, IP.1, IV.1, IX.1, IAD.1, IAF.1, IAJ.1, IAN.1, IAR.1, IAV.1, IAZ.1, IBD.1, IBH.1, IBL.1, and IBP.1 wherein (1) Ring (A) is selected from the group consisting of 1a to 33a, (2) the R$^9$—R$^{10}$— moiety is 50b, and (3) Ring (D) is selected from the group consisting of 1e to 8e.

Other embodiments of this invention are directed to any one of the embodiments directed to compounds IF.1, IH.1, IN.1, IP.1, IV.1, IX.1, IAD.1, IAF.1, IAJ.1, IAN.1, 1AR.1, IAV.1, IAZ.1, IBD.1, IBH.1, IBL.1, and IBP.1 wherein Ring (A) is 1a.

Other embodiments of this invention are directed to any one of the embodiments directed to any one of formulas (IA) to (IAR), (IB.1), (ID.1), (IF.1), (IH.1), (IJ.1), (IL.1), (IN.1), (IP.1), (IR.1), (IT.1), (IV.1), (IX.1), (IZ.1), (IAB.1), (IAD.1), (IAF.1), (IAH.1), (IAJ.1), (IAL.1), (IAN.1), (IAP.1), and (IAR.1) wherein Ring (A) is cycloalkyl.

Other embodiments of this invention are directed to any one of the embodiments directed to any one of formulas (IA) to (IAR), (IB.1), (ID.1), (IF.1), (IH.1), (IJ.1), (IL.1), (IN.1), (IP.1), (IR.1), (IT.1), (IV.1), (IX.1), (IZ.1), (IAB.1), (IAD.1), (IAF.1), (IAH.1), (IAJ.1), (IAL.1), (IAN.1), (IAP.1), and (IAR.1) wherein Ring (A) is cyclopropyl.

Other embodiments of this invention are directed to any one of the embodiments directed to any one of the formulas (IAG), (IAH), (IAI), (IAJ), (IAK), (IAL), (IAM), (IAN), (IAO), (IAP), (IAQ), (IAR), (IAN.1), (IAJ.1), (IAL.1), (IAN.1), (IAP.1) and (IAR.1) wherein Ring (A) is cycloalkyl.

Other embodiments of this invention are directed to any one of the embodiments directed to any one of the formulas (IAG), (IAH), (IAI), (IAJ), (IAK), (IAL), (IAM), (IAN), (IAO), (IAP), (IAQ), (IAR), (IAH.1), (IAJ.1), (IAL.1), (IAN.1), (IAP.1), and (IAR.1) wherein Ring (A) is cyclopropyl.

Other embodiments of this invention are directed to any one of the embodiment directed to any one of formulas (IA) to (IAR), (IB.1), (ID.1), (IF.1), (IH.1), (IJ.1), (IL.1), (IN.1), (IP.1), (IT.1), (IV.1), (IX.1), (IAB.1), (IAD.1), (IAF.1), (IAH.1), (IAJ.1), (IAL.1), (IAN.1), (IAP.1), and (IAR.1) wherein Ring (A) is cycloalkenyl.

Other embodiments of this invention are directed to any one of the embodiments directed to any one of formulas (IA) to (IAR), (IB.1), (ID.1), (IF.1), (IH.1), (IJ.1), (IL.1), (IN.1), (IP.1), (IR.1), (IT.1), (IV.1), (IX.1), (IZ.1), (IAB.1), (IAD.1), (IAF.1), (IAH.1), (IAJ.1), (IAL.1), (IAN.1), (IAP.1), and (IAR.1) wherein Ring (A) is heterocycloalkyl.

Other embodiments of this invention are directed to any one of the embodiments directed to any one of formulas (IA)

to (IAR), (IB.1), (ID.1), (IF.1), (IH.1), (IJ.1), (IL.1), (IN.1), (IP.1), (IR.1), (IT.1), (IV.1), (IX.1), (IZ.1), (IAB.1), (IAD.1), (IAF.1), (IAH.1), (IAJ.1), (IAL.1), (IAN.1), (IAP.1), and (IAR.1) wherein Ring (A) is heterocycloalkenyl.

Other embodiments of this invention are directed to any one of the embodiments directed to any one of formulas v wherein the —$R^{10}$—$R^9$ moiety is:

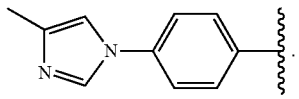 [SMILES: *c1ccc(-n2cnc(C)c2)cc1]

Other embodiments of this invention are directed to any one of the embodiments directed to any one of formulas (IA) to (IAR), (IB.1), (ID.1), (IF.1), (IH.1), (IJ.1), (IL.1), (IN.1), (IP.1), (IR.1), (IT.1), (IV.1), (IX.1), (IZ.1), (IAB.1), (IAD.1), (IAF.1), (IAH.1), (IAJ.1), (IAL.1), (IAN.1), (IAP.1), and (IAR.1) wherein the —$R^{10}$—$R^9$ moiety is:

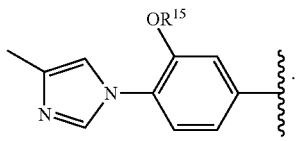

Other embodiments of this invention are directed to any one of the embodiments directed to any one of formulas (IA) to (IAR), (IB.1), (ID.1), (IF.1), (IH.1), (IJ.1), (IL.1), (IN.1), (IP.1), (IR.1), (IT.1), (IV.1), (IX.1), (IZ.1), (IAB.1), (IAD.1), (IAF.1), (IAH.1), (IAJ.1), (IAL.1), (IAN.1), (IAP.1), and (IAR.1) wherein the —$R^{10}$—$R^9$ moiety is:

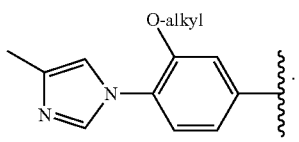

Other embodiments of this invention are directed to any one of the embodiments directed to any one of formulas (IA) to (IAR), (IB.1), (ID.1), (IF.1), (IH.1), (IJ.1), (IL.1), (IN.1), (IP.1), (IR.1), (IT.1), (IV.1), (IX.1), (IZ.1), (IAB.1), (IAD.1), (IAF.1), (IAH.1), (IAJ.1), (IAL.1), (IAN.1), (IAP.1), and (IAR.1) wherein the —$R^{10}$—$R^9$ moiety is:

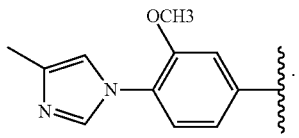 [SMILES: *c1ccc(-n2cnc(C)c2)c(OC)c1]

Other embodiments of this invention are directed to any one of the embodiments directed to any one of formulas (IA) to (ID), (II) to (IL), (IQ) to (IT), (IY) to (IAB), (IAG), (IAH), (IAK), (IAL), (IAO), (IAP), (IB.1), (ID.1), (IJ.1), (IL.1), (IR.1), (IT.1), (IZ.1), (IAB.1), (IAH.1), (IAL.1), and (IAP.1) wherein $R^6$ is alkyl.

Other embodiments of this invention are directed to any one of the embodiments directed to any one of formulas (IA) to (ID), (II) to (IL), (IQ) to (IT), (IY) to (IAB), (IAG), (IAH), (IAK), (IAL), (IAO), (IAP), (IB.1), (ID.1), (IJ.1), (IL.1), (IR.1), (IT.1), (IZ.1), (IAB.1), (IAH.1), (IAL.1), and (IAP.1) wherein $R^6$ is methyl.

Other embodiments of this invention are directed to any one of the embodiments directed to any one of formulas (IA) to (ID), (II) to (IL), (IQ) to (IT), (IY) to (IAB), (IAG), (IAH), (IAK), (IAL), (IAO), (IAP), (IB.1), (ID.1), (IJ.1), (IL.1), (IR.1), (IT.1), (IZ.1), (IAB.1), (IAH.1), (IAL.1), and (IAP.1) wherein $R^7$ is phenyl.

Other embodiments of this invention are directed to any one of the embodiments directed to any one of formulas (IA) to (ID), (II) to (IL), (IQ) to (IT), (IY) to (IAB), (IAG), (IAH), (IAK), (IAL), (IAO), (IAP), (IB.1), (ID.1), (IJ.1), (IL.1), (IR.1), (IT.1), (IZ.1), (IAB.1), (IAH.1), (IAL.1), and (IAP.1) wherein $R^7$ is phenyl substituted with 1 to 2 independently selected $R^2$ groups.

Other embodiments of this invention are directed to any one of the embodiments directed to any one of formulas (IA) to (ID), (II) to (IL), (IQ) to (IT), (IY) to (IAB), (IAG), (IAH), (IAK), (IAL), (IAO), (IAP), (IB.1), (ID.1), (IJ.1), (IL.1), (IR.1), (IT.1), (IZ.1), (IAB.1), (IAH.1), (IAL.1), and (IAP.1) wherein $R^7$ is phenyl substituted with 1 to 2 independently selected halos.

Other embodiments of this invention are directed to any one of the embodiments directed to any one of formulas (IA) to (ID), (II) to (IL), (IQ) to (IT), (IY) to (IAB), (IAG), (IAH), (IAK), (IAL), (IAO), (IAP), (IB.1), (ID.1), (IJ.1), (IL.1), (IR.1), (IT.1), (IZ.1), (IAB.1), (IAH.1), (IAL.1), and (IAP.1) wherein $R^7$ is phenyl substituted with 1 to 2 F.

Other embodiments of this invention are directed to any one of the embodiments directed to any one of formulas (IA) to (ID), (II) to (IL), (IQ) to (IT), (IY) to (IAB), (IAG), (IAH), (IAK), (IAL), (IAO), (IAP), (IB.1), (ID.1), (IJ.1), (IL.1), (IR.1), (IT.1), (IZ.1), (IAB.1), (IAH.1), (IAL.1), and (IAP.1) wherein $R^7$ is phenyl substituted with 1 F.

Other embodiments of this invention are directed to any one of the embodiments directed to any one of formulas (IA) to (ID), (II) to (IL), (IQ) to (IT), (IY) to (IAB), (IAG), (IAH), (IAK), (IAL), (IAO), (IAP), (IB.1), (ID.1), (IJ.1), (IL.1), (IR.1), (IT.1), (IZ.1), (IAB.1), (IAH.1), (IAL.1), and (IAP.1) wherein $R^7$ is p-F-phenyl.

Other embodiments of this invention are directed to any one of the embodiments directed to any one of formulas (IA) to (ID), (II) to (IL), (IQ) to (IT), (IY) to (IAB), (IAG), (IAH), (IAK), (IAL), (IAO), (IAP), (IB.1), (ID.1), (IJ.1), (IL.1), (IR.1), (IT.1), (IZ.1), (IAB.1), (IAH.1), (IAL.1), and (IAP.1) wherein:

Ring (A) is cycloalkyl (e.g., cyclopropyl);

the —$R^{10}$—$R^9$ moiety is:

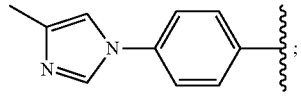

$R^6$ is alkyl (e.g., methyl); and $R^7$ is selected from the group consisting of: (1) phenyl, (2) phenyl substituted with 1 to 2 independently selected $R^{21}$ groups, (3) is phenyl substituted with 1 to 2 independently selected halos, (4) phenyl substituted with 1 to 2 F, (5) phenyl substituted with 1 F, and (6) p-F-phenyl.

Other embodiments of this invention are directed to any one of the embodiments directed to any one of formulas (IA) to (ID), (II) to (IL), (IQ) to (IT), (IY) to (IAB), (IAG), (IAH), (IAK), (IAL), (IAO), (IAP), (IB.1), (ID.1), (IJ.1), (IL.1), (IR.1), (IT.1), (IZ.1), (IAB.1), (IAH.1), (IAL.1), and (IAP.1) wherein:
Ring (A) is cycloalkyl (e.g., cyclopropyl);
the —R$^{10}$—R$^9$ moiety is:

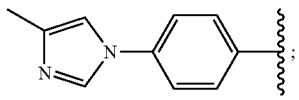 [SMILES: *c1ccc(-n2cnc(C)c2)cc1]

R$^6$ is alkyl (e.g., methyl); and
R$^7$ is selected from the group consisting of: (1) phenyl, (2) phenyl substituted with 1 to 2 F, (3) phenyl substituted with 1 F, and (4) p-F-phenyl.

Other embodiments of this invention are directed to any one of the embodiments directed to any one of formulas (IA) to (ID), (II) to (IL), (IQ) to (IT), (IY) to (IAB), (IAG), (IAH), (IAK), (IAL), (IAO), (IAP), (IB.1), (ID.1), (IJ.1), (IL.1), (IR.1), (IT.1), (IZ.1), (IAB.1), (IAH.1), (IAL.1), and (IAP.1) wherein:
Ring (A) is cycloalkyl (e.g., cyclopropyl);
the —R$^{10}$—R$^9$ moiety is:

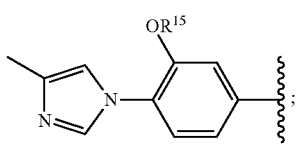

R$^6$ is alkyl (e.g., methyl); and
R$^7$ is selected from the group consisting of: (1) phenyl, (2) phenyl substituted with 1 to 2 independently selected R$^{21}$ groups, (3) is phenyl substituted with 1 to 2 independently selected halos, (4) phenyl substituted with 1 to 2 F, (5) phenyl substituted with 1 F, and (6) p-F-phenyl.

Other embodiments of this invention are directed to any one of the embodiments directed to any one of formulas (IA) to (ID), (II) to (IL), (IQ) to (IT), (IY) to (IAB), (IAG), (IAH), (IAK), (IAL), (IAO), (IAP), (IB.1), (ID.1), (IJ.1), (IL.1), (IR.1), (IT.1), (IZ.1), (IAB.1), (IAH.1), (IAL.1), and (IAP.1) wherein:
Ring (A) is cycloalkyl (e.g., cyclopropyl);
the —R$^{10}$—R$^9$ moiety is:

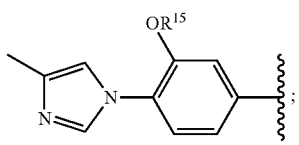

R$^6$ is alkyl (e.g., methyl); and
R$^7$ is selected from the group consisting of: (1) phenyl, (2) phenyl substituted with 1 to 2 F, (3) phenyl substituted with 1 F, and (4) p-F-phenyl.

Other embodiments of this invention are directed to any one of the embodiments directed to any one of formulas (IA) to (ID), (II) to (IL), (IQ) to (IT), (IY) to (IAB), (IAG), (IAH), (IAK), (IAL), (IAO), (IAP), (IB.1), (ID.1), (IJ.1), (IL.1), (IR.1), (IT.1), (IZ.1), (IAB.1), (IAH.1), (IAL.1), and (IAP.1) wherein:

Ring (A) is cycloalkyl (e.g., cyclopropyl);
the —R$^{10}$—R$^9$ moiety is:

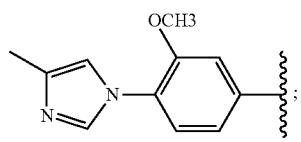

R$^6$ is alkyl (e.g., methyl); and
R$^7$ is selected from the group consisting of: (1) phenyl, (2) phenyl substituted with 1 to 2 independently selected R$^{21}$ groups, (3) is phenyl substituted with 1 to 2 independently selected halos, (4) phenyl substituted with 1 to 2 F, (5) phenyl substituted with 1 F, and (6) p-F-phenyl.

Other embodiments of this invention are directed to any one of the embodiments directed to any one of formulas (IA) to (ID), (II) to (IL), (IQ) to (IT), (IY) to (IAB), (IAG), (IAH), (IAK), (IAL), (IAO), (IAP), (IB.1), (ID.1), (IJ.1), (IL.1), (IR.1), (IT.1), (IZ.1), (IAB.1), (IAH.1), (IAL.1), and (IAP.1) wherein;
Ring (A) is cycloalkyl (e.g., cyclopropyl);
the —R$^{10}$—R$^9$ moiety is:

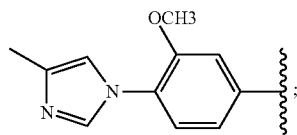

R$^6$ is alkyl (e.g., methyl); and
R$^7$ is selected from the group consisting of: (1) phenyl, (2) phenyl substituted with 1 to 2 F, (3) phenyl substituted with 1 F, and (4) p-F-phenyl.

In another embodiment of this invention the compound of formula (I) is selected from the group consisting of:

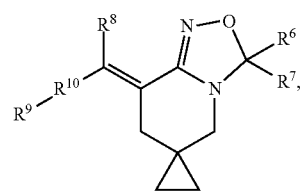

1c

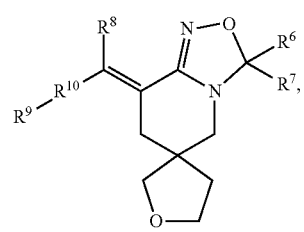

2c

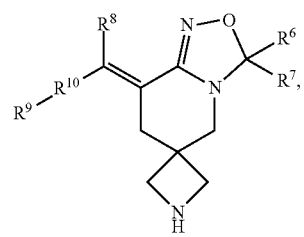

3c

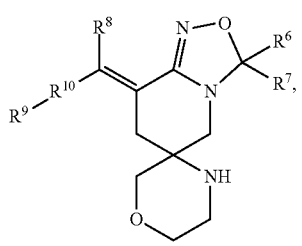
4c
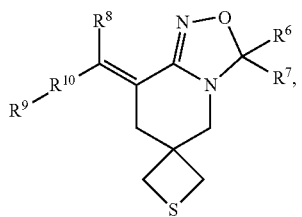
5c
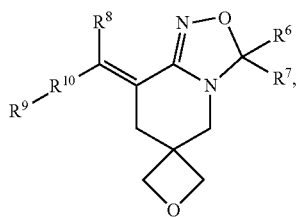
6c
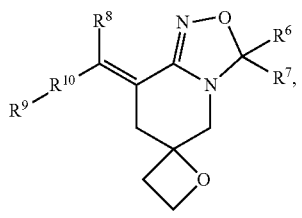
7c
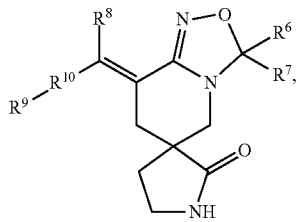
8c
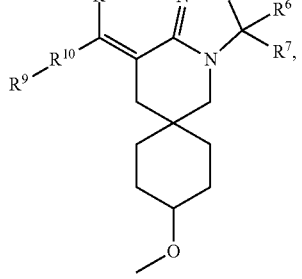
9c
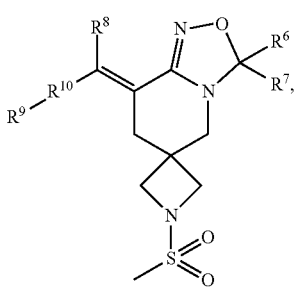
10c
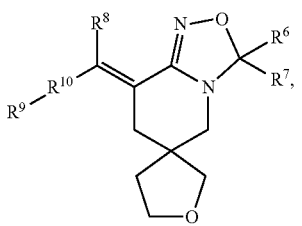
11c
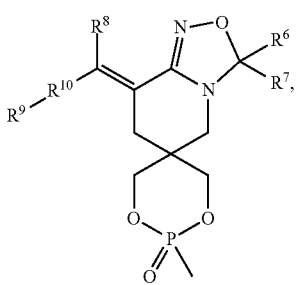
12c
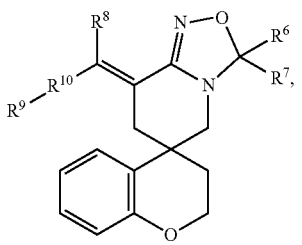
13c
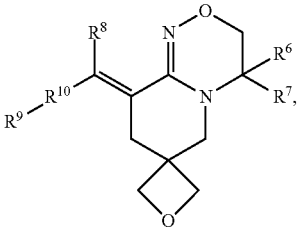
14c
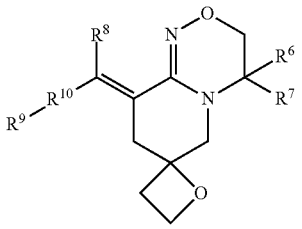
15c 16c
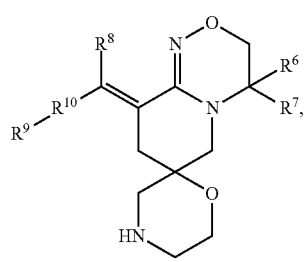
17c
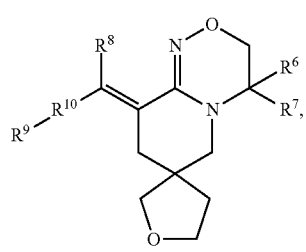
18c
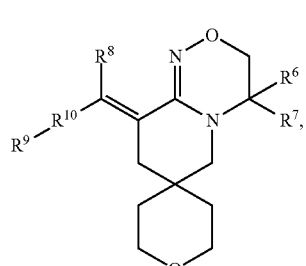
19c
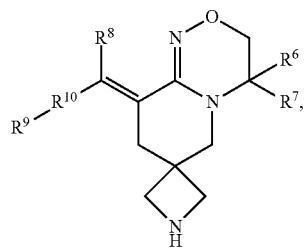
20c
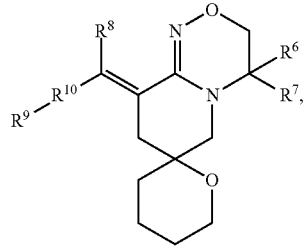
21c
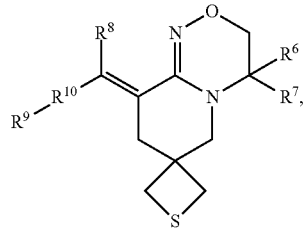
22c
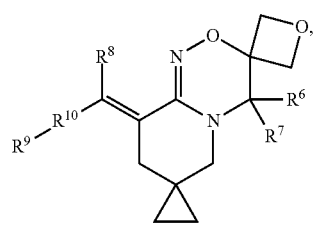
23c
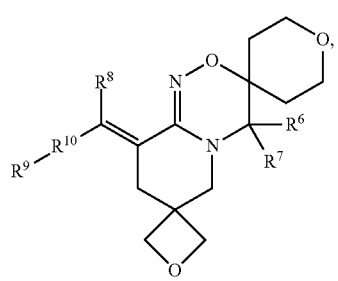
24c
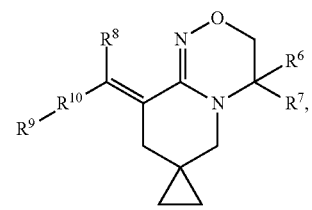
25c
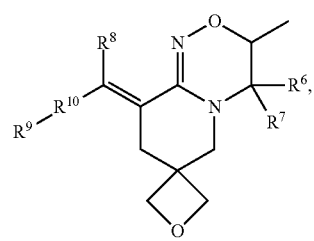
26c
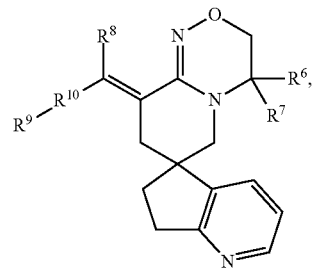
27c
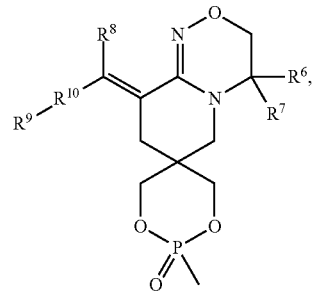

| | |
|---|---|
| 28c 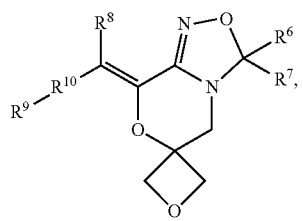 | 35c 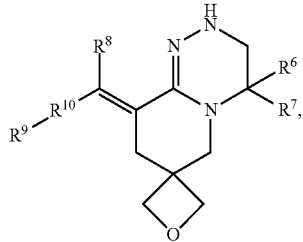 |
| 29c 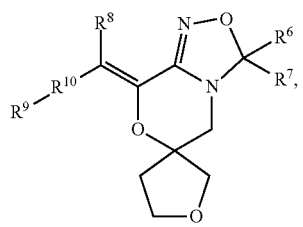 | 36c 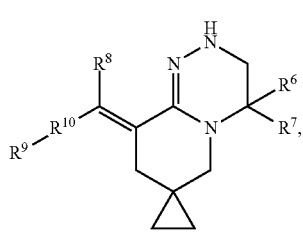 |
| 30c 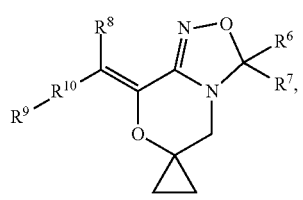 | 37c 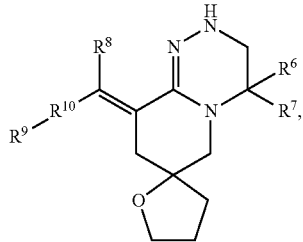 |
| 31c 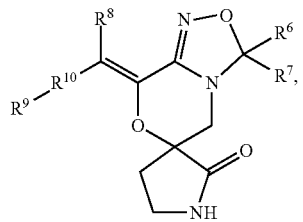 | 38c 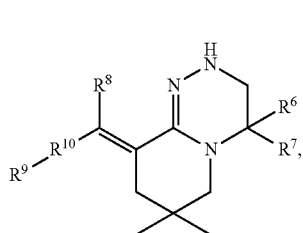 |
| 32c 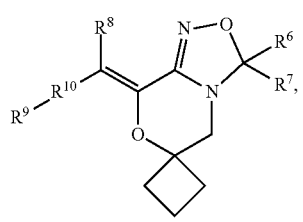 | 39c 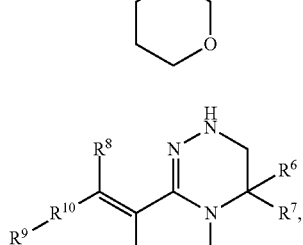 |
| 33c 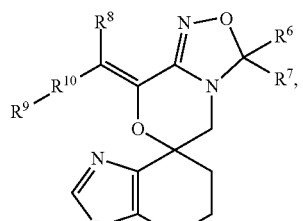 | 40c 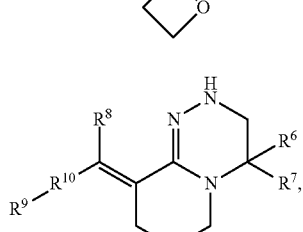 |
| 34c 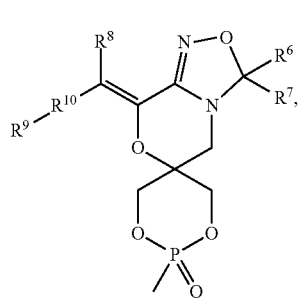 | |

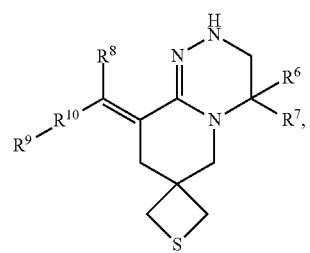
41c
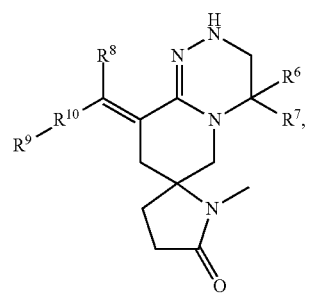
42c
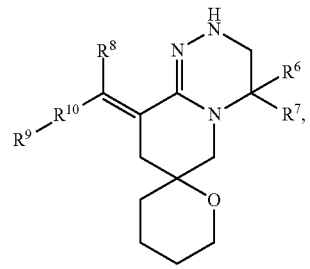
43c
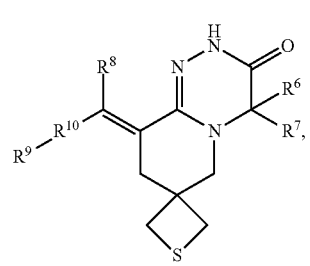
44c
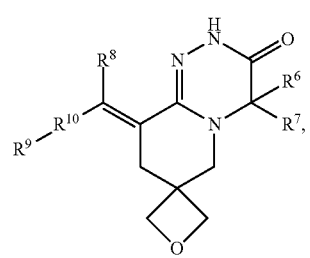
45c
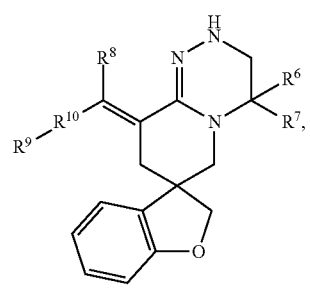
46c
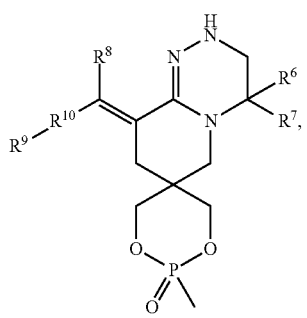
47c
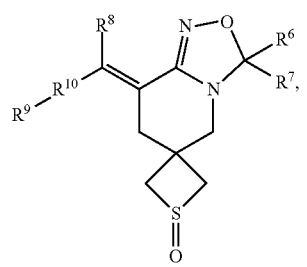
48c
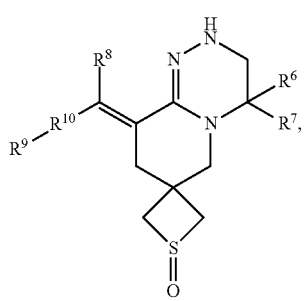
49c
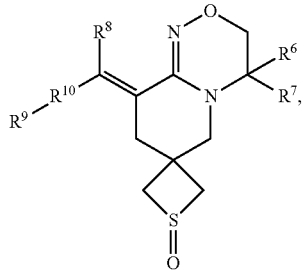
50c
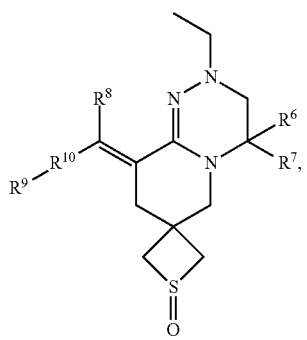
51c

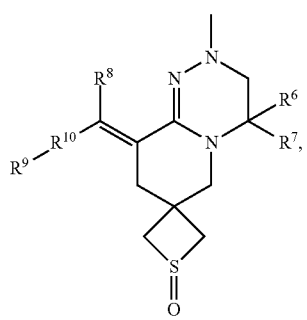
52c
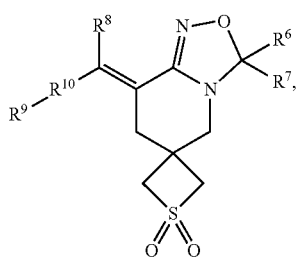
57c
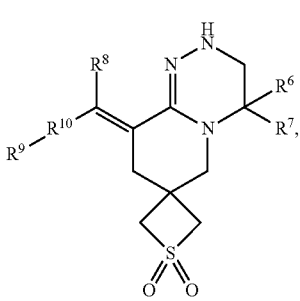
58c
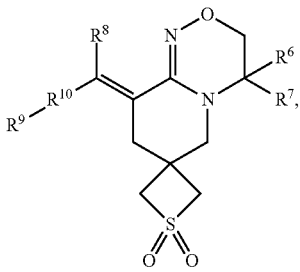
59c
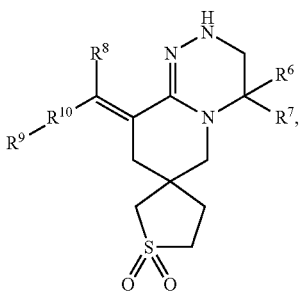
60c
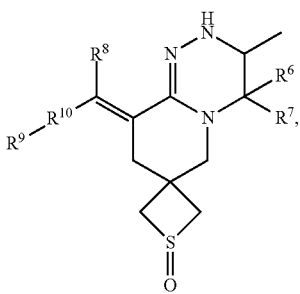
61c 62c 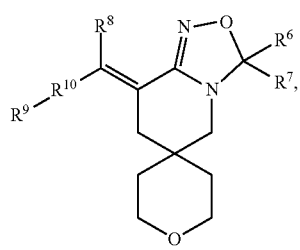
63c 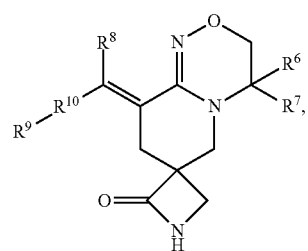
64c 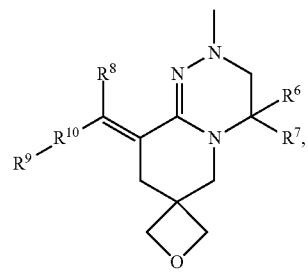
65c 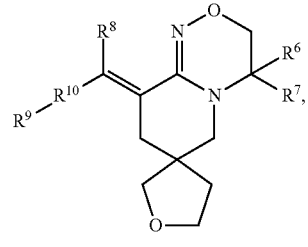
66c 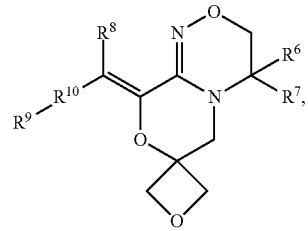
67c 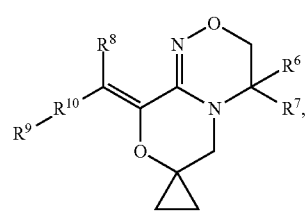
68c 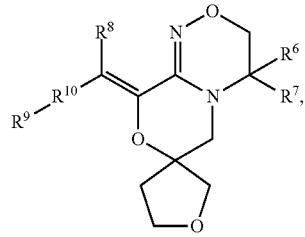
69c 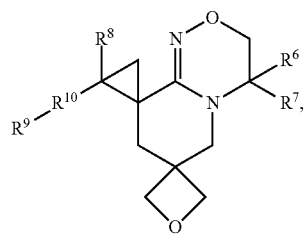
70c 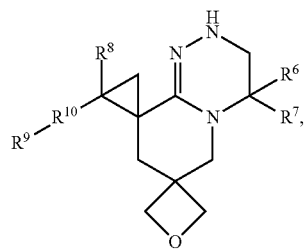
71c 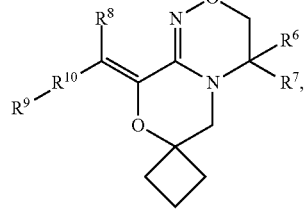
72c 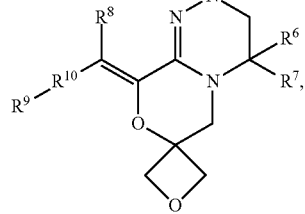
73c 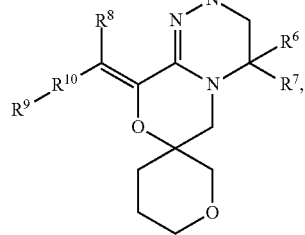

74c 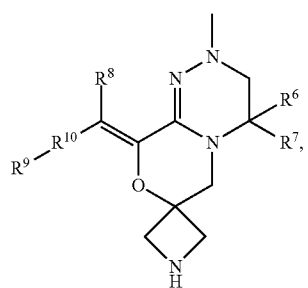
75c 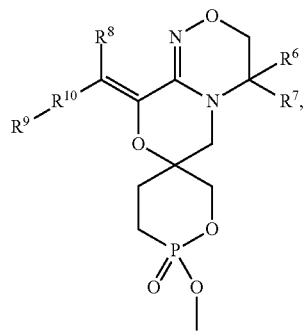
76c 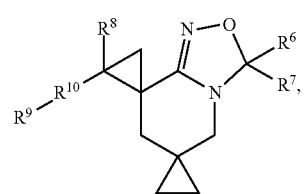
77c 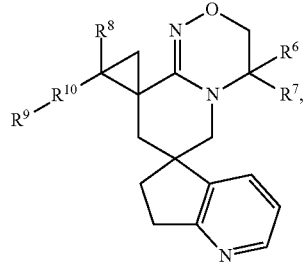
78c 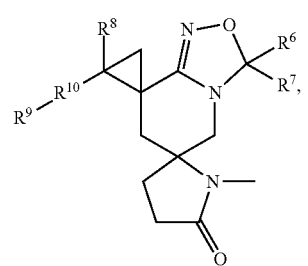
79c 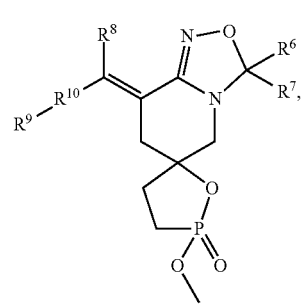
80c 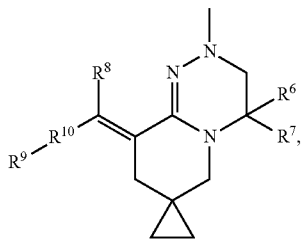
81c 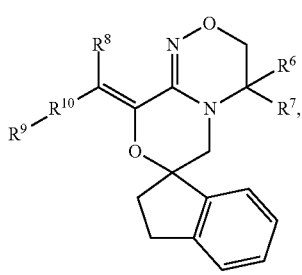
82c 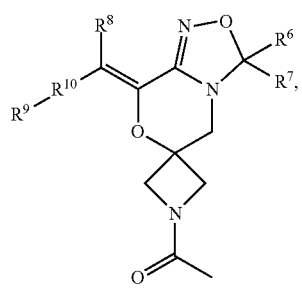
83c 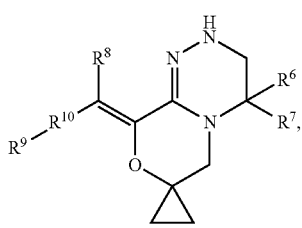
84c 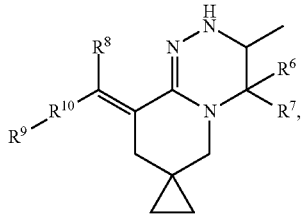
85c 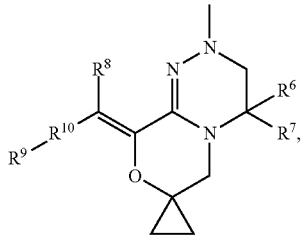

86c 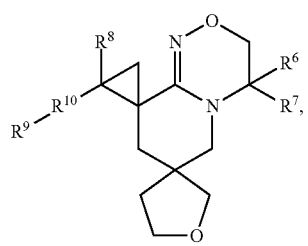
87c 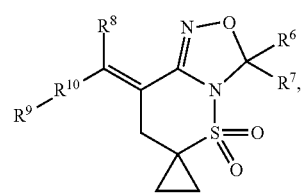
88c 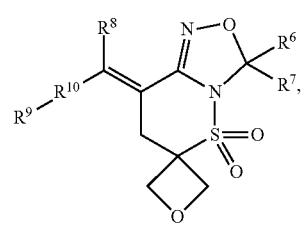
89c 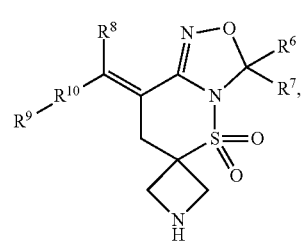
90c 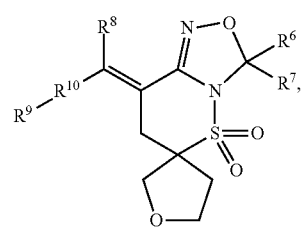
91c 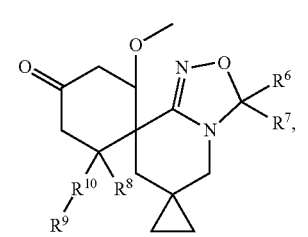
92c 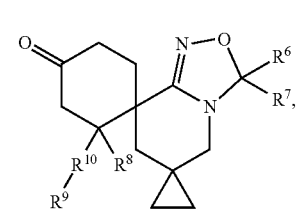
93c 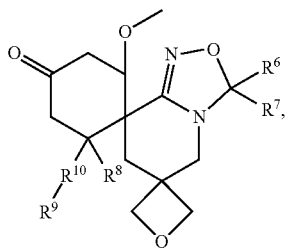
94c 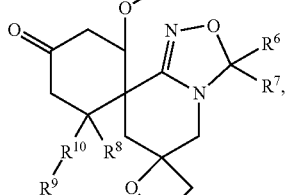
95c 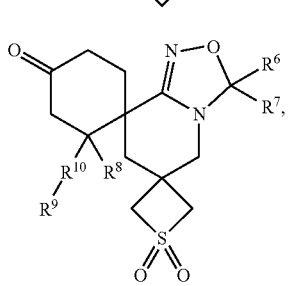
96c 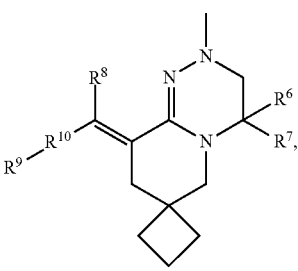
97c 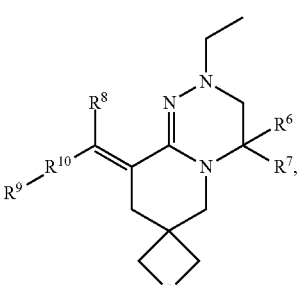
98c 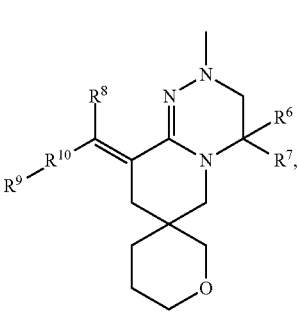

-continued

99c 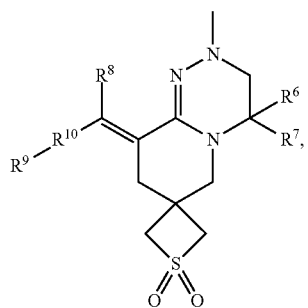

100c 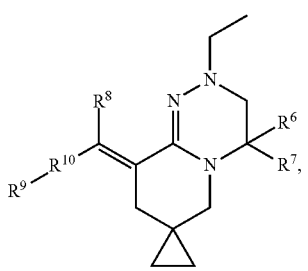

101c 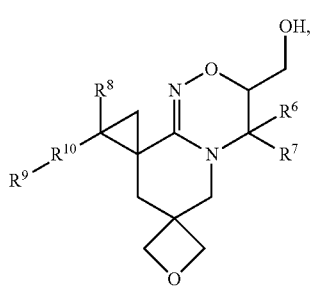

102c 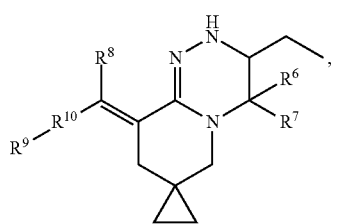

103c 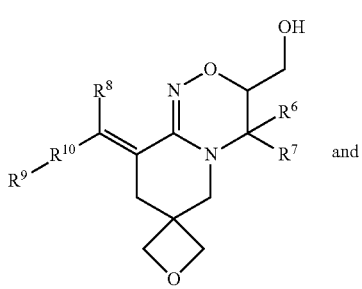 and

104c 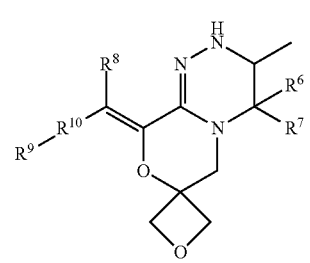

wherein all substituents are as defined for formula (I).

Another embodiment of this invention is directed to compound 1c. Another embodiment of this invention is directed to compound 2c. Another embodiment of this invention is directed to compound 3c. Another embodiment of this invention is directed to compound 4c. Another embodiment of this invention is directed to compound 5c. Another embodiment of this invention is directed to compound 6c. Another embodiment of this invention is directed to compound 7c. Another embodiment of this invention is directed to compound 8c. Another embodiment of this invention is directed to compound 9c. Another embodiment of this invention is directed to compound 10c. Another embodiment of this invention is directed to compound 11c. Another embodiment of this invention is directed to compound 12c. Another embodiment of this invention is directed to compound 13c. Another embodiment of this invention is directed to compound 14c. Another embodiment of this invention is directed to compound 15c. Another embodiment of this invention is directed to compound 16c. Another embodiment of this invention is directed to compound 17c. Another embodiment of this invention is directed to compound 18c. Another embodiment of this invention is directed to compound 19c. Another embodiment of this invention is directed to compound 20c. Another embodiment of this invention is directed to compound 21c. Another embodiment of this invention is directed to compound 22c. Another embodiment of this invention is directed to compound 23c. Another embodiment of this invention is directed to compound 24c. Another embodiment of this invention is directed to compound 25c. Another embodiment of this invention is directed to compound 26c. Another embodiment of this invention is directed to compound 27c. Another embodiment of this invention is directed to compound 28c. Another embodiment of this invention is directed to compound 29c. Another embodiment of this invention is directed to compound 30c. Another embodiment of this invention is directed to compound 31c. Another embodiment of this invention is directed to compound 32c. Another embodiment of this invention is directed to compound 33c. Another embodiment of this invention is directed to compound 34c. Another embodiment of this invention is directed to compound 35c. Another embodiment of this invention is directed to compound 36c. Another embodiment of this invention is directed to compound 37c. Another embodiment of this invention is directed to compound 38c. Another embodiment of this invention is directed to compound 39c. Another embodiment of this invention is directed to compound 40c. Another embodiment of this invention is directed to compound 41c. Another embodiment of this invention is directed to compound 42c. Another embodiment of this invention is directed to compound 43c. Another embodiment of this invention is directed to compound 44c. Another embodiment of this invention is directed to compound 45c. Another embodiment of this invention is directed to compound 46c. Another embodiment of this invention is directed to compound 47c. Another embodiment of this invention is directed to compound 48c. Another embodiment of this invention is directed to compound 49c. Another embodiment of this invention is directed to compound 50c. Another embodiment of this invention is directed to compound 51c. Another embodiment of this invention is directed to compound 52c. Another embodiment of this invention is directed to compound 53c. Another embodiment of this invention is directed to compound 54c. Another embodiment of this invention is directed to compound 55c. Another embodiment of this invention is directed to compound 56c. Another embodiment of this invention is directed to compound 57c. Another embodiment of this invention is directed to compound 58c. Another embodiment of this invention is directed to compound 59c. Another embodiment of this invention is directed to compound 60c. Another embodiment of this invention is directed to compound 61c. Another embodiment of this invention is directed to compound 62c. Another embodiment of this invention is directed to compound 63c. Another embodiment of this invention is directed to compound 64c. Another embodiment of this invention is directed to compound 65c. Another embodiment of this invention is directed to compound 66c. Another embodiment of this invention is directed to compound 67c. Another embodiment of this invention is directed to compound 68c. Another embodiment of this invention is directed to compound 69c. Another embodiment of this invention is directed to compound 70c. Another embodiment of this invention is directed to compound 71c. Another embodiment of this invention is directed to compound 72c. Another embodiment of this invention is directed to compound 73c. Another embodiment of this invention is directed to compound 74c. Another embodiment of this invention is directed to compound 75c. Another embodiment of this invention is directed to compound 76c. Another embodiment of this invention is directed to compound 77c. Another embodiment of this invention is directed to compound 78c. Another embodiment of this invention is directed to compound 79c. Another embodiment of this invention is directed to compound 80c. Another embodiment of this invention is directed to compound 81c. Another embodiment of this invention is directed to compound 82c. Another embodiment of this invention is directed to compound 83c. Another embodiment of this invention is directed to compound 84c. Another embodiment of this invention is directed to compound 85c. Another embodiment of this invention is directed to compound 86c. Another embodiment of this invention is directed to compound 87c. Another embodiment of this invention is directed to compound 88c. Another embodiment of this invention is directed to compound 89c. Another embodiment of this invention is directed to compound 90c. Another embodiment of this invention is directed to compound 91c. Another embodiment of this invention is directed to compound 92c. Another embodiment of this invention is directed to compound 93c. Another embodiment of this invention is directed to compound 94c. Another embodiment of this invention is directed to compound 95c. Another embodiment of this invention is directed to compound 96c. Another embodiment of this invention is directed to compound 97c. Another embodiment of this invention is directed to compound 98c. Another embodiment of this invention is directed to compound 99c. Another embodiment of this invention is directed to compound 100c. Another embodiment of this invention is directed to compound 101c. Another embodiment of this invention is directed to compound 102c. Another embodiment of this invention is directed to compound 103c. Another embodiment of this invention is directed to compound 104c.

Another embodiment of this invention is directed to compound 1c wherein $R^8$ is H. Another embodiment of this invention is directed to compound 2c wherein $R^8$ is H. Another embodiment of this invention is directed to compound 3c wherein $R^8$ is H. Another embodiment of this invention is directed to compound 4c wherein $R^8$ is H. Another embodiment of this invention is directed to compound 5c wherein $R^8$ is H. Another embodiment of this invention is directed to compound 6c wherein $R^8$ is H. Another embodiment of this invention is directed to compound 7c wherein $R^8$ is H. Another embodiment of this invention is directed to compound 8c wherein $R^8$ is H. Another embodiment of this invention is directed to compound 9c wherein $R^8$ is H. Another embodiment of this invention is directed to compound 10c wherein $R^8$ is H. Another embodiment of this invention is directed to compound 11c wherein $R^8$ is H. Another embodiment of this invention is directed to compound 12c wherein $R^8$ is H. Another embodiment of this invention is directed to compound 13c wherein $R^8$ is H. Another embodiment of this invention is directed to compound 14c wherein $R^8$ is H. Another embodiment of this invention is directed to compound 15c wherein $R^8$ is H. Another embodiment of this invention is directed to compound 16c wherein $R^8$ is H. Another embodiment of this invention is directed to compound 17c wherein $R^8$ is H. Another embodiment of this invention is directed to compound 18c wherein $R^8$ is H. Another embodiment of this invention is directed to compound 19c wherein $R^8$ is H. Another embodiment of this invention is directed to compound 20c wherein $R^8$ is H. Another embodiment of this invention is directed to compound 21c wherein $R^8$ is H. Another embodiment of this invention is directed to compound 22c wherein $R^8$ is H. Another embodiment of this invention is directed to compound 23c wherein $R^8$ is H. Another embodiment of this invention is directed to compound 24c wherein $R^8$ is H. Another embodiment of this invention is directed to compound 25c wherein $R^8$ is H. Another embodiment of this invention is directed to compound 26c wherein $R^8$ is H. Another embodiment of this invention is directed to compound 27c wherein $R^8$ is H. Another embodiment of this invention is directed to compound 28c wherein $R^8$ is H. Another embodiment of this invention is directed to compound 29c wherein $R^8$ is H. Another embodiment of this invention is directed to compound 30c wherein $R^8$ is H. Another embodiment of this invention is directed to compound 31c wherein $R^8$ is H. Another embodiment of this invention is directed to compound 32c wherein $R^8$ is H. Another embodiment of this invention is directed to compound 33c wherein $R^8$ is H. Another embodiment of this invention is directed to compound 34c wherein $R^8$ is H. Another embodiment of this invention is directed to compound 35c wherein $R^8$ is H. Another embodiment of this invention is directed to compound 36c wherein $R^8$ is H. Another embodiment of this invention is directed to compound 37c wherein $R^8$ is H. Another embodiment of this invention is directed to compound 38c wherein $R^8$ is H. Another embodiment of this invention is directed to compound 39c wherein $R^8$ is H. Another embodiment of this invention is directed to compound 40c wherein $R^8$ is H. Another embodiment of this invention is directed to compound 41c wherein $R^8$ is H. Another embodiment of this invention is directed to compound 42c wherein $R^8$ is H. Another embodiment of this invention is directed to compound 43c wherein $R^8$ is H. Another embodiment of this invention is directed to compound 44c wherein $R^8$ is H. Another embodiment of this invention is directed to compound 45c wherein $R^8$ is H. Another embodiment of this invention is directed to compound 46c wherein $R^8$ is H. Another embodiment of this invention is directed to compound 47c wherein $R^8$ is H. Another embodiment of this invention is directed to compound 48c wherein $R^8$ is H. Another embodiment of this invention is directed to compound 49c wherein $R^8$ is H. Another embodiment of this invention is directed to compound 50c wherein $R^8$ is H. Another embodiment of this invention is directed to compound 51c wherein $R^8$ is H. Another embodiment of this invention is directed to compound 52c wherein $R^8$ is H. Another embodiment of this invention is directed to compound 53c wherein $R^8$ is H. Another embodiment of this invention is directed to compound 54c wherein $R^8$ is H. Another embodiment of this invention is directed to compound 55c wherein $R^8$ is H. Another embodiment of this invention is directed to compound 56c wherein $R^8$ is H. Another embodiment of this invention is directed to compound 57c wherein $R^8$ is H. Another embodiment of this invention is directed to compound 58c wherein $R^8$ is H. Another embodiment of this invention is directed to compound 59c wherein $R^8$ is H. Another embodiment of this invention is directed to compound 60c wherein $R^8$ is H. Another embodiment of this invention is directed to compound 61c wherein $R^8$ is H. Another embodiment of this invention is directed to compound 62c wherein $R^8$ is H. Another embodiment of this invention is directed to compound 63c wherein $R^8$ is H. Another embodiment of this invention is directed to compound 64c wherein $R^8$ is H. Another embodiment of this invention is directed to compound 65c wherein $R^8$ is H. Another embodiment of this invention is directed to compound 66c wherein $R^8$ is H. Another embodiment of this invention is directed to compound 67c wherein $R^8$ is H. Another embodiment of this invention is directed to compound 68c wherein $R^8$ is H. Another embodiment of this invention is directed to compound 69c wherein $R^8$ is H. Another embodiment of this invention is directed to compound 70c wherein $R^8$ is H. Another embodiment of this invention is directed to compound 71c wherein $R^8$ is H. Another embodiment of this invention is directed to compound 72c wherein $R^8$ is H. Another embodiment of this invention is directed to compound 73c wherein $R^8$ is H. Another embodiment of this invention is directed to compound 74c wherein $R^8$ is H. Another embodiment of this invention is directed to compound 75c wherein $R^8$ is H. Another embodiment of this invention is directed to compound 76c wherein $R^8$ is H. Another embodiment of this invention is directed to compound 77c wherein $R^8$ is H. Another embodiment of this invention is directed to compound 78c wherein $R^8$ is H. Another embodiment of this invention is directed to compound 79c wherein $R^8$ is H. Another embodiment of this invention is directed to compound 80c wherein $R^8$ is H. Another embodiment of this invention is directed to compound 81c wherein $R^8$ is H. Another embodiment of this invention is directed to compound 82c wherein $R^8$ is H. Another embodiment of this invention is directed to compound 83c wherein $R^8$ is H. Another embodiment of this invention is directed to compound 84c wherein $R^8$ is H. Another embodiment of this invention is directed to compound 85c wherein $R^8$ is H. Another embodiment of this invention is directed to compound 86c wherein $R^8$ is H. Another embodiment of this invention is directed to compound 87c wherein $R^8$ is H. Another embodiment of this invention is directed to compound 88c wherein $R^8$ is H. Another embodiment of this invention is directed to compound 89c wherein $R^8$ is H. Another embodiment of this invention is directed to compound 90c wherein $R^8$ is H. Another embodiment of this invention is directed to compound 91c wherein $R^8$ is H. Another embodiment of this invention is directed to compound 92c wherein $R^8$ is H. Another embodiment of this invention is directed to compound 93c wherein $R^8$ is H. Another embodiment of this invention is directed to compound 94c wherein $R^8$ is H. Another embodiment of this invention is directed to compound 95c wherein $R^8$ is H. Another embodiment of this invention is directed to compound 96c wherein $R^8$ is H. Another embodiment of this invention is directed to compound 97c wherein $R^8$ is H. Another embodiment of this invention is directed to compound 98c wherein $R^8$ is H.

Another embodiment of this invention is directed to compound 99c wherein $R^5$ is H. Another embodiment of this invention is directed to compound 100c wherein $R^8$ is H. Another embodiment of this invention is directed to compound 101c wherein $R^8$ is H. Another embodiment of this invention is directed to compound 102c wherein $R^8$ is H. Another embodiment of this invention is directed to compound 103c wherein $R^8$ is H. Another embodiment of this invention is directed to compound 104c wherein $R^8$ is H.

Another embodiment of this invention is directed to compounds 1c to 104c wherein (1) the $R^9$ is selected from the group consisting of 1g to 13g, (2) $R^{10}$ is selected from the group consisting of 1f to 39f, (3) $R^6$ is selected from the group consisting of H, alkyl (e.g., methyl or ethyl), alkyl substituted with —$OR^{15}$ (e.g., —OH), and alkyl substituted with —$S(O)_2 R^{15A}$ (and in one example said $R^{15A}$ is alkyl (e.g., methyl, ethyl or propyl), and in another example said $R^{15A}$ is $(R^{18})_q$-alkyl- wherein $R^{18}$ is selected from the group consisting of halo (e.g., F) and cycloalkyl (e.g., cyclopropyl)), and (4) $R^7$ is selected from the group consisting of 1d to 35d.

Another embodiment of this invention is directed to compounds 1c to 104c wherein (1) the $R^9$ is H, (2) $R^{10}$ is selected from the group consisting of 1f to 39f, (3) $R^6$ is selected from the group consisting of H, alkyl (e.g., methyl or ethyl), alkyl substituted with —$OR^{15}$ (e.g., —OH), and alkyl substituted with —$S(O)_2R^{15A}$ (and in one example said $R^{15A}$ is alkyl (e.g., methyl, ethyl or propyl), and in another example said $R^{15A}$ is $(R^{18})_q$-alkyl- wherein $R^{18}$ is selected from the group consisting of halo (e.g., F) and cycloalkyl (e.g., cyclopropyl)), and (4) $R^7$ is selected from the group consisting of 1d to 35d.

Another embodiment of this invention is directed to compounds 1c to 104c wherein (1) the $R^9$ is selected from the group consisting of 1g to 13g, (2) $R^{10}$ is selected from the group consisting of 1f to 39f, (3) $R^6$ is selected from the group consisting of H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2$cyclopropyl, and (4) $R^7$ is selected from the group consisting of 1d to 35d.

Another embodiment of this invention is directed to compounds 1c to 104c wherein (1) the $R^9$ is H, (2) $R^{10}$ is selected from the group consisting of if to 39l, (3) $R^6$ is selected from the group consisting of H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —$(CH_2)_2S(O)_2CF_3$, and —$(CH_2)S(O)_2CH_2$cyclopropyl, and (4) $R^7$ is selected from the group consisting of 1d to 35d.

Another embodiment of this invention is directed to compounds 1c to 104c wherein (1) the $R^9$—$R^{10}$— moiety is selected from the group consisting of 1b to 50b, (2) $R^6$ is selected from the group consisting of H, alkyl (e.g., methyl or ethyl), alkyl substituted with —$OR^{15}$ (e.g., —OH), and alkyl substituted with —$S(O)_2R^{15A}$ (and in one example said $R^{15A}$ is alkyl (e.g., methyl, ethyl or propyl), and in another example said $R^{15A}$ is $(R^{18})_q$-alkyl- wherein $R^{18}$ is selected from the group consisting of halo (e.g., F) and cycloalkyl (e.g., cyclopropyl)), and (3) $R^7$ is selected from the group consisting of 1d to 35d.

Another embodiment of this invention is directed to compounds 1c to 104c wherein (1) the $R^9$—$R^{10}$— moiety is selected from the group consisting of 1b to 50b, (2) $R^6$ is selected from the group consisting of H, methyl, ethyl, —$CH_2OH$, —$CH(OH)CH_3$, —$(CH_2)_2S(O)_2CH_3$, —$CH(CH_3)CH_2S(O)_2CH_2CH_3$, —$(CH_2)_2S(O)_2(CH_2)_2CH_3$, —$CH_2CH(CH_3)S(O)_2CH_3$, —$(CH_2)_2S(O)_2CH_2CH_3$, —(CH$_2$)$_2$S(O)$_2$CF$_3$, and —(CH$_2$)S(O)$_2$CH$_2$cyclopropyl, and (3) R$^7$ is selected from the group consisting of 1d to 35d.

Another embodiment of this invention is directed to compounds 1c to 104c wherein (1) the R$^9$—R$^{10}$— moiety is 50b, (2) R$^6$ is selected from the group consisting of H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, and (3) R$^7$ is selected from the group consisting of 1d to 35d.

Another embodiment of this invention is directed to compounds 1c to 75c, 79c to 100c and 102c to 104c wherein (1) the R$^9$ is selected from the group consisting of 1g to 13g, (2) R$^{10}$ is selected from the group consisting of 1f to 39f, (3) R$^8$ is selected from the group consisting of H, alkyl (e.g., methyl or ethyl), alkyl substituted with —OR$^{15}$ (e.g., —OH), and alkyl substituted with —S(O)$_2$R$^{15A}$ (and in one example said R$^{15A}$ is alkyl (e.g., methyl, ethyl or propyl), and in another example said R$^{15A}$ is (R$^{18}$)$_q$-alkyl- wherein R$^{18}$ is selected from the group consisting of halo (e.g., F) and cycloalkyl (e.g., cyclopropyl)), and (4) R$^7$ is selected from the group consisting of 1d to 35d.

Another embodiment of this invention is directed to compounds 1c to 75c, 79c to 100c and 102c to 104c wherein (1) the R$^9$ is H, (2) R$^{10}$ is selected from the group consisting of 1f to 39f, (3) R$^6$ is selected from the group consisting of H, alkyl (e.g., methyl or ethyl), alkyl substituted with —OR$^{15}$ (e.g., —OH), and alkyl substituted with —S(O)$_2$R$^{15A}$ (and in one example said R$^{15A}$ is alkyl (e.g., methyl, ethyl or propyl), and in another example said R$^{15A}$ is (R$^{18}$)$_q$-alkyl- wherein R$^{18}$ is selected from the group consisting of halo (e.g., F) and cycloalkyl (e.g., cyclopropyl)), and (4) R$^7$ is selected from the group consisting of 1d to 35d.

Another embodiment of this invention is directed to compounds 1c to 75c, 79c to 100c and 102c to 104c wherein (1) the R$^9$ is selected from the group consisting of 1g to 13g, (2) R$^{10}$ is selected from the group consisting of 1f to 39f, (3) R$^6$ is selected from the group consisting of H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, and (4) R$^7$ is selected from the group consisting of 1d to 35d.

Another embodiment of this invention is directed to compounds 1c to 75c, 79c to 100c and 102c to 104c wherein (1) the R$^9$ is H, (2) R$^{10}$ is selected from the group consisting of 1f to 39f, (3) R$^6$ is selected from the group consisting of H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, and (4) R$^7$ is selected from the group consisting of 1d to 35d.

Another embodiment of this invention is directed to compounds 1c to 75c, 79c to 100c and 102c to 104c wherein (1) the R$^9$—R$^{10}$— moiety is selected from the group consisting of 1b to 50b, (2) R$^6$ is selected from the group consisting of H, alkyl (e.g., methyl or ethyl), alkyl substituted with —OR$^{15}$ (e.g., —OH), and alkyl substituted with —S(O)$_2$R$^{15A}$ (and in one example said R$^{15A}$ is alkyl (e.g., methyl, ethyl or propyl), and in another example said R$^{15A}$ is (R$^{18}$)$_q$-alkyl- wherein R$^{18}$ is selected from the group consisting of halo (e.g., F) and cycloalkyl (e.g., cyclopropyl)), and (3) R$^7$ is selected from the group consisting of 1d to 35d.

Another embodiment of this invention is directed to compounds 1c to 75c, 79c to 100c and 102c to 104c wherein (1) the R$^9$—R$^{10}$— moiety is selected from the group consisting of 1b to 50b, (2) R$^6$ is selected from the group consisting of H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, and (3) R$^7$ is selected from the group consisting of 1d to 35d.

Another embodiment of this invention is directed to compounds 1c to 75c, 79c to 100c and 102c to 104c wherein (1) the R$^9$—R$^{10}$— moiety is 50b, (2) R$^6$ is selected from the group consisting of H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, and (3) R$^7$ is selected from the group consisting of 1d to 35d.

Other embodiments of this invention are directed to any of the embodiments directed to compounds 1c to 75c, 79c to 100c and 102c to 104c wherein R$^8$ is H.

Another embodiment of this invention is directed to compounds 76c to 78c, and 101c wherein (1) the R$^9$ is selected from the group consisting of 1g to 13g, (2) R$^{10}$ is selected from the group consisting of 1f to 39f, (3) R$^6$ is selected from the group consisting of H, alkyl (e.g., methyl or ethyl), alkyl substituted with —OR$^{15}$ (e.g., —OH), and alkyl substituted with —S(O)$_2$R$^{15A}$ (and in one example said R$^{15A}$ is alkyl (e.g., methyl, ethyl or propyl), and in another example said R$^{15A}$ is (R$^{18}$)$_q$-alkyl- wherein R$^{18}$ is selected from the group consisting of halo (e.g., F) and cycloalkyl cyclopropyl)), and (4) R$^7$ is selected from the group consisting of 1d to 35d.

Another embodiment of this invention is directed to compounds 76c to 78c, and 101c wherein (1) the R$^9$ is H, (2) R$^{ic}$ is selected from the group consisting of 1f to 39f, (3) R$^6$ is selected from the group consisting of H, alkyl (e.g., methyl or ethyl), alkyl substituted with —OR$^{15}$ (e.g., —OH), and alkyl substituted with —S(O)$_2$R$^{15A}$ (and in one example said R$^{15A}$ is alkyl (e.g., methyl, ethyl or propyl), and in another example said R$^{15A}$ is (R$^{18}$)$_q$-alkyl- wherein R$^{18}$ is selected from the group consisting of halo (e.g., F) and cycloalkyl (e.g., cyclopropyl)), and (4) R$^7$ is selected from the group consisting of 1d to 35d.

Another embodiment of this invention is directed to compounds 76c to 78c, and 101c wherein (1) the R$^9$ is selected from the group consisting of 1g to 13g, (2) R$^{10}$ is selected from the group consisting of 1f to 39f, (3) R$^6$ is selected from the group consisting of H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, and (4) R$^7$ is selected from the group consisting of 1d to 35d.

Another embodiment of this invention is directed to compounds 76c to 78c, and 101c wherein (1) the R$^9$ is H, (2) R$^{10}$ is selected from the group consisting of 1f to 39f, (3) R$^6$ is selected from the group consisting of H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, and (4) R$^7$ is selected from the group consisting of 1d to 35d.

Another embodiment of this invention is directed to compounds 76c to 78c, and 101c wherein (1) the R$^9$—R$^{10}$— moiety is selected from the group consisting of 1b to 50b, (2) R$^6$ is selected from the group consisting of H, alkyl (e.g., methyl or ethyl), alkyl substituted with —OR$^{15}$ (e.g., —OH), and alkyl substituted with —S(O)$_2$R$^{15A}$ (and in one example said R$^{15A}$ is alkyl (e.g., methyl, ethyl or propyl), and in another example said $R^{15A}$ is $(R^{18})_q$-alkyl- wherein $R^{18}$ is selected from the group consisting of halo (e.g., F) and cycloalkyl (e.g., cyclopropyl)), and (3) $R^7$ is selected from the group consisting of 1d to 35d.

Another embodiment of this invention is directed to compounds 76c to 78c, and 101c wherein (1) the $R^9$—$R^{10}$— moiety is selected from the group consisting of 1b to 50b, (2) $R^6$ is selected from the group consisting of H, methyl, ethyl, —CH$_2$OH, —CH(OH)CH$_3$, —(CH$_2$)$_2$S(O)$_2$CH$_3$, —CH(CH$_3$)CH$_2$S(O)$_2$CH$_2$CH$_3$, —(CH$_2$)$_2$S(O)$_2$(CH$_2$)$_2$CH$_3$, —CH$_2$CH(CH$_3$)S(O)$_2$CH$_3$, —(CH$_2$)$_2$S(O)$_2$CH$_2$CH$_3$, —(CH$_2$)$_2$S(O)$_2$CF$_3$, and —(CH$_2$)S(O)$_2$CH$_2$cyclopropyl, and (3) $R^7$ is selected from the group consisting of 1d to 35d.

Another embodiment of this invention is directed to compounds 76c to 78c, and 101c wherein (1) the $R^9$—$R^{10}$— moiety is 50b, (2) $R^6$ is selected from the group consisting of H, methyl, ethyl, —CH$_2$OH, —CH(OH)CH$_3$, —(CH$_2$)$_2$S(O)$_2$ CH$_3$, —CH(CH$_3$)CH$_2$S(O)$_2$CH$_2$CH$_3$, —(CH$_2$)$_2$S(O)$_2$ (CH$_2$)$_2$CH$_3$, —CH$_2$CH(CH$_3$)S(O)$_2$CH$_3$, —(CH$_2$)$_2$S(O)$_2$ CH$_2$CH$_3$, —(CH$_2$)$_2$S(O)$_2$CF$_3$, and —(CH$_2$)S(O)$_2$ CH$_2$cyclopropyl, and (3) $R^7$ is selected from the group consisting of 1d to 35d.

Other embodiments of this invention are directed to any of the embodiments directed to compounds 76c to 78c, and 101c wherein $R^8$ is H.

Representative compounds of the invention include, but are not limited to:

A10
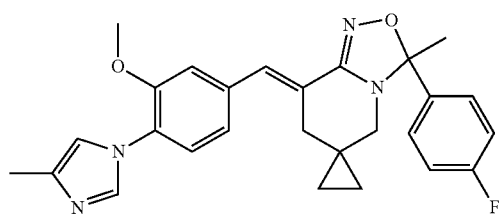

A11
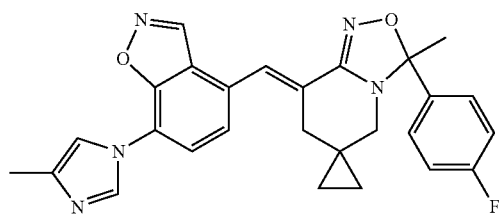

A12
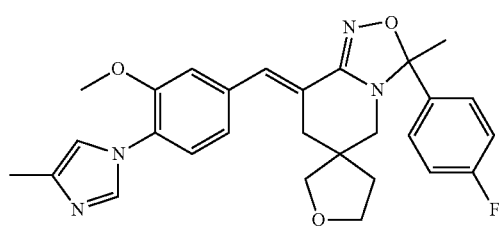

A13
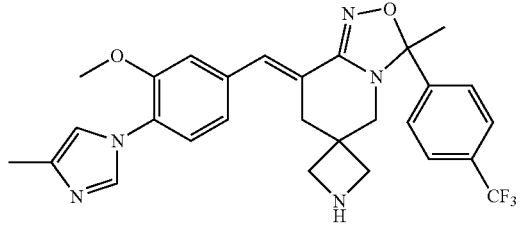

A14
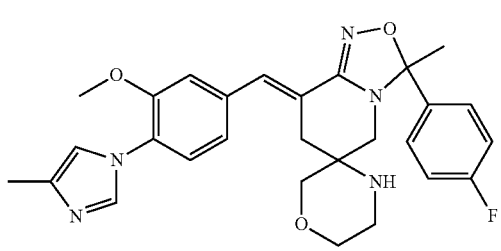

A15
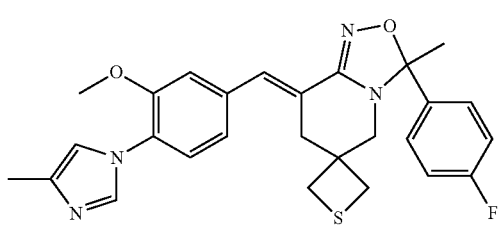

A16
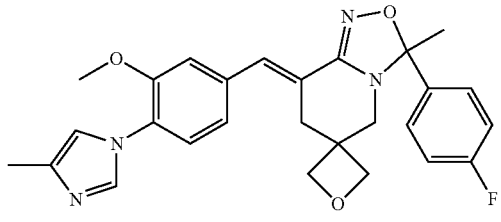

A17
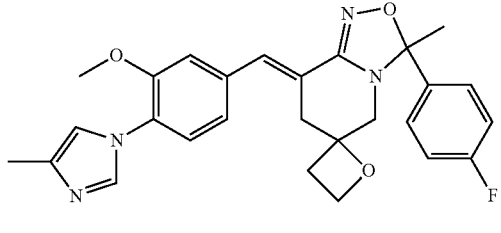

A18
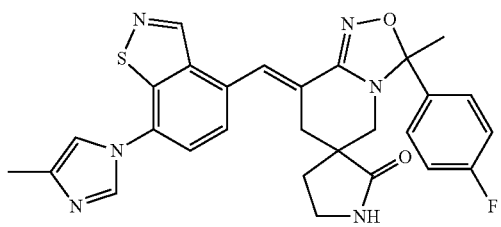

-continued
A19
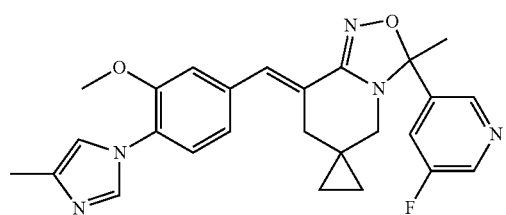
A20
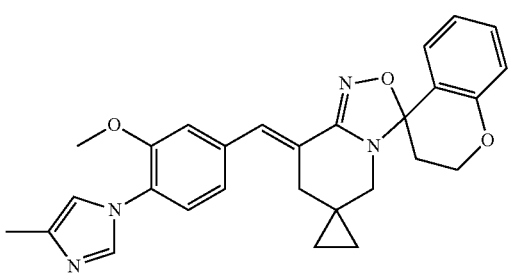
A21
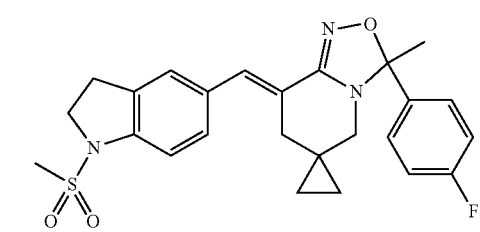
A22
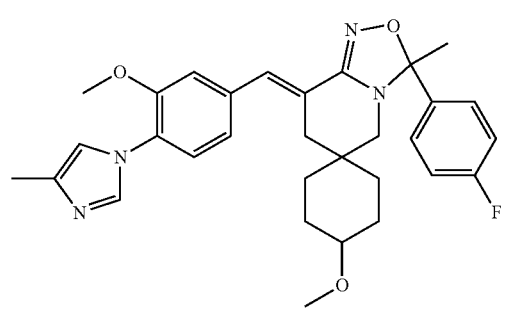
A23
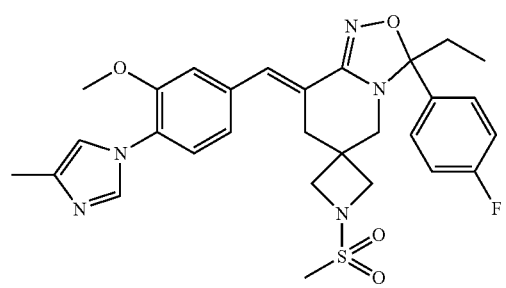
A24
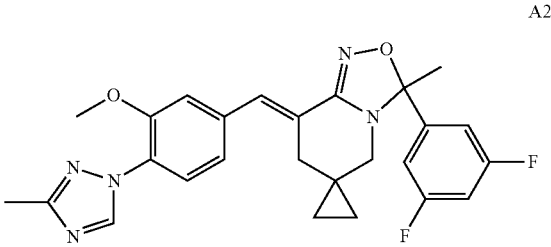
-continued
A25
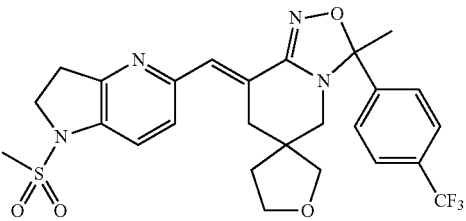
A26
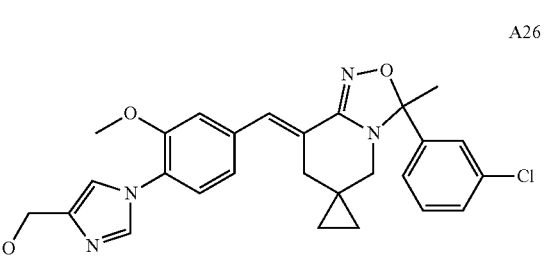
A27
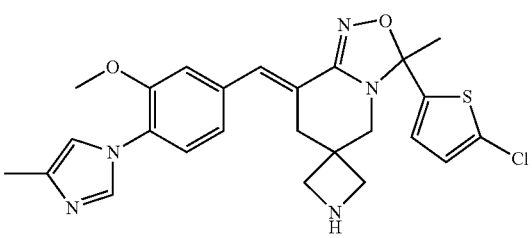
A28
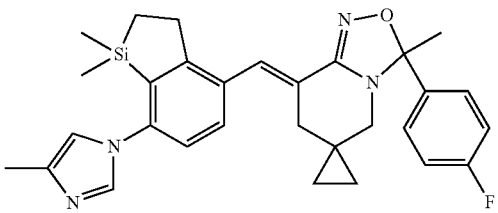
A29
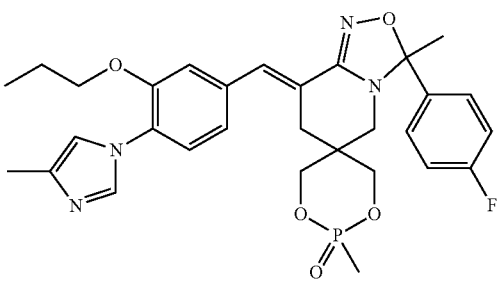
A30
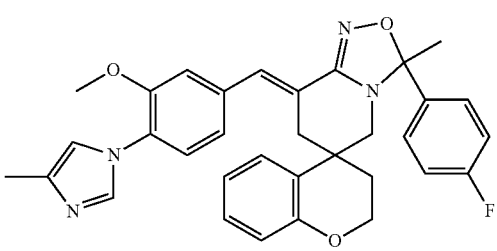

225
-continued
E11
E12
E13
E14
E15
E16
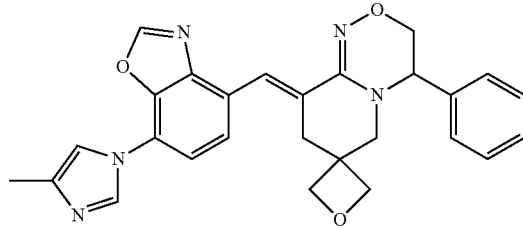
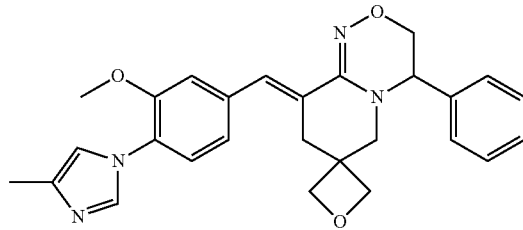
226
-continued
E17
E18
E19
E20
E21
E22
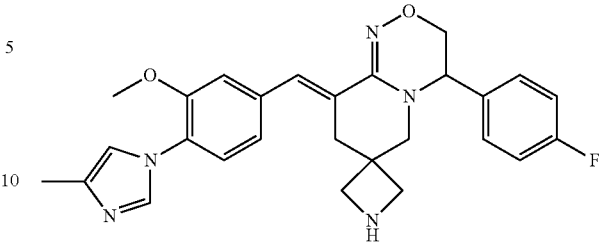
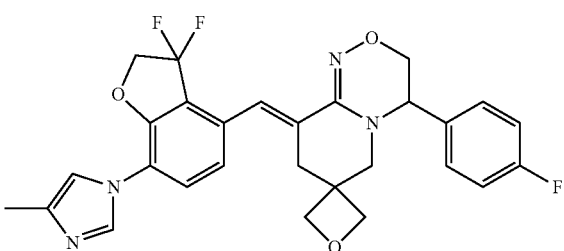

-continued
E23
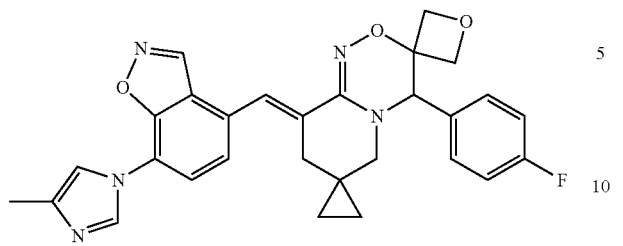
E24
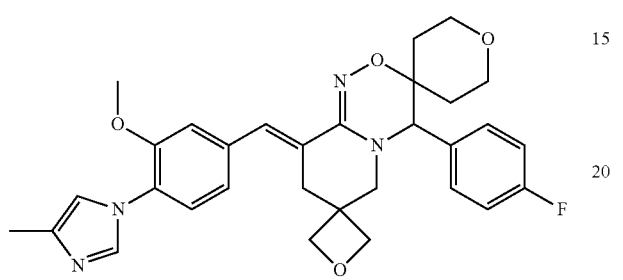
E25
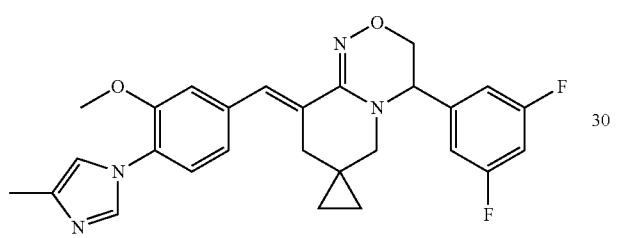
E26
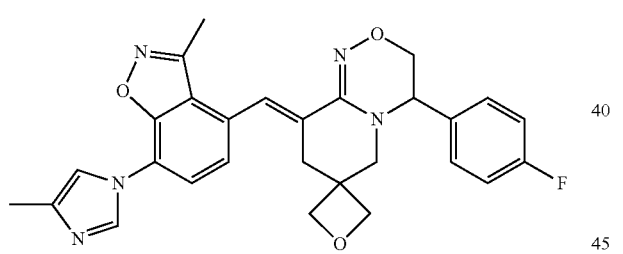
E27
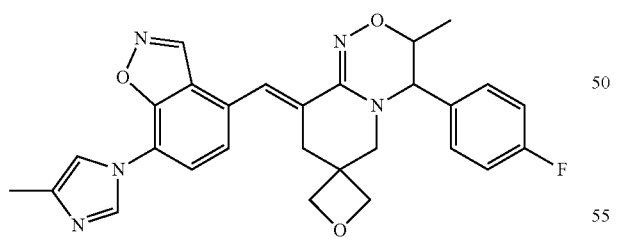
E28
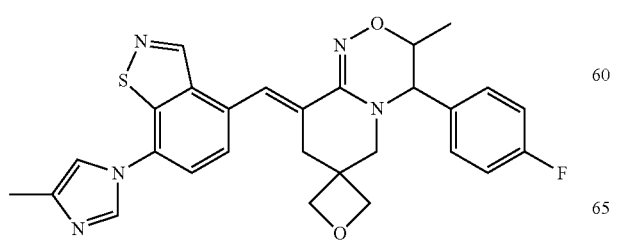
-continued
E29
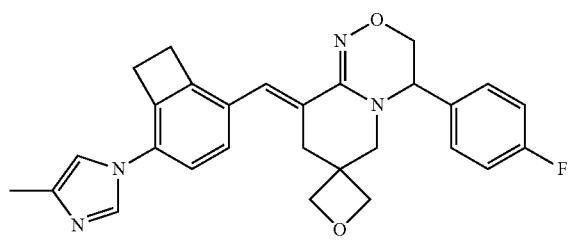
E30
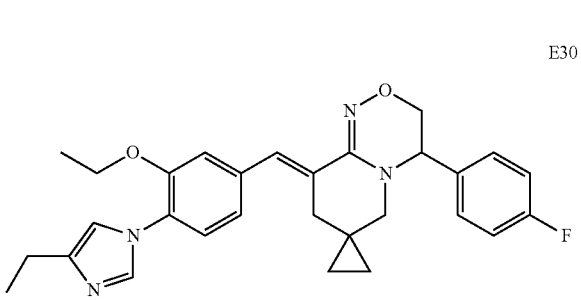
E31
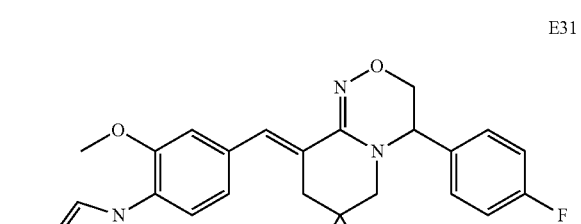
E32
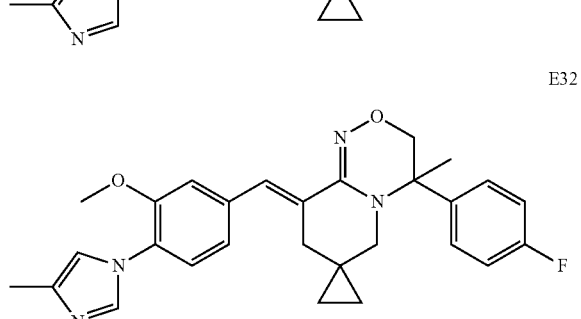
E33
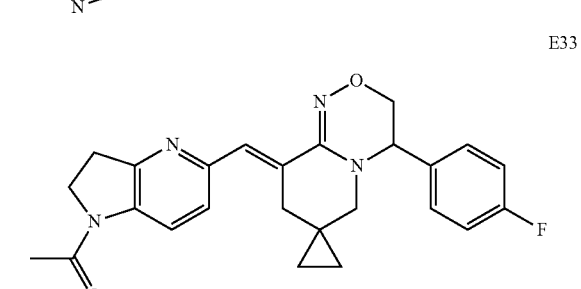
E34
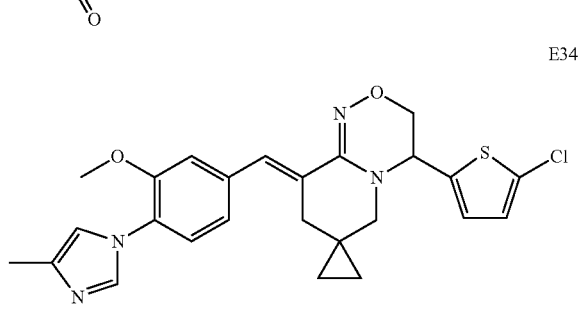

229
-continued
E35
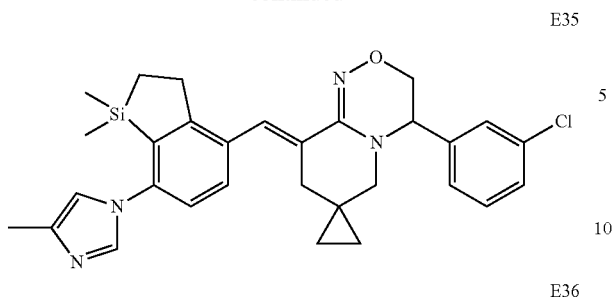
E36
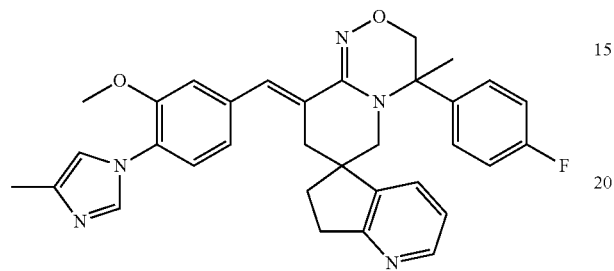
E37
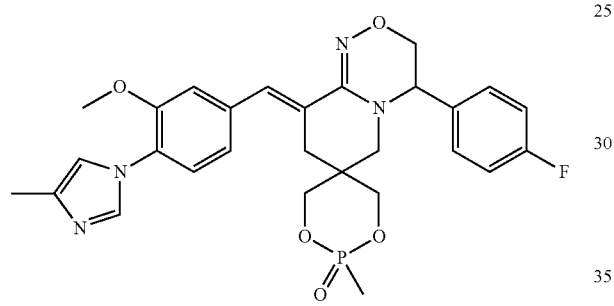
E38
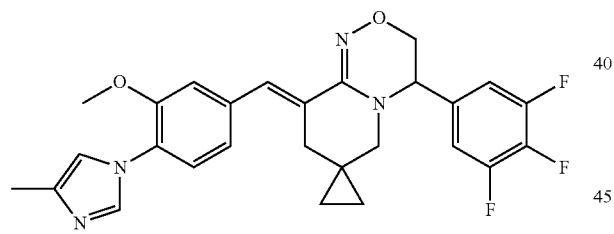
F8
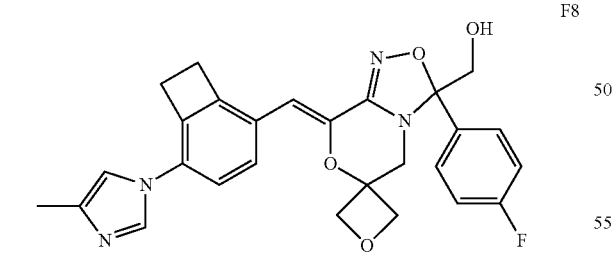
F9
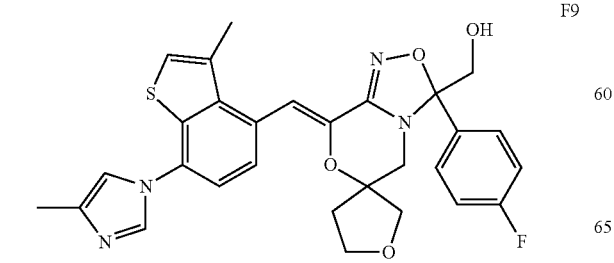
230
-continued
F10
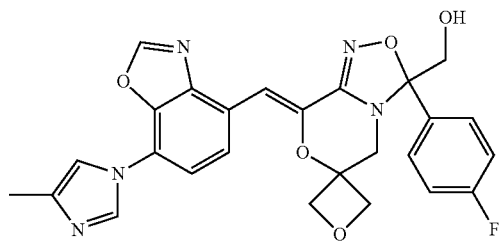
F11
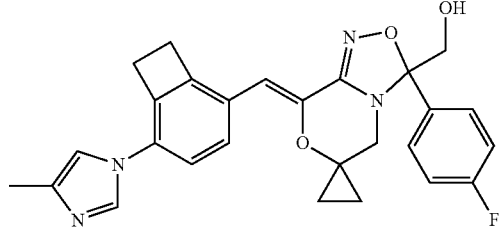
F12
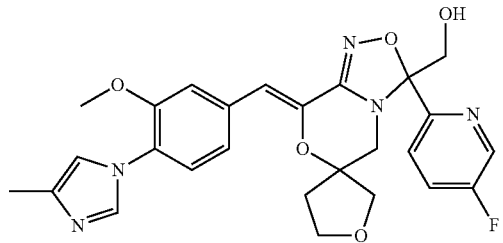
F13
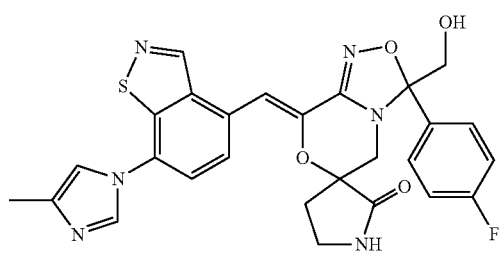
F14
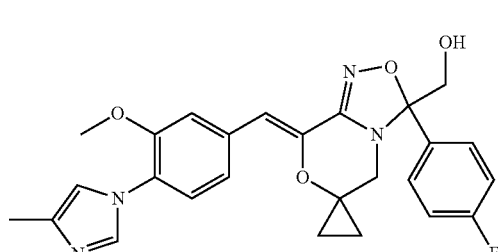
F15
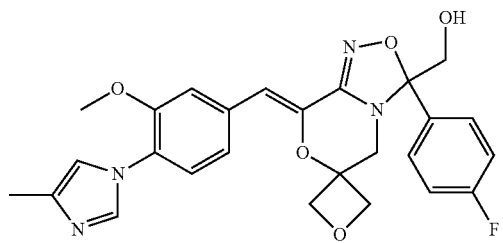

F16
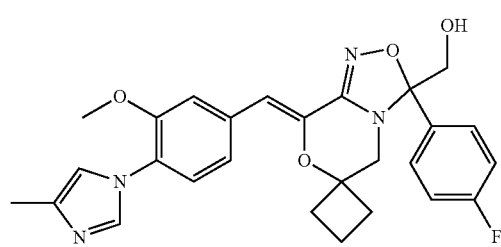
F17
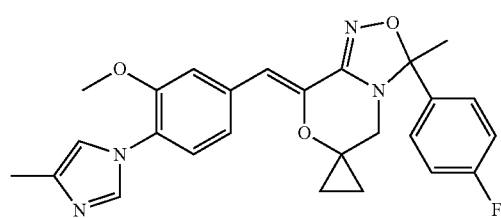
F18
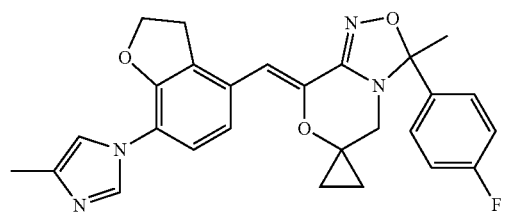
F19
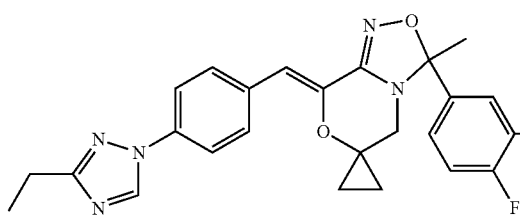
F20
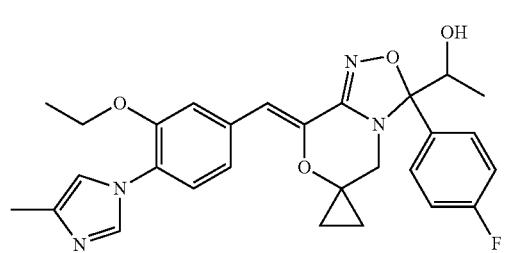
F21
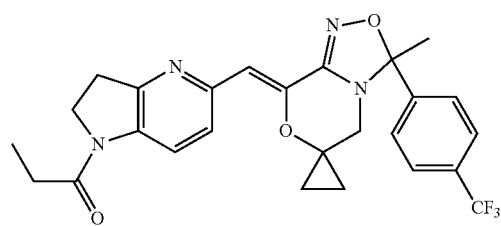
F22
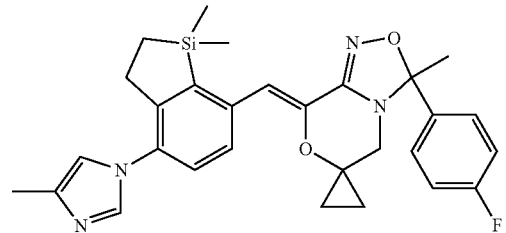
F23
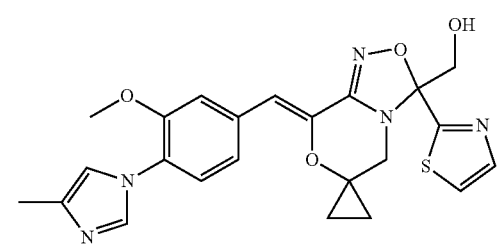
F24
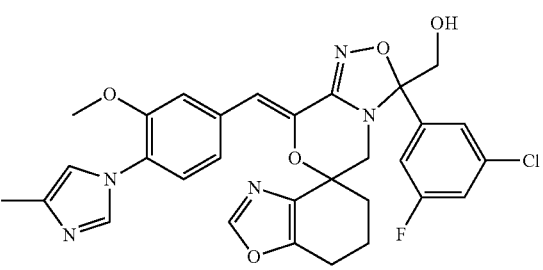
F25
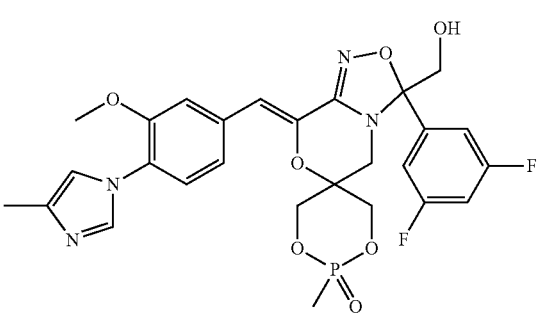
G3

233
-continued
G4
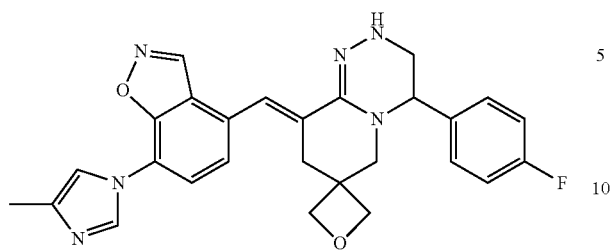
G5
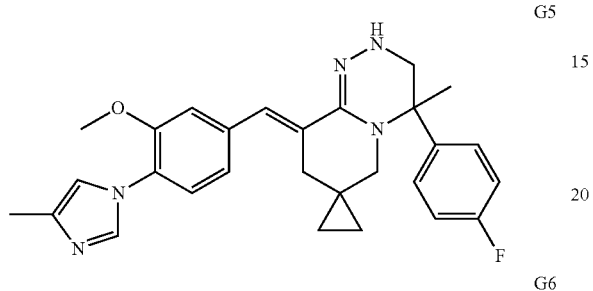
G6
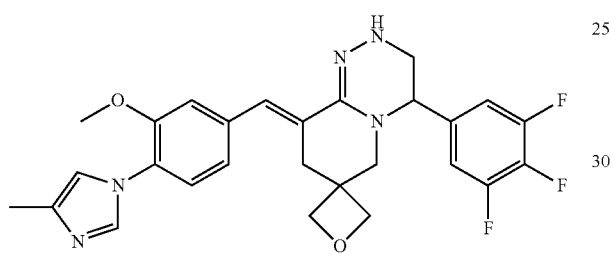
G7
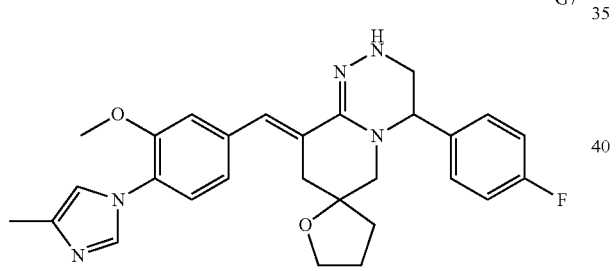
G8
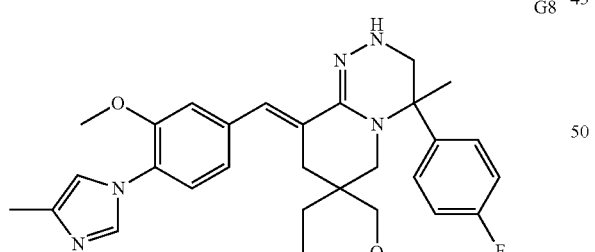
G9
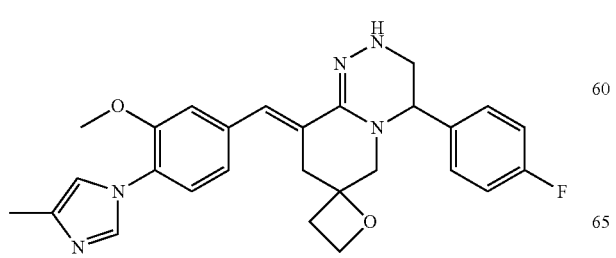
234
-continued
G10
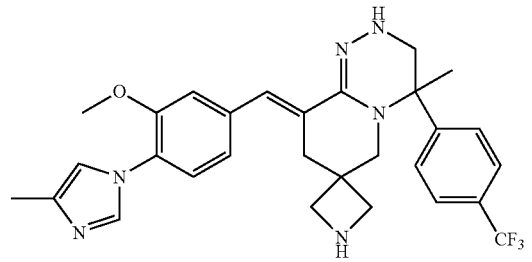
G11
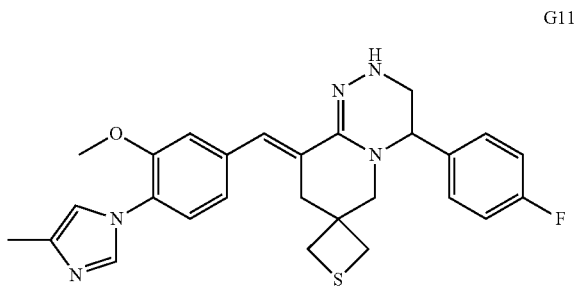
G14
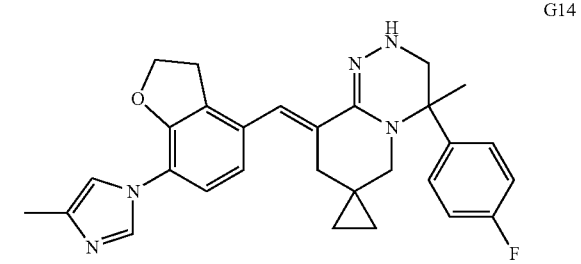
G15
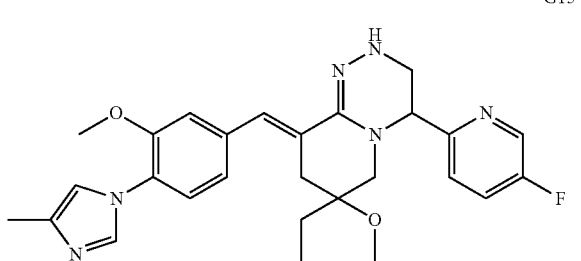
G16
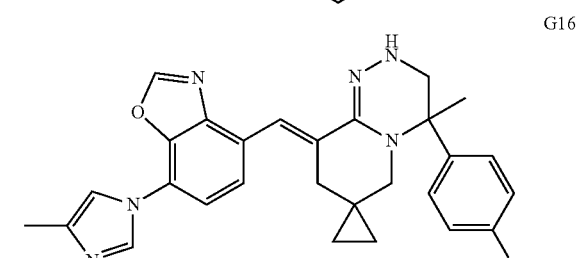
G17
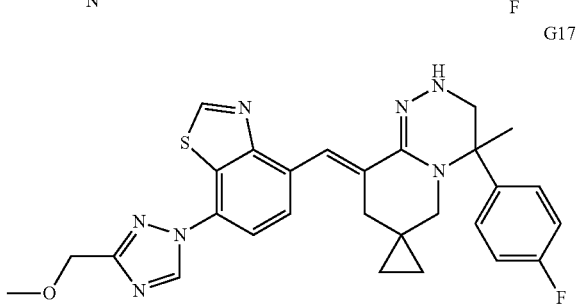

G18
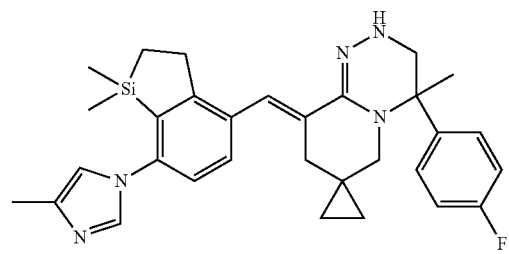
G19
G20
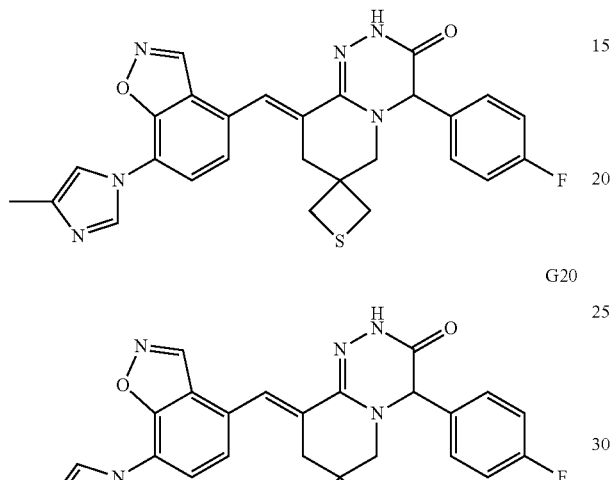
G21
G22
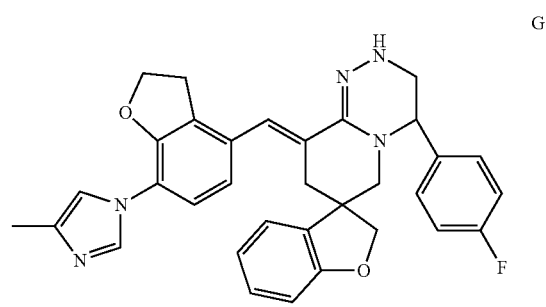
G23
G24
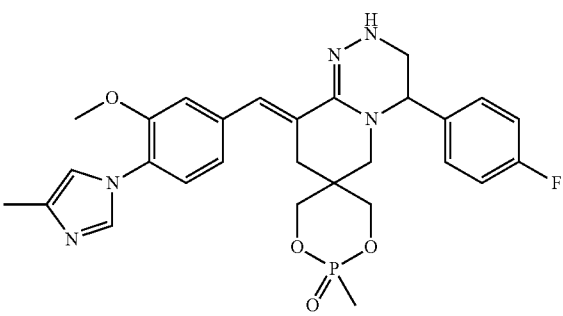
H1
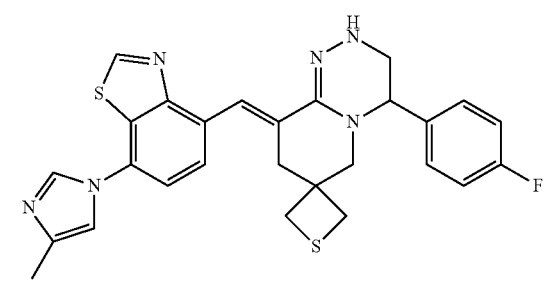
H2
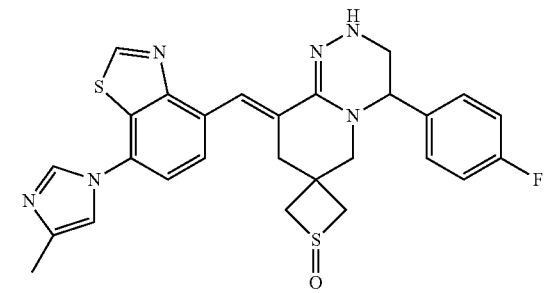
H3
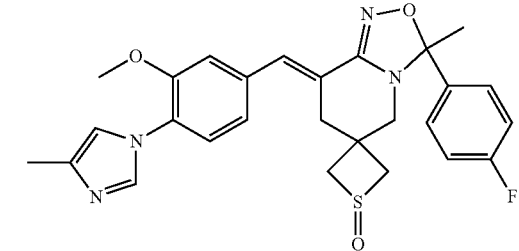
H4
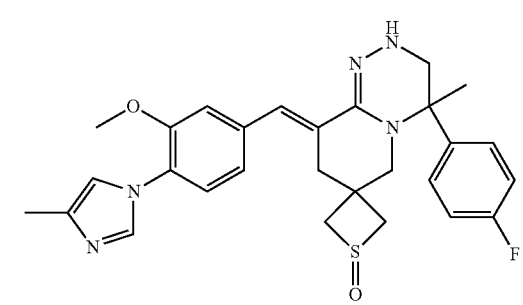

H5
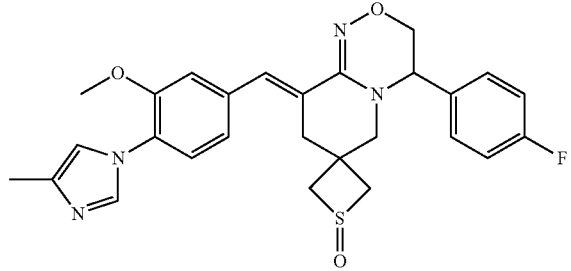
H6
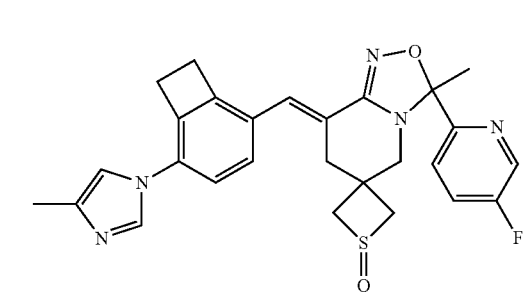
H7
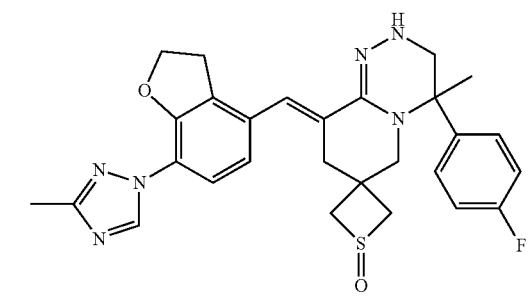
H8
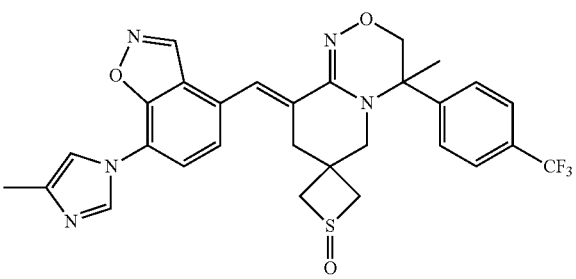
H9
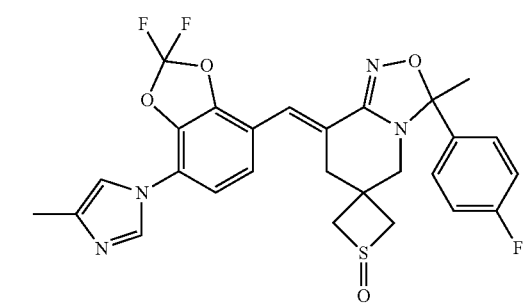
H10
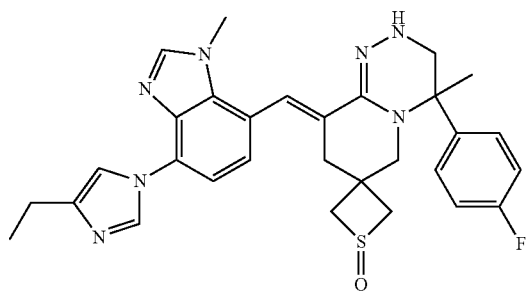
H11
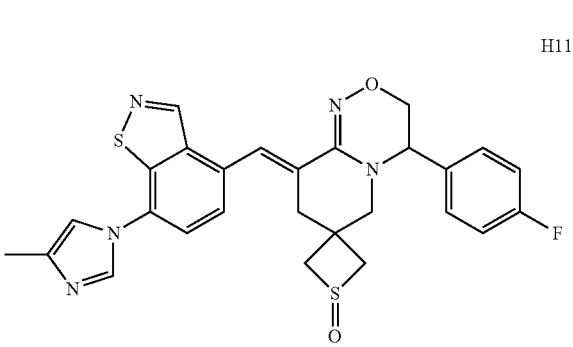
H12
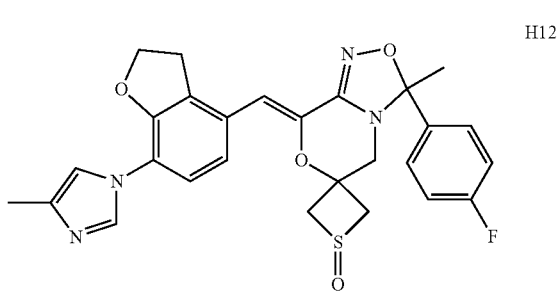
H13
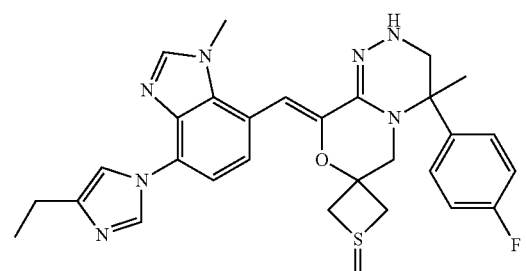
H14
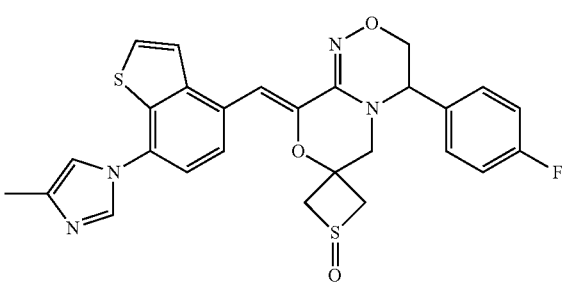

239
-continued
H15
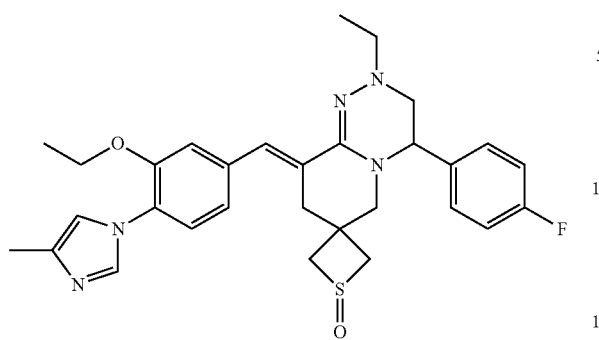
H16
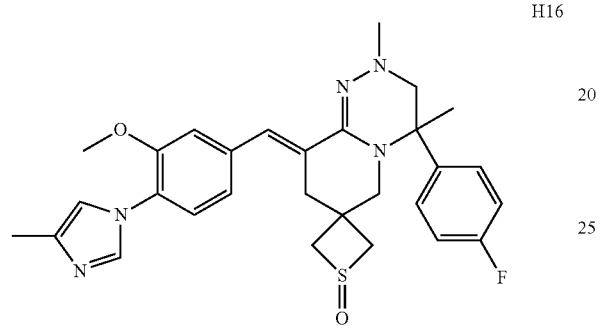
H17
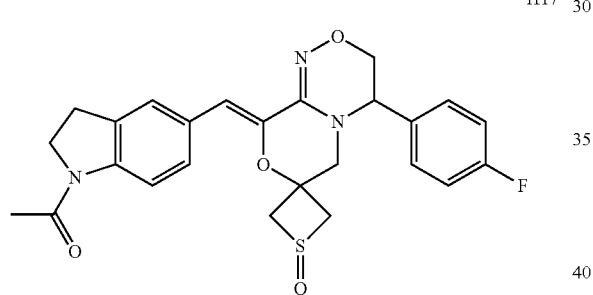
I1
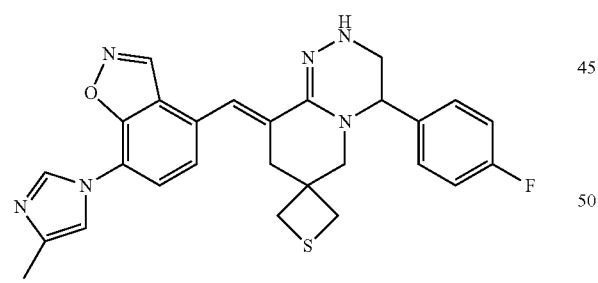
I2
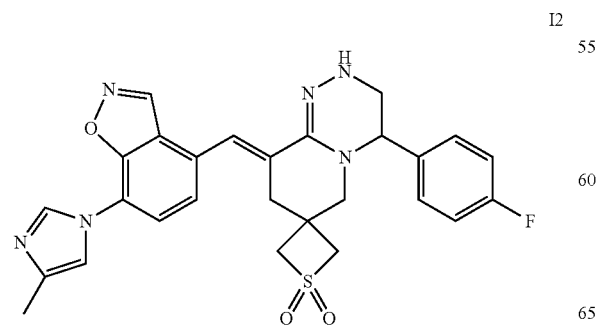
240
-continued
I3
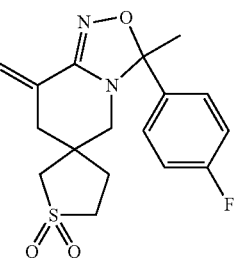
I4
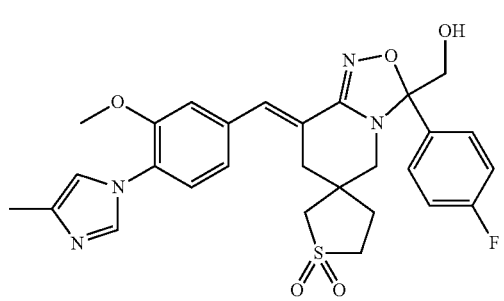
I5
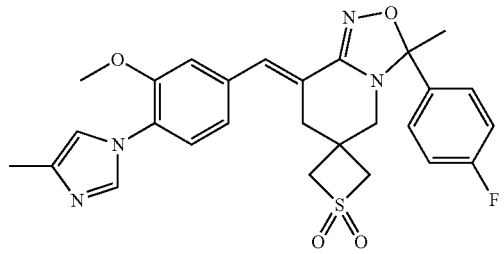
I6
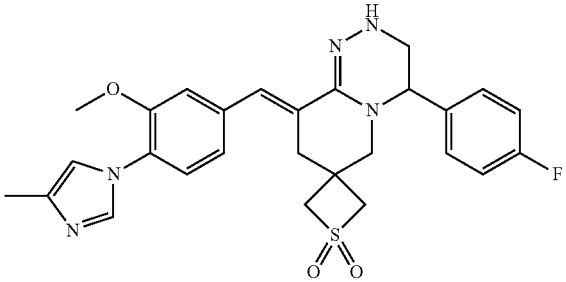
I7
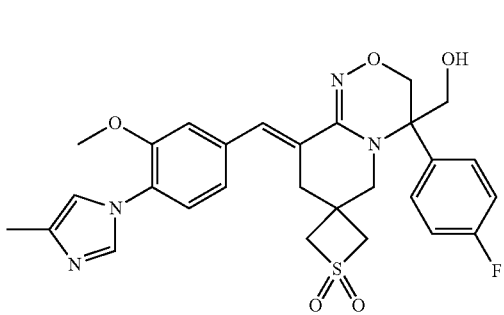

I8
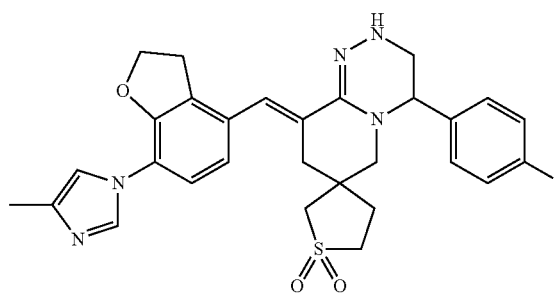
I9
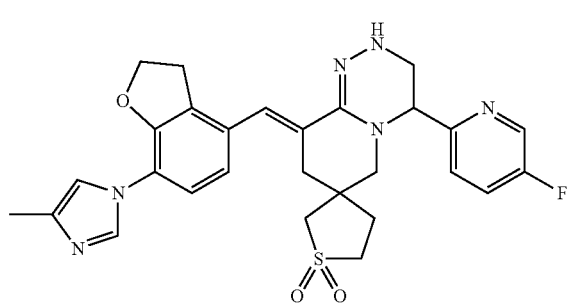
I10
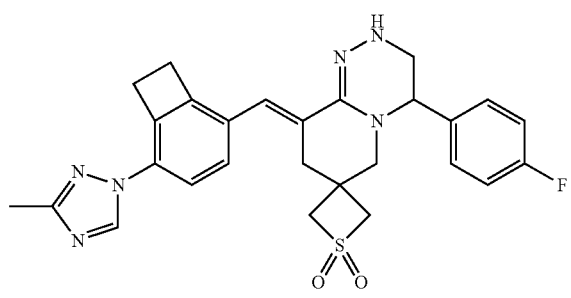
I11
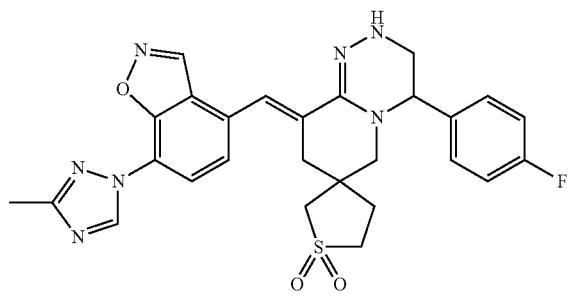
I12
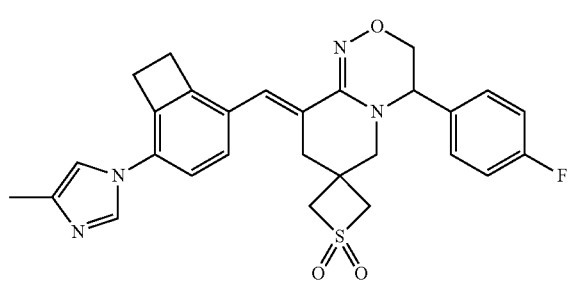
I13
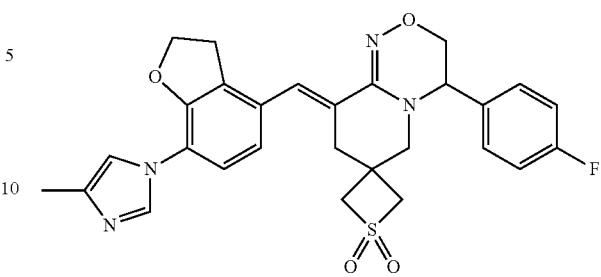
I14
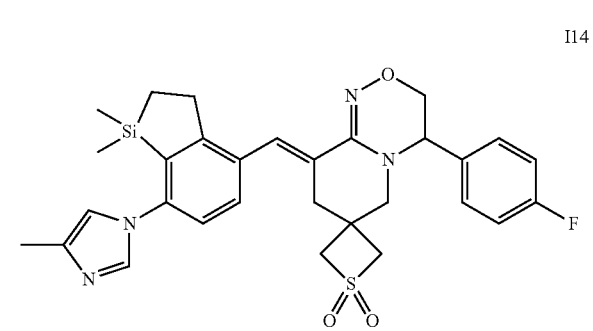
I15
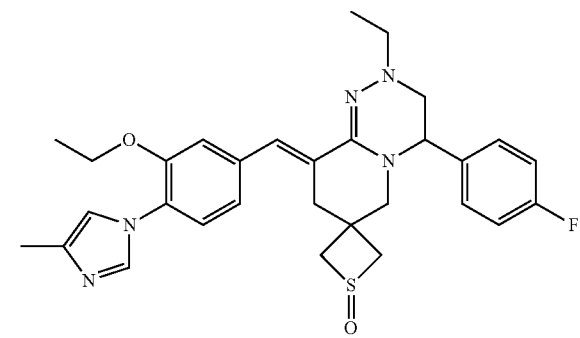
I16
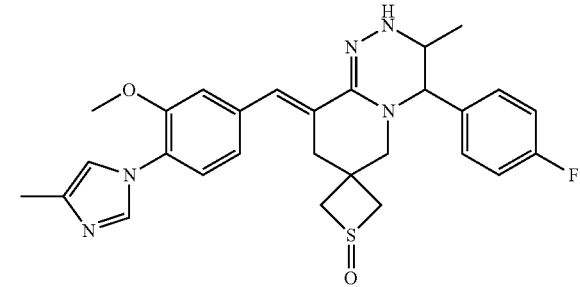
I17
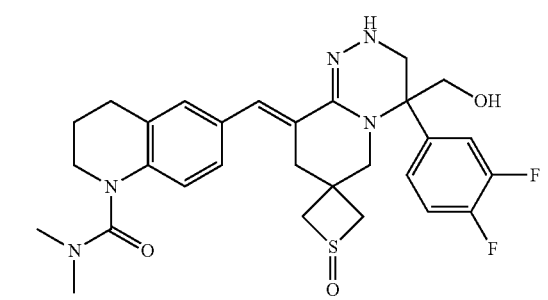

243
-continued
J1
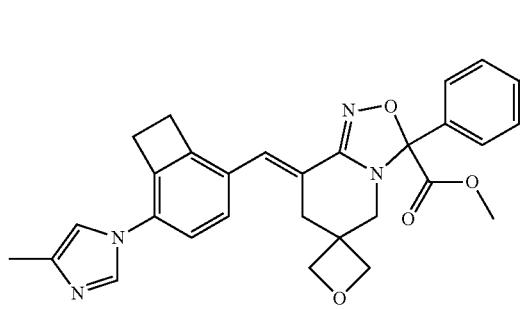
J3
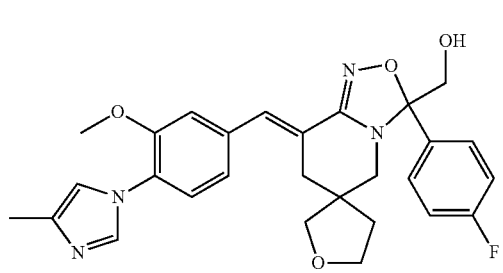
J4
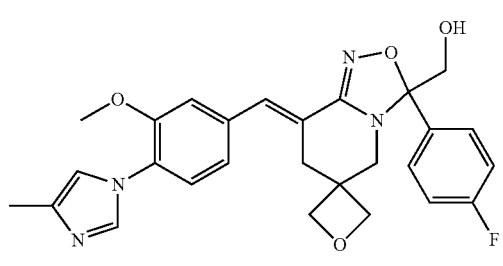
J5
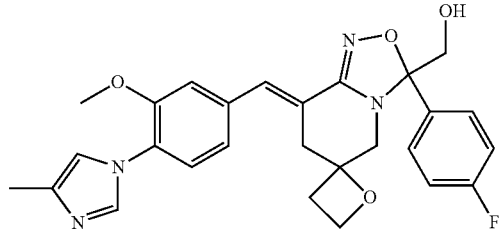
J6
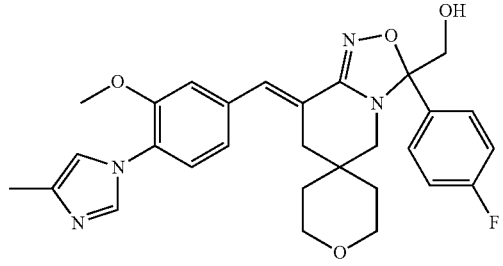
J7
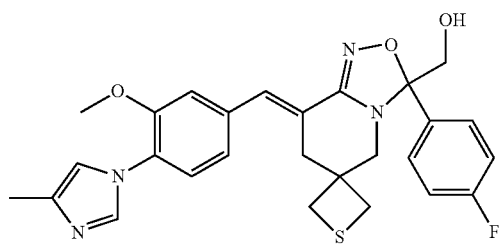
244
-continued
J8
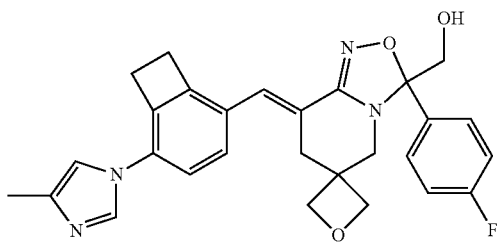
J9
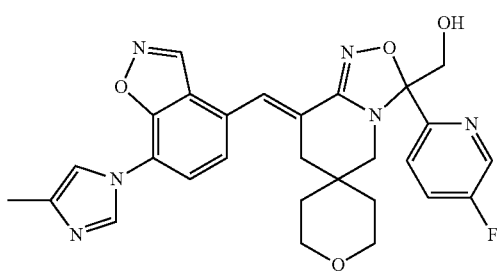
J10
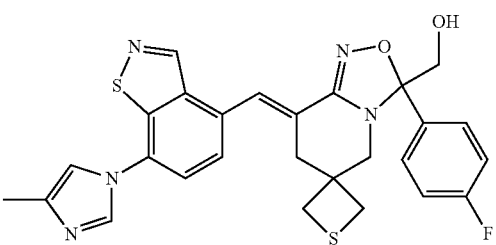
J11
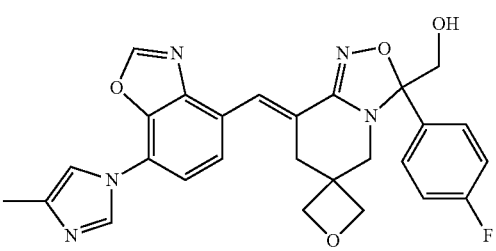
J12
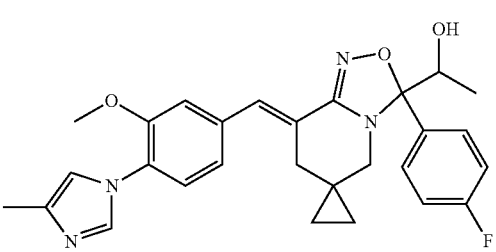
J13
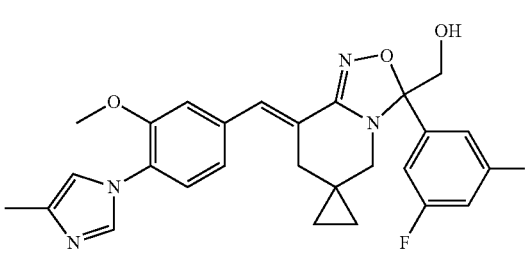

245
-continued
J14
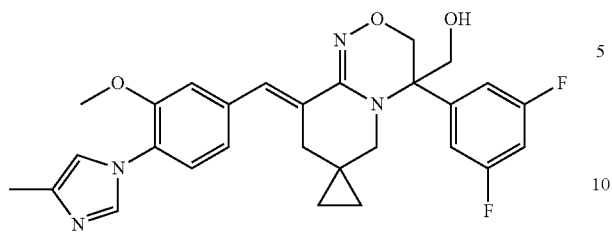
J15
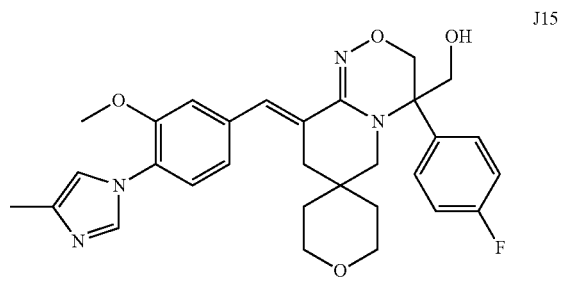
J16
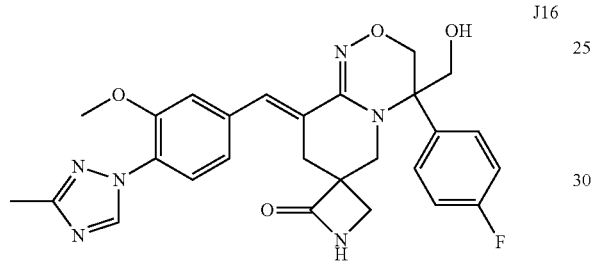
J17
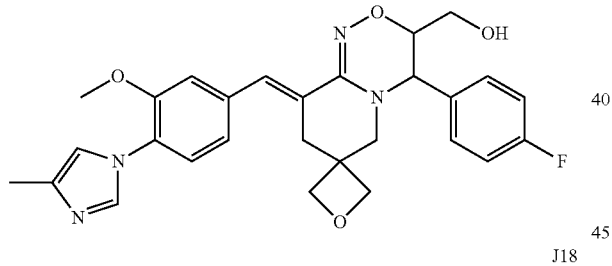
J18
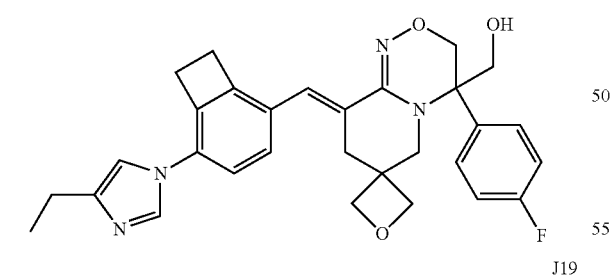
J19
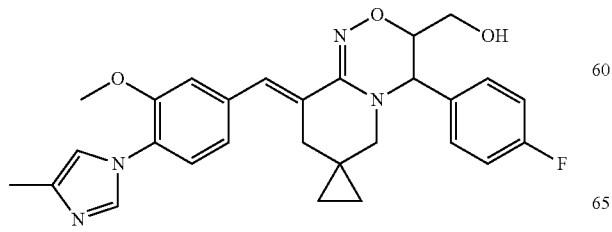
246
-continued
J20
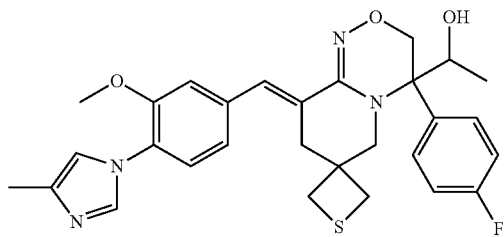
J21
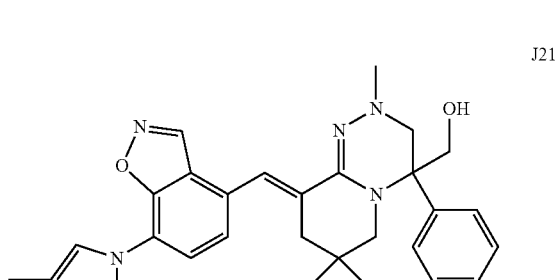
J22
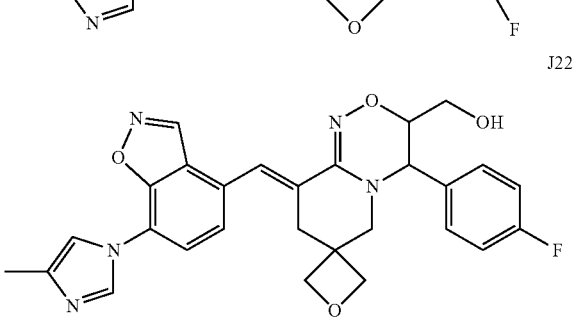
J23
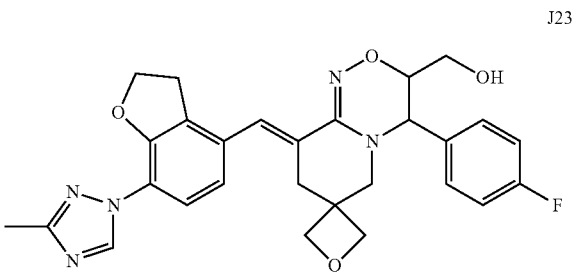
J24
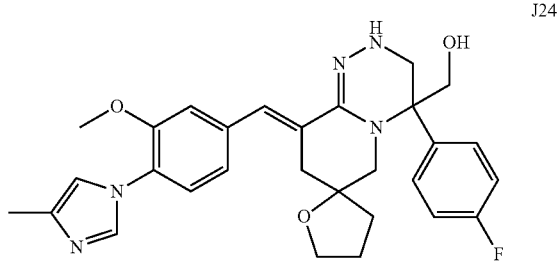
J25
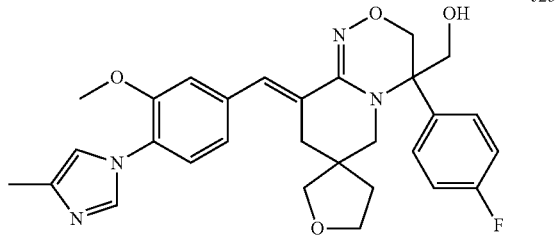

J26
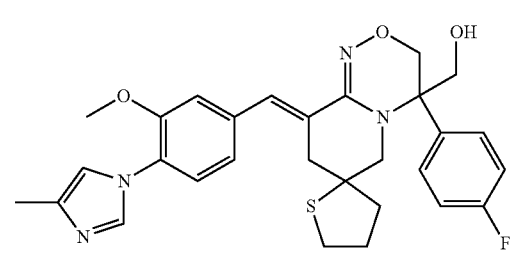
J27
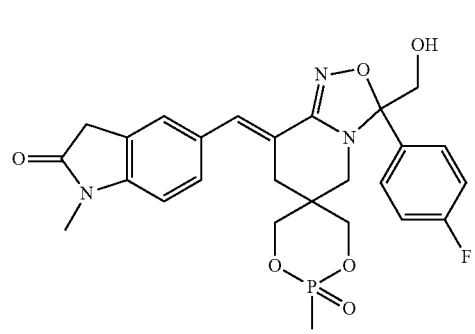
J28
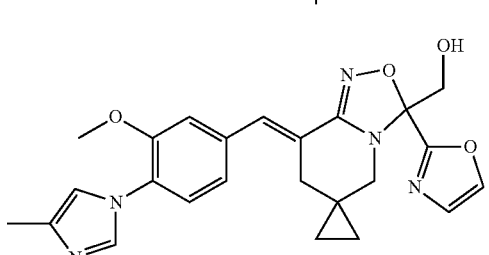
J29
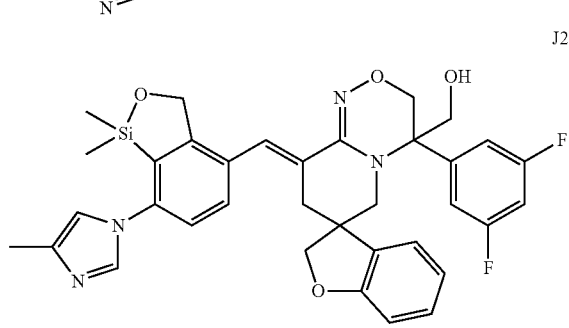
J30
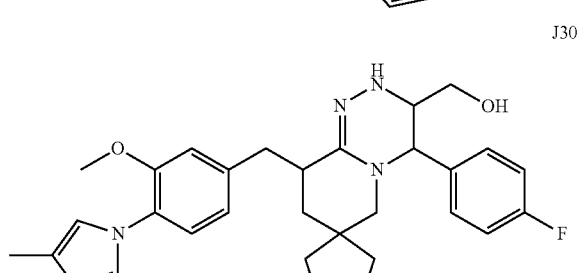
J31
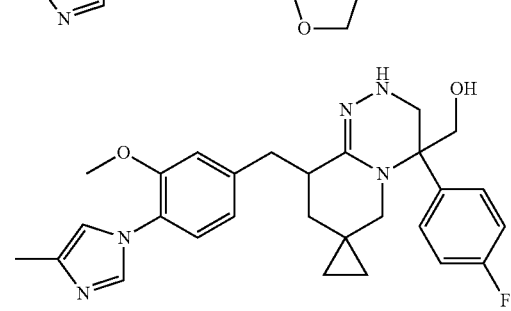
J32
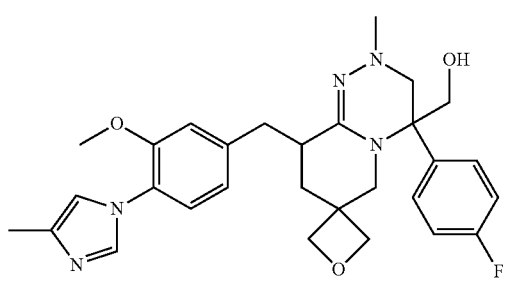
J33
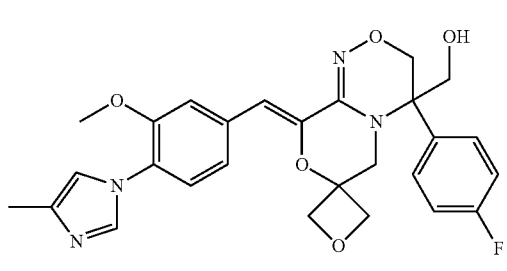
J34
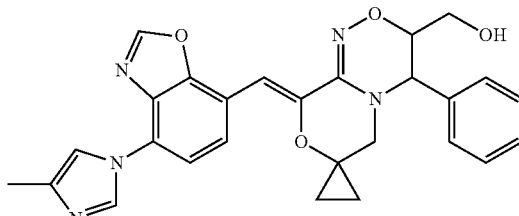
J35
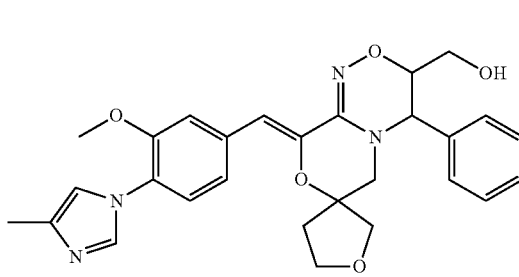
J36
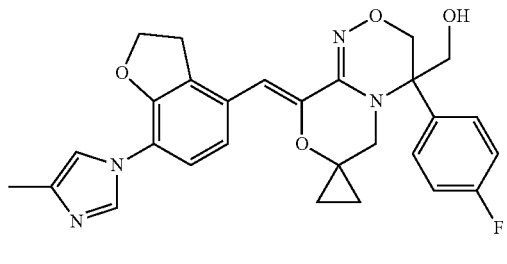
J37
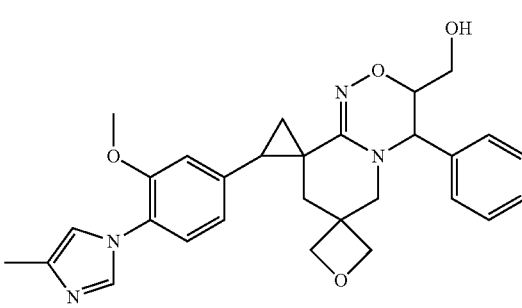

J38
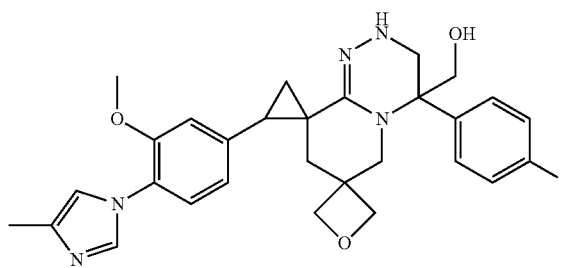
K9
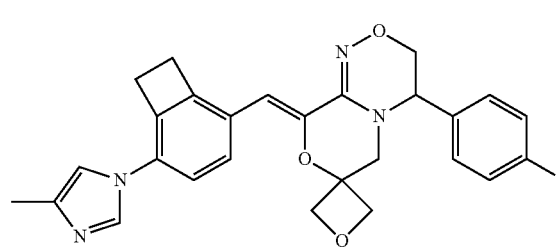
K10
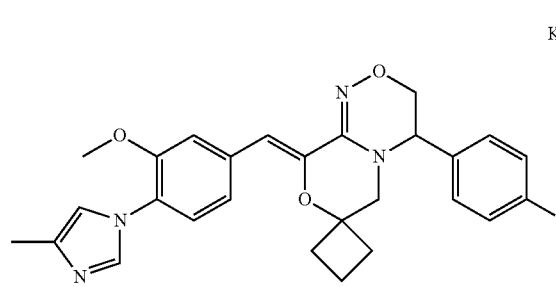
K11
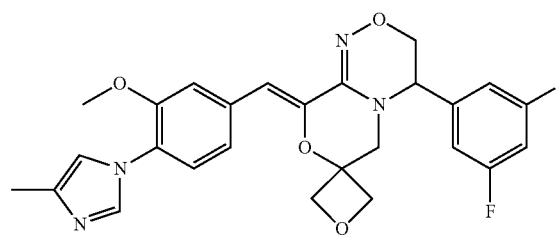
K12
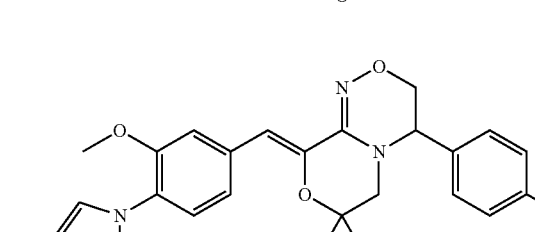
K13
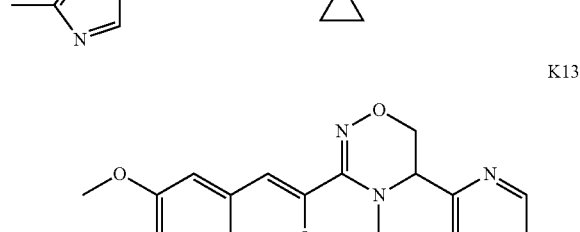
K14
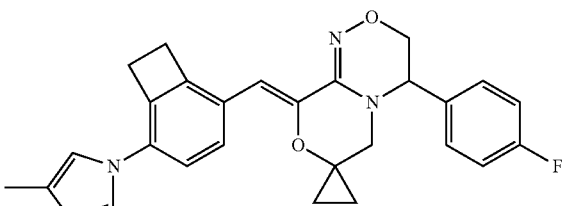
K15
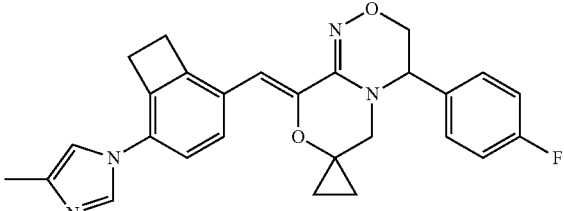
K16
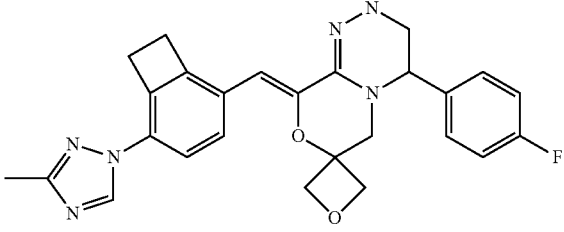
K17
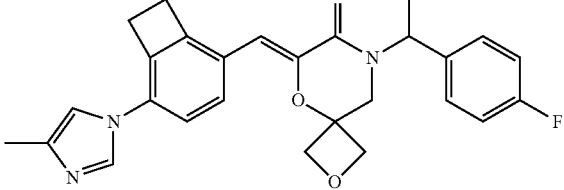
K18
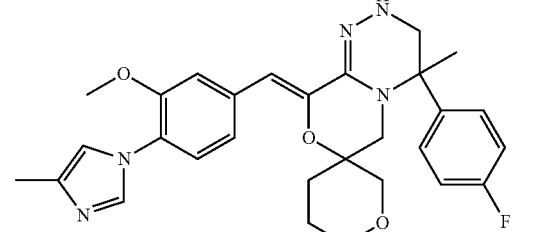
K19
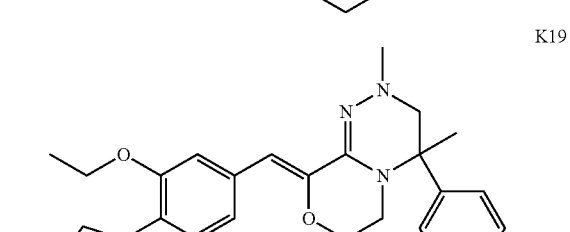

251
-continued
K20
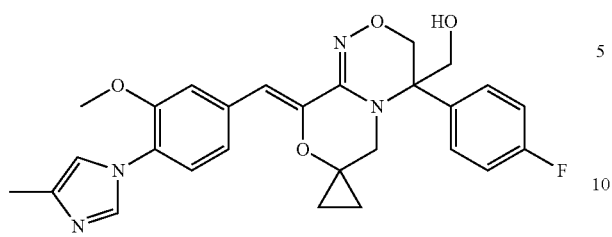
K21
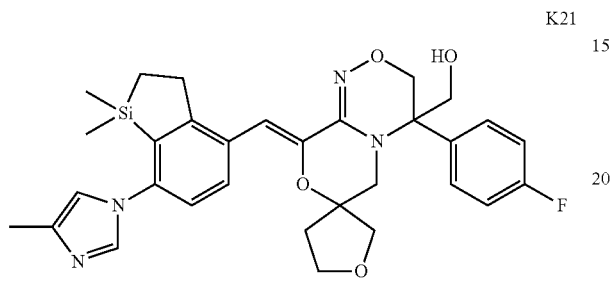
K22
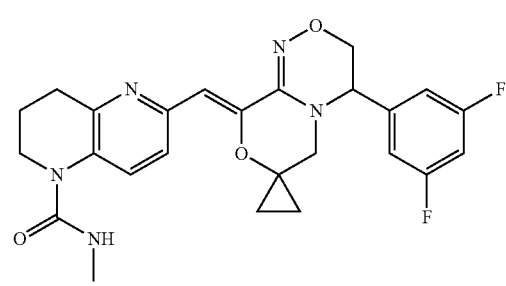
K23
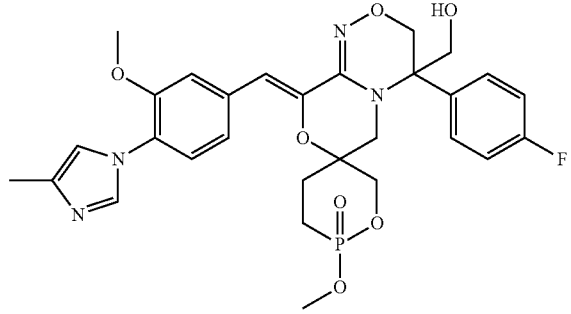
K24
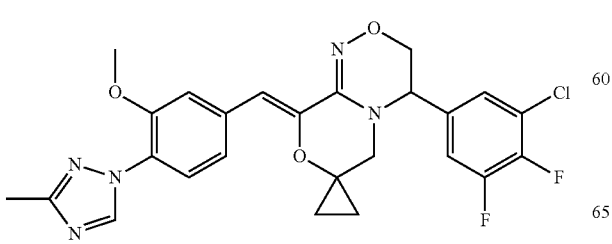
252
-continued
L8
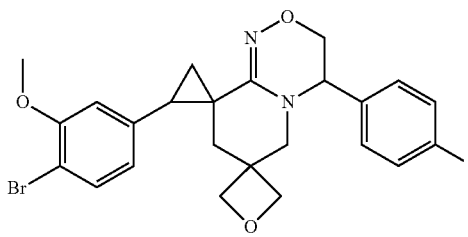
L9
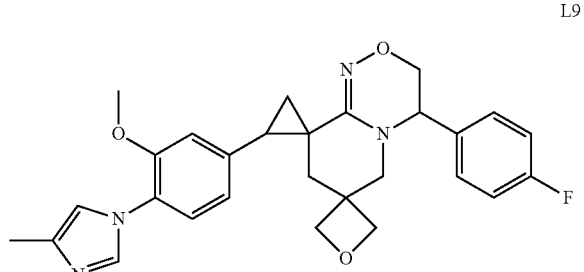
L10
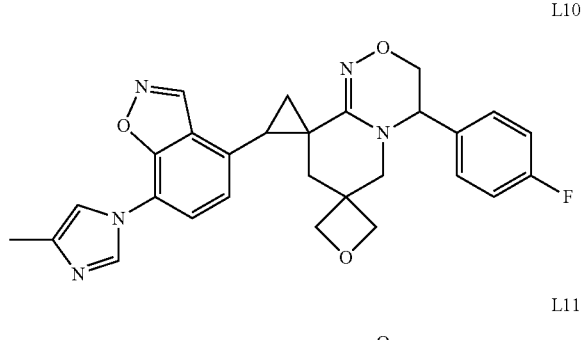
L11
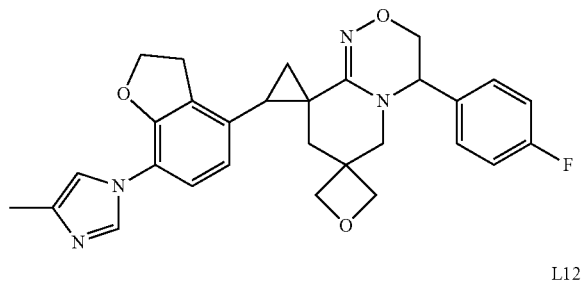
L12
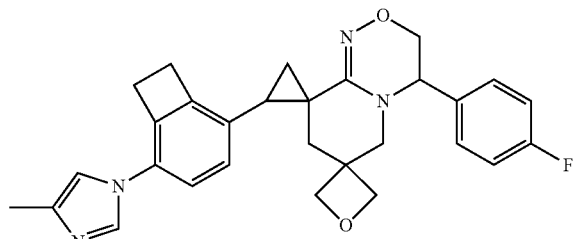
L13
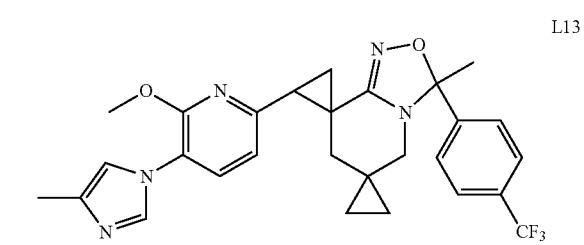

253
-continued
L14
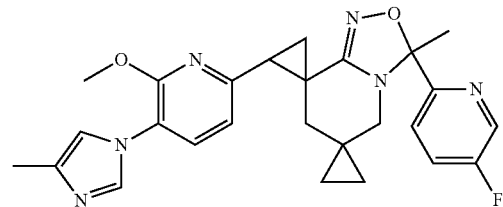
L15
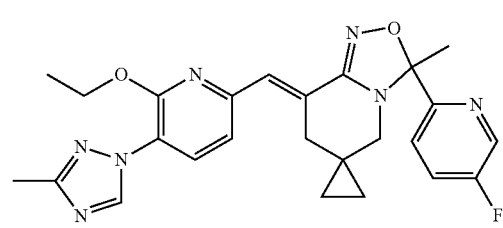
L16
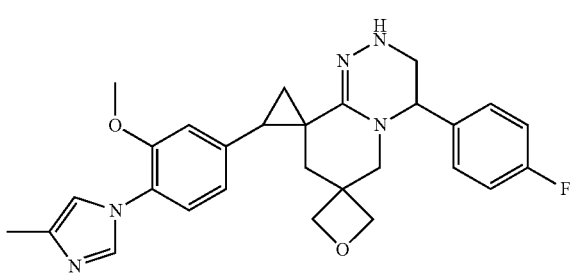
L17
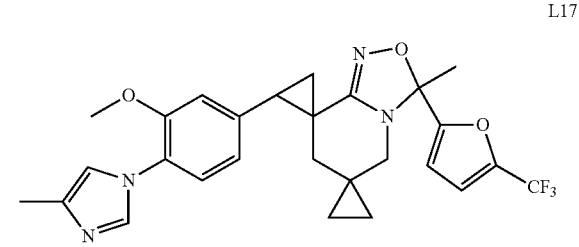
L18
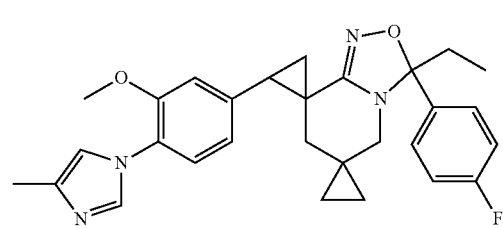
L19
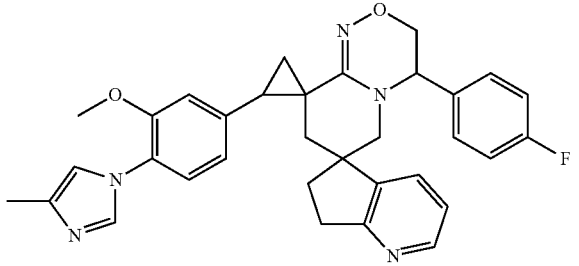
254
-continued
L20
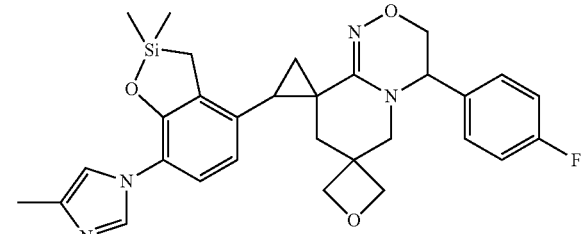
L21
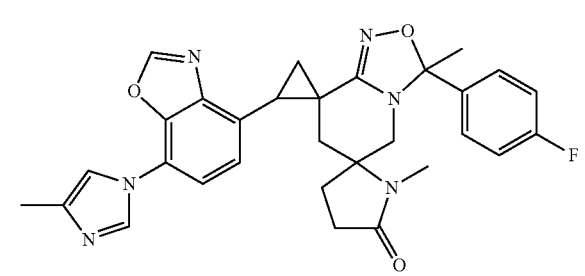
M1
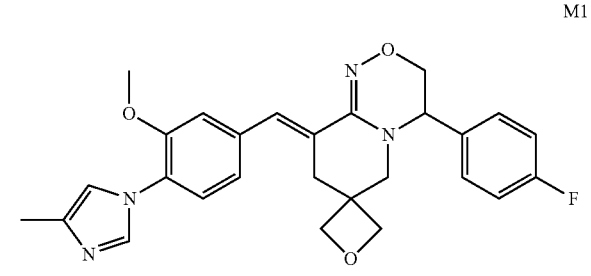
M2
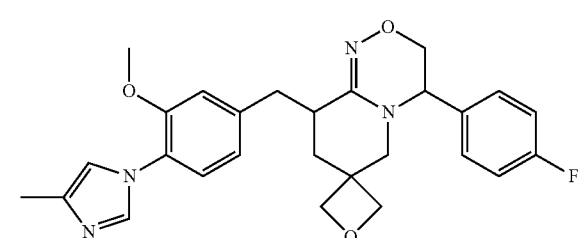
M3
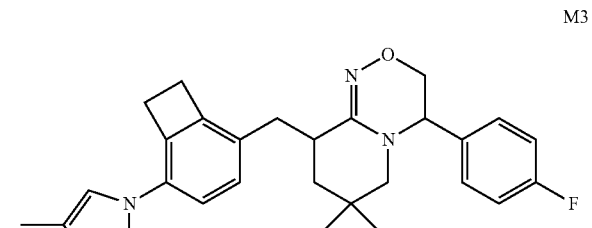
M4
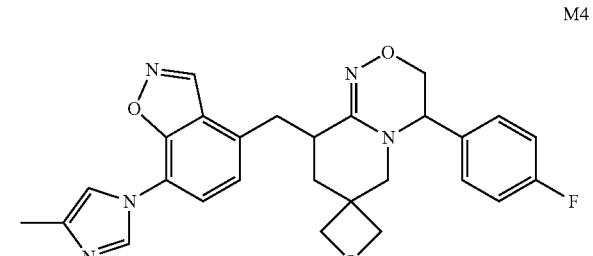

255 256
-continued -continued
M5
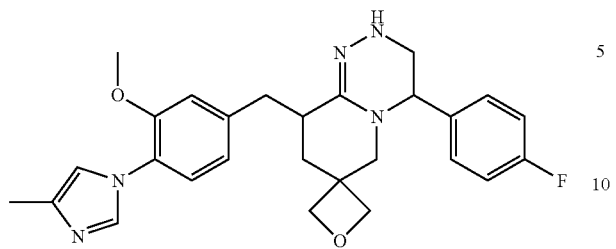
M11
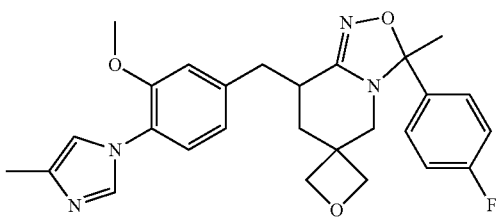
M6
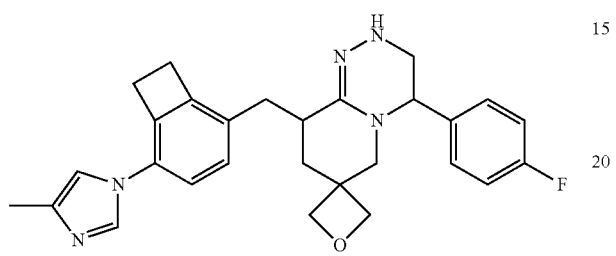
M12
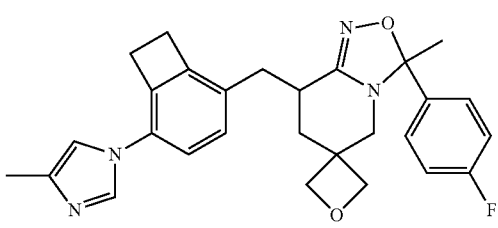
M7
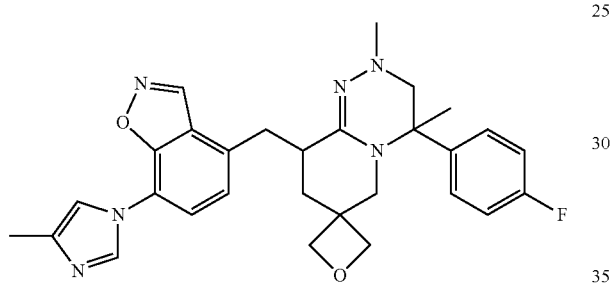
M13
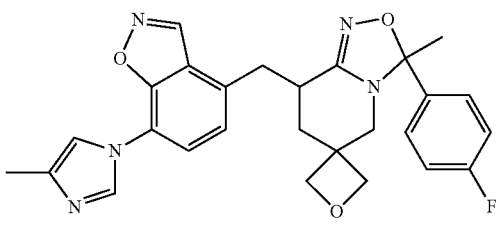
M8
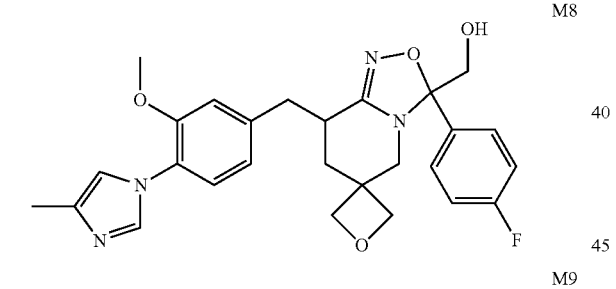
M14
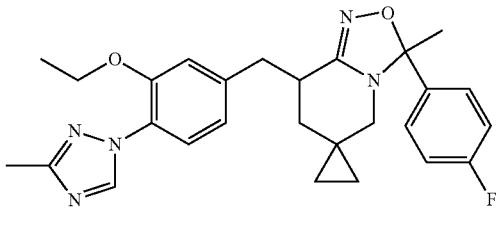
M9
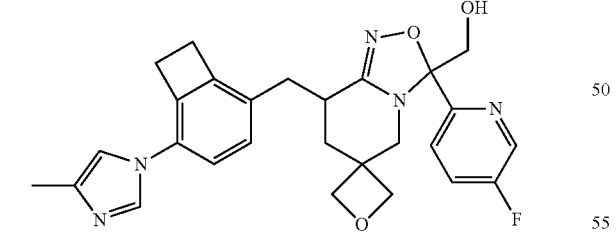
M15
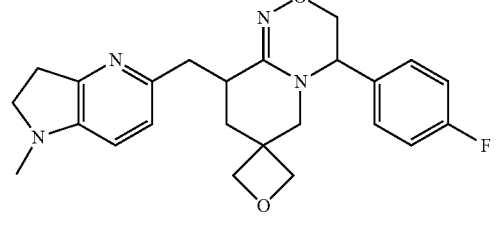
M10
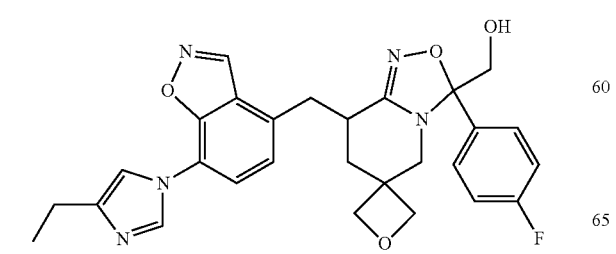
M16
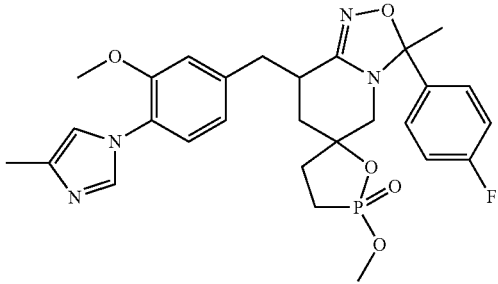

M17
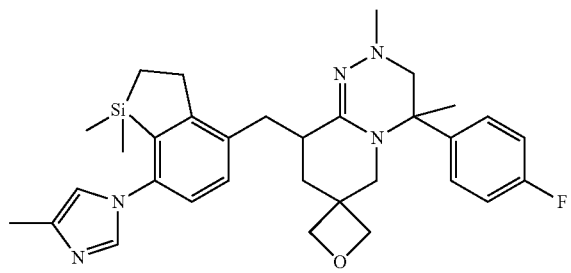
N1
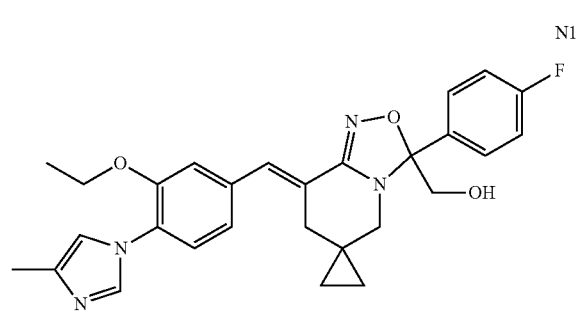
N2
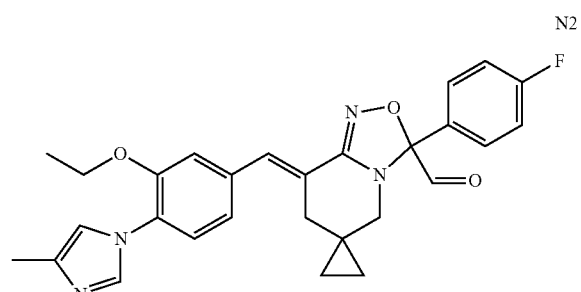
N3
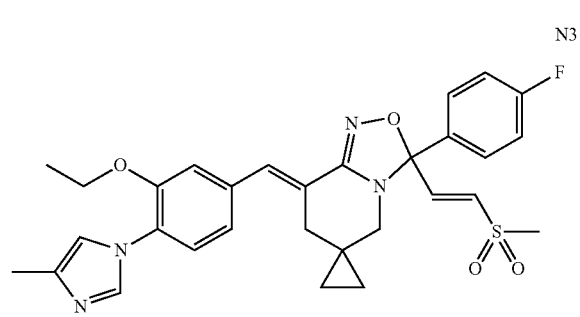
N4
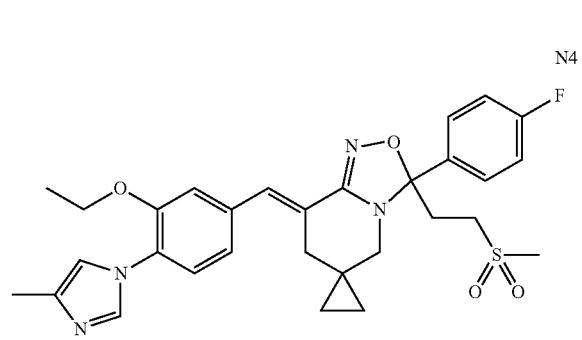
N5
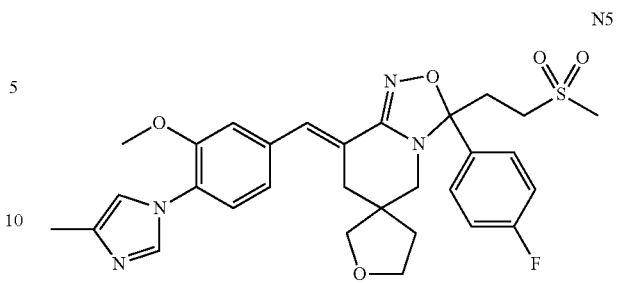
N6
N7
N8
N9
N10
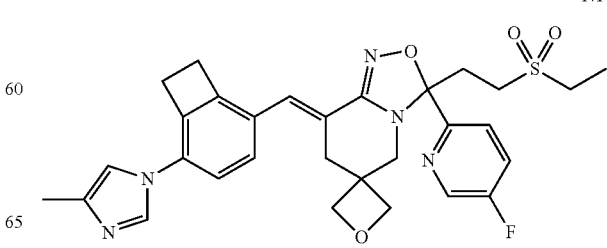

259
-continued
N11
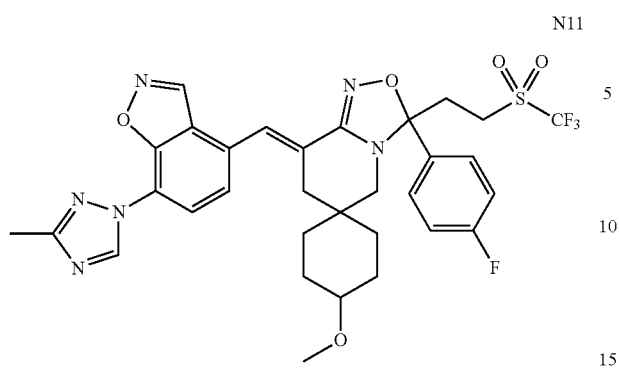
N12
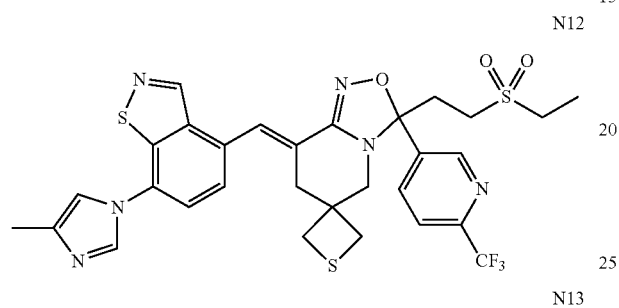
N13
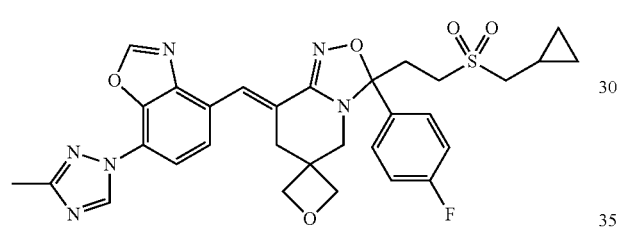
N14
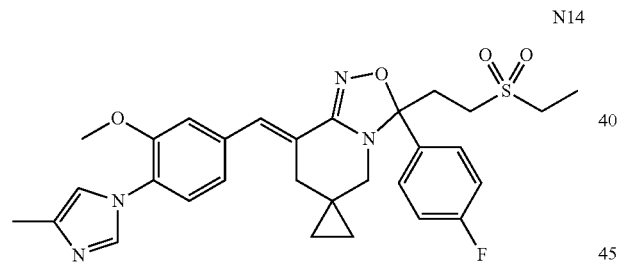
N15
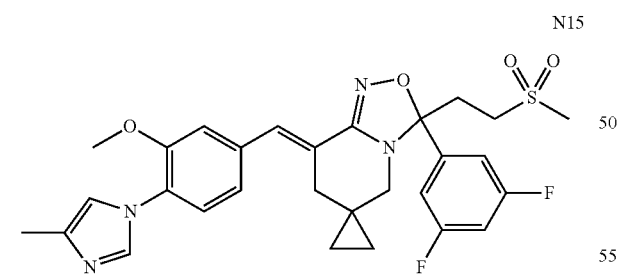
N16
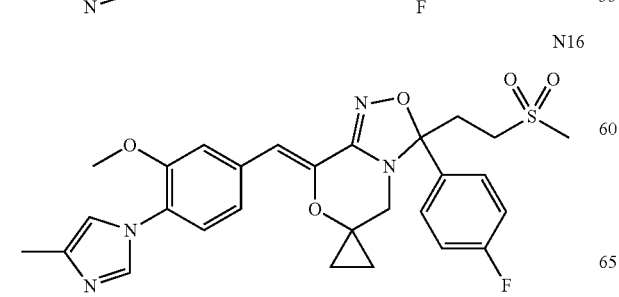
260
-continued
N17
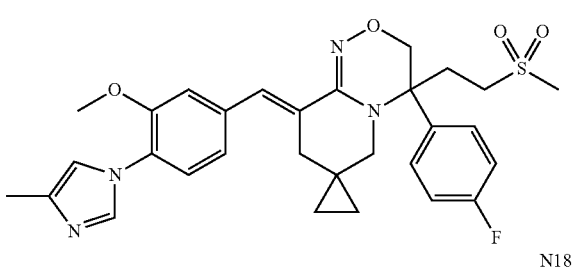
N18
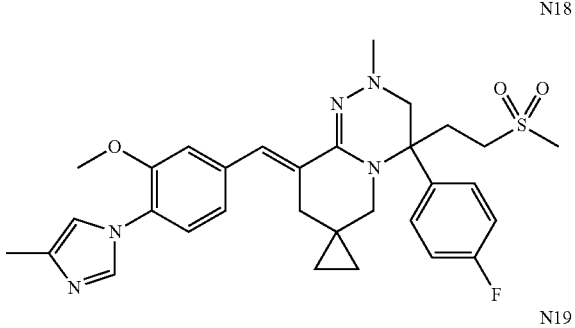
N19
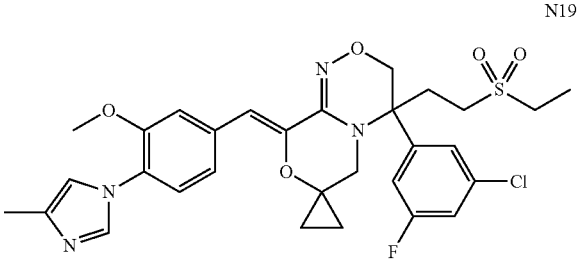
N20
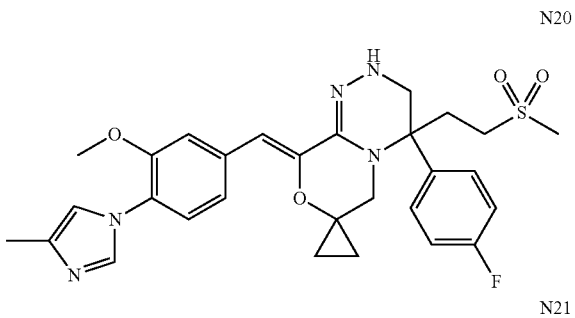
N21
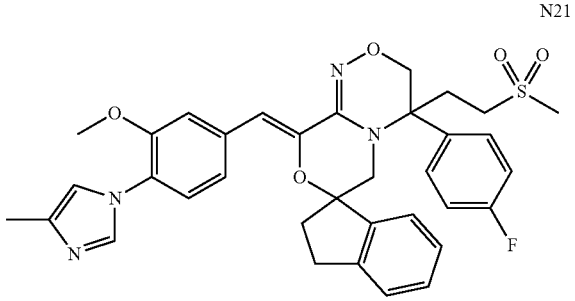
N22
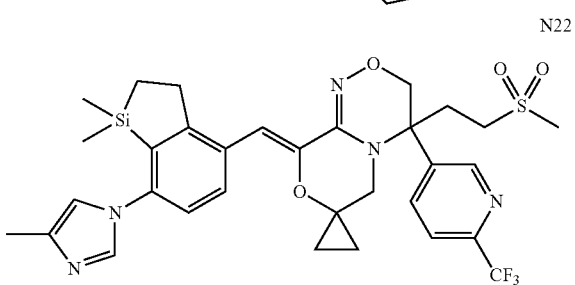

261
-continued
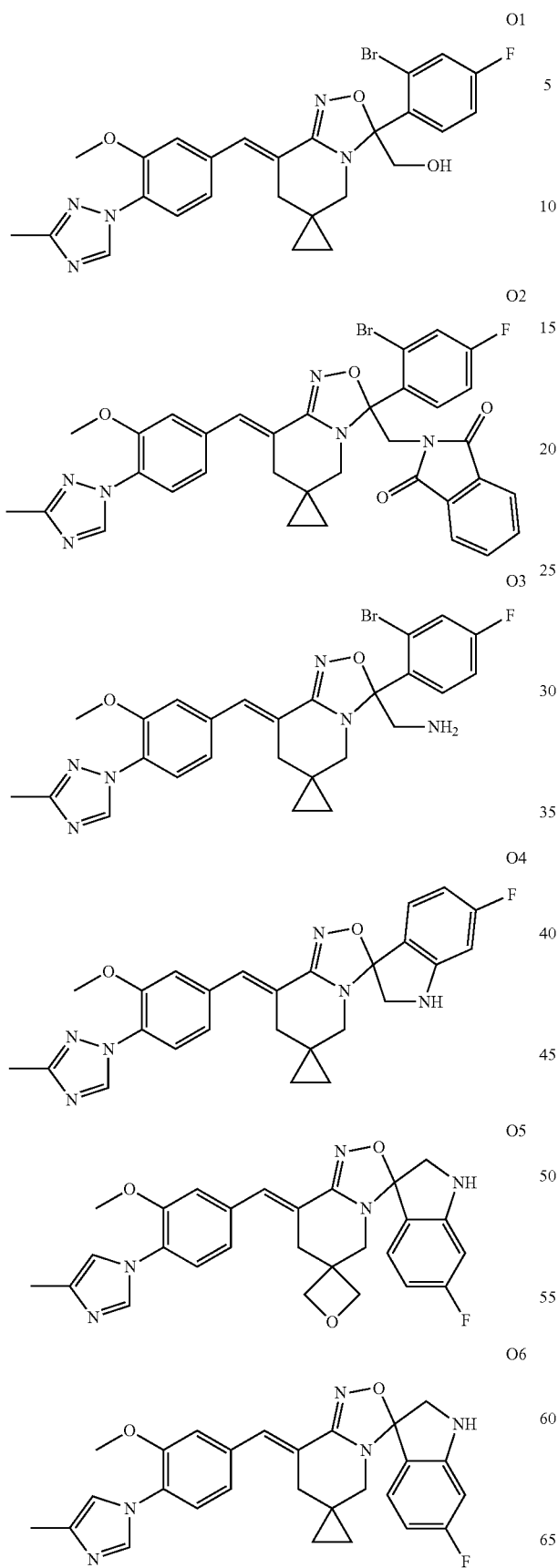
262
-continued
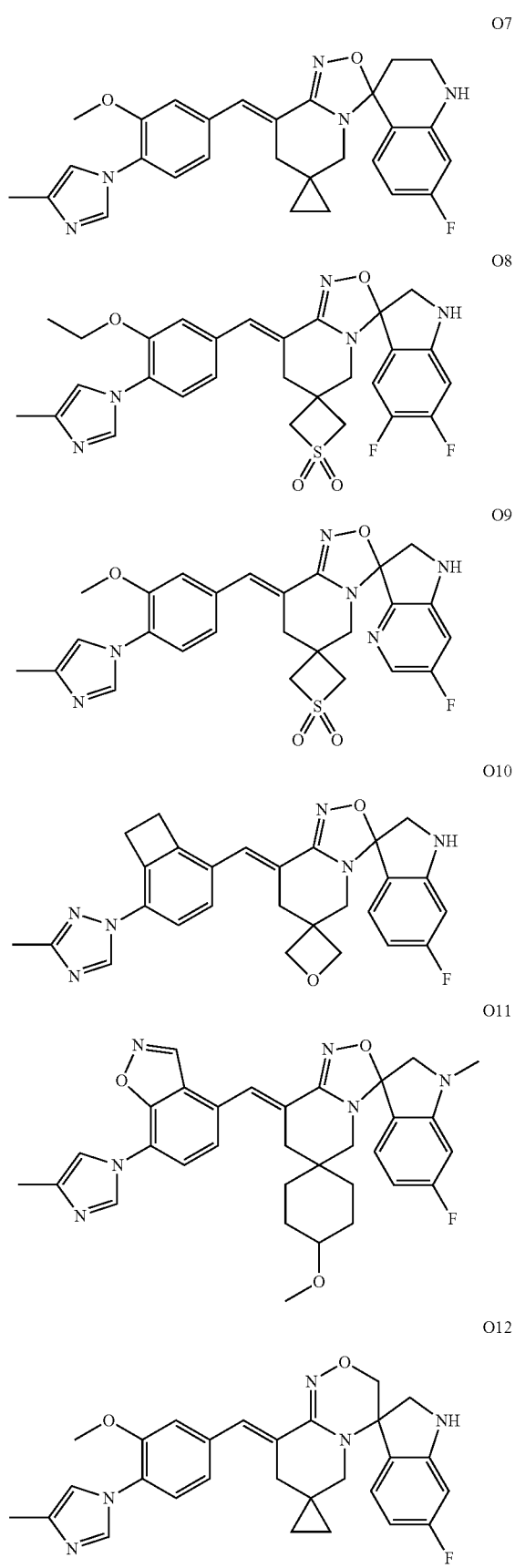

263
-continued
O13
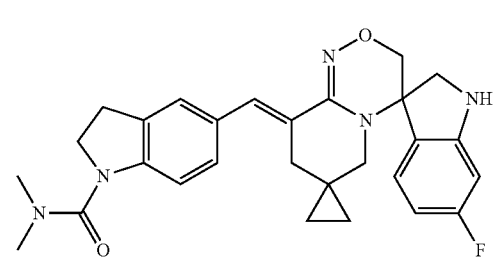
O14
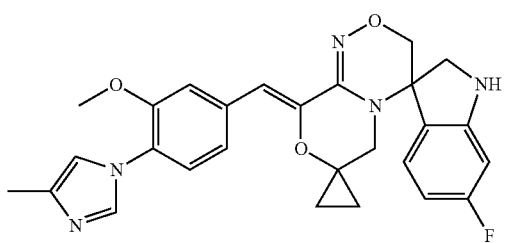
O15
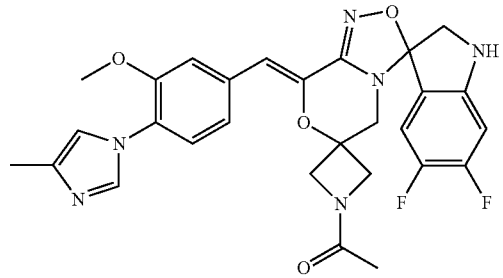
O16
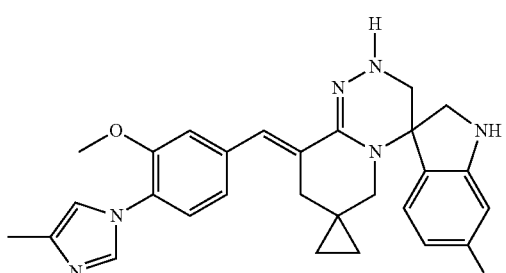
O17
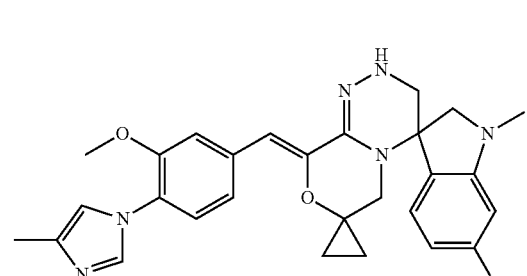
O18
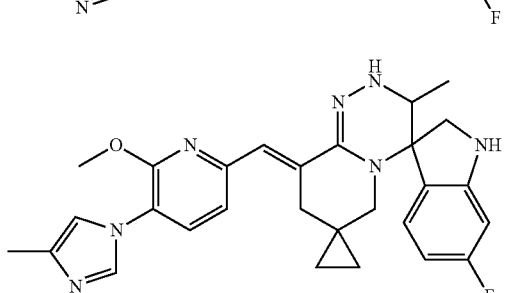
264
-continued
O19
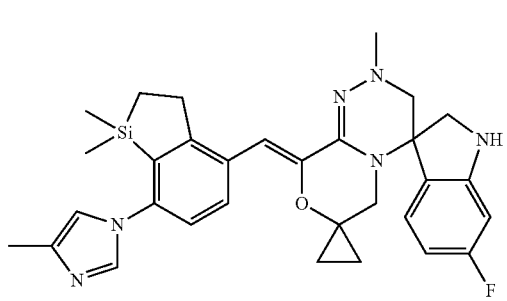
O20
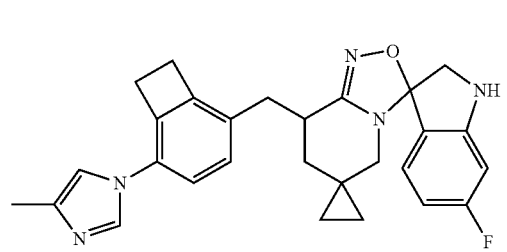
O21
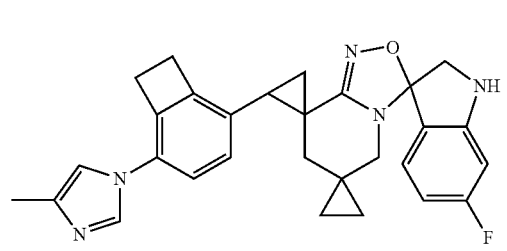
O22
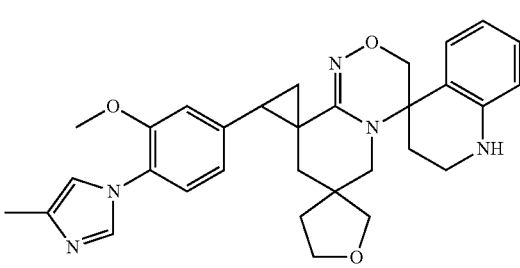
P6
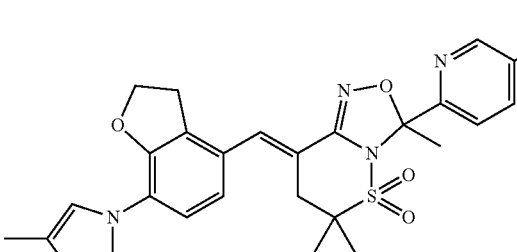
P7
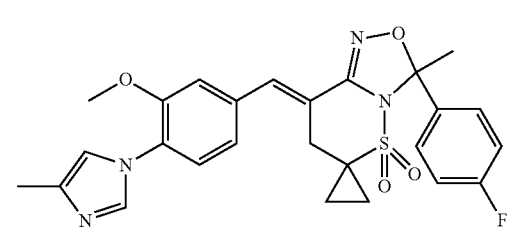

265
-continued
P8
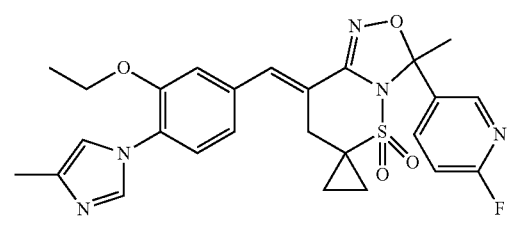
P9
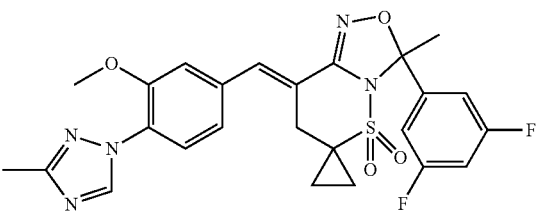
P10
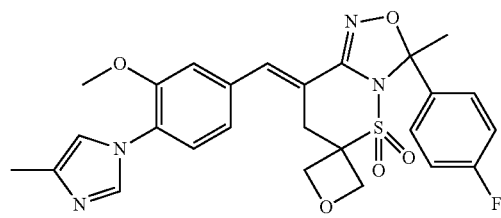
P11
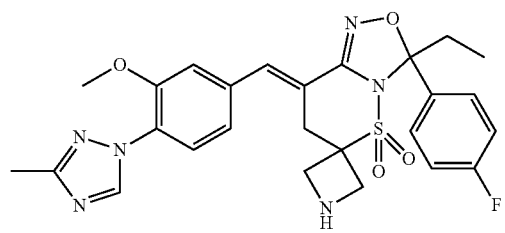
P12
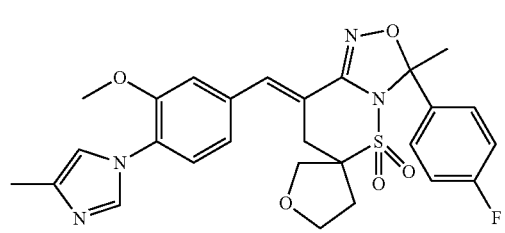
P13
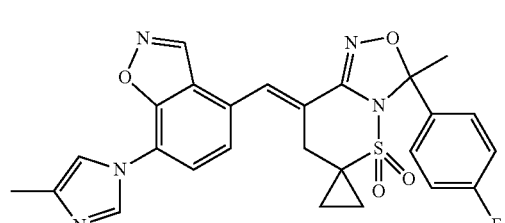
P14
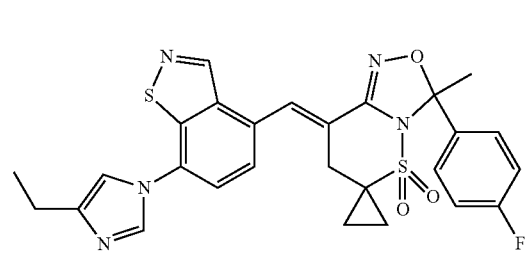
266
-continued
P15
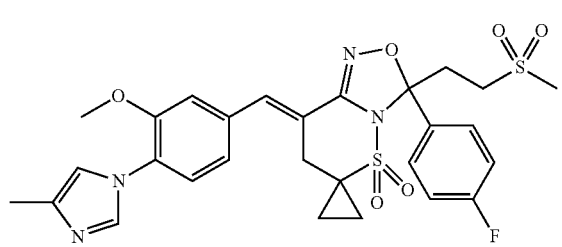
Q1
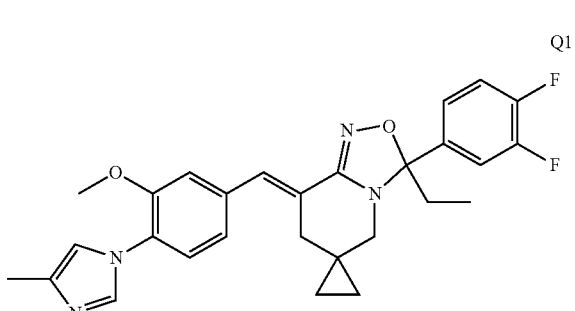
Q2
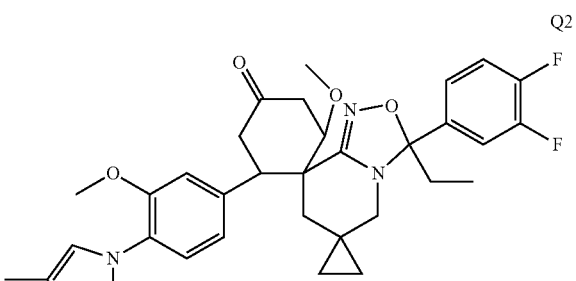
Q3
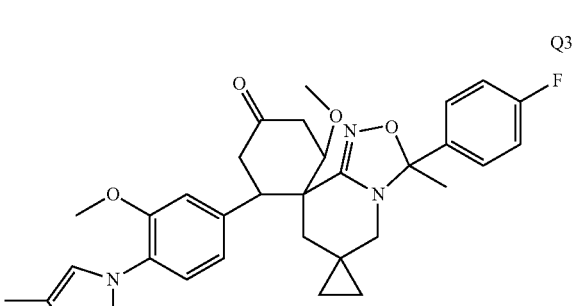
Q4
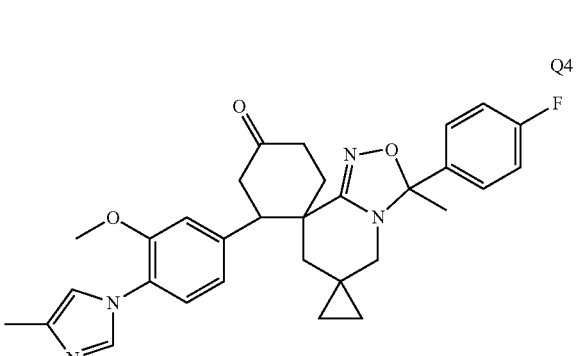

267
-continued
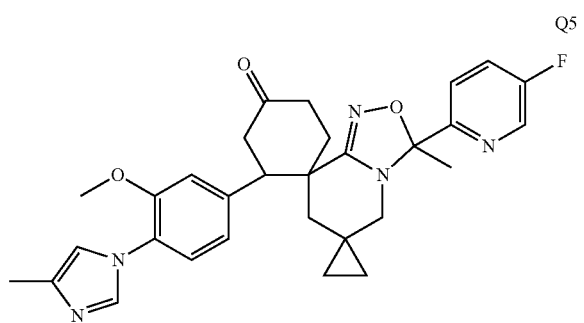
Q5
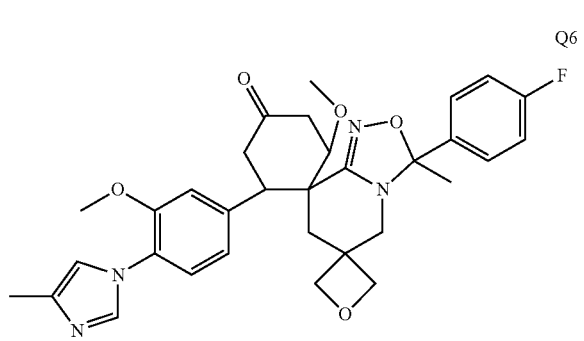
Q6
268
-continued
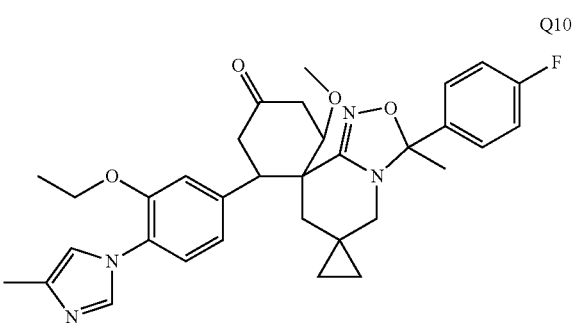
Q10
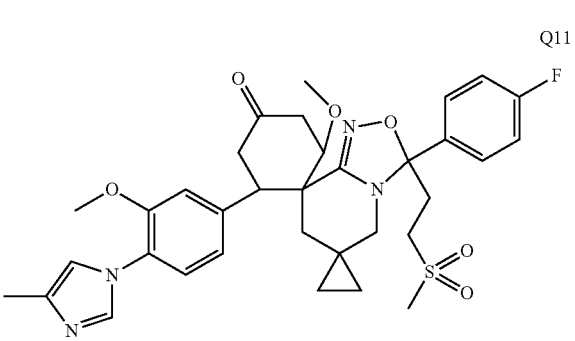
Q11
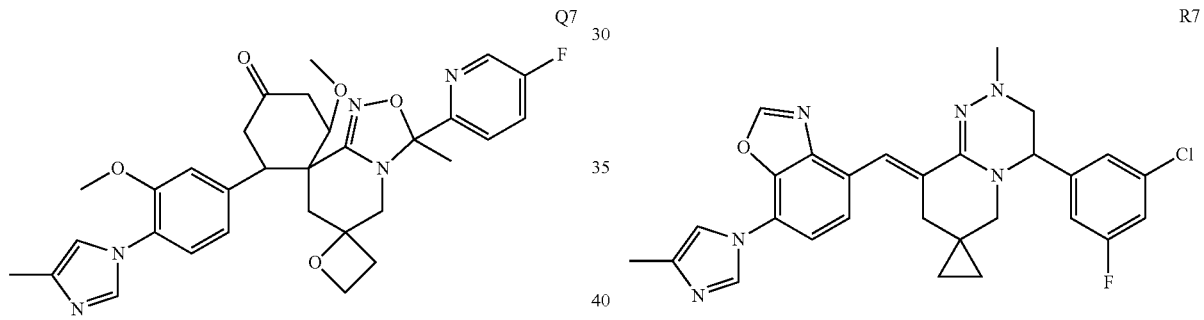
Q7
R7
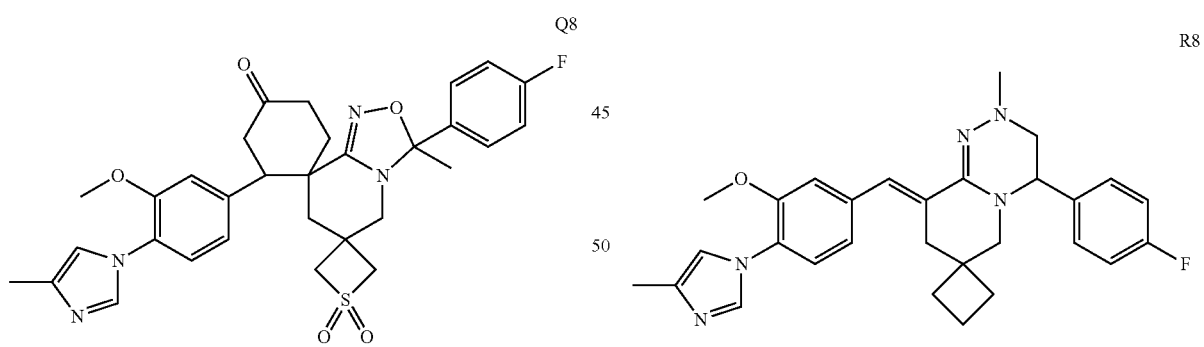
Q8
R8
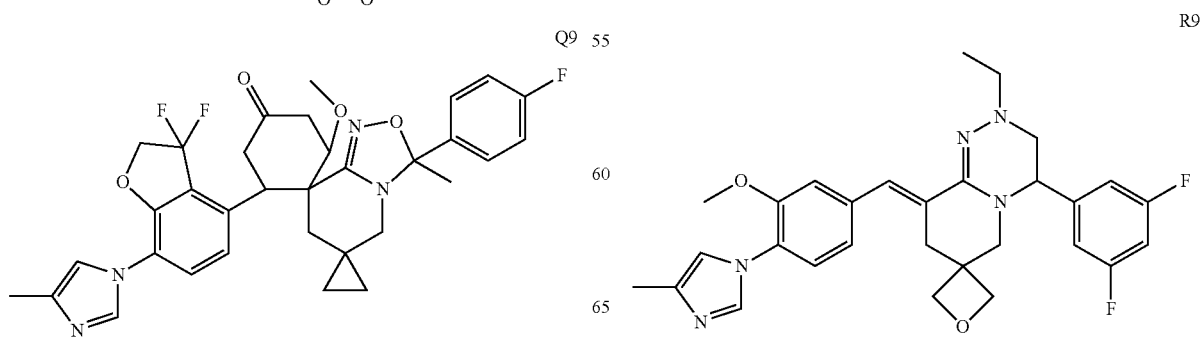
Q9
R9

269
-continued
R10
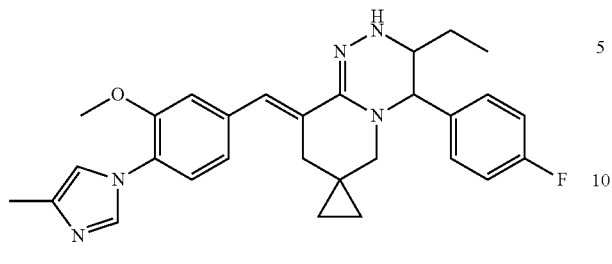
R11
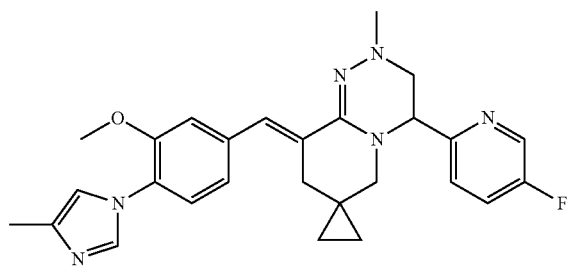
R12
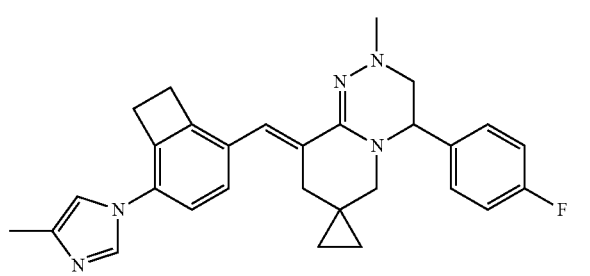
R13
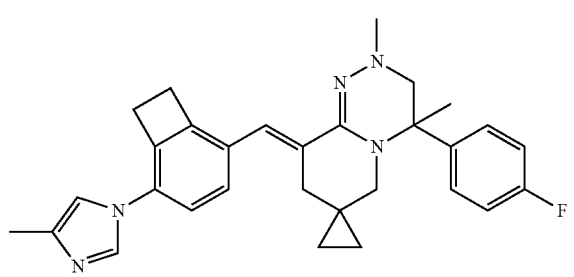
R14
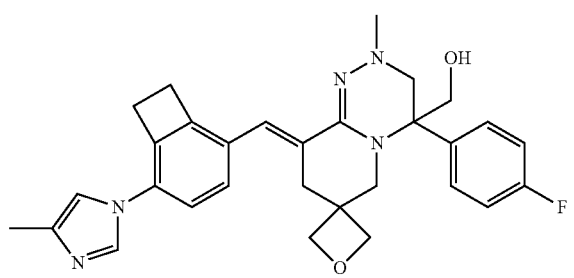
270
-continued
R15
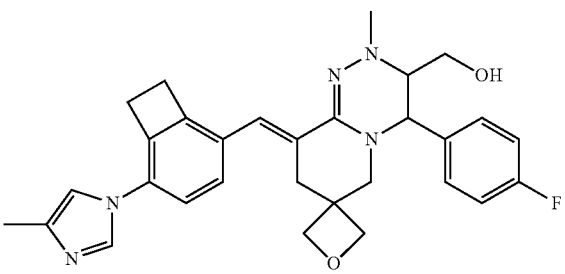
R16
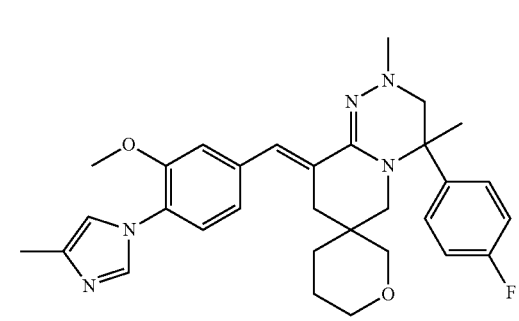
R17
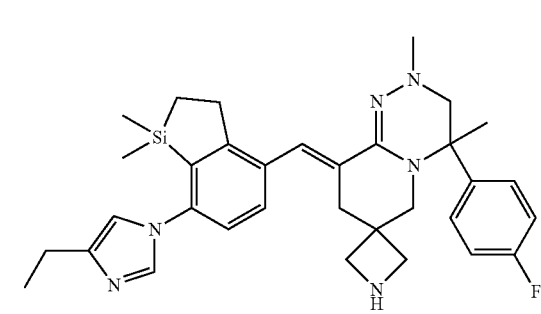
R18
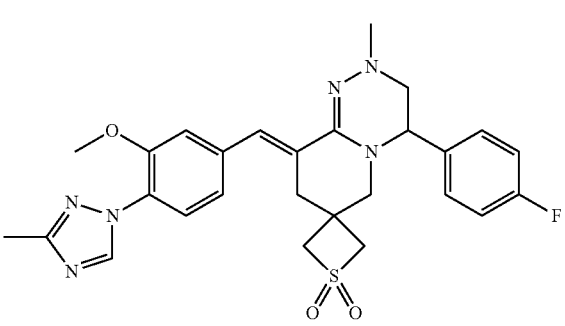
R19
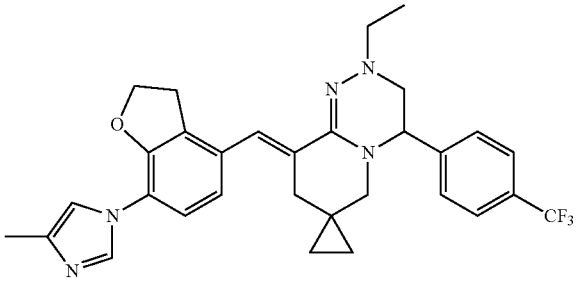

US 8,487,099 B2
271
-continued
S1
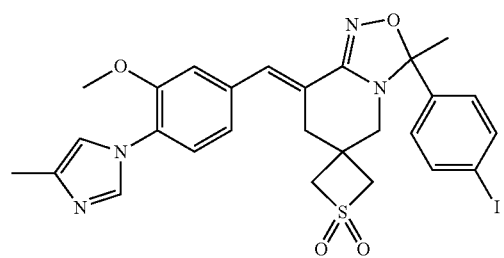
S2
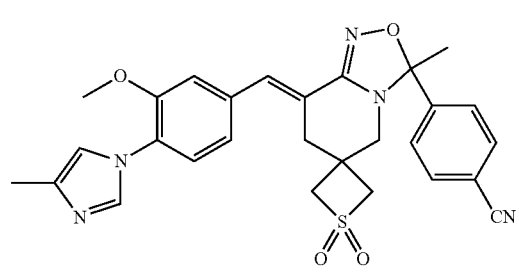
S3
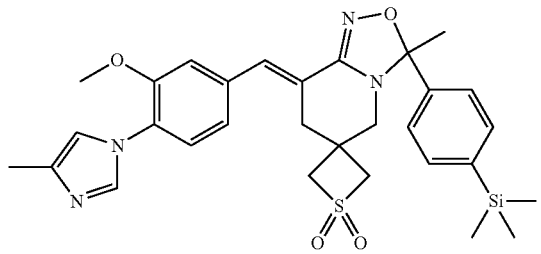
S4
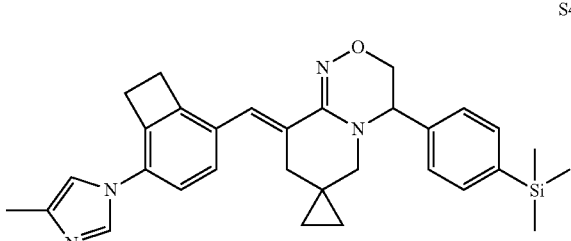
S5
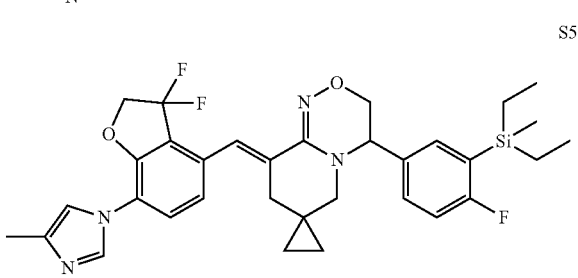
S6
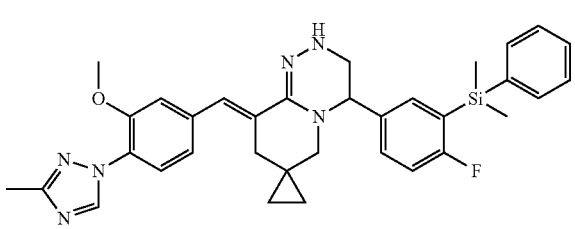
272
-continued
S7
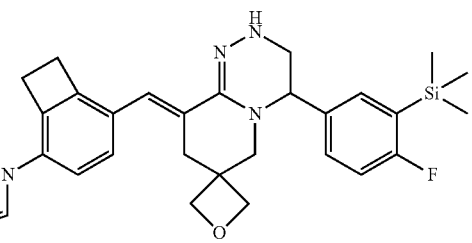
S8
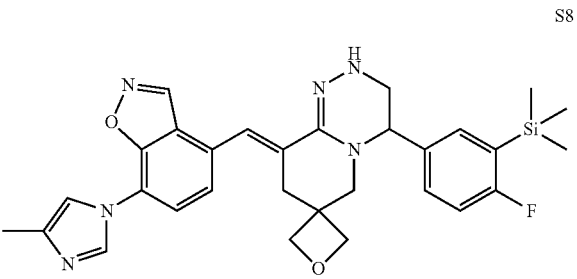
S9
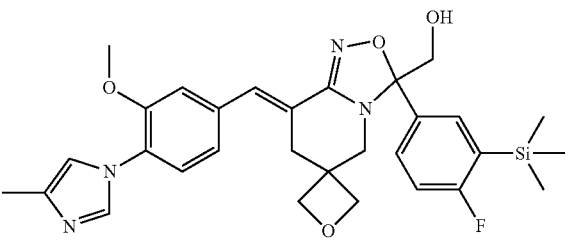
S10
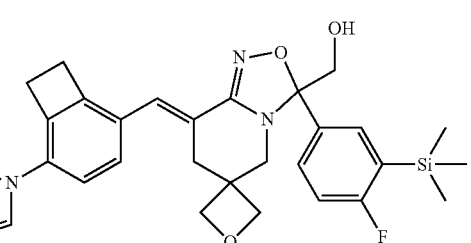
S11
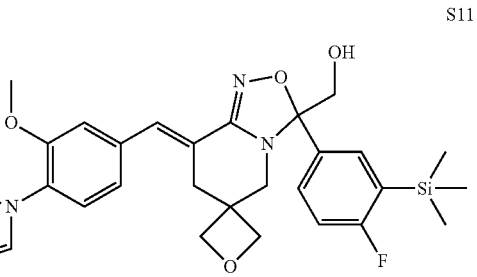
S12
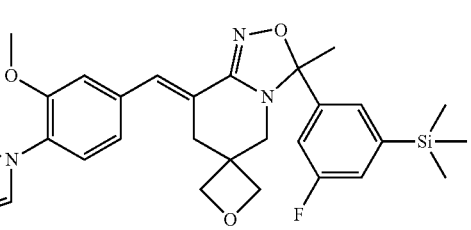

273
-continued
S13
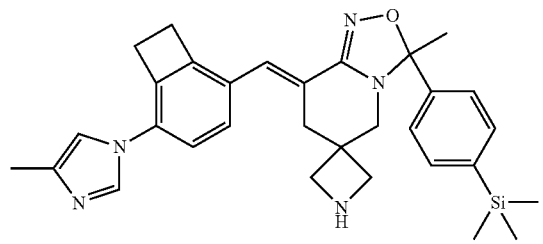
S14
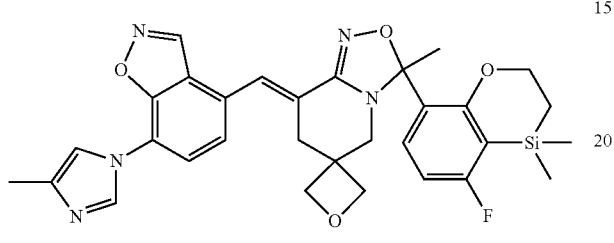
S15
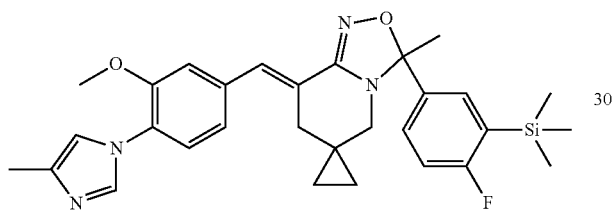
T3
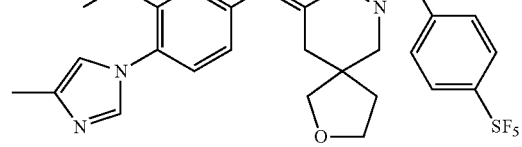
T4
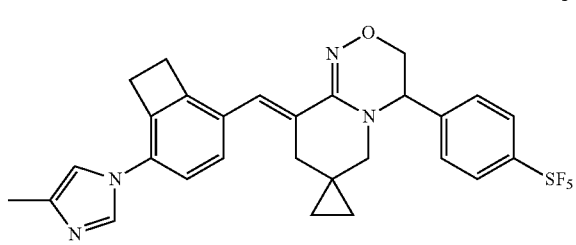
T5
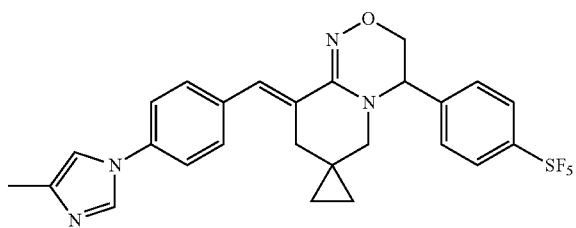
274
-continued
T6
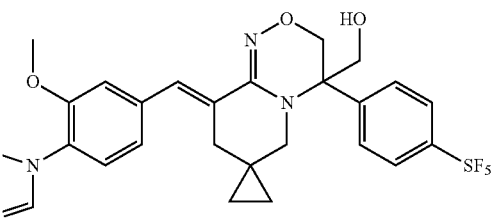
T7
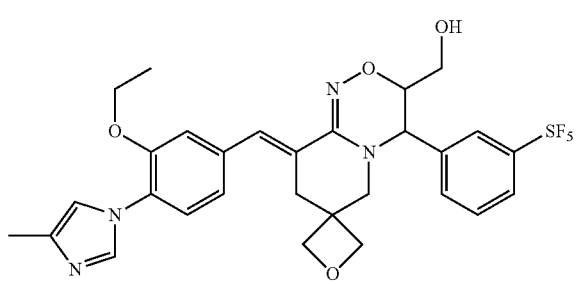
T8
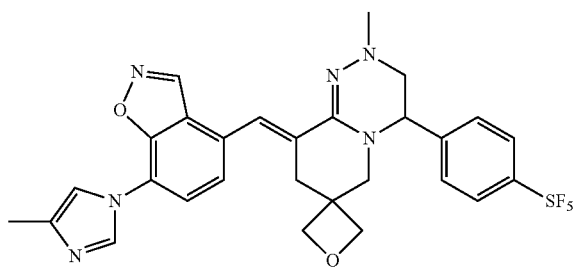
T9
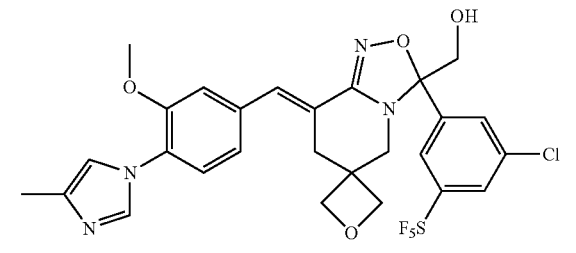
T10
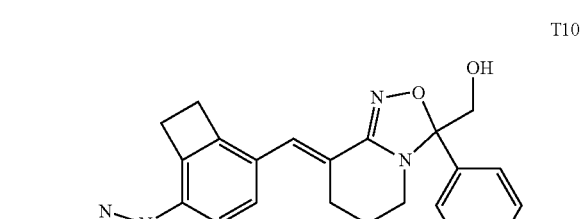

T11
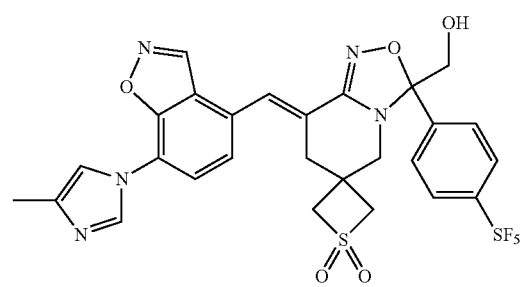

T12
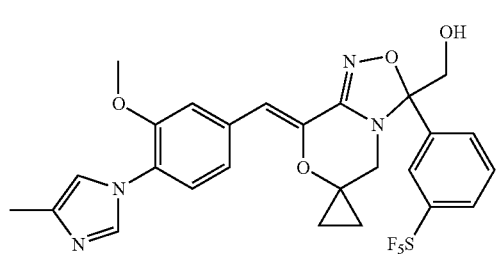

T13
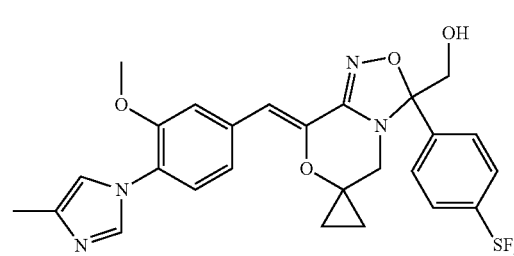

T14
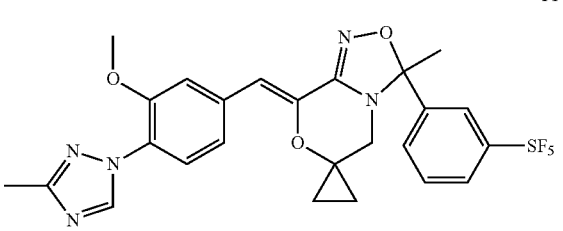

T15
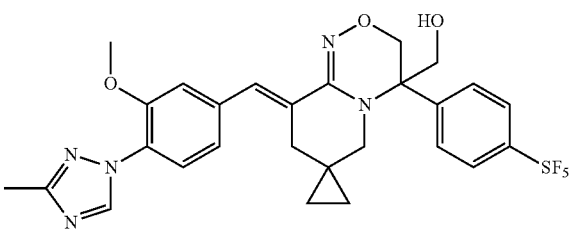

T16
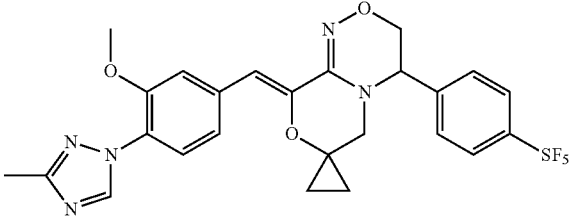

T17
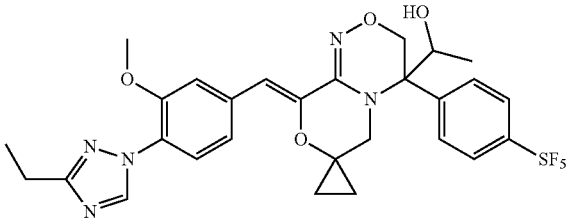

T18
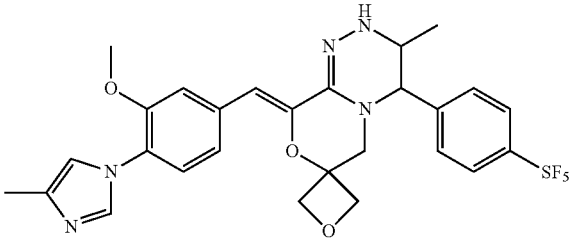

U1
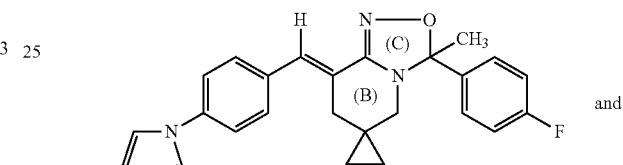

and

U2
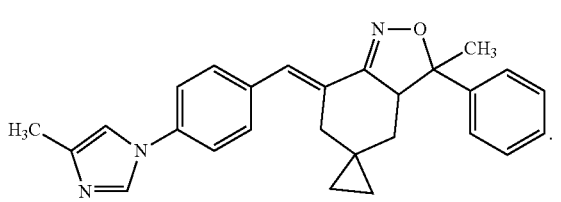

Another embodiment of this invention is directed to compound A10. Another embodiment of this invention is directed to compound A10a. Another embodiment of this invention is directed to compound A10b. Another embodiment of this invention is directed to compound A11. Another embodiment of this invention is directed to compound A12. Another embodiment of this invention is directed to compound A13. Another embodiment of this invention is directed to compound A14. Another embodiment of this invention is directed to compound A15. Another embodiment of this invention is directed to compound A16. Another embodiment of this invention is directed to compound A17. Another embodiment of this invention is directed to compound A18. Another embodiment of this invention is directed to compound A19. Another embodiment of this invention is directed to compound A20. Another embodiment of this invention is directed to compound A21. Another embodiment of this invention is directed to compound A22. Another embodiment of this invention is directed to compound A23. Another embodiment of this invention is directed to compound A24. Another embodiment of this invention is directed to compound A25. Another embodiment of this invention is directed to compound A26. Another embodiment of this invention is directed to compound A27. Another embodiment of this invention is directed to compound A28. Another embodiment of this invention is directed to compound A29. Another embodiment of this invention is directed to compound A30. Another embodiment of this invention is directed to compound E11. Another embodiment of this invention is directed to compound E12. Another embodiment of this invention is directed to compound E13. Another embodiment of this invention is directed to compound E14. Another embodiment of this invention is directed to compound E15. Another embodiment of this invention is directed to compound E16. Another embodiment of this invention is directed to compound E17. Another embodiment of this invention is directed to compound E18. Another embodiment of this invention is directed to compound E19. Another embodiment of this invention is directed to compound E20. Another embodiment of this invention is directed to compound E21. Another embodiment of this invention is directed to compound E22. Another embodiment of this invention is directed to compound E23. Another embodiment of this invention is directed to compound E24. Another embodiment of this invention is directed to compound E25. Another embodiment of this invention is directed to compound E26. Another embodiment of this invention is directed to compound E27. Another embodiment of this invention is directed to compound E28. Another embodiment of this invention is directed to compound E29. Another embodiment of this invention is directed to compound E30. Another embodiment of this invention is directed to compound E31. Another embodiment of this invention is directed to compound E32. Another embodiment of this invention is directed to compound E33. Another embodiment of this invention is directed to compound E34. Another embodiment of this invention is directed to compound E35. Another embodiment of this invention is directed to compound E36. Another embodiment of this invention is directed to compound E37. Another embodiment of this invention is directed to compound E38. Another embodiment of this invention is directed to compound F8. Another embodiment of this invention is directed to compound F9. Another embodiment of this invention is directed to compound F10. Another embodiment of this invention is directed to compound F11. Another embodiment of this invention is directed to compound F12. Another embodiment of this invention is directed to compound F13. Another embodiment of this invention is directed to compound F14. Another embodiment of this invention is directed to compound F15. Another embodiment of this invention is directed to compound F16. Another embodiment of this invention is directed to compound F17. Another embodiment of this invention is directed to compound F18. Another embodiment of this invention is directed to compound F19. Another embodiment of this invention is directed to compound F20. Another embodiment of this invention is directed to compound F21. Another embodiment of this invention is directed to compound F22. Another embodiment of this invention is directed to compound F23. Another embodiment of this invention is directed to compound F24. Another embodiment of this invention is directed to compound F25. Another embodiment of this invention is directed to compound G3. Another embodiment of this invention is directed to compound G4. Another embodiment of this invention is directed to compound G5. Another embodiment of this invention is directed to compound G6. Another embodiment of this invention is directed to compound G7. Another embodiment of this invention is directed to compound G8. Another embodiment of this invention is directed to compound G9. Another embodiment of this invention is directed to compound G10. Another embodiment of this invention is directed to compound G11. Another embodiment of this invention is directed to compound G12. Another embodiment of this invention is directed to compound G13. Another embodiment of this invention is directed to compound G14. Another embodiment of this invention is directed to compound G15. Another embodiment of this invention is directed to compound G16. Another embodiment of this invention is directed to compound G17. Another embodiment of this invention is directed to compound G18. Another embodiment of this invention is directed to compound G19. Another embodiment of this invention is directed to compound G20. Another embodiment of this invention is directed to compound G21. Another embodiment of this invention is directed to compound G22. Another embodiment of this invention is directed to compound G23. Another embodiment of this invention is directed to compound G24. Another embodiment of this invention is directed to compound H1. Another embodiment of this invention is directed to compound H2. Another embodiment of this invention is directed to compound H3. Another embodiment of this invention is directed to compound H4. Another embodiment of this invention is directed to compound H5. Another embodiment of this invention is directed to compound H6. Another embodiment of this invention is directed to compound H7. Another embodiment of this invention is directed to compound H8. Another embodiment of this invention is directed to compound H9. Another embodiment of this invention is directed to compound H10. Another embodiment of this invention is directed to compound H11. Another embodiment of this invention is directed to compound H12. Another embodiment of this invention is directed to compound H13. Another embodiment of this invention is directed to compound H14. Another embodiment of this invention is directed to compound H15. Another embodiment of this invention is directed to compound H16. Another embodiment of this invention is directed to compound H17. Another embodiment of this invention is directed to compound I1. Another embodiment of this invention is directed to compound I2. Another embodiment of this invention is directed to compound I3. Another embodiment of this invention is directed to compound I4. Another embodiment of this invention is directed to compound I5. Another embodiment of this invention is directed to compound I6. Another embodiment of this invention is directed to compound I7. Another embodiment of this invention is directed to compound I8. Another embodiment of this invention is directed to compound I9. Another embodiment of this invention is directed to compound I10. Another embodiment of this invention is directed to compound I11. Another embodiment of this invention is directed to compound I12. Another embodiment of this invention is directed to compound I13. Another embodiment of this invention is directed to compound I14. Another embodiment of this invention is directed to compound I15. Another embodiment of this invention is directed to compound I16. Another embodiment of this invention is directed to compound I17. Another embodiment of this invention is directed to compound J1. Another embodiment of this invention is directed to compound J3. Another embodiment of this invention is directed to compound J4. Another embodiment of this invention is directed to compound J5. Another embodiment of this invention is directed to compound J6. Another embodiment of this invention is directed to compound J7. Another embodiment of this invention is directed to compound J8. Another embodiment of this invention is directed to compound J9. Another embodiment of this invention is directed to compound J10. Another embodiment of this invention is directed to compound J11. Another embodiment of this invention is directed to compound J12. Another embodiment of this invention is directed to compound J13. Another embodiment of this invention is directed to compound J14. Another embodiment of this invention is directed to compound J15. Another embodiment of this invention is directed to compound J16. Another embodiment of this invention is directed to compound J17. Another embodiment of this invention is directed to compound J18. Another embodiment of this invention is directed to compound J19. Another embodiment of this invention is directed to compound J20. Another embodiment of this invention is directed to compound J21. Another embodiment of this invention is directed to compound J22. Another embodiment of this invention is directed to compound J23. Another embodiment of this invention is directed to compound J24. Another embodiment of this invention is directed to compound J25. Another embodiment of this invention is directed to compound J26. Another embodiment of this invention is directed to compound J27. Another embodiment of this invention is directed to compound J28. Another embodiment of this invention is directed to compound J29. Another embodiment of this invention is directed to compound J30. Another embodiment of this invention is directed to compound J31. Another embodiment of this invention is directed to compound J32. Another embodiment of this invention is directed to compound J33. Another embodiment of this invention is directed to compound J34. Another embodiment of this invention is directed to compound J35. Another embodiment of this invention is directed to compound J36. Another embodiment of this invention is directed to compound J37. Another embodiment of this invention is directed to compound J38. Another embodiment of this invention is directed to compound K9. Another embodiment of this invention is directed to compound K10. Another embodiment of this invention is directed to compound K11. Another embodiment of this invention is directed to compound K12. Another embodiment of this invention is directed to compound K13. Another embodiment of this invention is directed to compound K14. Another embodiment of this invention is directed to compound K15. Another embodiment of this invention is directed to compound K16. Another embodiment of this invention is directed to compound K17. Another embodiment of this invention is directed to compound K18. Another embodiment of this invention is directed to compound K19. Another embodiment of this invention is directed to compound K20. Another embodiment of this invention is directed to compound K21. Another embodiment of this invention is directed to compound K22. Another embodiment of this invention is directed to compound K23. Another embodiment of this invention is directed to compound K24. Another embodiment of this invention is directed to compound L8. Another embodiment of this invention is directed to compound L10. Another embodiment of this invention is directed to compound L11. Another embodiment of this invention is directed to compound L12. Another embodiment of this invention is directed to compound L13. Another embodiment of this invention is directed to compound L14. Another embodiment of this invention is directed to compound L15. Another embodiment of this invention is directed to compound L16. Another embodiment of this invention is directed to compound L17. Another embodiment of this invention is directed to compound L18. Another embodiment of this invention is directed to compound L19. Another embodiment of this invention is directed to compound L20. Another embodiment of this invention is directed to compound L21. Another embodiment of this invention is directed to compound M1. Another embodiment of this invention is directed to compound M2. Another embodiment of this invention is directed to compound M3. Another embodiment of this invention is directed to compound M4. Another embodiment of this invention is directed to compound M5. Another embodiment of this invention is directed to compound M6. Another embodiment of this invention is directed to compound M7. Another embodiment of this invention is directed to compound M8. Another embodiment of this invention is directed to compound M9. Another embodiment of this invention is directed to compound M10. Another embodiment of this invention is directed to compound M11. Another embodiment of this invention is directed to compound M12. Another embodiment of this invention is directed to compound M13. Another embodiment of this invention is directed to compound M14. Another embodiment of this invention is directed to compound M15. Another embodiment of this invention is directed to compound M16. Another embodiment of this invention is directed to compound M17. Another embodiment of this invention is directed to compound N1. Another embodiment of this invention is directed to compound N2. Another embodiment of this invention is directed to compound N3. Another embodiment of this invention is directed to compound N4. Another embodiment of this invention is directed to compound N5. Another embodiment of this invention is directed to compound N6. Another embodiment of this invention is directed to compound N7. Another embodiment of this invention is directed to compound N8. Another embodiment of this invention is directed to compound N9. Another embodiment of this invention is directed to compound N10. Another embodiment of this invention is directed to compound N11. Another embodiment of this invention is directed to compound N12. Another embodiment of this invention is directed to compound N13. Another embodiment of this invention is directed to compound N14. Another embodiment of this invention is directed to compound N15. Another embodiment of this invention is directed to compound N16. Another embodiment of this invention is directed to compound N17. Another embodiment of this invention is directed to compound N18. Another embodiment of this invention is directed to compound N19. Another embodiment of this invention is directed to compound N20. Another embodiment of this invention is directed to compound N21. Another embodiment of this invention is directed to compound N22. Another embodiment of this invention is directed to compound O1. Another embodiment of this invention is directed to compound O2. Another embodiment of this invention is directed to compound O3. Another embodiment of this invention is directed to compound O4. Another embodiment of this invention is directed to compound O5. Another embodiment of this invention is directed to compound O6. Another embodiment of this invention is directed to compound O7. Another embodiment of this invention is directed to compound O8. Another embodiment of this invention is directed to compound O9. Another embodiment of this invention is directed to compound O10. Another embodiment of this invention is directed to compound O11. Another embodiment of this invention is directed to compound O12. Another embodiment of this invention is directed to compound O13. Another embodiment of this invention is directed to compound O14. Another embodiment of this invention is directed to compound O15. Another embodiment of this invention is directed to compound O16. Another embodiment of this invention is directed to compound O17. Another embodiment of this invention is directed to compound O18. Another embodiment of this invention is directed to compound O19. Another embodiment of this invention is directed to compound O20. Another embodiment of this invention is directed to compound O21. Another embodiment of this invention is directed to compound O22. Another embodiment of this invention is directed to compound P6. Another embodiment of this invention is directed to compound P7. Another embodiment of this invention is directed to compound P8. Another embodiment of this invention is directed to compound P9. Another embodiment of this invention is directed to compound P10. Another embodiment of this invention is directed to compound P11. Another embodiment of this invention is directed to compound P12. Another embodiment of this invention is directed to compound P13. Another embodiment of this invention is directed to compound P14. Another embodiment of this invention is directed to compound P15. Another embodiment of this invention is directed to compound Q1. Another embodiment of this invention is directed to compound Q2. Another embodiment of this invention is directed to compound Q3. Another embodiment of this invention is directed to compound Q4. Another embodiment of this invention is directed to compound Q5. Another embodiment of this invention is directed to compound Q6. Another embodiment of this invention is directed to compound Q7. Another embodiment of this invention is directed to compound Q8. Another embodiment of this invention is directed to compound Q9. Another embodiment of this invention is directed to compound Q10. Another embodiment of this invention is directed to compound Q11. Another embodiment of this invention is directed to compound R7. Another embodiment of this invention is directed to compound R8. Another embodiment of this invention is directed to compound R9. Another embodiment of this invention is directed to compound R10. Another embodiment of this invention is directed to compound R11. Another embodiment of this invention is directed to compound R12. Another embodiment of this invention is directed to compound R13. Another embodiment of this invention is directed to compound R14. Another embodiment of this invention is directed to compound R15. Another embodiment of this invention is directed to compound R16. Another embodiment of this invention is directed to compound R17. Another embodiment of this invention is directed to compound R18. Another embodiment of this invention is directed to compound R19. Another embodiment of this invention is directed to compound S1. Another embodiment of this invention is directed to compound S2. Another embodiment of this invention is directed to compound S3. Another embodiment of this invention is directed to compound S4. Another embodiment of this invention is directed to compound S5. Another embodiment of this invention is directed to compound S6. Another embodiment of this invention is directed to compound S7. Another embodiment of this invention is directed to compound S8. Another embodiment of this invention is directed to compound S9. Another embodiment of this invention is directed to compound S10. Another embodiment of this invention is directed to compound S11. Another embodiment of this invention is directed to compound S12. Another embodiment of this invention is directed to compound S13. Another embodiment of this invention is directed to compound S14. Another embodiment of this invention is directed to compound S15. Another embodiment of this invention is directed to compound T3. Another embodiment of this invention is directed to compound T4. Another embodiment of this invention is directed to compound T5. Another embodiment of this invention is directed to compound T6. Another embodiment of this invention is directed to compound T7. Another embodiment of this invention is directed to compound T8. Another embodiment of this invention is directed to compound T9. Another embodiment of this invention is directed to compound T10. Another embodiment of this invention is directed to compound T11. Another embodiment of this invention is directed to compound T12. Another embodiment of this invention is directed to compound T13. Another embodiment of this invention is directed to compound T14. Another embodiment of this invention is directed to compound T15. Another embodiment of this invention is directed to compound T16. Another embodiment of this invention is directed to compound T17. Another embodiment of this invention is directed to compound T18. Another embodiment of this invention is directed to compound U1:

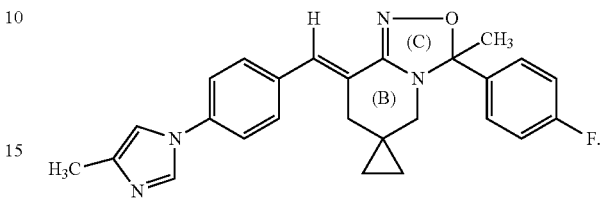

Another embodiment of this invention is directed to compound U2 (i.e., the final compound in Method U). Other embodiments of this invention are directed to any one of the embodiments to the compounds above wherein the embodiment is to a pharmaceutically acceptable salt of the compound. Other embodiments of this invention are directed to any one of the embodiments to the compounds above wherein the embodiment is to a pharmaceutically acceptable ester of the compound. Other embodiments of this invention are directed to any one of the embodiments to the compounds above wherein the embodiment is to a solvate of the compound.

In the embodiments below Groups A, B and C are as defined as follows:

(1) Group A: IA, IB, IC, ID, ID.1, ID.2, ID.3, IE, IF, IF.1, IG, IH, IH.1, II, IJ, IJ.1, IK, IL, IL.1, IM, IN, IN.1, IO, IP, IP.1, IQ, IR, IR.1, IS, IT, IT.1, IU, IV, IV.1, IW, IX, IX.1, IY, IZ, IZ.1, IAA, IAB, IAB.1, IAC, IAD, IAD.1, IAE, IAF, IAF.1, IAG, IAH, IAH.1, IAI, IAJ, IAJ.1, IAK, IAL, IAL.1, IAM, IAN, IAN.1, IAO, IAP, IAP.1, IAQ, IAR, IAR.1, IAS, IAT, IAT.1, IAU, IAV, IAV.1, IAW, IAX, IAX.1, IAY, IAZ, IAZ.1, IBA, IBB, IBB.1, IBC, IBD, IBD.1, IBE, IBF, IBF.1, IBG, IBH, IBH.1, IBI, IBJ, IBJ.1, IBK, IBL, IBL.1, IBM, IBN, IBN.1 IBO, IBP, and IBP.1;

(2) Group B: 1c to 104c; and (3) Group C: A10 (e.g., A10a and A10b) to A30, E11 to E38, F8 to F25, G3 to G24, H1 to H17, I1 to I17, J1, J3 to J38, K9 to K24, L8, L10 to L21, M1 to M17, N1 to N22, O1 to O22, P6 to P15, Q1 to Q11, R7 to R19, S1 to S15, T3 to T18, U1, and U2.

Another embodiment of this invention is directed to compounds of formula (I).

Another embodiment of this invention is directed to a compound of formula (I) selected from the group consisting of Group A.

Another embodiment of this invention is directed to a pharmaceutically acceptable salt of a compound of formula (I). And in one example the salt is a salt of a compound selected from the group consisting of Group A. And in another example the salt is a salt of a compound selected from the group consisting of Group B. And in another example the salt is a salt of a compound selected from the group consisting of Group C.

Another embodiment of this invention is directed to a pharmaceutically acceptable ester of a compound of formula (I). And in one example the ester is an ester of a compound selected from the group consisting of Group A. And in another example the ester is an ester of a compound selected from the group consisting of Group B. And in another example the ester is an ester of a compound selected from the group consisting of Group C.

Another embodiment of this invention is directed to a solvate of a compound of formula (I). And in one example the solvate is a solvate of a compound selected from the group consisting of Group A. And in another example the solvate is a solvate of a compound selected from the group consisting of Group B. And in another example the solvate is a solvate of a compound selected from the group consisting of Group C.

Another embodiment of this invention is directed to a compound of formula (I) in pure and isolated form. And in one example the compound of formula (I) is selected from the group consisting of Group C.

Another embodiment of this invention is directed to a compound of formula (I) in pure form. And in one example the compound of formula (I) is selected from the group consisting of Group C.

Another embodiment of this invention is directed to a compound of formula (I) in isolated form. And in one example the compound of formula (I) is selected from the group consisting of Group C.

Another embodiment of this invention is directed to a compound of formula (I) selected from the group consisting of Group C.

Another embodiment of this invention is directed to a pharmaceutical composition comprising a therapeutically effective amount of at least one compound of Formula (I), or a pharmaceutically acceptable salt, solvate, or ester thereof, and at least one pharmaceutically acceptable carrier.

Another embodiment of this invention is directed to a pharmaceutical composition comprising an effective amount of one or more (e.g., one) compounds of formula (I) and a pharmaceutically acceptable carrier.

Another embodiment of this invention is directed to a pharmaceutical composition comprising an effective amount of a pharmaceutically acceptable salt of one or more (e.g., one) compounds of formula (I) and a pharmaceutically acceptable carrier.

Another embodiment of this invention is directed to a pharmaceutical composition comprising an effective amount of a pharmaceutically acceptable ester of one or more (e.g., one) compounds of formula (I) and a pharmaceutically acceptable carrier.

Another embodiment of this invention is directed to a pharmaceutical composition comprising an effective amount of a solvate of one or more (e.g., one) compounds of formula (I) and a pharmaceutically acceptable carrier.

Another embodiment of this invention is directed to a pharmaceutical composition comprising an effective amount of one or more (e.g., one) compounds of formula (I), and an effective amount of one or more (e.g., one) other pharmaceutically active ingredients (e.g., drugs), and a pharmaceutically acceptable carrier. Examples of the other pharmaceutically active ingredients include, but are not limited to drugs selected form the group consisting of: (a) drugs useful for the treatment of Alzheimer's disease, (b) drugs useful for inhibiting the deposition of amyloid protein (e.g., amyloid beta protein) in, on or around neurological tissue (e.g., the brain), (c) drugs useful for treating neurodegenerative diseases, and (d) drugs useful for inhibiting gamma-secretase.

Another embodiment of this invention is directed to a pharmaceutical composition comprising a therapeutically effective amount of at least one compound of Formula (I), or a pharmaceutically acceptable salt, solvate, or ester thereof, and at feast one pharmaceutically acceptable carrier, and a therapeutically effective amount of one or more compounds selected from the group consisting of cholinesterase inhibitors, Aβ antibody inhibitors, gamma secretase inhibitors and beta secretase inhibitors.

Another embodiment of this invention is directed to a pharmaceutical composition comprising an effective amount of one or more (e.g., one) compounds of formula (I), and effective amount of one or more BACE inhibitors, and a pharmaceutically acceptable carrier.

Another embodiment of this invention is directed to a pharmaceutical composition comprising an effective amount of one or more (e.g., one) compounds of formula (I), and effective amount of one or more cholinesterase inhibitors (e.g., acetyl- and/or butyrylchlolinesterase inhibitors), and a pharmaceutically acceptable carrier.

Another embodiment of this invention is directed to a pharmaceutical composition comprising an effective amount of one or more (e.g., one) compounds of formula (I), and effective amount of one or more muscarinic antagonists (e.g., $m_1$ or $m_2$ antagonists), and a pharmaceutically acceptable carrier.

Another embodiment of this invention is directed to a pharmaceutical composition comprising an effective amount of one or more (e.g., one) compounds of formula (I), and effective amount of Exelon (rivastigmine), and a pharmaceutically acceptable carrier.

Another embodiment of this invention is directed to a pharmaceutical composition comprising an effective amount of one or more (e.g., one) compounds of formula (I), and effective amount of Cognex (tacrine), and a pharmaceutically acceptable carrier.

Another embodiment of this invention is directed to a pharmaceutical composition comprising an effective amount of one or more (e.g., one) compounds of formula (I), and effective amount of a Tau kinase inhibitor, and a pharmaceutically acceptable carrier.

Another embodiment of this invention is directed to a pharmaceutical composition comprising an effective amount of one or more (e.g., one) compounds of formula (I), and effective amount of one or more Tau kinase inhibitor (e.g., GSK3beta inhibitor, cdk5 inhibitor, ERK inhibitor), and a pharmaceutically acceptable carrier.

Another embodiment of this invention is directed to a pharmaceutical composition comprising an effective amount of one or more (e.g., one) compounds of formula (I), and effective amount of one anti-Abeta vaccine (active immunization), and a pharmaceutically acceptable carrier.

Another embodiment of this invention is directed to a pharmaceutical composition comprising an effective amount of one or more (e.g., one) compounds of formula (I), and effective amount of one or more APP ligands, and a pharmaceutically acceptable carrier.

Another embodiment of this invention is directed to a pharmaceutical composition comprising an effective amount of one or more (e.g., one) compounds of formula (I), and effective amount of one or more agents that upregulate insulin degrading enzyme and/or neprilysin, and a pharmaceutically acceptable carrier.

Another embodiment of this invention is directed to a pharmaceutical composition comprising an effective amount of one or more (e.g., one) compounds of formula (I), and effective amount of one or more cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe), and a pharmaceutically acceptable carrier.

Another embodiment of this invention is directed to a pharmaceutical composition comprising an effective amount of one or more (e.g., one) compounds of formula (I), and effective amount of one or more fibrates (for example, clofibrate, Clofibride, Etofibrate, Aluminium Clofibrate), and a pharmaceutically acceptable carrier An ter embodiment of this invention is directed to a pharmaceutical composition comprising an effective amount of one or more (e.g., one) compounds of formula (I), and effective amount of one or more LXR agonists, and a pharmaceutically acceptable carrier.

Another embodiment of this invention is directed to a pharmaceutical composition comprising an effective amount of one or more (e.g., one) compounds of formula (I), and effective amount of one or more LRP mimics, and a pharmaceutically acceptable carrier.

Another embodiment of this invention is directed to a pharmaceutical composition comprising an effective amount of one or more (e.g., one) compounds of formula (I), and effective amount of one or more 5-HT6 receptor antagonists, and a pharmaceutically acceptable carrier.

Another embodiment of this invention is directed to a pharmaceutical composition comprising an effective amount of one or more (e.g., one) compounds of formula (I), and effective amount of one or more nicotinic receptor agonists, and a pharmaceutically acceptable carrier.

Another embodiment of this invention is directed to a pharmaceutical composition comprising an effective amount of one or more (e.g., one) compounds of formula (I), and effective amount of one or more H3 receptor antagonists, and a pharmaceutically acceptable carrier.

Another embodiment of this invention is directed to a pharmaceutical composition comprising an effective amount of one or more (e.g., one) compounds of formula (I), and effective amount of one or more histone deacetylase inhibitors, and a pharmaceutically acceptable carrier.

Another embodiment of this invention is directed to a pharmaceutical composition comprising an effective amount of one or more (e.g., one) compounds of formula (I), and effective amount of one or more hsp90 inhibitors, and a pharmaceutically acceptable carrier.

Another embodiment of this invention is directed to a pharmaceutical composition comprising an effective amount of one or more (e.g., one) compounds of formula (I), and effective amount of one or more m1 muscarinic receptor agonists, and a pharmaceutically acceptable carrier.

Another embodiment of this invention is directed to combinations, i.e., a pharmaceutical composition, comprising a pharmaceutically acceptable carrier, an effective (i.e., therapeutically effective) amount of one or more compounds of formula (I), in combination with an effective (i.e., therapeutically effective) amount of one or more compounds selected from the group consisting of cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), Aβ antibody inhibitors, gamma secretase inhibitors and beta secretase inhibitors.

Another embodiment of this invention is directed to a pharmaceutical composition comprising an effective amount of one or more (e.g., one) compounds of formula (I), and effective amount of one or more 5-HT6 receptor antagonists mGluR1 or mGluR5 positive allosteric modulators or agonists, and a pharmaceutically acceptable carrier.

Another embodiment of this invention is directed to a pharmaceutical composition comprising an effective amount of one or more (e.g., one) compounds of formula (I), and effective amount of one or more one mGluR2/3 antagonists, and a pharmaceutically acceptable carrier.

Another embodiment of this invention is directed to a pharmaceutical composition comprising an effective amount of one or more (e.g., one) compounds of formula (I), and effective amount of one or more anti-inflammatory agents that can reduce neuroinflammation, and a pharmaceutically acceptable carrier.

Another embodiment of this invention is directed to a pharmaceutical composition comprising an effective amount of one or more (e.g., one) compounds of formula (I), and effective amount of one or more Prostaglandin EP2 receptor antagonists, and a pharmaceutically acceptable carrier.

Another embodiment of this invention is directed to a pharmaceutical composition comprising an effective amount of one or more (e.g., one) compounds of formula and effective amount of one or more PAI-1 inhibitors, and a pharmaceutically acceptable carrier.

Another embodiment of this invention is directed to a pharmaceutical composition comprising an effective amount of one or more (e.g., one) compounds of formula (I), and effective amount of one or more agents that can induce Abeta efflux such as gelsolin, and a pharmaceutically acceptable carrier.

Other embodiments of this invention are directed to any one of the above embodiments directed to pharmaceutical compositions wherein the compound of formula (I) is selected from the group consisting of Group A.

Other embodiments of this invention are directed to any one of the above embodiments directed to pharmaceutical compositions wherein the compound of formula (I) is selected from the group consisting of Group B.

Other embodiments of this invention are directed to any one of the above embodiments directed to pharmaceutical compositions wherein the compound of formula (I) is selected from the group consisting of Group C.

The compounds of formula (I) can be useful as gamma secretase modulators and can be useful in the treatment and prevention of diseases such as, for example, central nervous system disorders (such as Alzheimers disease and Downs Syndrome), mild cognitive impairment, glaucoma, cerebral amyloid angiopathy, stroke, dementia, microgliosis, brain inflammation, and olfactory function loss.

Another embodiment of this invention is directed to a method of treating a central nervous system disorder comprising administering a therapeutically effective amount of at least one compound of Formula (I) to a patient in need of such treatment.

Another embodiment of this invention is directed to a method of treating a central nervous system disorder comprising administering a therapeutically effective amount of a pharmaceutical composition comprising a therapeutically effective amount of at least one compound of Formula (I), or a pharmaceutically acceptable salt, solvate, or ester thereof, and at least one pharmaceutically acceptable carrier.

Another embodiment of this invention is directed to a method of treating a central nervous system disorder comprising administering a therapeutically effective amount of a pharmaceutical composition comprising a therapeutically effective amount of at least one compound of Formula (I), or a pharmaceutically acceptable salt, solvate, or ester thereof, and at least one pharmaceutically acceptable carrier, and a therapeutically effective amount of one or more compounds selected from the group consisting of cholinesterase inhibitors, Aβ antibody inhibitors, gamma secretase inhibitors and beta secretase inhibitors.

Another embodiment of this invention is directed to a method for modulating (including inhibiting, antagonizing and the like) gamma-secretase comprising administering an effective amount of one or more (e.g., one) compounds of formula (I) to a patient in need of such treatment.

Another embodiment of this invention is directed to a method for modulating (including inhibiting, antagonizing and the like) gamma-secretase, comprising administering an effective amount of a compound of formula (I) to a patient in need of treatment.

Another embodiment of this invention is directed to a method of treating one or more neurodegenerative diseases, comprising administering an effective amount of one or more (e.g., one) compounds of formula (I) to a patient in need of treatment.

Another embodiment of this invention is directed to a method of treating one or more neurodegenerative diseases, comprising administering an effective amount of a compound of formula (I) to a patient in need of treatment.

Another embodiment of this invention is directed to a method of inhibiting the deposition of amyloid protein (e.g., amyloid beta protein) in, on or around neurological tissue (e.g., the brain), comprising administering an effective amount of one or more (e.g., one) compounds of formula (I) to a patient in need of treatment.

Another embodiment of this invention is directed to a method of inhibiting the deposition of amyloid protein (e.g., amyloid beta protein) in, on or around neurological tissue (e.g., the brain), comprising administering an effective amount of a compound of formula (I) to a patient in need of treatment.

Another embodiment of this invention is directed to a method of treating Alzheimer's disease, comprising administering an effective amount of one or more (e.g., one) compounds of formula (I) to a patient in need of treatment.

Another embodiment of this invention is directed to a method of treating Alzheimer's disease, comprising administering an effective amount of a compound of formula (I) to a patient in need of treatment.

Another embodiment of this invention is directed to a method of treating mild cognitive impairment, glaucoma, cerebral amyloid angiopathy, stroke, dementia, microgliosis, brain inflammation, or olfactory function loss, comprising administering an effective (i.e., therapeutically effective) amount of one or more (e.g., one) compounds of formula (I) to a patient in need of treatment.

Another embodiment of this invention is directed to a method of treating mild cognitive impairment, glaucoma, cerebral amyloid angiopathy, stroke, dementia, microgliosis, brain inflammation, or olfactory function loss, comprising administering an effective (i.e., therapeutically effective) amount of a compound of formula (I) to a patient in need of treatment.

Another embodiment of this invention is directed to a method of treating mild cognitive impairment, comprising administering an effective amount of one or more (e.g., one) compounds of formula (I) to a patient in need of treatment.

Another embodiment of this invention is directed to a method of treating glaucoma, comprising administering an effective amount of one or more (e.g., one) compounds of formula (I) to a patient in need of treatment.

Another embodiment of this invention is directed to a method of treating cerebral amyloid angiopathy, comprising administering an effective amount of one or more (e.g., one) compounds of formula (I) to a patient in need of treatment.

Another embodiment of this invention is directed to a method of treating stroke, comprising administering an effective amount of one or more (e.g., one) compounds of formula (I) to a patient in need of treatment.

Another embodiment of this invention is directed to a method of treating dementia, comprising administering an effective amount of one or more (e.g., one) compounds of formula (I) to a patient in need of treatment.

Another embodiment of this invention is directed to a method of treating microgliosis, comprising administering an effective amount of one or more (e.g., one) compounds of formula (I) to a patient in need of treatment.

Another embodiment of this invention is directed to a method of treating brain inflammation, comprising administering an effective amount of one or more (e.g., one) compounds of formula (I) to a patient in need of treatment.

Another embodiment of this invention is directed to a method of treating olfactory function loss, comprising administering an effective amount of one or more (e.g., one) compounds of formula (I) to a patient in need of treatment.

Another embodiment of this invention is directed to a method of treating Downs syndrome, comprising administering an effective amount of one or more (e.g., one) compounds of formula (I) to a patient in need of treatment.

Another embodiment of this invention is directed to a method of treating Downs syndrome, comprising administering an effective amount of a compound of formula (I) to a patient in need of treatment.

Other embodiments of this invention are directed to any one of the above embodiments directed to methods of treating wherein the compound of formula (I) is selected from the group consisting of Group A.

Other embodiments of this invention are directed to any one of the above embodiments directed to methods of treating wherein the compound of formula (I) is selected from the group consisting of Group B.

Other embodiments of this invention are directed to any one of the above embodiments directed to methods of treating wherein the compound of formula (I) is selected from the group consisting of Group C.

This invention also provides combination therapies for (1) modulating gamma-secretase, or (2) treating one or more neurodegenerative diseases, or (3) inhibiting the deposition of amyloid protein (e.g., amyloid beta protein) in, on or around neurological tissue (e.g., the brain), or (4) treating Alzheimer's disease. The combination therapies are directed to methods comprising the administration of an effective amount of one or more (e.g. one) compounds of formula (I) and the administration of an effective amount of one or more (e.g., one) other pharmaceutical active ingredients (e.g., drugs). The compounds of formula (I) and the other drugs can be administered separately (i.e., each is in its own separate dosage form), or the compounds of formula (I) can be combined with the other drugs in the same dosage form.

Thus, other embodiments of this invention are directed to any one of the methods of treatment, or methods of inhibiting, described herein, wherein an effective amount of the compound of formula (I) is used in combination with an effective amount of one or more other pharmaceutically active ingredients (e.g., drugs). The other pharmaceutically active ingredients (i.e., drugs) are selected from the group consisting of: BACE inhibitors (beta secretase inhibitors), muscarinic antagonists (e.g., $m_1$ agonists or $m_2$ antagonists), cholinesterase inhibitors (e.g., acetyl- and/or butyrylcholinesterase inhibitors); gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Exelon (rivastigmine); Cognex (tacrine); Tau kinase inhibitors (e.g., GSK3beta inhibitors, cdk5 inhibitors, or ERK inhibitors); anti-Abeta vaccine; APP ligands; agents that upregulate insulin cholesterol lowering agents (for example, statins such as Atorvastatin, Fluvastatin, Lovastatin, Mevastatin, Pitavastatin, Pravastatin, Rosuvastatin, Simvastatin); cholesterol absorption inhibitors (such as Ezetimibe); fibrates (such as, for example, for example, clofibrate, Clofibride, Etofibrate, and Aluminium Clofibrate); LXR agonists; LRP mimics; nicotinic receptor agonists; H3 receptor antagonists; histone deacetylase inhibitors; hsp90 inhibitors; m1 muscarinic receptor agonists; 5-HT6 receptor antagonists; mGluR1; mGluR5; positive allosteric modulators or agonists; mGluR2/3 antagonists; anti-inflammatory agents that can reduce neuroinflammation; Prostaglandin EP2 receptor antagonists; PAI-1 inhibitors; and agents that can induce Abeta efflux such as gelsolin.

Another embodiment of this invention is directed to a method of treating Alzheimer's disease, comprising administering an effective amount of one or more (e.g., one) compounds of formula (I), in combination with an effective (i.e., therapeutically effective) amount of one or more cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective amount of a compound of formula (I), in combination with an effective amount of one or more (e.g., one) cholinesterase inhibitors (such as, for example, (±)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Alzheimer's disease, comprising administering an effective amount of one or more (e.g., one) compounds of formula (I), in combination with an effective amount of one or more compounds selected from the group consisting of Aβ antibody inhibitors, gamma secretase inhibitors and beta secretase inhibitors.

Another embodiment of this invention is directed to a method of treating Alzheimer's disease, comprising administering an effective amount of one or more (e.g., one) compounds of formula (I), in combination with an effective amount of one or more PACE inhibitors.

Another embodiment of this invention is directed to a method of treating Alzheimer's disease, comprising administering an effective amount of one or more compounds of formula (I), in combination with an effective amount of Exelon (rivastigmine).

Another embodiment of this invention is directed to a method of treating Alzheimer's disease, comprising administering an effective amount of one or more compounds of formula (I), in combination with an effective amount of Cognex (tacrine).

Another embodiment of this invention is directed to a method of treating Alzheimer's disease, comprising administering an effective amount of one or more compounds of formula (I), in combination with an effective amount of a Tau kinase inhibitor.

Another embodiment of this invention is directed to a method of treating Alzheimer's disease, comprising administering an effective amount of one or more compounds of formula (I), in combination with an effective amount of one or more Tau kinase inhibitor (e.g., GSK3beta inhibitor, cdk5 inhibitor, ERK inhibitor).

This invention also provides a method of treating Alzheimer's disease, comprising administering an effective amount of one or more compounds of formula (I), in combination with an effective amount of one anti-Abeta vaccination (active immunization).

Another embodiment of this invention is directed to a method of treating Alzheimer's disease, comprising administering an effective amount of one or more compounds of formula (I), in combination with an effective amount of one or more APP ligands.

Another embodiment of this invention is directed to a method of treating Alzheimer's disease, comprising administering an effective amount of one or more compounds of formula (I), in combination with an effective amount of one or more agents that upregulate insulin degrading enzyme and/or neprilysin.

Another embodiment of this invention is directed to a method of treating Alzheimer's disease, comprising administering an effective amount of one or more compounds of formula (I), in combination with an effective amount of one or more cholesterol lowering agents (for example, statins such as Atorvastatin, Fluvastatin, Lovastatin, Mevastatin, Pitavastatin, Pravastatin, Rosuvastatin, Simvastatin, and cholesterol absorption inhibitor such as Ezetimibe).

This invention also provides a method of treating Alzheimer's disease, comprising administering an effective amount of one or more compounds of formula (I), in combination with an effective amount of one or more fibrates (for example, clofibrate, Clofibride, Etofibrate, Aluminium Clofibrate).

Another embodiment of this invention is directed to a method of treating Alzheimer's disease, comprising administering an effective amount of one or more compounds of formula (I), in combination with an effective amount of one or more LXR agonists.

Another embodiment of this invention is directed to a method of treating Alzheimer's disease, comprising administering an effective amount of one or more compounds of formula (I), in combination with an effective amount of one or more LRP mimics.

Another embodiment of this invention is directed to a method of treating Alzheimer's disease, comprising administering an effective amount of one or more compounds of formula (I), in combination with an effective amount of one or more 5-HT6 receptor antagonists.

Another embodiment of this invention is directed to a method of treating Alzheimer's disease, comprising administering an effective amount of one or more compounds of formula (I), in combination with an effective amount of one or more nicotinic receptor agonists.

Another embodiment of this invention is directed to a method of treating Alzheimer's disease, comprising administering an effective amount of one or more compounds of formula (I), in combination with an effective amount of one or more H3 receptor antagonists.

This invention also provides a method of treating Alzheimer's disease, comprising administering an effective amount of one or more compounds of formula (I), in combination with an effective amount of one or more histone deacetylase inhibitors.

Another embodiment of this invention is directed to a method of treating Alzheimer's disease, comprising administering an effective amount of one or more compounds of formula (I), in combination with an effective amount of one or more hsp90 inhibitors.

Another embodiment of this invention is directed to a method of treating Alzheimer's disease, comprising administering at 55 effective amount of one or more compounds of formula (I), in combination with an effective amount of one or more ml muscarinic receptor agonists.

Another embodiment of this invention is directed to a method of treating Alzheimer's disease, comprising administering an effective amount of one or more compounds of formula (I), in combination with an effective amount of one or more 5-HT6 receptor antagonists mGluR1 or mGluR5 positive allosteric modulators or agonists Another embodiment of this invention is directed to a method of treating Alzheimer's disease, comprising administering an effective amount of one or more compounds of formula (I), in combination with an effective amount of one or more mGluR2/3 antagonists.

Another embodiment of this invention is directed to a method of treating Alzheimer's disease, comprising administering an effective amount of one or more compounds of formula (I), in combination with an effective amount of one or more anti-inflammatory agents that can reduce neuroinflammation.

Another embodiment of this invention is directed to a method of treating Alzheimer's disease, comprising administering an effective amount of one or more compounds of formula (I), in combination with an effective amount of one or more Prostaglandin EP2 receptor antagonists.

Another embodiment of this invention is directed to a method of treating Alzheimer's disease, comprising administering an effective amount of one or more compounds of formula (I), in combination with an effective amount of one or more PAI-1 inhibitors.

Another embodiment of this invention is directed to a method of treating Alzheimer's disease, comprising administering an effective amount of one or more compounds of formula (I), in combination with an effective amount of one or more agents that can induce Abeta efflux such as gelsolin.

Another embodiment of this invention is directed to a method of treating Downs syndrome, comprising administering an effective amount of one or more (e.g., one) compounds of formula (I), in combination with an effective amount of one or more cholinesterase inhibitors (such as, for example, ($\pm$)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Another embodiment of this invention is directed to a method of treating Downs syndrome, comprising administering an effective amount of a compound of formula (I), in combination with an effective amount of one or more (e.g., one) cholinesterase inhibitors (such as for example, ($\pm$)-2,3-dihydro-5,6-dimethoxy-2-[[1-(phenylmethyl)-4-piperidinyl]methyl]-1H-inden-1-one hydrochloride, i.e., donepezil hydrochloride, available as the Aricept® brand of donepezil hydrochloride), to a patient in need of treatment.

Other embodiments of this invention are directed to any one of the above embodiments directed to combination therapies (i.e., the above methods of treating wherein compounds of formula (I) are used in combination with other pharmaceutically active ingredients, i.e., drugs) wherein the compound of formula (I) is selected from the group consisting of Group A.

Other embodiments of this invention are directed to any one of the above embodiments directed to combination therapies (i.e., the above methods of treating wherein compounds of formula (I) are used in combination with other pharmaceutically active ingredients, i.e., drugs) wherein the compound of formula (I) is selected from the group consisting of Group B.

Other embodiments of this invention are directed to any one of the above embodiments directed to combination therapies (i.e., the above methods of treating wherein compounds of formula (I) are used in combination with other pharmaceutically active ingredients, i.e., drugs) wherein the compound of formula (I) is selected from the group consisting of Group C.

This invention also provides a kit comprising, in separate containers, in a single package, pharmaceutical compositions for use in combination, wherein one container comprises an effective amount of a compound of formula (I) in a pharmaceutically acceptable carrier, and another container (i.e., a second container) comprises an effective amount of another pharmaceutically active ingredient (as described above), the combined quantities of the compound of formula (I) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase, or (e) mild cognitive impairment, or (f) glaucoma, or (g) cerebral amyloid angiopathy, or (h) stroke, or (i) dementia, or (j) microgliosis, or (k) brain inflammation, or (l) olfactory function loss.

This invention also provides a kit comprising, in separate containers, in a single package, pharmaceutical compositions for use in combination, wherein one container comprises an effective amount of a compound of formula (I) in a pharmaceutically acceptable carrier, and another container (i.e., a second container) comprises an effective amount of another pharmaceutically active ingredient (as described above), the combined quantities of the compound of formula (I) and the other pharmaceutically active ingredient being effective to: (a) treat Alzheimer's disease, or (b) inhibit the deposition of amyloid protein (e.g., amyloid beta protein) in, on or around neurological tissue (e.g., the brain), or (c) treat neurodegenerative diseases, or (d) modulate the activity of gamma-secretase.

Other embodiments of this invention are directed to any one of the above embodiments directed to kits wherein the compound of formula (I) is selected from the group consisting of Group A.

Other embodiments of this invention are directed to any one of the above embodiments directed to kits wherein the compound of formula (I) is selected from the group consisting of Group B.

Other embodiments of this invention are directed to any one of the above embodiments directed to kits wherein the compound of formula (I) is selected from the group consisting of Group C.

Examples of cholinesterase inhibitors are tacrine, donepezil, rivastigmine, galantamine, pyridostigmine and neostigmine, with tacrine, donepezil, rivastigmine and galantamine being preferred.

Examples of $m_1$ antagonists are known in the art. Examples of $m_2$ antagonists are also known in the art; in particular, $m_2$ antagonists are disclosed in U.S. Pat. Nos. 5,883,096; 6,037,352; 5,889,006; 6,043,255; 5,952,349; 5,935,958; 6,066,636; 5,977,138; 6,294,554; 6,043,255; and 6,458,812; and in WO 03/031412, all of which are incorporated herein by reference.

Examples of BACE inhibitors include those described in: US2005/0119227 published Jun. 2, 2005 (see also WO2005/

016876 published Feb. 24, 2005). US2005/0043290 published Feb. 24, 2005 (see also WO2005/014540 published Feb. 17, 2005), WO2005/058311 published Jun. 30, 2005 (see also US2007/0072852 published Mar. 29, 2007), US2006/0111370 published May 25, 2006 (see also WO2006/065277 published Jun. 22, 2006), U.S. application Ser. No. 11/710,582 filed Feb. 23, 2007, US2006/0040994 published Feb. 23, 2006 (see also WO20061014762 published Feb. 9, 2006), WO2006/014944 published Feb. 9, 2006 (see also US2006/0040948 published Feb. 23, 2006), WO2006/138266 published Dec. 28, 2006 (see also US2007/0010667 published Jan. 11, 2007), WO2006/138265 published Dec. 28, 2006, WO2006/138230 published Dec. 28, 2006, WO2006/138195 published Dec. 28, 2006 (see also US2006/0281729 published Dec. 14, 2006), WO2006/138264 published Dec. 28, 2006 (see also US2007/0060575 published Mar. 15, 2007), WO2006/138192 published Dec. 28, 2006 (see also US2006/0281730 published Dec. 14, 2006), WO2006/138217 published Dec. 28, 2006 (see also US2006/0287294 published Dec. 21, 2006), US2007/0099898 published May 3, 200 (see also WO2007/050721 published May 3, 2007), WO2007/053506 published May 10, 2007 (see also US2007/099875 published May 3, 2007), U.S. application Ser. No. 11/759,336 filed Jun. 7, 2007, U.S. Application Ser. No. 60/874,362 filed Dec. 12, 2006, and U.S. Application Ser. No. 60/874,419 filed Dec. 12, 2006, the disclosures of each being incorporated herein by reference thereto.

As used above, and throughout this disclosure, the following terms, unless otherwise indicated, shall be understood to have the following meanings:

"DCE" means 1,2-dichloroethane.
"DCM" means dichloromethane.
"DEAD" means diethyl azodicarboxylate.
"DIAD" means diisopropylazodicarboxylate.
"DMAP" means 4-dimethylaminopyridine.
"DMF" means N,N-dimethylformamide.
"DMSO" means dimethylsulfoxide.
"DPPA" means diphenylphosphorylazide
"EDCI" means (3-(dimethylamino)propyl)ethyl carbodiimide hydrochloride.
"LDA" means lithium diisopropylamide.
"MCPBA" means meta-chloroperoxybenzoic acid.
"MOM" means methoxymethyl,
"NBS" means N-bromosuccinimide.
"SM" means starting material.
"TBAF" means tetrabutylammonium fluoride.
"TBDPSCl" means chloro tert-butyldiphenylsilane
"TBDPSO" or "OTPDPS" means tert-butyldiphenylsilyloxy.
"TBS" means tert-butyldimethylsilyl.
"TBSCl" means chloro tert-butyldimethylsilane.
"TEA" means triethylamine.
"Tf" means triflic.
"TFA" means trifluoroacetic acid.
"Tf$_2$O" means triflic anhydride.
"THF" means tetrahydrofuran.
"Patient" includes both human and animals.
"Mammal" means humans and other mammalian animals.
"One or more" means that there is at least one and there can be more than one, and examples include 1, 2 or 3, or 1 and 2, or 1.
"At least one" means there is at least one and there can be more than one, and examples include 1, 2 or 3, or 1 and 2, or 1.

It is noted that the carbons of formula (I) and other formulas herein may be replaced with 1 to 3 silicon atoms so long as all valency requirements are satisfied.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, oxime (e.g., =N—OH), —NH(alkyl), —NH(cycloalkyl), —N(alkyl)$_2$, —O—C(O)-alkyl, —O—C(O)-aryl, —O—C(O)-cycloalkyl, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide, "Heteroaryl" may also include a heteroaryl as defined above fused to an aryl as defined above. Non-limiting examples of suitable heteroaryls include pyridyl, pyrazinyl, uranyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl- group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like, Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine. "Halo" refers to fluoro, chloro, bromo or iodo.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), oxime (e.g., =N—OH), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

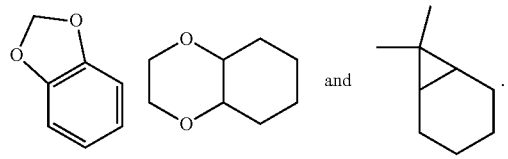

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl"

may also mean a single moiety (e.g., carbonyl) which simultaneously replaces two available hydrogens on the same carbon atom on a ring system. Examples of such heterocyclyls include, for example,

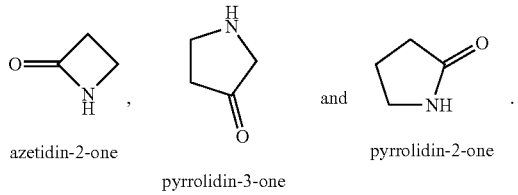 [SMILES: O=C1CCN1 ; O=C1CCNC1 ; O=C1CCCN1]

azetidin-2-one pyrrolidin-3-one pyrrolidin-2-one

"Heterocyclylalkyl" (or heterocycloalkylalkyl) means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" (or heterocycloalkenyl) means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

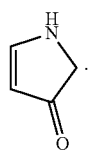

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

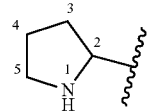

there is no —OH attached directly to carbons marked 2 and 5.

It should also be noted that tautomeric forms such as, for example, the moieties:

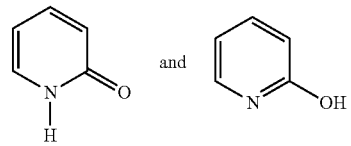 [SMILES: O=c1cccc[nH]1 ; Oc1ccccn1]

are considered equivalent in certain embodiments of this invention.

"Alkynylalkyl" means an alkynyl-alkyl- group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described, Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified" "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula (I), its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g., a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, ($C_1$-$C_8$)alkyl, ($C_2$-$C_{12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-(C1-C2)alkyl and piperidino-, pyrrolidino- or morpholino($C_2$-$C_3$) alkyl, and the like.

Similarly, if a compound of Formula (I) contains an alcohol functional group, a prodrug can be formed by the replacement of the hydrogen atom of the alcohol group with a group such as, for example, ($C_1$-$C_6$)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino ($C_1$-$C_4$)alkanyl, arylacyl and α-aminoacyl, or α-aminoacyl-α-aminoacyl, where each α-aminoacyl group is independently selected from the naturally occurring L-amino acids, P(O)(OH)$_2$, —P(O)(0($C_1$-$C_6$)alkyl)$_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl, —C(OH)C(O)O$Y^1$ wherein $Y^1$ is H, ($C_1$-$C_6$)alkyl or benzyl, —C(O$Y^2$)$Y^3$ wherein $Y^2$ is ($C_1$-$C_4$) alkyl and $Y^3$ is ($C_1$-$C_6$)alkyl, carboxy($C_1$-$C_6$)alkyl, amino ($C_1$-$C_4$)alkyl or mono-N— or di-N,N—($C_1$-$C_6$)alkylaminoalkyl, —C($Y^4$)$Y^5$ wherein $Y^4$ is H or methyl and $Y^5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula (I) can form salts which are also within the scope of this invention. Reference to a compound of Formula (I) herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts*. Properties, Selection and Use. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula (I), and salts, solvates, esters and prodrugs thereof, may exist in their tautomeric form (for example, as an amide, enol, keto or imino ether), All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for t ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula (I), and of the salts, solvates, esters and prodrugs of the compounds of Formula (I), are intended to be included in the present invention.

The compounds according to the invention can have pharmacological properties; in particular, the compounds of Formula (I) can be modulators of gamma secretase (including inhibitors, antagonists and the like).

More specifically, the compounds of Formula (I) can be useful in the treatment of a variety of disorders of the central nervous system including, for example, including, but not limited to, Alzheimer's disease, AIDS-related dementia, Parkinson's disease, amyotrophic lateral sclerosis, retinitis pigmentosa, spinal muscular atrophy and cerebellar degeneration and the like.

Another aspect of this invention is a method of treating a mammal (e.g., human) having a disease or condition of the central nervous system by administering a therapeutically effective amount of at least one compound of Formula (I), or a pharmaceutically acceptable salt, solvate, ester or prodrug of said compound to the mammal.

A preferred dosage is about 0.001 to 500 mg/kg of body weight/day of the compound of Formula (I). An especially preferred dosage is about 0.01 to 25 mg/kg of body weight/day of a compound of Formula (I), or a pharmaceutically acceptable salt or solvate of said compound.

The compounds of this invention may also be useful in combination (administered together or sequentially) with one or more additional agents listed above.

The compounds of this invention may also be useful in combination (administered together or sequentially) with one or more compounds selected from the group consisting of Aβ antibody inhibitors, gamma secretase inhibitors and beta secretase inhibitors.

If formulated as a fixed dose, such combination products employ the compounds of this invention within the dosage range described herein and the other pharmaceutically active agent or treatment within its dosage range.

Accordingly, in an aspect, this invention includes combinations comprising an amount of at least one compound of Formula (I), or a pharmaceutically acceptable salt, solvate, ester or prodrug thereof, and an amount of one or more additional agents listed above wherein the amounts of the compounds/treatments result in desired therapeutic effect.

The pharmacological properties of the compounds of this invention may be confirmed by a number of pharmacological assays. Certain assays are exemplified later in this document.

This invention is also directed to pharmaceutical compositions which comprise at least one compound of Formula (I), or a pharmaceutically acceptable salt, solvate, ester or prodrug of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula (I), or a pharmaceutically acceptable salt, solvate, ester or prodrug of said compound and a pharmaceutically acceptable carrier, vehicle or diluent.

Yet another aspect of this invention is a kit comprising an amount of at least one compound of Formula (I), or a pharmaceutically acceptable salt, solvate, ester or prodrug of said compound and an amount of at least one additional agent listed above, wherein the amounts of the two or more ingredients result in desired therapeutic effect.

The invention disclosed herein is exemplified by the following illustrative processes which should not be construed to limit the scope of the disclosure. Alternative mechanistic pathways and analogous structures will be apparent to those skilled in the art.

Method A

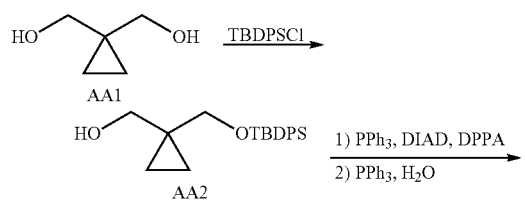

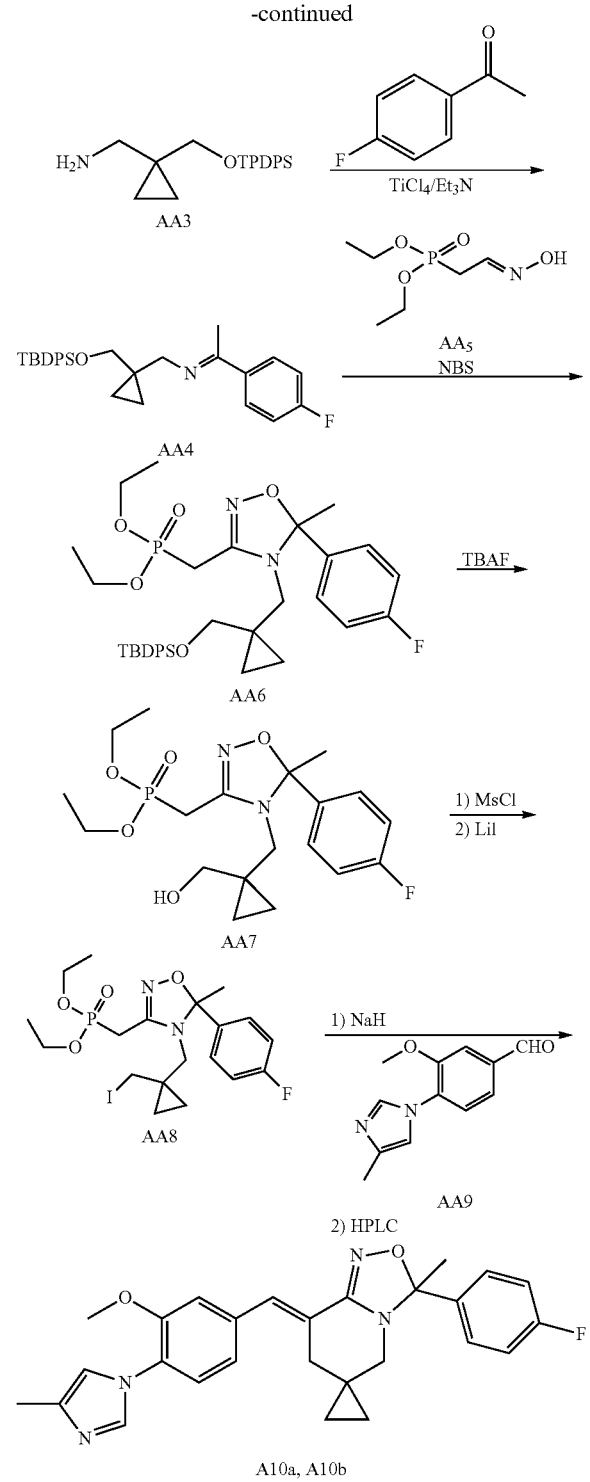

Method A, Step 1

To a solution of 1-hydroxymethylcyclopropylmethanol AA1 (10 g, 98 mmol) in DMF (300 mL) was added Pert-butylchlorodiphenylsilane (26.3 mL, 100 mmol) followed by diisopropylethylamine (170 mL) and the reaction was stirred at RT overnight. The final mixture was quenched with water and extracted with EtOAc. The organic layer was washed with 3N HCl, sat NaHCO$_3$, brine, dried over Na$_2$SO$_4$ and concentrated. The residue was purified by chromatography over silica gel (eluted with DCM/MeOH 100:0 to 80:20) to give 18.5 g (55%) of product AA2.

Method A, Step 2

To a solution of AA2 (18.5 g, 54.32 mmol) in THF (500 mL) at 0° C. was added triphenylphosphine (17 g, 65.15 mmol) followed by diisopropylazodicarboxylate (13 mL, 65.15 mmol) and diphenylphosphorylazide (14 mL, 65.15 mmol) and the mixture was stirred at RT overnight. After addition of water (250 mL) and triphenylphosphine (35.6 g, 135.7 mmol), the reaction was heated at reflux for 4 h and stirred at RT overnight. The final mixture was diluted with 1N NaOH, extracted with EtOAc, dried over $Na_2SO_4$ and concentrated and the residue was purified by chromatography over silica gel (eluted with DCM/MeOH 100:0 to 20:80) to give 12.8 g (70%) of product AA3.

Method A, Step 3

To a solution of AA3 (7 g, 20.6 mmol) and 4-fluoroacetophenone (2.56 g, 18.54 mmol) in DMF (18 mL) and DCM (5 mL) was added triethylamine (18.2 mL, 129.8 mmol) slowly. The reaction was cooled to 0° C., then a solution of $TiCl_4$ (1.93 mL, 17.6 mmol) in DCM (15 mL) was added slowly. The reaction was heated at 40 C for an hour and left to stir at RT overnight. The final mixture was diluted with $Et_2O$, washed with water, and filtered over Celite. The aqueous layer was extracted twice with $Et_4O$. The combined organic layers were washed with water and brine, dried over $Na_2SO_4$ and concentrated to give 9.4 g (100%) of product AA4.

Method A, Step 4

To a solution of 3-diethyl 2-(hydroxyimino)ethylphosphonate AA5 (3.83 g, 19.6 mmol) in DMF (50 mL) at −20° C. was added a solution of N-bromosuccinimide (3.48 g, 19.6 mmol) in DMF (20 mL) and the reaction was stirred 1 h at −10° C. and 2 h at 0° C. A mixture of triethylamine (2.73 mL, 19.6 mmol) and AA4 (9 g, 19.6 mmol) in DCM (30 mL) was added dropwise at 0° C. The reaction was allowed to warm to RT overnight then worked-up with 1:1 $Et_2O$/EtOAc and brine. The residue was purified by chromatography over silica gel (eluted with Hexanes/EtOAc 99:1 to EtOAc) to provide 4.8 g (37%) of product AA6.

Method A, Step 5

To a solution of AA6 (4.75 g, 7.27 mmol) in THF (30 mL) was added TBAF 1N in THF (10.9 mL, 10.9 mmol) and the reaction was stirred 2 h then concentrated. After concentration, the residue was taken up in EtOAc and 0.5 N glacial HCl and brine, extracted with EtOAc, dried over $Na_2SO_4$ and concentrated. The residue was purified by chromatography over silica gel (eluted with DCM/MeOH 100:0 to 80:20) to give 1.2 g (40%) of product AA7.

Method A, Step 6

To a solution of AA7 (880 mg, 2.20 mmol) in DCM (20 mL) at 0° C. was added methanesulfonyl chloride (0.22 mL, 2.87 mmol) followed by triethylamine (0.45 mL, 3.3 mmol) and the reaction was stirred at 0° C. for an hour. The final mixture was diluted with sat. $NH_4Cl$, extracted with DCM, dried over $Na_2SO_4$ and concentrated to provide an intermediate mesylate. This intermediate was treated with LiI (411 mg, 3.075 mmol) and $CaCO_3$ (410 mg, 4.1 mmol) in acetonitrile (20 mL) and heated 1 h at 80° C., then diluted with sat. $Na_2S_2O_3$ and sat. $NaHCO_3$, extracted with EtOAc, dried over $Na_2SO_4$ and concentrated then purified by chromatography over silica gel (eluted with EtOAc/MeOH 100:0 to 80:20) to provide 920 mg (84%) of product AA8.

Method A, Step 7

To a solution of NaH 60% in hexanes (53 mg, 1.32 mmol) in THF (2 mL) at 0° C. was added AA8 (470 mg, 0.90 mmol) in THF (7 mL) and the reaction was stirred 30 min. The resulting mixture was then added to a stirred solution of 3-methoxy-4-(4-methyl-1H-imidazol-1-yl)benzaldehyde AA9 (240 mg, 0.90 mmol) and NaH 60% in hexanes (53 mg, 1.32 mmol) in THF (7 mL) at 0° C. The final mixture was stirred at 0° C. for 30 min, and then it was poured onto ice water, diluted with brine, extracted with EtOAc, dried over $Na_2SO_4$ and concentrated. The residue was purified by chromatography over silica gel (eluted with DCM/MeOH 100:0 to 80:20) to give 640 mg of crude product. This was purified by HPLC over Chiracel OD column (eluted with Hexanes/isopropanol 15:85) to provide, in order of elution:

A10a, enantiomer 1, 176 mg: $[\alpha]_D$=+12.16 (c=1, DCM); $^1$H NMR (CDCl$_3$ 400 MHz) δ 7.70 (s, 1H), 7.50-7.60 (m, 3H), 7.21 (d, J=8.4 Hz, 1H), 7.07 (t, J=8.4 Hz, 2H), 6.90-6.95 (m, 3H), 3.83 (s, 3H), 3.06 (d, J=11 Hz, 1H), 2.64 (br d, 1H), 2.43 (m, 2H), 2.29 (s, 3H), 1.87 (s, 3H), 0.30-0.50 (m, 4H); LCMS (MH$^+$)=459.3; retention time=3.09 min.

A10b, enantiomer 2, 150 mg: $^1$H NMR and LCMS identical to A10a.

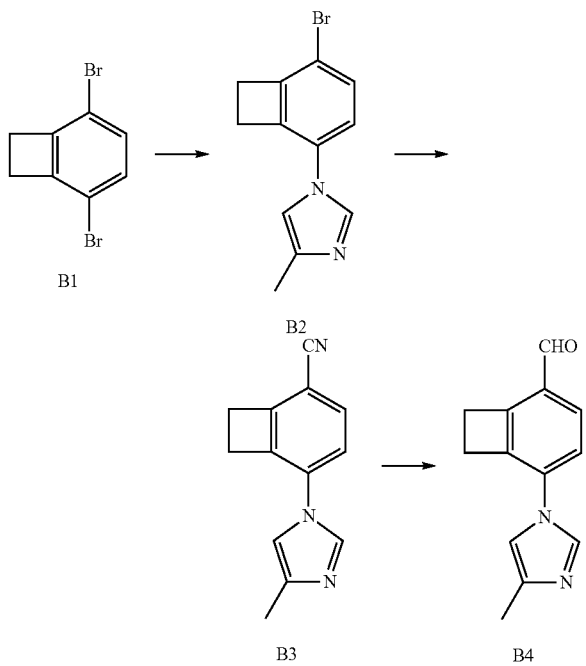

Method B

Compound B1 is obtained using a literature method by K. Walker, L., Markoski and J. Moore *Synthesis*, 1992, 1265.

Method B, Step 1

To a solution of B1 (0.11 mmol) in dry 0.5 mL will be added 4-methyl imidazole (5 eq, 0.546 mmol, 44 mg), $Cu_2O$ (0.4 equiv, 0.044 mmol, 6 mg), 4,7-dimethoxyl-1,8-phenanthracene (0.4 equiv, 0.044 mmol, 10 mg), $Cs_2CO_3$ (1.4 equiv, 0.154 mmol, 50 mg) and PEG (40 mg). The resulting solution will be degassed and heated at 110° C. for 40 h to give compound B1 after purification.

Method B, Step 2

A procedure from P. Schirch and V. Bockelheide is adapted (*J. Amer. Chem. Soc.* 1981, 103, 6873). To a solution of B2 (1.5 g) will be added 5.0 eq of cuprous cyanide in 100 ml of N-methyl-2-pyrrolidinone. The mixture will be heated at 115° C. with stirring under nitrogen to give B3 after workup and purification.

Method B, Step 3

To a 140 mg of B3 in ether will be added 1 eq of DiBAL in hexane. After 1 h, 5 mL of MeOH will be added and the mixture will be poured into ice water followed by acidification with 10% HCl and extraction with ether. The organic layers will be combined and solvent evaporated to give a residue which will be chromatographed to give compound B4.

The following intermediates will be synthesized using methods similar to Method B.

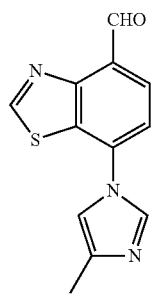
B9

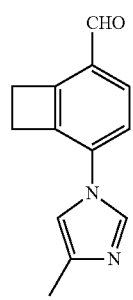
B5

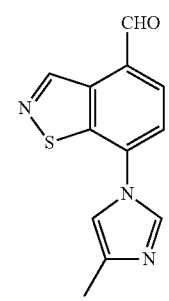
B10

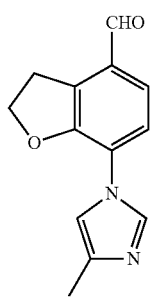
B6

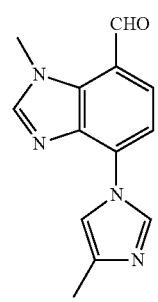
B11

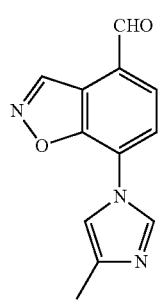
B7

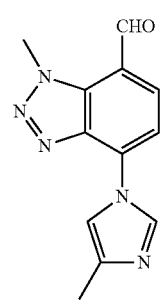
B12

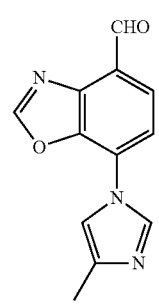
B8

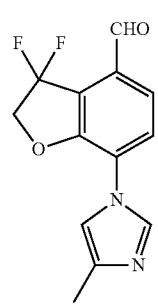
B13

-continued

B14 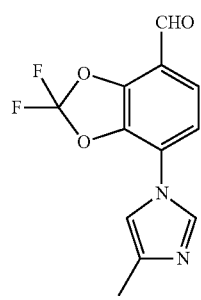

B15 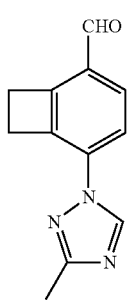

B16 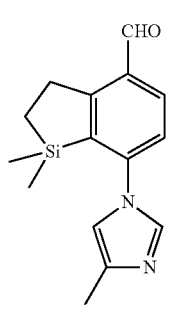

B17 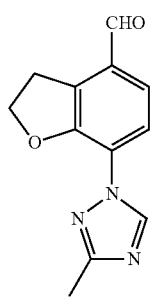

B18 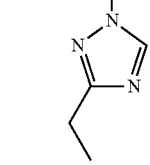

-continued

B19 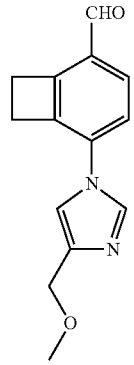

Method C

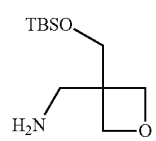

Method C, Step 1
Commercially available C1 will be treated with TBSCl and imidazole in DCM to give C2 after purification.

Method C, Step 2
Compound C2 will be treated with NaN$_3$ in MeOH to give C3 after purification.

Method C, Step 3
Compound C3 will be hydrogenated under H$_2$ over Pd/C to give compound C4 after purification.

The following intermediates will be synthesized using method similar to Method C.

C4 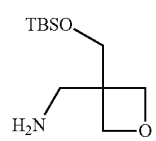

C6 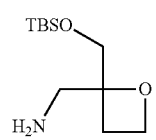

C7 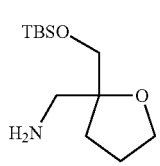

C8 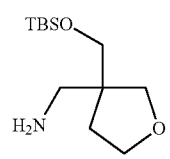
C9 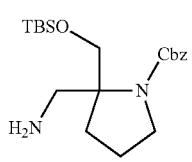
C10 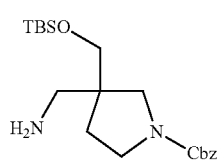
C11 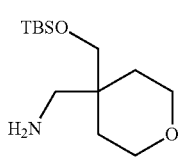
C12 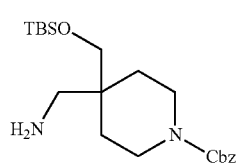
C13 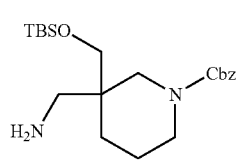
C14 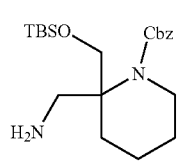
C15 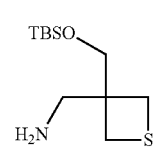
C16 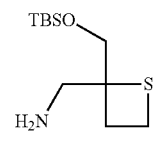
C17 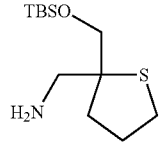
C18 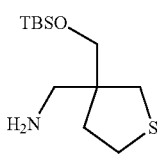
C19 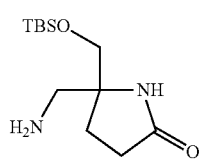
C20 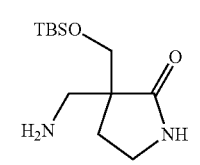
C21 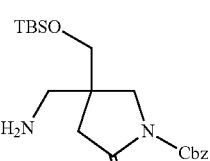
C22 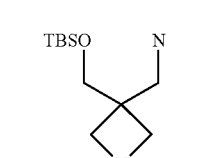
C23 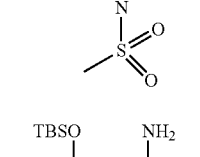
C24 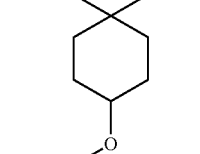
C25 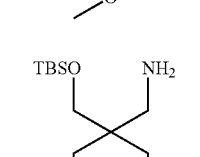

Method D

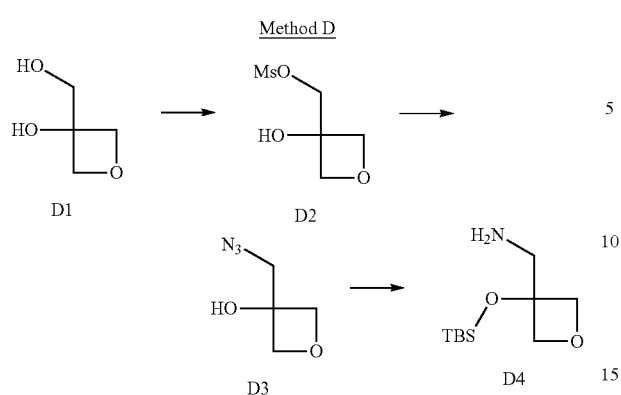

Method D, Step 1

Compound D1 will be treated with 1 eq of methylsulfonyl chloride in ether with DMAP (1.2 eq) to give D2 after workup, D2 will be used for next step without purification.

Method D, Step 2

Compound D2 will be treated with NaN₃ in MeOH to give D3 after purification.

Method O, Step 3

Compound D3 will be treated with TBSCl and imidazole to give the TBS-ether which will be hydrogenated with Pd/C to give D4 after purification.

The following intermediates will be synthesized using methods similar to Method D.

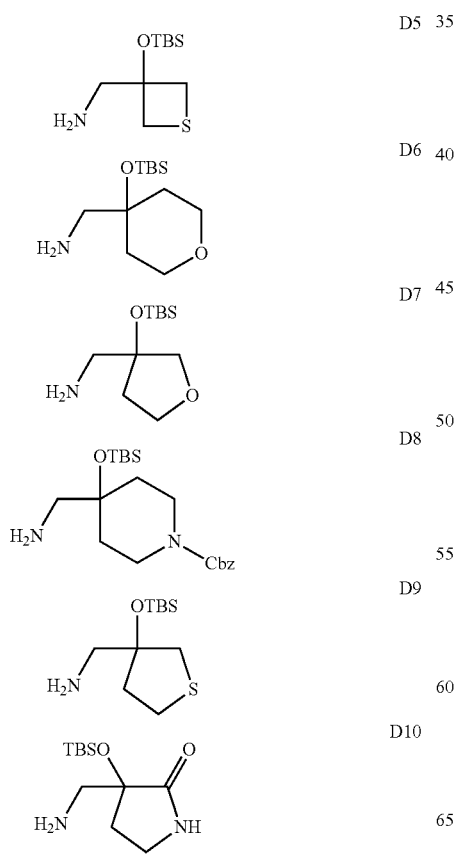

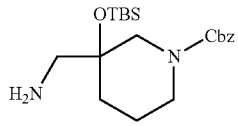

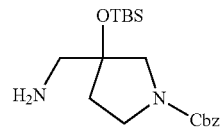

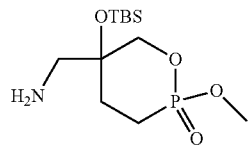

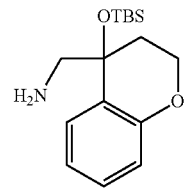

Method E

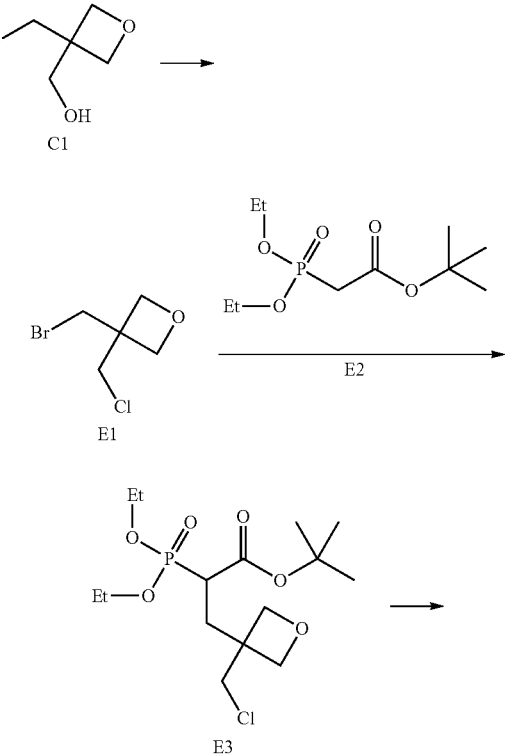

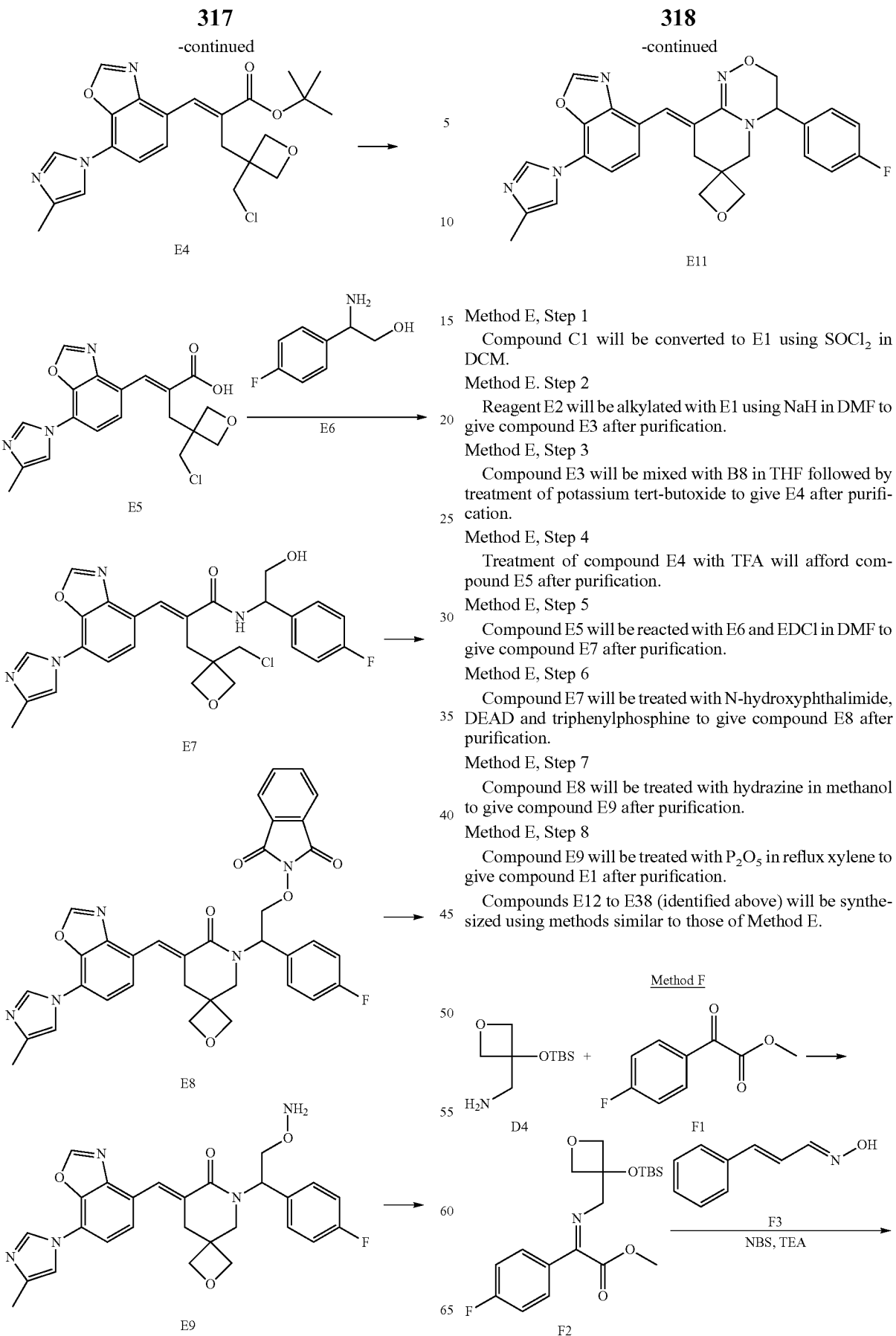

Method E, Step 1
Compound C1 will be converted to E1 using SOCl$_2$ in DCM.
Method E. Step 2
Reagent E2 will be alkylated with E1 using NaH in DMF to give compound E3 after purification.
Method E, Step 3
Compound E3 will be mixed with B8 in THF followed by treatment of potassium tert-butoxide to give E4 after purification.
Method E, Step 4
Treatment of compound E4 with TFA will afford compound E5 after purification.
Method E, Step 5
Compound E5 will be reacted with E6 and EDCl in DMF to give compound E7 after purification.
Method E, Step 6
Compound E7 will be treated with N-hydroxyphthalimide, DEAD and triphenylphosphine to give compound E8 after purification.
Method E, Step 7
Compound E8 will be treated with hydrazine in methanol to give compound E9 after purification.
Method E, Step 8
Compound E9 will be treated with P$_2$O$_5$ in reflux xylene to give compound E1 after purification.
Compounds E12 to E38 (identified above) will be synthesized using methods similar to those of Method E.

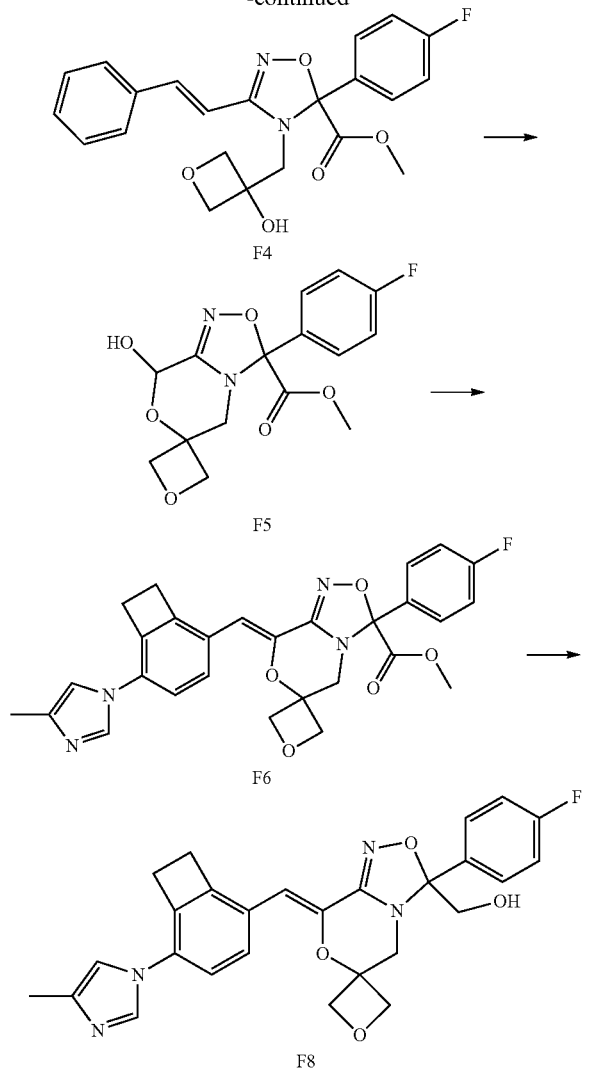

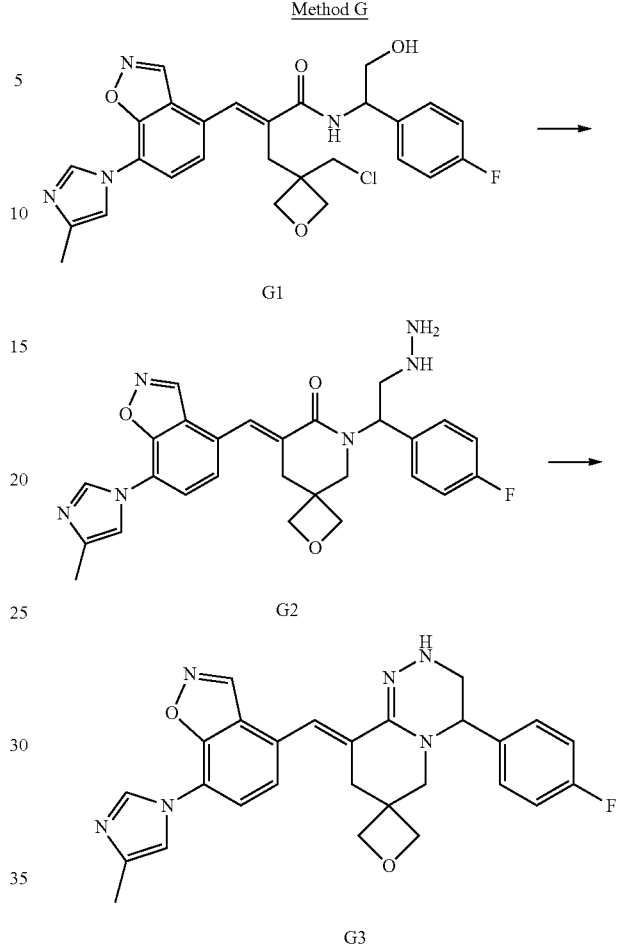

Method F, Step 1

Compound D4 will be reacted with 2.1 eq of TMSCl in presence of 2.5 eq of triethylamine in ether. After the removal of solid precipitate and organic solvent, the residue will be mixed with F1 in DOE under reflux conditions to give compound F2.

Method F, Step 2

Compound F2 will be reacted with a mixture of 1 eq of F3 and 1 eq of NBS in DMF to give the product of [2+3]cycloaddition after purification. The TBS group on the product will be removed using TFA or 1 eq of TBAF to afford compound F4.

Method F, Step 3

Compound F4 will be treated with $O_3$ followed by dimethylsulfide to give compound F5 after purification.

Method F, Step 4

Compound F5 will be reacted with $Ph_3P.HBr$ followed by B5 and potassium tert-butoxide to give compound F6 after workup and purification.

Method F, Step 5

Compound F6 will be reacted with $NaBH_4$ to afford compound F8 after workup and purification.

Compounds F9 to F25 (identified above) will be synthesized using methods similar to those of Method F.

Method G, Step 1

Compound G1 will be obtained using a method similar to the preparation of compound E7. G1 will be treated with $SOCl_2$ followed by hydrazine to give compound G2 after purification.

Method G, Step 2

Compound G2 will be converted to G3 through treatment with $P_2O_5$ in xylene under reflux conditions followed by workup and purification.

Compounds G4 to G24 (identified above) will be synthesized using methods similar to those of Method G.

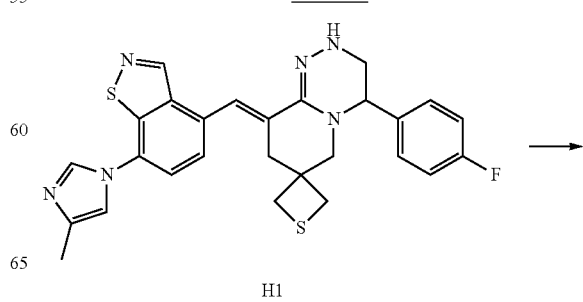

Method J

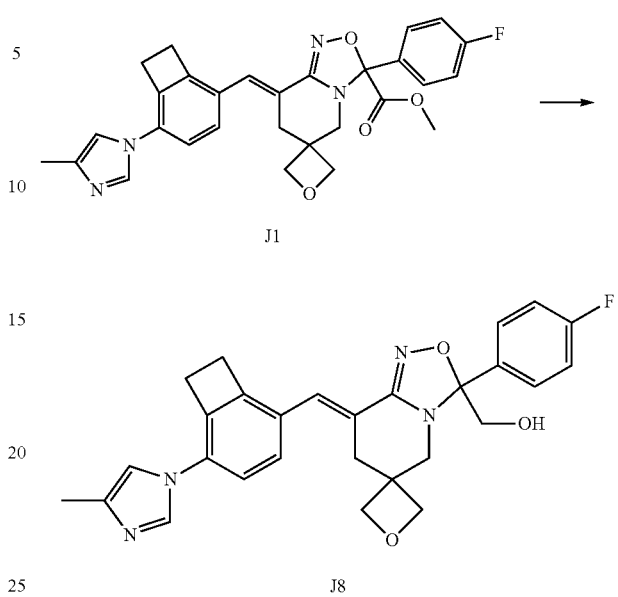

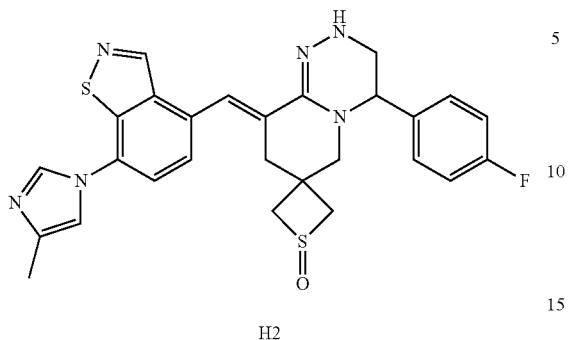

Method H, Step 1
Compound H1 will be obtained using a method similar to Method G. H1 will be dissolved in acetic acid followed by addition of H₂O₂ to give compound H2.
Compounds H3 to H17 (identified above) will be synthesized using methods similar to those of Method H.

Method J, Step 1
Compound J1 will be obtained using a method similar to Method A. J1 will be reacted with NaBH₄ to afford compound J8 after workup and purification.
Compounds J3 to J7, and J9 to J38 (identified above) will be synthesized using methods similar to those of Method J.

Method I

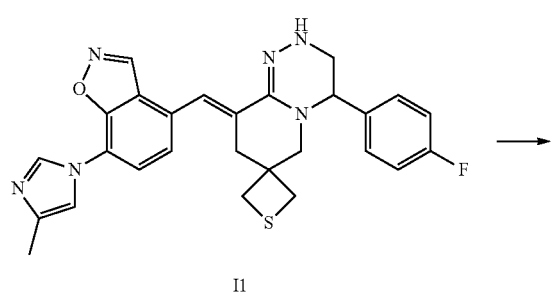

Method K

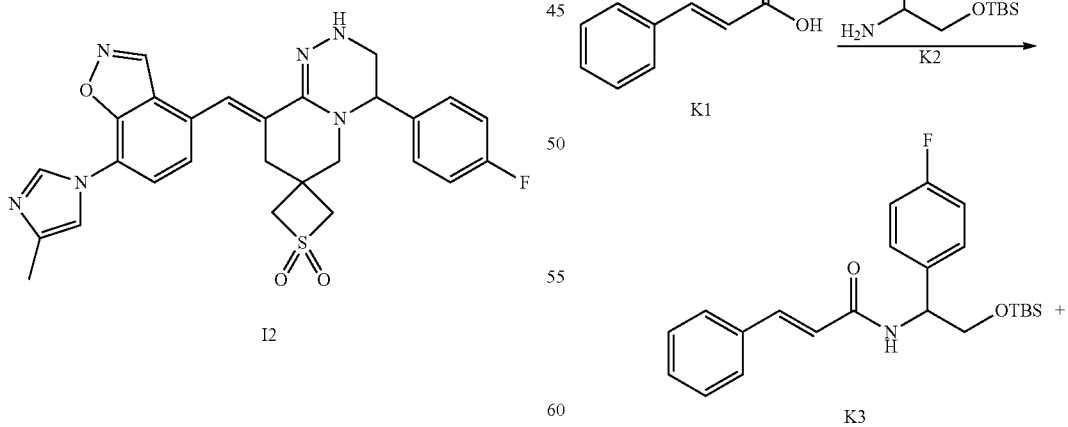

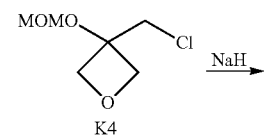

Method I, Step 1
Compound I1 will be prepared using a method similar to method G. I1 be treated with acetic acid and MCPBA to give compound I2 after workup and purification.
Compounds I13 to I17 (identified above) will be synthesized using methods similar to those of Method 1.

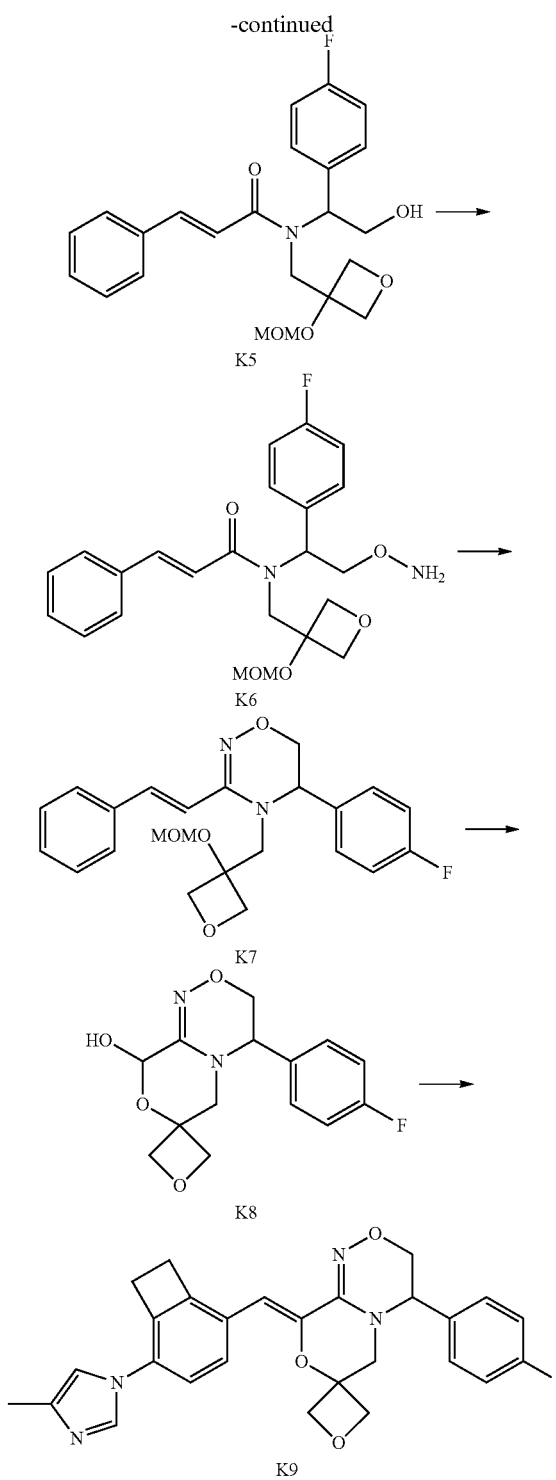

Method K, Step 3

Compound K5 will be reacted with N-hydroxylphthalimide under Mitsunobu conditions such as DEAD and triphenylphosphine to give a product which upon treatment with hydrazine in methanol will give compound K6 after workup and purification.

Method K, Step 4

Compound K6 will be converted to compound K7 through treatment with $P_2O_5$ followed by workup and purification.

Method K, Step 5

Compound K7 will be treated with HCl in methanol to deprotect the MOM-group. The product will be treated with $O_3$ followed by dimethylsulfide to generate compound K8.

Method K, Step 6

Compound K8 will be treated with $Ph_3P.HBr$ followed by compound B4 to afford compound K9 after workup and purification.

Compounds K10 to K24 (identified above) will be synthesized using methods similar to those of Method K.

Method L

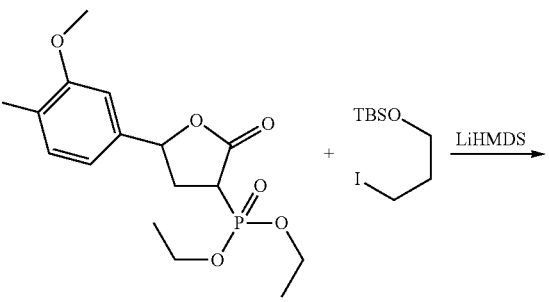

L1

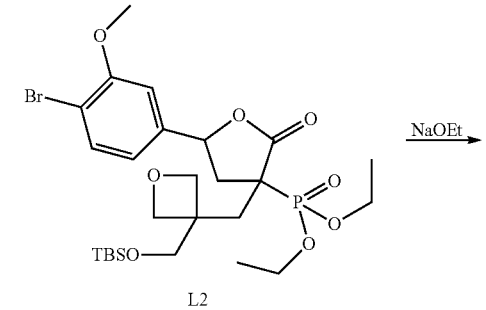

L2

Method K, Step 1

Compound K1 will be reacted with K2 using peptide coupling conditions such as EDCl/TEA in DMF to give compound K3 after workup and purification.

Method K, Step 2

Compound K3 will be treated with K4 and NaH in DMF to give a TBS-protected product which will be treated with TBAF or alternate conditions such as α-chloroethylchloroformate in methanol to give compound K5 after workup and purification.

L3

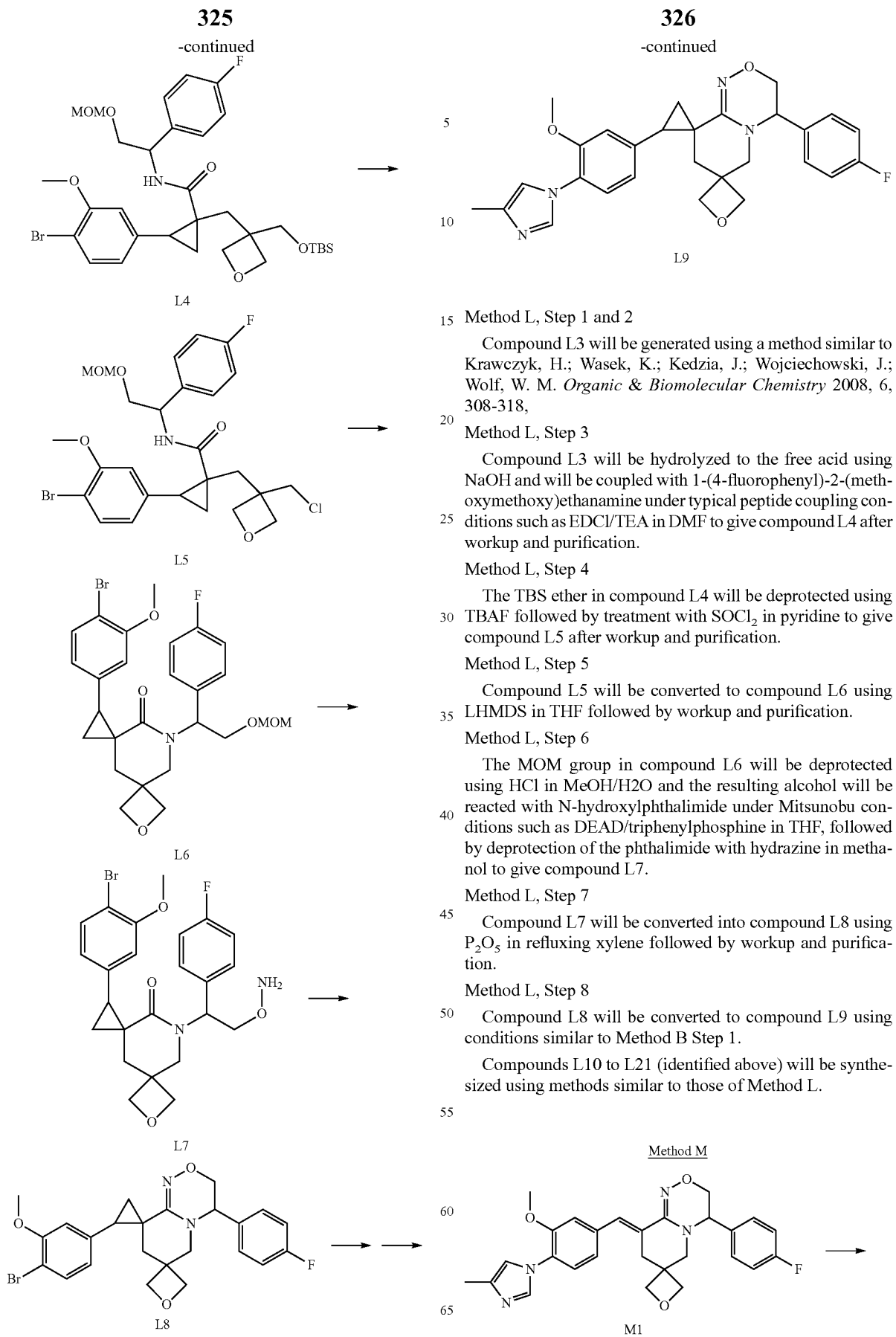

Method L, Step 1 and 2

Compound L3 will be generated using a method similar to Krawczyk, H.; Wasek, K.; Kedzia, J.; Wojciechowski, J.; Wolf, W. M. *Organic & Biomolecular Chemistry* 2008, 6, 308-318, Method L, Step 3

Compound L3 will be hydrolyzed to the free acid using NaOH and will be coupled with 1-(4-fluorophenyl)-2-(methoxymethoxy)ethanamine under typical peptide coupling conditions such as EDCl/TEA in DMF to give compound L4 after workup and purification.

Method L, Step 4

The TBS ether in compound L4 will be deprotected using TBAF followed by treatment with $SOCl_2$ in pyridine to give compound L5 after workup and purification.

Method L, Step 5

Compound L5 will be converted to compound L6 using LHMDS in THF followed by workup and purification.

Method L, Step 6

The MOM group in compound L6 will be deprotected using HCl in MeOH/H2O and the resulting alcohol will be reacted with N-hydroxylphthalimide under Mitsunobu conditions such as DEAD/triphenylphosphine in THF, followed by deprotection of the phthalimide with hydrazine in methanol to give compound L7.

Method L, Step 7

Compound L7 will be converted into compound L8 using $P_2O_5$ in refluxing xylene followed by workup and purification.

Method L, Step 8

Compound L8 will be converted to compound L9 using conditions similar to Method B Step 1.

Compounds L10 to L21 (identified above) will be synthesized using methods similar to those of Method L.

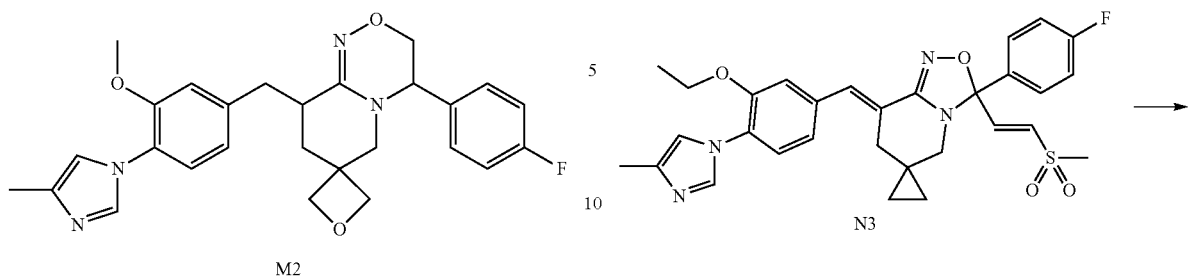

Method M, Step 1

Compound M1 will be obtained using a method similar to method E. M1 will be hydrogenated over Pd/C in EtOAc to give compound M2 after workup and purification.

Compounds M3 to M17 (identified above) will be synthesized using methods similar to those of Method M.

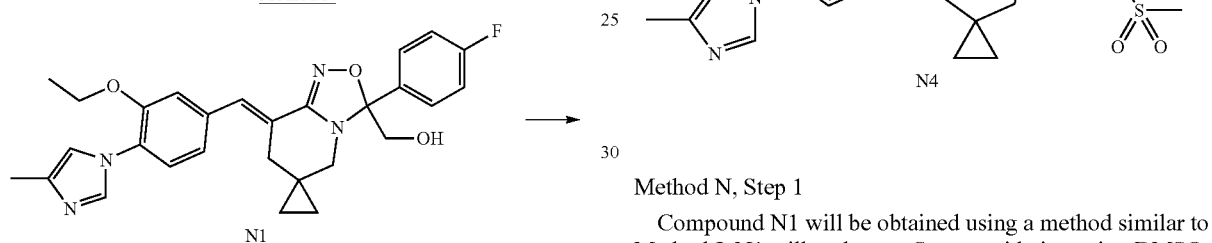

Method N, Step 1

Compound N1 will be obtained using a method similar to Method J. N1 will undergo a Swern oxidation using DMSO, oxalyl chloride and triethylamine in DCM to give compound N2 after workup.

Method N, Step 2

Compound N2 will be reacted with lithium hexamethyldisilazide and [(methylsulfonyl)methyl]-phosphonic acid dimethyl ester to afford compound N3 after workup and purification.

Method N, Step 3

Compound N3 will be reduced with sodium borohydride to afford compound N4 after workup and purification.

Compounds N5 to N22 (identified above) will be synthesized using methods similar to those of Method N.

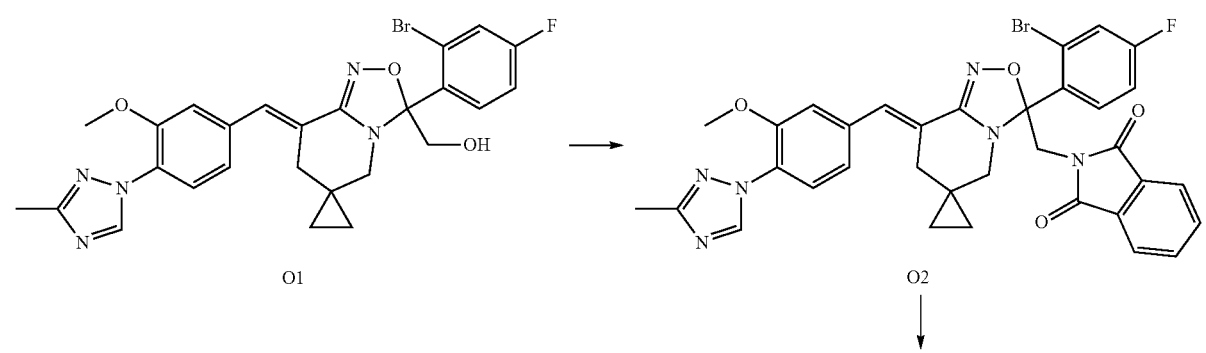

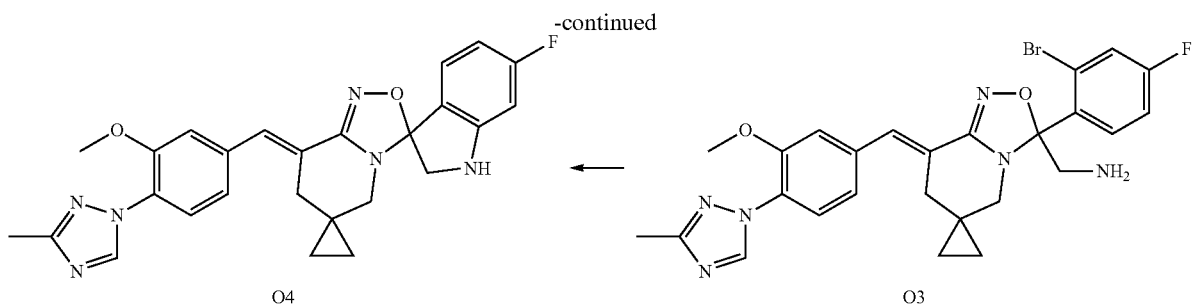

O4 ← O3

Method O, Step 1

Compound O1 will be obtained using a method similar to Method J. O1 will be reacted with phthalimide, DEAD and tributylphosphine to give compound O2 after workup and purification.

Method O, Step 2

Compound O2 will be reacted with hydrazine to afford compound O3 after workup.

Method O, Step 3

Compound O3 will be cyclized with copper iodide, potassium carbonate and N1,N2-dimethylethane-1,2-diamine to afford compound O4 after workup and purification.

Compounds O5 to O22 (identified above) will be synthesized using methods similar to those of Method O.

Method P

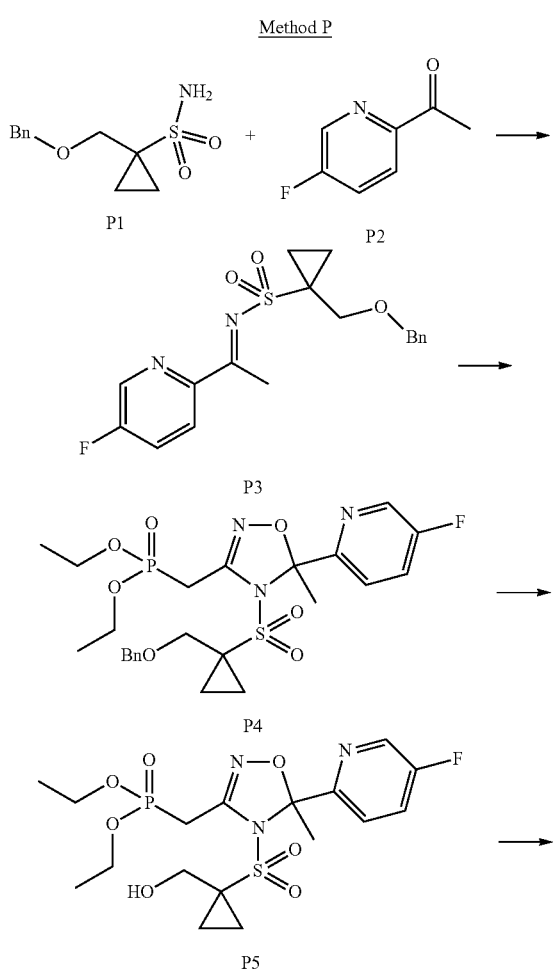

-continued

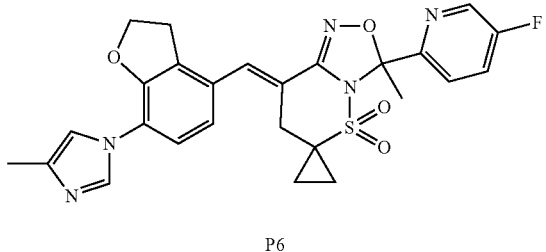

P6

Method P, Step 1

Compound P1 will be obtained using a method similar to Li, J.; Smith, D.; Wong, H. S.; Campbell, J. A.; Meanwell, N. A.; Scola, P. M. *Synlett* 2006, 5, 725-728, and using chloro(benzyloxy)methane instead of chloro(methoxy)methane. P1 will be reacted with 1-(5-fluoropyridin-2-yl)ethanone P2 under conditions described in method A to provide compound P3.

Method P, Step 2

Compound P3 will be reacted with A4 under conditions described in method A to afford compound P4, after workup and purification.

Method P, Step 3

Compound P3 with be hydrogenated on palladium hydroxide overnight to give P5.

Method P, Step 4

Compound P5 with be converted to compound P6 following conditions described in method A and using B6 as intermediate.

Compounds P7 to P15 (identified above) will be synthesized using methods similar to those of Method P.

Method Q

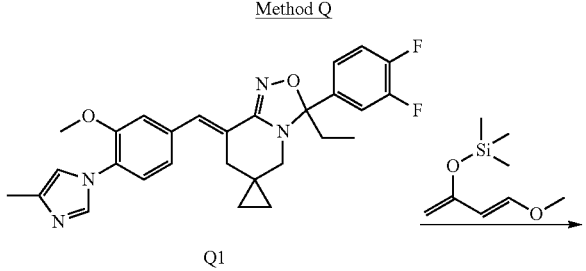

Q1

331

-continued

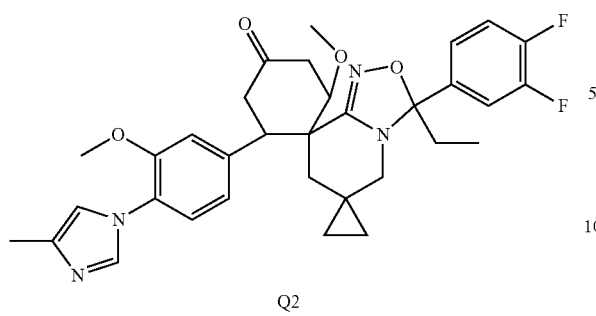

Q2

Method Q, Step 1

Compound Q1 will be prepared according to Method A. Q1 will be reacted with (E)-(4-methoxybuta-1,3-dien-2-yloxy) trimethylsilane (Danishefsky, S.; Morris, J.; Mullen, G.; Gammill, R. *J Am Chem Soc* 1980, 102, 2838) to afford compound Q2, after workup and purification.

Compounds Q3 to Q11 (identified above) will be synthesized using methods similar to those of Method Q.

Method R

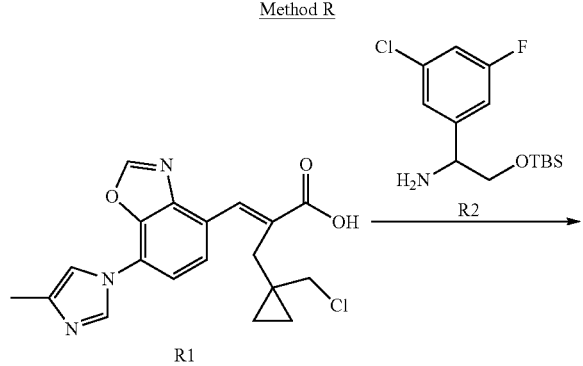

R1

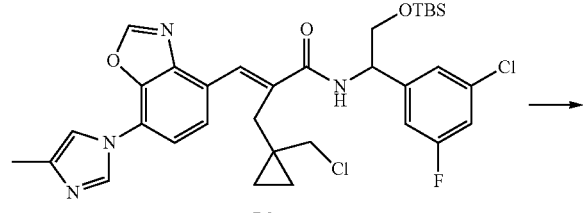

R3

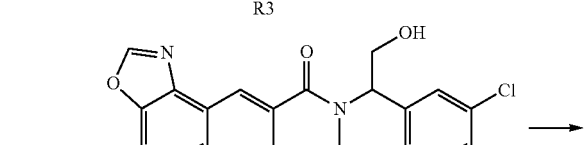

R4

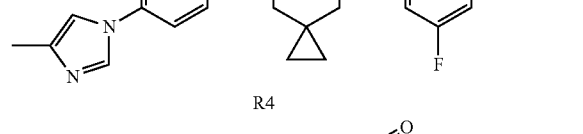

R5

332

-continued

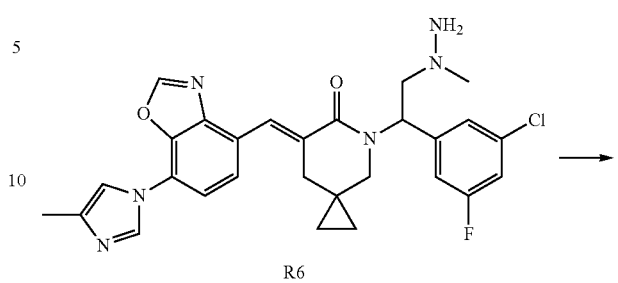

R6

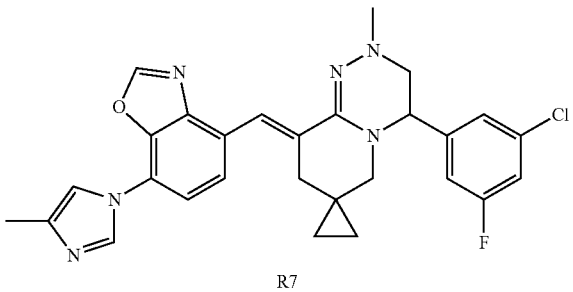

R7

Method R, Step 1

Compound R1 will be obtained using a method similar to the preparation of compound E7. Compound R1 will be reacted with R2 using peptide coupling conditions such as EDCI/TEA in DMF to give compound R3 after workup and purification.

Method R, Step 2

Compound R3 will be cyclized to an O-protected intermediate through treatment with a base such as NaH followed by workup and purification. This intermediate will be treated with TBAF or alternate conditions such as α-chloroethylchloroformate in methanol to give compound R4 after workup and purification.

Method R, Step 3

Compound R4 will undergo a Swern oxidation using DMSO, oxalyl chloride and triethylamine in DCM, or alternate conditions such as Dess-Martin periodinane in DCM, to give compound R5.

Method R, Step 4

Compound R5 will be treated with benzaldehyde (E)-methylhydrazone and trimethylaluminum in DCM following conditions similar to the ones from E I Kaim, L.; Grimaud, L.; Perroux, Y.; Tirla, C.; *J Org Chem* 2003, 68, 8733-8735. The resulting intermediate will then be hydrolyzed with hydroxylamine hydrochloride and HCl in acetonitrile to afford compound R6.

Method R, Step 5

Compound R6 will be converted to compound R7 through treatment with $P_2O_5$ or alternate dehydrating agents followed by workup and purification.

Compounds R8 to R19 (identified above) will be synthesized using methods similar to those of Method R.

333

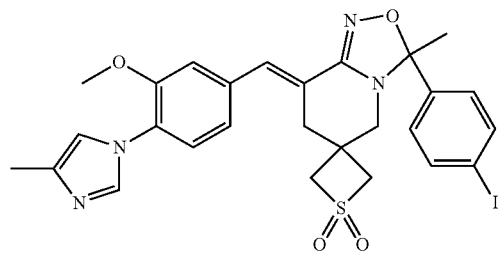

S1

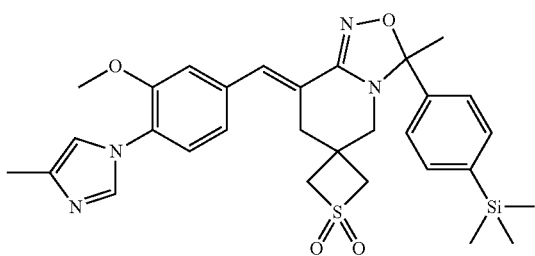

S3

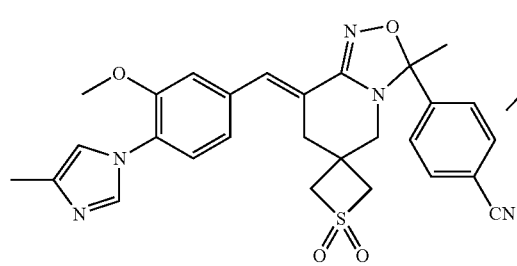

S2

Method S, Step 1

Compound S1 will be obtained using a method similar to method A. S1 will be reacted with trimethylsilane following conditions similar to the ones from Murala, M.; Ohara, H.; Oiwa, R.; Watanabe, S.; Masuda, Y.; *Synthesis* 2006, 11, 1771 to give compound S3 after purification.

Alternatively, compound S2 will be obtained using a method similar to method A. S2 will be reacted with hexamethyldisilane following conditions similar to the ones from Tobisu, M.; Kita, Y.; Chatani, N.; *J Am Chem Sac* 2006, 128, 8152 to give compound S3 after purification.

Compounds S4 to S15 (identified above) will be synthesized using methods similar to those of Method S.

Method T

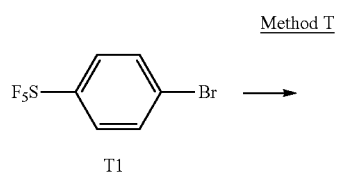

T1

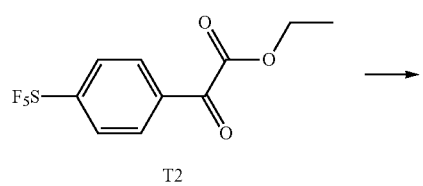

T2

334

-continued

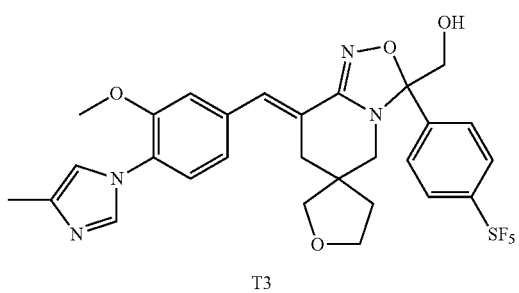

T3

Method T, Step 1

1-Bromo-4-(pentafluorothio)benzene T1 will be treated with isopropylmagnesium chloride and lithium chloride to generate a Grignard reagent that will be coupled with diethyloxalate to give compound T2 after workup and purification.

Method T, Step 2

Compound T2 will be converted to compound T3 using conditions similar to methods A and J.

Compounds T4 to T18 (identified above) will be synthesized using methods similar to those of Method T.

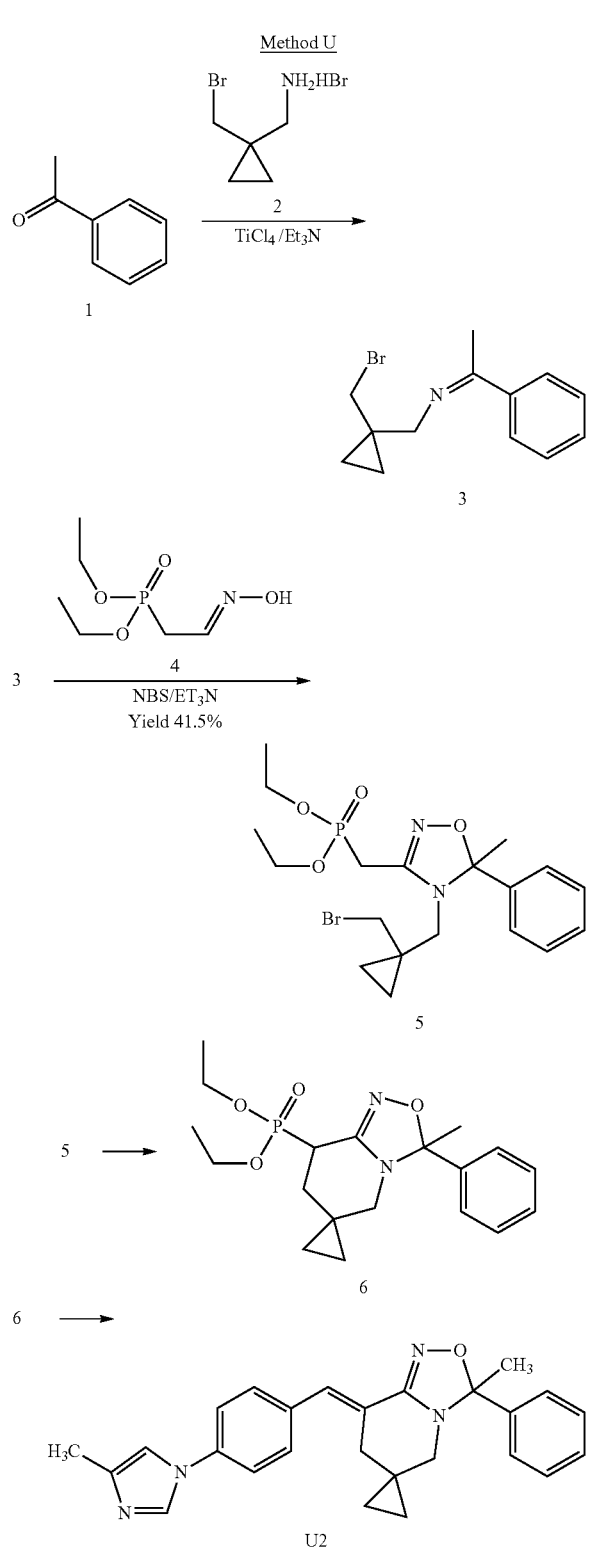

ASSAY

Secretase Reaction and Aβ Analysis in Whole Cells: HEK293 cells overexpressing APP with Swedish and London mutations were treated with the specified compounds for 5 hour at 37° C. In 100 ml of DMEM medium containing 10% fetal bovine serum. At the end of the incubation, total Aβ, Aβ40 and Aβ42 were measured using electrochemiluminescence (ECL) based sandwich immunoassays. Total Aβ was determined using a pair of antibodies TAG-W02 and biotin-4G8, Aβ40 was identified with antibody pairs TAG-G2-10 and biotin-4G8, while Aβ42 was identified with TAG-G2-11 and biotin-4G8. The ECL signal was measured using Sector Imager 2400 (Meso Scale Discovery).

MS Analysis of Aβ Profile: Aβ profile in conditioned media was determined using surface enhanced laser desorption/ionization (SELDI) mass spectrometry. Conditioned media was incubated with antibody W02 coated PS20 ProteinChip array. Mass spectra of Aβ captured on the array was read on SELDI ProteinChip Reader (Bio-Rad) according to manufacturer's instructions.

CSF Aβ Analysis: Aβ in rat CSF was determined using MSD technology as described above. Aβ40 was measured using antibody pair Tag-G2-10 and biotin-4G8, while Aβ42 was measured using Tag-anti Aβ42 (Meso Scale Discovery) and biotin-4G8. The ECL signal was measured using Sector Imager 2400 (Meso Scale Discovery).

Matrix-assisted laser desorption/ionization mass spectrometric (MALDI MS) analysis of Aβ was performed on a Voyager-DE STR mass spectrometer (ABI, Framingham, Mass.). The instrument is equipped with a pulsed nitrogen laser (337 nm). Mass spectra was acquired in the linear mode with an acceleration voltage of 20 kV. Each spectrum presented in this work represents an average of 256 laser shots. To prepare the sample-matrix solution, 1 μL of immunoprecipitated Aβ sample was mixed with 3 μL of saturated α-cyano-4-hydroxycinnamic add solution in 0.1% TFA/acetonitrile. The sample-matrix solution was then applied to the sample plate and dried at ambient temperature prior to mass spectrometric analysis. All the spectra are externally calibrated with a mixture of bovine insulin and ACTH (18-39 clip).

Certain compounds had a Cellular Aβ42 IC$_{50}$ of less than 1 micromolar, and a ratio of total Aβ versus Aβ42 higher than 39.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound of the formula

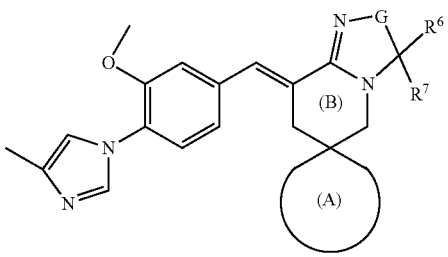

or a pharmaceutically acceptable salt thereof, wherein
G is —O— or O—C—(R3)$_2$ each R$^3$ is taken together with the carbon atom to which they are bound to form a 3 to 8 membered cycloalkyl or heterocycloalkyl ring, said heterocycloalkyl ring comprising 1 to 3 ring members independently selected from the group consisting of: O, S, NR$^2$, P(O)alkyl, P(O)Oalkyl, S(O), and S(O)$_2$, and wherein the remaining ring members are selected from the group consisting of carbon and C(O);

Spiro Ring (A) is selected from the group consisting of: cycloalkyl, cycloalkenyl, heterocycloalkyl, and heterocycloalkenyl, wherein:

(a) said cycloalkyl ring (A) is a 3 to 8 carbon membered ring (including the carbon atom common to both rings (A) and (B)), and (b) said cycloalkenyl ring (A) is a 5 to 8 carbon membered ring (including the carbon atom common to both rings (A) and (B)) comprising one or two double bonds, provided that there is no double bond to the carbon common to Rings (A) and (B) and (c) said heterocycloalkyl Ring (A) is a 4 to 8 membered ring (including the carbon atom common to Rings (A) and (B)) comprising 1 to 3 ring members independently selected from the group consisting of: O, S, $NR^2$, P(O) alkyl, P(O)Oalkyl, S(O), and $S(O)_2$, and wherein the remaining ring members are independently selected from the group consisting of carbon and C(O), and (d) said heterocycloalkenyl Ring (A) is a 5 to 8 membered ring (including the carbon atom common to Rings (A) and (B)) comprising one or two double bonds, and comprising 1 to 3 ring members independently selected from the group consisting of: O, S, $NR^2$, P(O)alkyl, P(O)Oalkyl, S(O), and $S(O)_2$, and wherein the remaining ring members are independently selected from the group consisting of carbon and C(O), provided that there is no double bond to the carbon common to Rings (A) and (B), and (e) wherein said Spiro Ring (A) is optionally fused with an aryl ring, or is optionally fused with a heteroaryl ring, to form a fused Spiro Ring (A) moiety, and (f) wherein said Spiro Ring (A) is optionally substituted with 1 to 3 substituents independently selected from the group consisting of: alkyl, alkenyl, alkynyl, —CN, halo, —C(O)$R^{15}$, —C(O)O$R^{15}$, —C(O)N($R^{15}$)($R^{16}$), —S(O)N($R^{15}$)($R^{16}$), —S(O)$_2$N($R^{15}$) ($R^{16}$), —C(=NO$R^{15}$)$R^{16}$, —P(O)(O$R^{15}$)(O$R^{16}$), —O$R^{15}$ (e.g., —OCH$_3$), and —S(O)$_2$ $R^{15A}$ (e.g., —S(O)$_2$CH$_3$);

$R^6$ and $R^7$ are each independently selected from the group consisting of: H, alkyl-, alkenyl-, alkynyl-, phenyl, pyridinyl or thiophenyl, wherein the alkyl, alkenyl, alkynyl, phenyl, pyridinyl or thiophenyl is optionally substituted with 1 to 5 independently selected $R^{21}$ groups selected from the group consisting of alkyl, alkenyl, alkynyl, alkoxyl and halo; or $R^6$ and $R^7$, together with the carbon atom to which they are bound, form 6-membered heterocycloalkyl fused to a phenyl;

$R^{15}$ and $R^{16}$ are each independently selected from hydrogen, alkyl, alkenyl and alkynyl; and $R^{15A}$ is selected from alkyl, alkenyl and alkynyl.

2. The compound according to claim 1 or a pharmaceutically acceptable salt thereof, wherein $R^6$ is an alkyl and $R^7$ is phenyl optionally substituted with a fluoro, chloro, or trifluoromethyl group.

3. The compound according to claim 1 or a pharmaceutically acceptable salt thereof, wherein $R^6$ is an alkyl and $R^7$ is a pyridinyl optionally substituted with a fluoro group.

4. The compound according to claim 1 or a pharmaceutically acceptable salt thereof, wherein G is —O—.

5. The compound according to claim 1 or a pharmaceutically acceptable salt thereof, wherein the spiro ring A is a cyclopropyl.

6. The compound according to claim 1 or a pharmaceutically acceptable salt thereof, wherein the spiro ring A is a heterocycloalkyl selected from tetrahydrofuran, azetidine, thietane, oxetane, and morpholine.

7. The compound according to claim 1 or a pharmaceutically acceptable salt thereof, wherein the compound is selected from the group consisting of:

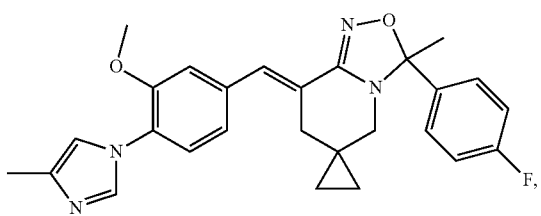

A10

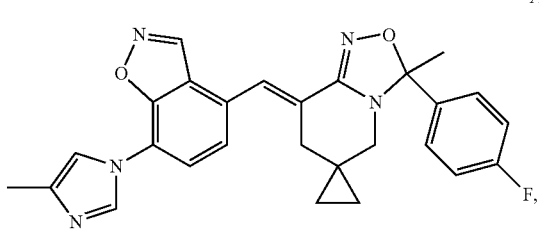

A11

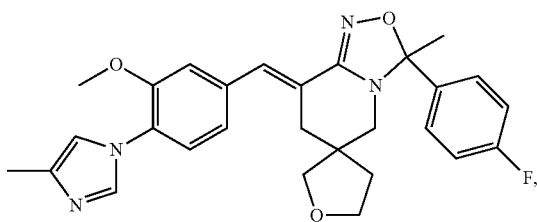

A12

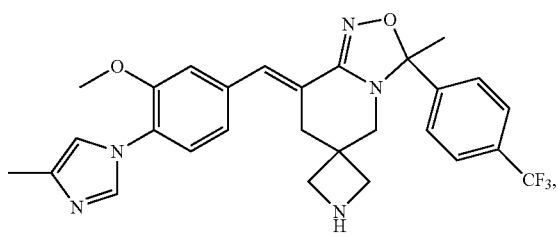

A13

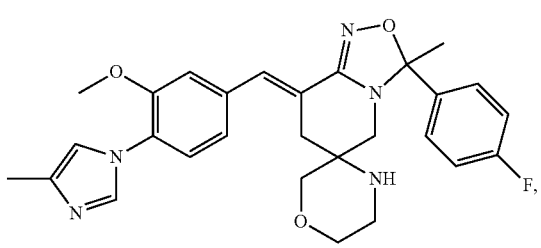

A14

-continued

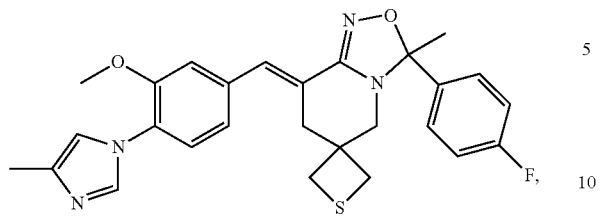
A15

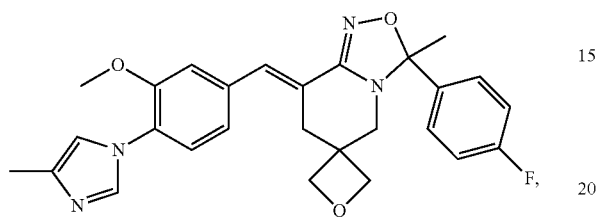
A16

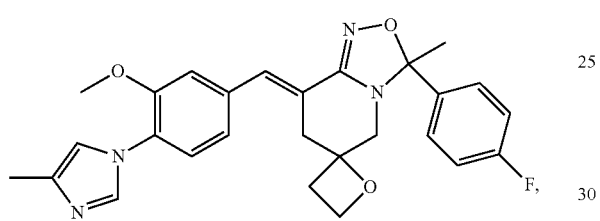
A17

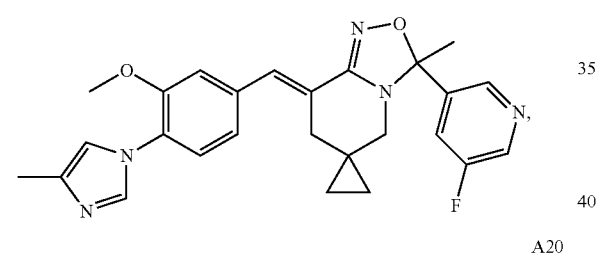
A19

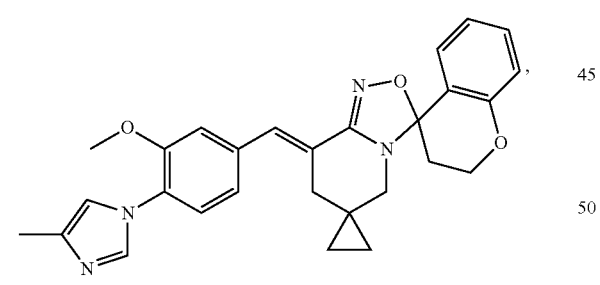
A20

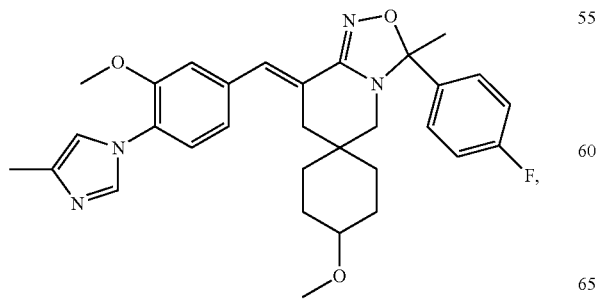
A22

-continued

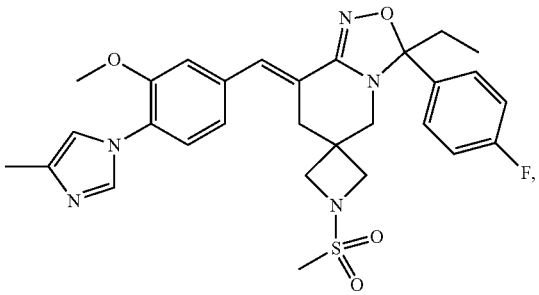
A23

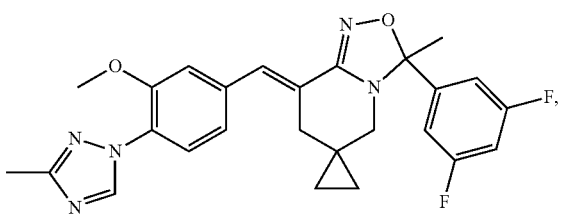
A24

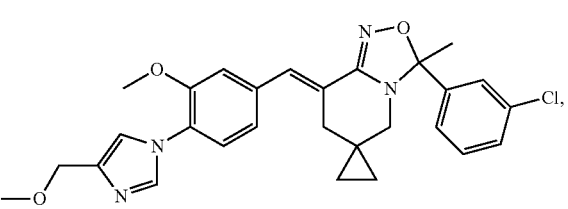
A26

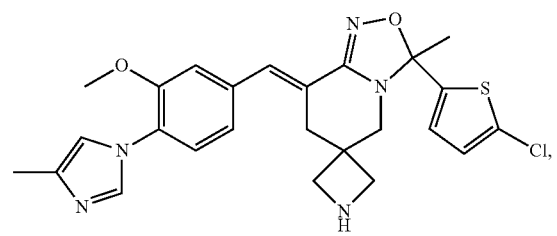
A27 and

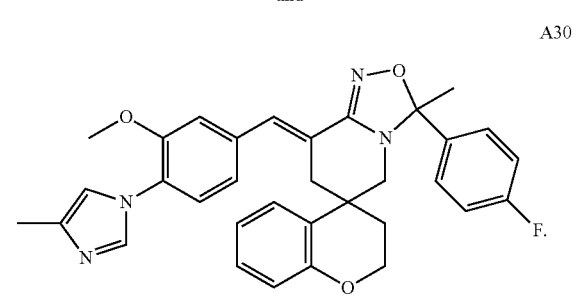
A30

8. A pharmaceutical composition comprising a compound according to claim 1 or a pharmaceutically acceptable salt thereof and a pharmaceutically acceptable carrier.

9. A method of treating Alzheimer's disease in a patient in need thereof, the method comprising administering to the patient a therapeutically effective amount of a compound according to claim 1 or a pharmaceutically acceptable salt thereof.

10. A method of treating Alzheimer's disease in a patient in need thereof, the method comprising administering to the patient a therapeutically effective amount of a compound according to claim 1 or a pharmaceutically acceptable salt thereof in combination with an effective amount of one or more other pharmaceutically active ingredients selected from the group consisting of: BACE inhibitors; muscarinic antagonists; cholinesterase inhibitors; gamma secretase inhibitors; gamma secretase modulators; HMG-CoA reductase inhibitors; non-steroidal anti-inflammatory agents; N-methyl-D-aspartate receptor antagonists; anti-amyloid antibodies; vitamin E; nicotinic acetylcholine receptor agonists; CB1 receptor inverse agonists or CB1 receptor antagonists; an antibiotic; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors and cholesterol absorption inhibitors.

* * * * *